US011497762B2

(12) United States Patent
Van Battum et al.

(10) Patent No.: US 11,497,762 B2
(45) Date of Patent: Nov. 15, 2022

(54) MIRNA MOLECULE, EQUIVALENT, ANTAGOMIR, OR SOURCE THEREOF FOR TREATING AND/OR DIAGNOSING A CONDITION AND/OR A DISEASE ASSOCIATED WITH NEURONAL DEFICIENCY OR FOR NEURONAL (RE)GENERATION

(71) Applicant: INTERNA TECHNOLOGIES B.V., Nijmegen (NL)

(72) Inventors: Eljo Y. Van Battum, Zeist (NL); Vamshi R. Vangoor, Zeist (NL); Alwin A. H. A. Derijck, Driebergen-Rijsenburg (NL); Roeland Quirinus Jozef Schaapveld, Bussum (NL); R. Jeroen Pasterkamp, Vleuten (NL)

(73) Assignee: INTERNA TECHNOLOGIES B.V., Nijmegen (NL)

( * ) Notice: Subject to any disclaimer, the term of this patent is extended or adjusted under 35 U.S.C. 154(b) by 73 days.

(21) Appl. No.: 16/760,396

(22) PCT Filed: Nov. 2, 2018

(86) PCT No.: PCT/EP2018/080007
§ 371 (c)(1),
(2) Date: Apr. 29, 2020

(87) PCT Pub. No.: WO2019/086603
PCT Pub. Date: May 9, 2019

(65) Prior Publication Data
US 2020/0352978 A1 Nov. 12, 2020
US 2021/0315917 A9 Oct. 14, 2021

(30) Foreign Application Priority Data
Nov. 3, 2017 (EP) .................................. 17199997

(51) Int. Cl.
*A61K 31/713* (2006.01)
*C12N 15/113* (2010.01)
*C12Q 1/68* (2018.01)

(52) U.S. Cl.
CPC .......... *A61K 31/713* (2013.01); *C12N 15/113* (2013.01); *C12N 2310/113* (2013.01); *C12N 2310/141* (2013.01)

(58) Field of Classification Search
None
See application file for complete search history.

(56) References Cited

U.S. PATENT DOCUMENTS

| 10,792,298 B2* | 10/2020 | De Pietri Tonelli .... A61P 35/00 |
| 2016/0348101 A1* | 12/2016 | Chen ...................... A61P 25/18 |

FOREIGN PATENT DOCUMENTS

| WO | 2013/018060 A2 | 2/2013 |
| WO | 2014/096418 A2 | 6/2014 |
| WO | 2015/118537 A2 | 8/2015 |

OTHER PUBLICATIONS

Alsharafi, W., et al., "Dynamic Expression of MicroRNAs (183, 135a, 125b, 128, 30c and 27a) in the Rat Pilocarpine Model and Temporal Lobe Epilepsy Patients," CNS & Neurological Disorders—Drug Targets, vol. 14, pp. 1096-1102 (2015).
Issler, O., et al., "MicroRNA 135 Is Essential for Chronic Stress Resiliency, Antidepressant Effficacy, and Intact Serotonergic Activity," Neuron, vol. 83, No. 2, pp. 344-360 (Jun. 19, 2014).
Huang, Y., et al., "Myocyte-Specific Enhancer Binding Factor 2A Expression is Downregulated During Temporal Lobe Epilepsy," International Journal of Neuroscience, vol. 126, No. 9, pp. 1-11 (Published online Oct. 6, 2015).
Van Battum, E., et al., "An Image-Based miRNA Screen Identifies miRNA-135s as Regulators of CNS Axon Growth and Regeneration by Targeting Kruppel-like Factor 4," Journal of Neuroscience, vol. 38, No. 3, pp. 613-630 (Jan. 17, 2018).

* cited by examiner

*Primary Examiner* — Sean McGarry
(74) *Attorney, Agent, or Firm* — Christopher M. Cabral; Much Shelist, PC

(57) ABSTRACT

The invention relates to the diagnostic and therapeutic uses of a miRNA molecule, an equivalent or a source thereof in a neuronal deficiency or a disease and condition associated with neuronal deficiency.

9 Claims, 37 Drawing Sheets
Specification includes a Sequence Listing.

C

B

MIRNA MOLECULE, EQUIVALENT, ANTAGOMIR, OR SOURCE THEREOF FOR TREATING AND/OR DIAGNOSING A CONDITION AND/OR A DISEASE ASSOCIATED WITH NEURONAL DEFICIENCY OR FOR NEURONAL (RE)GENERATION

CROSS REFERENCE TO RELATED APPLICATIONS

The present application is the 35 U.S.C. 371 National Stage of International Application Number PCT/EP2018/080007, filed Nov. 2, 2018, which claims priority from European patent application 17199997.2, filed Nov. 3, 2017, the contents of each of which are incorporated herein by reference.

Sequence Listing Submission via EFS-Web

A computer readable text file, entitled "105811-5020-Sequence-Listing.txt", created on or about Apr. 28, 2020, with a file size of about 75,000 bytes contains the sequence listing for this application and is hereby incorporated by reference in its entirety.

FIELD OF THE INVENTION

The invention relates to a miRNA molecule, equivalent, antagomir, or source thereof for treating and/or diagnosing a neuronal deficiency or for neuronal (re)generation.

BACKGROUND OF THE INVENTION

Deficient neuronal function is involved in several diseases or conditions. For example, loss of cognition, neurodegenerative disorders such as Alzheimer's disease and Parkinson's disease or the traumatic spinal cord injury are all characterized by a loss of neurons and their connections. Current therapeutic options are still very limited and display a limited if any efficacy.

To tentatively restore complete neuronal function (neurorestoration), different therapeutic approaches are considered (Enciu et al, BMC Neurology 2011, 11:75; Kraev et al, PLoS ONE, 10 Aug. 2011, Vol 6, Issue 8).

Neuroplasticity could be improved. Neuroplasticity is a comprehensive term that illustrates the brain's capacity to adapt, structurally and functionally, to environmental enhancement. Neuroplasticity is particularly important for cognitive abilities such as learning and memory formation.

Neuronal regeneration could be improved. It implies that new neurons or new projections, generated either through proliferation of endogenous stem/progenitor cells or by administration of exogenous stem/precursor cells with potential to substitute for lost tissue, will differentiate, survive, and integrate into existing neural networks. Neuroprotection could be promoted using growth factors (Nerve Growth Factor (NGF), Brain-Derived Nerve Factor (BDNF), Glial-Derived Nerve Factor (GDNF)) and their pro-survival effect on neuronal cells.

Neurite extension, or neurite outgrowth, plays a fundamental role in embryonic development, neuronal differentiation, and nervous system function. Neurite outgrowth is also critical in some neuropathological disorders as well as neuronal injury and regeneration. A variety of neurite parameters, including length and number of neurites, are sensitive to the intra- or extracellular environment and pharmacological agents. Retinoic acid, plannexin and neuropeptide galanin are examples of these candidates which are able to induce neurite outgrowth of neuronal cells.

However, the mechanisms and factors that regulate the regeneration of neurons in the adult after nerve injury remain poorly understood. Damage to a peripheral nerve causes major changes within the cell bodies of the sensory neurons which are thought to promote regeneration by stimulating neurite outgrowth and enhancing survival of the damaged neuron.

Another neuronal disfunction is epilepsy. Epilepsy is a chronic neurological disorder and is characterized by recurrent unprovoked seizures, caused due to abnormal and synchronous neuronal discharges within the brain (Chang and Lowenstein, 2003). In some cases, epilepsy is caused by single gene mutations mainly of genes encoding ion channels, but the reason for most epilepsies is unknown. Temporal lobe Epilepsy (TLE) is a subclass of epilepsy, accounts for about one third of all patients with epilepsy (Engel, 2001). It consists of several subgroups of which Mesial Temporal Lobe Epilepsy with Hippocampal Sclerosis (MTLE-HS) is the most severe one. MTLE-HS presents with a typical set of diagnostics, clinical and pathological characteristics (neuron loss, gliosis and axonal sprouting) and is known to be most resistant to pharmacological treatment (Wieser and Epilepsy, 2004). For many patients, surgical removal of the hippocampus is the only alternative to achieve seizure control (Semah et al., 1998). The pathological mechanisms underlying TLE are largely unknown. Anticonvulsant and anti-epileptic drugs are used to treat these patients. But, unfortunately these only reduce the occurrence of seizures but do not treat the underlying pathophysiology. Hence there is an urgent need to develop novel treatment strategies for this disabling condition. A need for developing disease-modifying drugs is increasingly recognized by research community and in clinical practice (Loscher et al., 2013).

The pathological mechanisms underlying MTLE are still largely unknown. Animal models of epilepsy and human tissue studies suggest that epileptogenesis involves a cascade of molecular, cellular and neuronal network alterations (Rakhade and Jensen, 2009). Approaches starting from the transcriptome have revealed that patterns of gene expression are significantly altered in human MTLE (van Gassen et al., 2008) and during epileptogenesis in animal models for TLE (Gorter et al., 2006; Pitkanen and Lukasiuk, 2009; Rakhade and Jensen, 2009). This dysregulation effects entire gene regulatory networks that normally control gene expression that regulate pathways involving inflammation, gliosis, synaptic structure and neuronal function. Insight into whether or how these mechanisms are altered may not only provide important new insights into the pathogenesis of TLE, but could also yield novel targets for therapy.

Examples of known drugs for managing epilepsy are lamotrigine, phenytoin, carbamazepine, levetiracetam, oxcarbazepine, clobazam, diazepam, lorazepam, Seroquel, pregabaline, and restoril. These drugs are generally antiseizure or anticonvulsant agents. For example, lamotrigine suppresses the release of glutamate and aspartate, two of the dominant excitatory neurotransmitters in the CNS; phenytoin is believed to protect against seizures by causing voltage-dependent block of voltage gated sodium channels. Carbamazepine and oxcarbazepine are sodium channel blockers, levetiracetam inhibits presynaptic calcium channels. Clobazam is a $GABA_A$ receptor agonist and may affect sodium channels and voltage-sensitive calcium channels. These drugs are generally prone to causing drug-drug interactions because they are metabolized via e.g. CYP2C19, CYP3A4 and CYP3A5. Also they mostly treat symptoms, not underlying causes of epilepsy.

MicroRNAs (miRNAs) are small RNA molecules, approximately 20-22 nucleotides long. They function as translational repressor, and thereby control many cellular processes. In humans, around 1500 miRNAs have been identified of which approximately 50% is present in the brain. This suggests that these miRNAs are part of all kinds of neuronal development and maintenance; however the actual function of most miRNA is unknown. Several brain specific miRNAs are described, of which miR-124 is the most popular. The domestic pig is considered to be an excellent, alternate, large mammal model for human-related neurological studies, due to its similarity in both brain development and the growth curve when compared to humans. Considering these similarities, studies examining microRNA expression during porcine brain development have been performed to predict the expression profile and role of microRNAs in the human brain (Podolska et al., PLoS One. 2011 Jan. 6; 6(1): e14494, doi: 10.1371/journal-.pone.0014494). Numerous developmental stage or tissue-specific microRNAs including, miR-17, miR-18a, miR-29c, miR-106a, the miR-135s, miR-221 and miR-222 were detected by microarray analysis. However, no biological functions in neuron development have been identified so far. At least two miR-135s are known, namely miR-135a and miR-135b. The main description of the miR-135 family has been reported in cancer cells such as the regulation of the Adenomatous Polyposis Coli gene in the colorectal cancer (Meijer and Agami, Cancer Res 2008; 68(14): 5795-802). Inactivation of the adenomatous polyposis coli (APC) gene is a major initiating event in colorectal tumorigenesis. Most of the mutations in APC generate premature stop codons leading to truncated proteins that have lost β-catenin binding sites. APC-free β-catenin stimulates the Wnt signaling pathway, leading to active transcription of target genes. miR-135a and miR-135b target the 3' untranslated region of APC, suppress its expression, and induce downstream Wnt pathway activity. Interestingly, a considerable up-regulation of miR-135a and miR-135b in colorectal adenomas and carcinomas significantly correlated with low APC mRNA levels. This genetic interaction is also preserved in full-blown cancer cell lines expressing miR-135a and miR-135b, regardless of the mutational status of APC. miR-135a is also reported to contribute to anticancer drug resistance in tumor cells (Holleman et al, 2011 Oncogene). miRNA arrays were used to screen for differentially expressed miRNAs in paclitaxel-resistant cell lines. The role of miRNA-135a was evaluated in an in vivo model of paclitaxel resistance. In paclitaxel-resistant cell lines, established either in vitro or in vivo, blockage of miR-135a sensitized resistant cell lines to paclitaxel-induced cell death. Upregulation of miR-135a was associated with reduced expression of the adenomatous polyposis coli gene (APC). APC knockdown increased paclitaxel resistance in parental cell lines. These results indicate that paclitaxel resistance is associated with upregulation of miR-135a, both in vitro and in vivo.

miRNA-124 is downregulated in nerve-injured motor neurons and it potentially targets mRNAs for KLF6 and STAT3 (Nagata et al., doi: 10.1016/j.neuroscience.2013.10.055). Also, it was demonstrated that HDAC5 acts as an inhibitor of neurite elongation and that HDAC5 is regulated by the brain enriched microRNA miR-124 (Gu et al., doi: 10.1002/jcp.25927). Additionally, brain regeneration in planarians (flatworms) is mediated by precise spatiotemporal control of gene expression and is crucial for multiple aspects of neurogenesis. The role of the miR-124 family of microRNAs in planarian brain regeneration has been reported by Sasidharan et al., (doi: 10.1242/dev.144758). The miR-124 family (miRNA-124) is highly conserved in animals and regulates neurogenesis.

There is a need for better diagnostic markers for assessing the generation or regeneration of a neuronal cell, as well as better strategies for promoting generation, regeneration, or functionality of a neuronal cell.

DESCRIPTION OF THE INVENTION

The present invention focused on a family of miRNAs that promote generation or regeneration of a neuronal cell and that promote restoration of the functional activity of a neuronal cell, and that could be used in therapeutic and diagnostic activities of diseases and/or conditions associated with neuronal deficiency.

The invention encompasses several uses of a miRNA molecule, mimic, isomiR, or antagomir, or a source thereof, as identified herein. The invention also encompasses each of the newly identified miRNA molecules mimic, isomiR or antagomir per se, as well as each of those miRNA molecules, mimics, isomiRs, or antagomirs for use according to the invention.

In a first aspect, there is provided a miRNA, an antagomir, or a source thereof, for treating, reverting, preventing, curing, and/or delaying a neuronal deficiency or a disease and/or condition associated with neuronal deficiency, wherein said miRNA or antagomir is a miRNA molecule, an isomiR, or a mimic thereof, and is an oligonucleotide with a seed sequence comprising at least 6 of the 7 nucleotides of the seed sequence represented by SEQ ID NOs: 14-56, or is an antagomir thereof,
wherein said miRNA or antagomir is:
a miRNA-135 or an isomiR thereof, or a mimic thereof, or an antagomir thereof, or
a miRNA-196a-5p or an isomiR thereof, or a mimic thereof, or an antagomir thereof. Such a miRNA, an antagomir, or a source thereof for use are referred to herein as a miRNA, an antagomir, or a source thereof according to the invention. In preferred embodiments the miRNA, antagomir, or a source thereof is for treating, reverting, curing, and/or delaying a neuronal deficiency or a disease and/or condition associated with neuronal deficiency.

In preferred embodiments there is provided a miRNA, an antagomir, or a source thereof, for treating, reverting, preventing, curing, and/or delaying a neuronal deficiency or a disease and/or condition associated with neuronal deficiency,
wherein said miRNA is a miRNA molecule, an isomiR, or a mimic thereof, and is an oligonucleotide with a seed sequence comprising at least 6 of the 7 nucleotides of the seed sequence represented by SEQ ID NOs: 14-56, or an antagomir thereof,
wherein said miRNA or antagomir is:
a miRNA-135a or an isomiR thereof, or a mimic thereof, or an antagomir thereof, or
miRNA-135b or an isomiR thereof, or a mimic thereof, or an antagomir thereof, or
a miRNA-196a-5p or an isomiR thereof, or a mimic thereof, or an antagomir thereof.

In particularly preferred embodiments the invention provides an antagomir of a miRNA-135, or a source of such an antagomir, for treating, reverting, preventing, curing, and/or delaying epilepsy,
wherein said miRNA-135 is a miRNA-135 molecule or a miRNA-135 isomiR, and is an oligonucleotide with a seed sequence comprising at least 6 of the 7 nucleotides of the seed sequence represented by SEQ ID NOs: 14-17, 19-42, 52-56, or is a source thereof.

In preferred embodiments the invention provides a miRNA, an antagomir, or a source thereof for use according to the invention, wherein said miRNA or antagomir is a miRNA-135a molecule, a miRNA-135b molecule, a miRNA-196a-5p molecule, an isomiR of miRNA-135a, or an isomiR of miRNA-135b, an isomiR of miRNA-196a-5p molecule, a miRNA-196a-5p isomiR, an antagomir of miRNA-135a, an antagomir of miRNA-135b, an antagomir of miRNA-196a-5p, or a mimic thereof. More particularly, in preferred embodiments the invention provides a miRNA, an antagomir, or a source thereof for use according to the invention, wherein said miRNA or antagomir is:

i) a miRNA-135a molecule, a miRNA-135b molecule, a miRNA-196a-5p molecule, an isomiR of miRNA-135a, an isomiR of miRNA-135b, an isomiR of miRNA-196a-5p, an antagomir of miRNA-135a, an antagomir of miRNA-135b, an antagomir of miRNA-196a-5p, or a mimic thereof, or ii) a miRNA-135a molecule, a miRNA-135b molecule, a miRNA-196a-5p molecule, an isomiR of miRNA-135a, an isomiR of miRNA-135b, an isomiR of miRNA-196a-5p, or a mimic thereof, or iii) a miRNA-135a molecule, a miRNA-135b molecule, an isomiR of miRNA-135a, or an isomiR of miRNA-135b, or optionally a mimic thereof, or iv) a miRNA-196a-5p molecule, a miRNA-196a-5p isomiR, or a mimic thereof, or v) a miRNA-135a antagomir, a miRNA-135b antagomir, or a mimic thereof.

In further preferred embodiments the invention provides a miRNA, an antagomir, or a source thereof for use according to the invention, wherein a source of a miRNA is a precursor of a miRNA and is an oligonucleotide of at least 50 nucleotides in length, preferably wherein a source of an antagomir is an oligonucleotide of at least 50 nucleotides in length.

In preferred embodiments of this aspect is provided a miRNA-135a and/or miRNA-135b and/or miRNA-196a-5p molecule, a mimic, isomiR, antagomir, or a source thereof or a composition comprising said miRNA molecule miRNA-135a and/or miRNA-135b and/or miRNA-196a-5p, said mimic, isomiR, antagomiR, or said source thereof, preferably for use as a medicament for preventing, treating, reverting, curing and/or delaying a neuronal deficiency or a disease and/or condition associated with neuronal deficiency. In further preferred embodiments, a miRNA, an antagomir, or a source thereof for use according to the invention are provided, wherein said miRNA is a miRNA-135a molecule, a miRNA-135b molecule, a miRNA-196a-5p molecule, an isomiR of miRNA-135a, an isomiR of miRNA-135b, an isomiR of miRNA-196a-5p, or a mimic thereof, and/or wherein a source of a miRNA is a precursor of a miRNA-135a or of a miRNA-135b or of a miRNA-196a-5p and is an oligonucleotide of at least 50 nucleotides in length.

In preferred embodiments of this aspect is provided a miRNA-196a-5p molecule, a mimic, isomiR, antagomir, or a source thereof, more preferably a miRNA-196a-5p molecule, a mimic, isomiR or a source thereof, or a composition comprising said miRNA-196a-5p molecule, mimic, isomiR, antagomir, or said source thereof, more preferably a miRNA-196a-5p molecule, a mimic, isomiR or a source thereof, preferably for use as a medicament for preventing, treating, reverting, curing and/or delaying a neuronal deficiency or a disease and/or condition associated with neuronal deficiency. In further preferred embodiments, a miRNA, an antagomir, or a source thereof for use according to the invention are provided, wherein said miRNA or antagomir is a miRNA-196a-5p molecule, an isomiR, an antagomir, or a mimic thereof, and/or wherein a source of a miRNA is a precursor of a miRNA-196a-5p and is an oligonucleotide of at least 50 nucleotides in length.

In preferred embodiments of this aspect is provided a miRNA-135a and/or a miRNA-135b molecule, a mimic, isomiR, antagomir, or a source thereof, more preferably a miRNA-135a and/or a miRNA-135b antagomir or a source thereof, or a composition comprising said miRNA-135a and/or miRNA-135b molecule, mimic, isomiR, antagomir, or said source thereof, more preferably a miRNA-135a and/or a miRNA-135b antagomir or a source thereof, preferably for use as a medicament for preventing, treating, reverting, curing and/or delaying a neuronal deficiency or a disease and/or condition associated with neuronal deficiency, preferably epilepsy. In further preferred embodiments, a miRNA, an antagomir, or a source thereof for use according to the invention are provided, wherein said miRNA or antagomir is a miRNA-135a and/or a miRNA-135b molecule, an isomiR, an antagomir, or a mimic thereof, and/or wherein a source of a miRNA is a precursor of a miRNA-135a and/or a miRNA-135b and is an oligonucleotide of at least 50 nucleotides in length.

MicroRNAs (miRNAs) are small RNAs of 17-25 nucleotides, which function as regulators of gene expression in eukaryotes. miRNAs are initially expressed in the nucleus as part of long primary transcripts called primary miRNAs (pri-miRNAs). Inside the nucleus, pri-miRNAs are partially digested by the enzyme Drosha, to form 65-120 nucleotide-long hairpin precursor miRNAs (pre-miRNAs) that are exported to the cytoplasm for further processing by Dicer into shorter, mature miRNAs, which are the active molecules. In animals, these short RNAs comprise a 5' proximal "seed" region (generally nucleotides 2 to 8) which appears to be the primary determinant of the pairing specificity of the miRNA to the 3' untranslated region (3'-UTR) of a target mRNA. A more detailed explanation is given in the part dedicated to general definitions.

Each of the definitions given below concerning a miRNA molecule, a miRNA mimic or a miRNA isomiR or a miRNA antagomir or a source of any of those is to be used for each of the identified miRNAs, molecules or mimics or isomiRs or antagomirs or sources thereof of this application: miRNA-135a, miRNA-135b, miRNA-196a-5p or isomiRs or mimics or antagomirs or sources thereof. Preferred mature or mimic sequences (as identified in Table 2 as SEQ ID NOs: 5-9), seed sequences (as identified in Tables 4 and 5 as SEQ ID NO: 14-56), isomiR sequences (as identified in Tables 5 and 6 as SEQ ID NOs: 57-241), antagomir sequences (as identified in table 6 as SEQ ID NOs: 242-341), or source sequences (as identified in Table 1 (RNA precursor as SEQ ID NOs: 1-4) or 3 (DNA encoding a RNA precursor as SEQ ID NOs: 10-13)) of said miRNA molecule or mimic or isomiR or antagomir thereof respectively are identified in corresponding tables.

Within the whole text of the application unless otherwise indicated, a miRNA may also be named a miRNA molecule, a miR, an isomiR, an antagomir, or a mimic, or a source or a precursor thereof. Each sequence identified herein may be identified as being SEQ ID NO as used in the text of the application or as corresponding SEQ ID NO in the sequence listing. A SEQ ID NO as identified in this application may refer to the base sequence of said miRNA, isomiR, antagomir, mimic, or source thereof such as a precursor.

For all SEQ ID NOs, a skilled person knows that some bases can be interchanged. For example, each instance of T can be individually substituted by U, and vice versa. An RNA sequence provided for a mature miRNA can for example be synthesized as a DNA oligonucleotide using DNA nucleotides instead of RNA nucleotides. In such a case, thymine bases can be used instead of uracil bases. Alternately, thymine bases on deoxyribose scaffolds can be used. A skilled person understands that the base pairing behaviour is more important than the exact sequence, and that T and U are generally interchangeable for such purposes. Accordingly, an antagomir can be either a DNA or an RNA molecule, or a further modified oligonucleotide as defined later herein. Accordingly, a mimic can be either a DNA or an RNA molecule, or a further modified oligonucleotide as defined later herein.

MiRNA antagomirs are also referred to in the present invention. This term relates to miRNA molecules of this invention whose expression is not to be up-regulated/overexpressed/increased and/or whose activity is not to be increased in order to be used in therapeutic applications as identified herein. In contrast, the endogenous expression of these miRNA molecules needs to be down-regulated/decreased and/or an activity of such miRNA molecule needs to be decreased or reduced or inhibited to obtain a therapeutically desirable effect. This is preferably carried out as explained later herein using an antagomir. Therefore, in the invention when reference is made to any of these miRNA molecules in a therapeutic use, one always refers to a use of an antagomir of a miRNA-135a, miRNA-135b, or miRNA-196a-5p molecule or of a mimic of an antagomir of these miRNAs or a source of an antagomir of these miRNAs. Accordingly, when one refers to an antagomir, one always refers to a use of an antagomir of a miRNA-135a, miRNA-135b, or miRNA-196a-5p molecule or a mimic or a source thereof as indicated herein. Each of the definitions given herein concerning a miRNA molecule or a mimic or an isomiR or a source of any of those may also apply for any of the miRNA molecules to be used as an antagomir as identified in this paragraph. Each definition given herein concerning a given antagomir of a miRNA molecule also holds for other antagomir of a distinct miRNA molecule, each as defined herein. An antagomir is preferably complementary or reverse complementary to a miRNA, isomiR, or mimic thereof.

In the context of the invention, a miRNA molecule or a mimic or an isomiR or an antagomir thereof may be a synthetic or natural or recombinant or mature or part of a mature miRNA or a human miRNA or derived from a human miRNA as further defined in the part dedicated to the general definitions. A human miRNA molecule is a miRNA molecule which is found in a human cell, tissue, organ or body fluids (i.e. endogenous human miRNA molecule). A human miRNA molecule may also be a human miRNA molecule derived from an endogenous human miRNA molecule by substitution, deletion and/or addition of a nucleotide. A miRNA molecule or a mimic or an isomiR or an antagomir thereof may be a single stranded or double stranded RNA molecule.

Preferably a miRNA molecule or a mimic or an isomiR thereof is from 6 to 30 nucleotides in length, preferably 12 to 30 nucleotides in length, preferably 15 to 28 nucleotides in length, more preferably said molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Preferably an antagomir of a miRNA molecule is from 8 to 30 nucleotides in length, preferably 10 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more.

In a preferred embodiment, a miRNA molecule or a mimic or isomiR comprises at least 6 of the 7 nucleotides present in the seed sequence of said miRNA molecule or a mimic or isomiR thereof (Tables 4 and 5 show preferred seed sequence of each of the miRNAs molecule identified herein as SEQ ID NOs: 14-56), or is an antagomir thereof. Preferably in this embodiment, a miRNA molecule or a mimic or isomiR is from 6 to 30 nucleotides in length and more preferably comprises at least 6 of the 7 nucleotides present in the seed sequence of said miRNA molecule or mimic or isomiR, or is an antagomir thereof of the same length. Even more preferably a miRNA molecule or a mimic or isomiR is from 15 to 28 nucleotides in length and more preferably comprises at least 6 of the 7 nucleotides present in the seed sequence, even more preferably a miRNA molecule has a length of at least 6, 7, 8, 9, 10, 11, 12, 13, 14, 15, 16, 17, 18, 19, 20, 21, 22, 23, 24, 25, 26, 27, 28, 29, 30 nucleotides or more, or is an antagomir thereof of the same length.

In this context, to comprise at least 6 of the 7 nucleotides present in a seed sequence is intended to refer to a continuous stretch of 7 nucleotides that differs from the seed sequence in at most one position. Alternately, this can refer to a continuous stretch of 6 nucleotides that differs from the seed sequence only through omission of a single nucleotide. Throughout the application, more preferred miRNA molecules, isomiRs, mimics, or precursors thereof comprise all 7 of the 7 nucleotides present in an indicated seed sequence, or in other words have 100% sequence identity with said seed sequences. Preferably, when comprised in a miRNA, isomiR, or mimic, a seed sequence starts at nucleotide number 1, 2, or 3, and ends at nucleotide number 7, 8, 9, 10, or 11; most preferably such a seed sequence starts at nucleotide number 2 and ends at nucleotide number 8.

Accordingly a preferred miRNA-135 is a miRNA-135 molecule, isomiR, or mimic thereof and comprises at least 6 of the 7 nucleotides present in the seed sequence identified as SEQ ID NOs: 14-17 or 19-42 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. Preferably, for an antagomir, a sequence reverse complementary to at least 6 of the 7 nucleotides present in the seed sequence identified as SEQ ID NOs: 14-17 or 19-42 is comprised instead. A preferred antagomir of miRNA-135 is complementary or reverse complementary to the miRNA-135 molecule, isomiR, or mimic thereof as described above.

Accordingly a preferred miRNA-135a is a miRNA-135a molecule, isomiR, or mimic thereof and comprises at least 6 of the 7 nucleotides present in the seed sequence identified as SEQ ID NOs: 14 or 15 or 19-31 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. Preferably, for an antagomir, a sequence reverse complementary to at least 6 of the 7 nucleotides present in the seed sequence identified as SEQ ID NO: 14 or 15 or 19-31 is comprised instead. A preferred antagomir of miRNA-135a is complementary or reverse complementary to the miRNA-135a molecule, isomiR, or mimic thereof as described above.

Accordingly a preferred miRNA-135b is a miRNA-135b molecule, isomiR, or mimic thereof and comprises at least 6 of the 7 nucleotides present in the seed sequence identified as SEQ ID NOs: 16 or 17 or 32-42 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. Preferably, for an antagomir, a sequence reverse complementary to at least 6 of the 7 nucleotides present in the seed sequence identified as SEQ ID NO: 16 or 17 or 32-42 is comprised instead. A preferred antagomir of miRNA-135b is complementary or reverse complementary to the miRNA-135b molecule, isomiR, or mimic thereof as described above.

Accordingly a preferred miRNA-196a-5p is a miRNA-196a-5p molecule, isomiR, or mimic thereof and comprises at least 6 of the 7 nucleotides present in the seed sequence identified as SEQ ID NOs: 18 or 43-51 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more. Preferably, for an antagomir, a sequence reverse complementary to at least 6 of the 7 nucleotides present in the seed sequence identified as SEQ ID NO: 18 or 43-51 is comprised instead. A preferred antagomir of miRNA-196a-5p is complementary or reverse complementary to the miRNA-196a-5p molecule, isomiR, or mimic thereof as described above.

The inventors found that a miRNA-124 molecule, isomiR, or mimic thereof can advantageously be used as part of the present invention. Accordingly a preferred miRNA-124 molecule, isomiR, or mimic thereof comprises at least 6 of the 7 nucleotides present in the seed sequence identified as SEQ ID NOs: 349-350 and more preferably has a length of at least 6, 7, 8, 9, 10, 11, 12, 13, 14, 15, 16, 17, 18, 19, 20, 21, 22, 23, 24, 25, 26, 27, 28, 29, 30 nucleotides or more, and optionally has at least 70% identity over the whole mature sequence as represented by any one of SEQ ID NOs: 347-348. Preferably, identity is at least 75%, 80%, 85%, 90%, 95%, 97%, 98%, 99% or 100%.

Preferably, a miRNA molecule, isomiR, or mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more, comprises at least 6 of the 7 nucleotides present in a given seed sequence as identified in Tables 4 and 5 as SEQ ID NOs: 14-56 and has at least 70% identity over the whole mature sequence as identified in Table 6 as SEQ ID NOs: 147-241. Preferably, identity is at least 75%, 80%, 85%, 90%, 95%, 97%, 98%, 99% or 100%.

Alternatively, preferably, a miRNA molecule, isomiR, or mimic thereof has a length of not more than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides, comprises at least 6 of the 7 nucleotides present in a given seed sequence as identified in Tables 4 and 5 as SEQ ID NOs: 14-56 and has at least 70% identity over the whole mature sequence as identified in Table 6 as SEQ ID NOs: 147-241. Preferably, identity is at least 75%, 80%, 85%, 90%, 95%, 97%, 98%, 99% or 100%.

In another preferred embodiment, an isomiR of a miRNA molecule has at least 70% identity over the whole isomiR sequence (Table 5 shows preferred isomiR of each of the mature miRNAs identified as SEQ ID NOs: 57-146. Preferably, identity is at least 75%, 80%, 85%, 90%, 95% or higher. Preferably in this embodiment, an isomiR of a miRNA molecule or a mimic thereof has a length of at least 6, 7, 8, 9, 10, 11, 12, 13, 14, 15, 16, 17, 18, 19, 20, 21, 22, 23, 24, 25, 26, 27, 28, 29, 30 nucleotides or more.

Accordingly a preferred miRNA-135 molecule, isomiR, or mimic thereof comprises at least 6 of the 7 nucleotides present in the seed sequence identified as SEQ ID NOs: 14-17 and/or has at least 70%, 75%, 80%, 85%, 90%, 95%, 97%, 98%, 99% or 100% identity over SEQ ID NOs: 147-214 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-135a molecule, isomiR, or mimic thereof comprises at least 6 of the 7 nucleotides present in the seed sequence identified as SEQ ID NO: 14 or 15 or 19-31 and/or has at least 70%, 75%, 80%, 85%, 90%, 95%, 97%, 98%, 99% or 100% identity over SEQ ID NOs: 147-187 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-135b molecule, isomiR, or mimic thereof comprises at least 6 of the 7 nucleotides present in the seed sequence identified as SEQ ID NOs: 16 or 17 or 32-42 and/or has at least 70%, 75%, 80%, 85%, 90%, 95%, 97%, 98%, 99% or 100% identity over SEQ ID NOs:188-214 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Accordingly a preferred miRNA-196a-5p molecule, isomiR, or mimic thereof comprises at least 6 of the 7 nucleotides present in the seed sequence identified as SEQ ID NOs: 18 or 43-51 and/or has at least 70%, 75%, 80%, 85%, 90%, 95%, 97%, 98%, 99% or 100% identity over SEQ ID NOs: 215-241 and/or has a length of at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 nucleotides or more.

Another preferred miRNA molecule, isomiR, or mimic thereof has at least 60% identity with a seed sequence (as identified in Tables 4 and 5 as SEQ ID NOs: 14-56 or with a mature sequence (as identified in Table 2 as SEQ ID NOs: 5-9 or with a precursor sequence (as identified in Table 1 as SEQ ID NOs: 1-4 or with a DNA encoding an RNA precursor (as identified in Table 3 as SEQ ID NOs: 10-13 or with an isomiR sequence (as identified in Table 5 as SEQ ID NOs: 57-146. Identity may be at least 65%, 70%, 75%, 80%, 85%, 90%, 95%, 99% or 100%. Identity is preferably assessed on the whole SEQ ID NO as identified in a given table. However, identity may also be assessed on part of a given SEQ ID NO. Part may mean at least 50% of the length of the SEQ ID NO, at least 60%, at least 70%, at least 80%, at least 90% or 100%.

A precursor sequence may result in more than one isomiR sequences depending on the maturation process—see for example miRNA-135a where in certain tissues multiple isomiRs have been identified (Table 5). IsomiRs of a miRNA molecule stem from the same precursor, and conversely a precursor can lead to multiple miRNA molecules, one of which is referred to as the canonical miRNA (such as miRNA-135a-5p, SEQ ID NO: 5) and others being referred to as isomiRs (such as the oligonucleotide represented by SEQ ID NOs: 57-88). The difference between a canonical miRNA and its isomiRs can be said lie only in their prevalence—generally, the most prevalent molecule is called the canonical miRNA, while the others are isomiRs. Dependent on the type, environment, position in its life cycle, or pathological state of a cell, individual isomiRs or miRNAs can be expressed at different levels; expression can even differ between population groups or gender (Loher et al., Oncotarget (2014) DOI: 10.18632/oncotarget.2405).

A mimic is a molecule which has a similar or identical activity with a miRNA molecule. In this context a similar activity is given the same meaning as an acceptable level of an activity. A mimic is, in a functional determination, opposed to an antagomir. Preferred mimics are synthetic oligonucleotides, preferably comprising one or more nucleotide analogues such as locked nucleic acid monomers, and/or nucleotides comprising scaffold modifications and/or nucleotides comprising base modifications. An antagomir of a miRNA molecule, isomiR, mimic, or source thereof is therefore a molecule which has an activity which is opposite or reverse to the one of the corresponding miRNA molecule it derives from. An antagomir of a miRNA, isomiR, or mimic may also be defined as a molecule which is able to antagonize or silence or decrease an activity of said miRNA molecule or isomiR or mimic. An activity which is opposite or reverse to the one of the corresponding miRNA molecule it derives from or an activity which is able to antagonize an activity of said miRNA molecule it derives from is preferably an activity which is able to decrease an activity of said miRNA molecule or isomiR or mimic or source thereof. In this context, decrease means at least 5%, 10%, 20%, 30%, 40%, 50%, 60%, 70%, 80%, 90%, 95% or 100% decrease of the activity of said miRNA molecule or isomiR or mimic or source thereof. A mimic of an antagomir can be a synthetic oligonucleotide that has chemical modifications such as later defined herein. Preferred activities and preferred assays for assessing said activities are later on defined herein.

An antagomir of a miRNA molecule or mimic or isomiR or source thereof may be a nucleic acid, preferably a RNA which is complementary or reverse complementary to a part of the corresponding miRNA molecule or isomiR or mimic thereof. An antagomir preferably hybridizes with a part of the corresponding miRNA molecule or isomiR or mimic thereof. Preferred antagomir are complementary or reverse complementary to a part of sequences of mature miRNAs or isomiR identified in Table 6 as SEQ ID NOs: 147-241. A part may mean at least 50% of the length of the SEQ ID NO, at least 60%, at least 70%, at least 80%, at least 90% or 100%. In a preferred embodiment, an antagomir or a mimic thereof is complementary or reverse complementary to a seed sequence or a part of said seed sequence of a miRNA molecule or isomiR or mimic thereof. A part may mean at least 50% of the length of the seed sequence, at least 60%, at least 70%, at least 80%, at least 90% or 100%.

Preferably, an antagomir is from 8 to 30 nucleotides in length, preferably 10 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more and is complementary or reverse complementary to a part of sequences of mature miRNAs or isomiR identified in Table 6 (as SEQ ID NOs: 147-241). A part may mean at least 50% of the length of a given sequence, at least 60%, at least 70%, at least 80%, at least 90% or 100%.

Preferably, an antagomir is from 8 to 30 nucleotides in length, preferably 10 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more and is complementary or reverse complementary to a part of a seed sequence (as identified in Tables 4 and 5 as SEQ ID NOs: 14-56). A part may mean at least 50% of the length of the seed sequence, at least 60%, at least 70%, at least 80%, at least 90% or 100%.

Preferably an antagomir or mimic thereof has at least 60% identity with an antagomir sequence (as identified in Table 6 as SEQ ID NOs: 242-341). Identity may be at least 65%, 70%, 75%, 80%, 85%, 90%, 95%, 99% or 100%. Identity is preferably assessed on the whole SEQ ID NO as identified in Table 6. However, identity may also be assessed on a part of a given SEQ ID NO. A part may mean at least 50% of the length of the SEQ ID NO, at least 60%, at least 70%, at least 80%, at least 90% or 100%.

Preferably, an antagomir is from 8 to 30 nucleotides in length, preferably 12 to 28 nucleotides in length, more preferably said molecule has a length of at least 8, 9, 10, 11, 12, 13, 14, 15, 16, 17, 18, 19, 20, 21, 22, 23, 24, 25, 26, 27, 28, 29, 30 nucleotides or more and has at least 60% identity with an antagomir sequence (as identified in Table 6 as SEQ ID NOs: 242-341). Identity may be at least 65%, 70%, 75%, 80%, 85%, 90%, 95%, 99% or 100%. Identity is preferably assessed on the whole SEQ ID NO as identified in Table 6. However, identity may also be assessed on a part of a given SEQ ID NO. A part may mean at least 50% of the length of the SEQ ID NO, at least 60%, at least 70%, at least 80%, at least 90% or 100%.

The chemical structure of the nucleotides of an antagomir of a miRNA molecule or mimics or sources thereof may be modified to increase stability, binding affinity and/or specificity. Said antagomir may comprise or consists of a RNA molecule or preferably a modified RNA molecule. A preferred modified RNA molecule comprises a modified sugar. One example of such modification is the introduction of a 2'-O-methyl or 2'-O-methoxyethyl group or 2' fluoride group on the nucleic acid to improve nuclease resistance and binding affinity to RNA. Another example of such modification is the introduction of a methylene bridge connecting the 2'-O atom and the 4'-C atom of the nucleic acid to lock the conformation (Locked Nucleic Acid (LNA)) to improve affinity towards complementary single-stranded RNA. A third example is the introduction of a phosphorothioate group as linker between nucleic acid in the RNA-strand to improve stability against a nuclease attack. A fourth modification is conjugation of a lipophilic moiety on the 3' end of the molecule, such as cholesterol to improve stability and cellular delivery. In a preferred embodiment, an antagomir of miRNA molecule consists of a fully LNA-modified phosphorotioate oligonucleotide, termed tiny LNA as described in Obad et al. An antagomir as defined herein may comprise 1, 2, 3, 4, 5, 6, 7, 8, 9, 10 or more sugar modifications. It is also encompassed by the invention to introduce more than one distinct sugar modification in one antagomir. In preferred embodiments, an antagomir has a conjugated lipophilic moiety such as cholesterol on the 3' end of the molecule, and comprises a modified sugar such as LNA.

In preferred embodiments this aspect provides a miRNA, an antagomir, or a source thereof for use according to the invention, wherein said miRNA shares at least 70% sequence identity with any one of SEQ ID NOs:147-241, wherein said antagomir shares at least 70% sequence identity with any one of SEQ ID NOs: 242-341, and/or wherein said miRNA or antagomir is from 15-30 nucleotides in length, and/or wherein said source of a miRNA is a precursor of said miRNA and shares at least 70% sequence identity with any one of SEQ ID NOs: 1-4 or 10-13.

Even more preferably this aspect provides an antagomir or a source thereof, for use according to the invention, preferably for treating, reverting, preventing, curing, and/or delaying epilepsy, wherein said miRNA is a miRNA-135 and shares at least 70% sequence identity with any one of SEQ ID NOs: 147-214, and/or wherein said antagomir shares at least 70% sequence identity with any one of SEQ ID NOs: 242-245, 247-314, and/or wherein said miRNA or antagomir is from 15-30 nucleotides in length, and/or wherein said source of a miRNA is a precursor of said miRNA and shares at least 70% sequence identity with any one of SEQ ID NOs: 1-3 or 10-12.

Each of the miRNA molecules or mimics or isomiRs or antagomirs thereof as identified herein has an acceptable level of an activity of a given miRNA they derive from. An acceptable level of an activity is preferably that said miRNA or mimics or isomiRs or antagomirs thereof is still able to exhibit an acceptable level of said activity of said miRNA. An activity of a given miRNA or an mimic or isomiR or antagomir is for example the ability to exhibit a detectable promotion or induction of generation or regeneration of a neuronal cell or restore normal (dis)charges within a neuronal cell or in the brain as later defined herein. An acceptable level of an activity is preferably at least 30%, 40%, 50%, 60%, 70%, 80%, 90%, 95% or 100% of the activity of the miRNA they derive from, or of the miRNA they mimic, or of the miRNA of which they are an isomiR or an antagomir. An isomiR may be more active than a canonical miRNA under certain circumstances. An isomiR may have an increased resistance to degradation.

A preferred activity of any of the miRNA molecule or isomiR or antagomir or mimic thereof as identified herein (i.e. miRNA-135a, miRNA-135b, miRNA-196a-5p, miR-124) is to exhibit a detectable promotion or induction of generation or regeneration of a neuronal cell in a subject as later defined herein. In this context, a preferred miRNA molecule is a miRNA or equivalent or isomiR or mimic of miRNA-135a or of miRNA-135b or of miRNA-196a-5p. A preferred activity is an ability to suppress expression of Kruppel-like factor 4 (KLF4). In preferred embodiments of this aspect, the invention provides a miRNA, an antagomir, or a source thereof for use according to the invention, wherein said use is for suppressing expression of Kruppel-like factor 4 (KLF4). In preferred embodiments, KLF4 is detected as a protein by techniques such as those used in the examples, for example western blot. In other preferred embodiments, KLF4 is detected indirectly through quantification of mRNA levels, for example through qPCR.

A preferred activity of any of the antagomir, miRNA molecule, isomer or mimic thereof or source thereof as identified herein (i.e. antagomir of miRNA-135a) is to exhibit a detectable promotion or induction of generation or regeneration of a neuronal cell in a subject as later defined herein. A preferred activity of any of the antagomirs or mimics thereof or sources thereof as identified herein (i.e. antagomir of miRNA-135a or of miRNA-135b) is to exhibit a detectable promotion of correct neuronal (dis)charge.

A preferred activity of any of the miRNA molecules, antagomirs, or sources thereof for use according to the invention is the ability to promote normal (dis)charges within a neuronal cell or in the brain. This is useful for treating, reverting, preventing, curing, and/or delaying epilepsy. Such promotion preferably leads to an increase in correct neuronal (dis)charge, which can be an increase in the amount of cells that exhibit correct or improved neuronal (dis)charge, or it can be an increase in correct (dis)charge behaviour in a set population of cells. In this context, a preferred miRNA or antagomir molecule is a miRNA or mimic or isomiR or antagomir of miRNA-135, or a precursor thereof. More preferred is an antagomir of miRNA-135 or a mimic thereof or a source thereof, such as an antagomir of miRNA-135a, a mimic of an antagomir of miRNA-135a, or a source thereof, or an antagomir of miRNA-135b, a mimic of an antagomir of miRNA-135b, or a source thereof.

As used herein, epilepsy refers to a condition with a diverse set of chronic neurological disorders characterized by seizures. Such seizures may be recurrent and unprovoked. They may alternatively constitute single seizures combined with brain alterations and thus increase the chance of future seizures. Epileptic seizures may, for example, result from abnormal, excessive or hypersynchronous neuronal activity in the brain. Epilepsy may further be classified according to seizure types or forms. Seizure types are typically organized according to whether the source of the seizure within the brain is localized (partial or focal onset seizures) or distributed (generalized seizures). Epilepsy comprising partial seizures may further be divided on the extent to which awareness is affected. If awareness is unaffected, then it is an epilepsy comprising simple partial seizure. If awareness is affected, it is an epilepsy comprising complex partial or psychomotor seizure. A partial seizure may typically spread within the brain, i.e. lead to secondary generalization. Generalized seizures typically involve loss of consciousness and may further be divided according to the effect on the body. Examples include absence (petit mal), myoclonic, clonic, tonic, tonic-clonic (grand mal), and atonic seizures.

The following are preferred indications and uses for the miRNA molecules, antagomirs, or sources thereof for use according to the invention; more preferably for antagomirs of miRNA-135, or a source of such an antagomir, wherein said miRNA-135 is a miRNA-135 molecule or a miRNA-135 isomiR, and is an oligonucleotide with a seed sequence comprising at least 6 of the 7 nucleotides of the seed sequence represented by SEQ ID NOs: 14-17, 19-42, 52-56, or is a source thereof; more preferably wherein the use is for treating, reverting, preventing, curing, and/or delaying epilepsy:

i) The miRNA molecules, antagomirs, or sources thereof for use according to the invention wherein the use is for reducing, reverting, preventing, curing, and/or delaying seizure propagation. Such use is for treatment of epilepsy beyond a single status epilepticus. In this context, status epilepticus should be seen as a single epileptic seizure lasting more than thirty, preferably more than five minutes, or two or more seizures within a thirthy, preferably five-minute period without the subject returning to normal between them. Such treatment is beneficial because it reduces required drug regimens by removing an underlying cause of epilepsy instead of suppressing symptoms.

ii) The miRNA molecules, antagomirs, or sources thereof for use according to the invention wherein the use is for reducing seizure count. A reduced seizure frequency can be beneficial for subjects suffering or expected to suffer multiple seizures within a given period of time such as within a week or a day; or for subjects who do not respond to known medication such as channel blockers. Seizure count is preferably reduced by at least 10, 20, 30, 40, 50, 60, 70, 80, 90, or 100%, more preferably by at least 30, 40, 50, 60, 70, 80, 90, or 100%, even more preferably by at least 50, 60, 70, 80, 90, or 100%, such as by at least 75%. Such a reduction is preferably assessed at least 1, 2, 3, 4, 5, or 6 days after administration, more preferably at least 3, 4, 5, or 6 days after administration, such as 6 days after administration.

iii) The miRNA molecules, antagomirs, or sources thereof for use according to the invention wherein the use is for reducing seizure duration. Seizure duration is preferably average seizure duration over more than one seizure. Reduction of seizure duration can be beneficial for subjects suffering or expected to suffer from low frequency of seizures, rendering reduction of seizure count less effective; or for subjects who do not respond to known medication such as channel blockers. Seizure duration is preferably reduced by at least 5, 10, 15, 20, 25, 30, 35, 40, 50, 60, 70, 80, 90, or 100%, more preferably by at least 20, 25, 30, 25, 40, 50, 60, 70, 80, 90, or 100%, even more preferably by at least 30, 35, 40, 50, 60, 70, 80, 90, or 100%, such as by at least 36%. Such a reduction is preferably assessed at least 1, 2, 3, 4, 5, or 6 days after administration, more preferably at least 3, 4, 5, or 6 days after administration, such as 6 days after administration.

iv) The miRNA molecules, antagomirs, or sources thereof for use according to the invention wherein the use is for reducing total time in seizure. This can be seen as reducing total time of ictal activity, or as increasing the length of interictal periods. Reduction of total time in seizure can be beneficial for subjects who do not respond to known medication such as channel blockers. Preferably, total time in seizure is reduced by at least 10, 20, 30, 40, 50, 60, 70, 80, 90, or 100%, more preferably by at least 40, 50, 60, 70, 80, 90, or 100%, even more preferably by at least 60, 70, 80, 90, or 100%, such as by at least 75%. Such a reduction is preferably assessed at least 1, 2, 3, 4, 5, or 6 days after administration, more preferably at least 3, 4, 5, or 6 days after administration, such as 6 days after administration.

v) The miRNA molecules, antagomirs, or sources thereof for use according to the invention wherein the use is for restoring expression of myocyte-specific enhancer factor 2A (Mef2a). Myocyte-specific enhancer factor 2A (Mef2a) is a transcription factor that, when mutated, can lead to coronary artery disease or myocardial infarction. The inventors have surprisingly found that Mef2a expression is reduced for subjects suffering from epilepsy. Restoring Mef2a expression reduced seizure duration, seizure count, total time spent in seizure, and improved neuronal spine maturation, preventing neuronal spine loss. Restoration of Mef2a expression can be beneficial for subjects who do not respond to known medication such as channel blockers; it can reduce required drug regimens by removing an underlying cause of epilepsy instead of suppressing symptoms. Restoration of Mef2a expression in this context is preferably an increase in the Mef2a expression as compared to expression prior to treatment. Preferably, this increase is by at least 2, 4, 6, 8, 10, 12, 14, 16, 18, 20, 22, 24, 26, 28, 30% or more. Restoration preferably results in Mef2a expression that is about the same as average Mef2a expression for healthy subjects, more preferably it is within 25, 20, 15, 10, or 5% of expression for healthy subjects, most preferably within 10% or 5%.

vi) The miRNA molecules, antagomirs, or sources thereof for use according to the invention wherein the use is for preventing, reverting, curing, and/or delaying neuronal spine loss. Neuronal spines are also known as dendritic spines, and are small membranous protrusions from a neuron's dendrite. Neuronal spines typically receive input from an axon, at a synapse. Neuronal spines serve as a storage site for synaptic strength and help transmit electrical signals to the neuron's cell body. MiRNA-135 (over)expression associated with epilepsy was found to lead to loss of neuronal spines. Prevention of neuronal spine loss can be beneficial for subjects who do not respond to known medication such as channel blockers; it can reduce required drug regimens by removing an underlying cause of epilepsy instead of suppressing symptoms. Neuronal spine loss is preferably prevented entirely, wherein comparison can be made to a healthy individual or a population of healthy individuals or set values based upon such populations. Spine loss is preferably prevented for at least 5, 10, 15, 20, 25, 30, 35, 40, 45, 50, 55, 60, 65, 70, 75, 80, 85, 90, 95, or 100%. Prevention of spine loss can also be expressed as increase of spine density.

vii) The miRNA molecules, antagomirs, or sources thereof for use according to the invention wherein the use is for increasing neuronal spine maturation. Increasing neuronal spine maturation can be beneficial for subjects who do not respond to known medication such as channel blockers; it can reduce required drug regimens by removing an underlying cause of epilepsy instead of suppressing symptoms. Neuronal spines start as filopodium, then mature to thin, then to stubby, then to muschroom, culminating in a cupshaped spine. Mature spines are considered to be cupshaped, mushroom, and stubby; immature spines are considered to be thin and filopodium. The increase is preferably expressed as increase in percentage of spine type after treatment as compared to percentage of spine type before treatment. Accordingly the use is preferably for increasing the amount of stubby, mushroom, and cupshaped spines, more preferably for increasing the amount of mushroom and cupshaped spines, most preferably for increasing the amount of cupshaped spines. Preferably the amount of mature spines is increased by at least 5, 10, 15, 20, 25, 30, 35, 40, 45, 50, 55, 60% or more, more preferably by at least 20, 25, 30, 35, 40, 45, 50, 55, 60% or more, most preferably by at least 50, 55, 60% or more. In preferred embodiments the amount of cupshaped spines is increased by at least 5, 10, 15, 20, 25, 30, 35, 40, 50, 60, 70, 80, 90, or 100% or more, more preferably by at least 30, 35, 40, 50, 60, 70, 80, 90, or 100% or more, most preferably by at least 80, 90, or 100% or more, such as by at least 100%. In preferred embodiments the amount of mushroom spines is increased by at least 5, 10, 15, 20, 25, 30, 35, 40, 50, 60, 70, 80, 90, or 100% or more, more preferably by at least 30, 35, 40, 50, 60, 70, 80, 90, or 100% or more, most preferably by at least 80, 90, or 100% or more, such as by at least 90%.

viii) The miRNA molecules, antagomirs, or sources thereof for use according to the invention wherein the use is for preventing, delaying, curing, and/or reverting abnormal neuronal spine formation. This can be beneficial for subjects who do not respond to known medication such as channel blockers; it can reduce required drug regimens by removing an underlying cause of epilepsy instead of suppressing symptoms.

ix) The miRNA molecules, antagomirs, or sources thereof for use according to the invention wherein the use is for treating subjects known to not respond to treatment with channel blockers, or suspected of not responding to treatment with channel blockers. The failure to respond to channel blockers can be a partial response to channel blockers, or an absence of response to channel blockers. In preferred embodiments, subjects respond at most 90, 85, 80, 75, 70, 65, 60, 55, 50, 45, 40, 35, 30, 25, 20, 15, 10, 5%, or fewer as compared to known efficacy of channel blockers.

A source of a miRNA molecule or a source of a mimic or an isomiR may be any molecule which is able to induce the production of a miRNA molecule or of a mimic or isomiR as identified herein and which preferably comprises a hairpin-like structure and/or a double stranded nucleic acid molecule. The presence of a hairpin-like structure may be assessed using the RNAshapes program (Steffen P. et al 2006) using sliding windows of 80, 100 and 120 nt or more. The hairpin-like structure is usually present in a natural or endogenous source of a miRNA molecule whereas a double-stranded nucleic acid molecule is usually present in a recombinant or synthetic source of a miRNA molecule or of an isomiR or mimic thereof.

A source of an antagomir of a miRNA molecule or a source of a mimic of an antagomir of a miRNA molecule may be any molecule which is able to induce the production of said antagomir, such as an appropriate vector.

A source of a miRNA molecule or of a mimic or an isomiR or an antagomir thereof may be a single stranded, a double stranded RNA or a partially double stranded RNA or may comprise three strands, an example of which is described in WO2008/10558. As used herein partially double stranded refers to double stranded structures that also comprise single stranded structures at the 5' and/or at the 3' end. It may occur when each strand of a miRNA molecule does not have the same length. In general, such partial double stranded miRNA molecule may have less than 75% double stranded structure and more than 25% single stranded structure, or less than 50% double stranded structure and more than 50% single stranded structure, or more preferably less than 25%, 20% or 15% double stranded structure and more than 75%, 80%, 85% single stranded structure.

Alternatively, a source of a miRNA molecule or of a mimic or an isomiR thereof is a DNA molecule encoding a precursor of a miRNA molecule or a mimic or an isomiR thereof. Preferred DNA molecules in this context are identified in Table 3 as SEQ ID NOs: 10-13. The invention encompasses the use of a DNA molecule encoding a precursor of a miRNA molecule that has at least 70% identity with said sequence as identified in Table 3. Preferably, the identity is at least 75%, 80%, 85%, 90%, 95%, 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400 nucleotides or more and has at least 70% identity with a DNA sequence as identified in Table 3 as SEQ ID NOs: 10-13.

The induction of the production of a given miRNA molecule or of a mimic or an isomiR, or the inductions of the production of a given antagomir thereof is preferably obtained when said source is introduced into a cell using one assay as defined below. Cells encompassed by the present invention are later on defined.

A preferred source of a miRNA molecule or of a mimic or an isomiR thereof is a precursor thereof, more preferably a nucleic acid encoding said miRNA molecule or a mimic or an isomiR thereof. A preferred precursor is a naturally-occurring precursor. A precursor may be a synthetic or recombinant precursor. A synthetic or recombinant precursor may be a vector that can express a naturally-occurring precursor.

A preferred precursor of a given miRNA molecule is identified in Table 1 as SEQ ID NOs: 1-4. The invention encompasses the use of a precursor of a miRNA molecule or of an isomiR or mimic thereof that has at least 70% identity with said sequence. Preferably, identity is at least 75%, 80%, 85%, 90%, 95%, 97%, 98%, 99% or 100%. Preferably in this embodiment, a DNA molecule has a length of at least 50, 55, 60, 70, 75, 80, 85, 90, 95, 100, 130, 150, 200, 250, 300, 350, 400 nucleotides or more and has at least 70% identity with a sequence as identified in Table 1 as SEQ ID NOs: 1-4. Preferably, in this embodiment, a precursor comprises a seed sequence that shares at least 6 of the 7 nucleotides with a seed sequence selected from the group represented by SEQ ID NOs: 14-56. More preferably, a precursor comprises a seed sequence selected from the group represented by SEQ ID NOs: 14-56.

Accordingly, a preferred source of a miRNA-135 molecule has at least 70%, 75%, 80%, 85%, 90%, 95%, 97%, 98%, 99% or 100% identity with SEQ ID NOs: 1-3 or 10-12 and/or has a length of at least 50, 55, 60, 70, 75, 80, 85, 90, 95, 100, 130, 150, 200, 250, 300, 350, 400 nucleotides or more and/or comprises a seed sequence that shares at least 6 of the 7 nucleotides of any one of SEQ ID NOs:14-17 or 19-42. Such a source is a precursor of a miRNA-135a molecule and of miRNA-135a isomiRs.

Accordingly, a preferred source of a miRNA-135a molecule has at least 70%, 75%, 80%, 85%, 90%, 95%, 97%, 98%, 99% or 100% identity with SEQ ID NOs: 1 or 2 or 10 or 11 and/or has a length of at least 50, 55, 60, 70, 75, 80, 85, 90, 95, 100, 130, 150, 200, 250, 300, 350, 400 nucleotides or more and/or comprises a seed sequence that shares at least 6 of the 7 nucleotides of any one of SEQ ID NOs:14 or 15 or 19-31. Such a source is a precursor of a miRNA-135a molecule and of miRNA-135a isomiRs.

Accordingly, a preferred source of a miRNA-135b molecule has at least 70%, 75%, 80%, 85%, 90%, 95%, 97%, 98%, 99% or 100% identity with SEQ ID NOs: 3 or 12 and/or has a length of at least 50, 55, 60, 70, 75, 80, 85, 90, 95, 100, 130, 150, 200, 250, 300, 350, 400 nucleotides or more and/or comprises a seed sequence that shares at least 6 of the 7 nucleotides of any one of SEQ ID NOs: 16 or 17 or 32-42. Such a source is a precursor of a miRNA-135b molecule and of miRNA-135b isomiRs.

Accordingly, a preferred source of a miRNA-196a-5p molecule has at least 70%, 75%, 80%, 85%, 90%, 95%, 97%, 98%, 99% or 100% identity with SEQ ID NOs: 4 or 13 and/or has a length of at least 50, 55, 60, 70, 75, 80, 85, 90, 95, 100, 130, 150, 200, 250, 300, 350, 400 nucleotides or more and/or comprises a seed sequence that shares at least 6 of the 7 nucleotides of any one of SEQ ID NOs: 18 or 43-51. Such a source is a precursor of a miRNA-196a-5p molecule and of miRNA-196a-5p isomiRs.

In this context, it is pointed that several precursors of a given mature miRNA molecule may lead to an identical miRNA molecule. For example, miRNA-135a may originate from precursor miRNA-135a-1 or miRNA-135a-2 (preferably identified as being SEQ ID NO:1 or SEQ ID NO: 2, respectively). In a preferred embodiment, a miRNA-135a-1 or a molecule having at least 70%, 75%, 80%, 85%, 90%, 95%, 97%, 98%, 99% or 100% identity with miRNA-135a-1 or SEQ ID NO: 1 is used as a precursor of a miRNA-135a-5p molecule.

Also in this context, it is pointed that several isomers of a given mature miRNA molecule may lead to miRNA molecules with identical seed sequences. For example, mature miRNA-135a-5p (SEQ ID NO: 5) and at least isomers with SEQ ID NOs: 58-67 or 96-98, all share the same seed sequence (preferably identified as being SEQ ID NO: 19).

Preferred sources or precursors have been defined later herein. A preferred source includes or comprises an expression construct comprising a nucleic acid, i.e. DNA encoding said precursor of said miRNA or encoding said antagomir, more preferably said expression construct is a viral gene therapy vector selected from gene therapy vectors based on an adenovirus, an adeno-associated virus (AAV), a herpes virus, a pox virus and a retrovirus. A preferred viral gene therapy vector is an AAV or Lentiviral vector. Other preferred vectors are oncolytic viral vectors. Such vectors are further described herein below.

Alternatively, a source may be a synthetic miRNA molecule or a chemical mimic as further defined in the part dedicated to general definitions.

The detection of the presence of a miRNA molecule or of a mimic or an isomiR or the presence of an antagomir of a miRNA molecule or mimic thereof may be carried out using any technique known to the skilled person. The assessment of the expression level or of the presence of such molecule is preferably performed using classical molecular biology techniques such as (real time Polymerase Chain Reaction) qPCR, microarrays, bead arrays, RNAse protection analysis or Northern blot analysis or cloning and sequencing. The skilled person will understand that alternatively or in combination with the quantification of a miRNA molecule or of a mimic or isomiR thereof, the quantification of a substrate of a corresponding miRNA molecule or of a mimic or isomiR thereof of any compound known to be associated with a function of said miRNA molecule or of said isomiR or mimic thereof or the quantification of a function or activity of said miRNA molecule or of said isomiR or mimic thereof using a specific assay is encompassed within the scope of the invention. The same holds for an antagomir of a miRNA molecule.

Preferred compositions and formulations are all defined later herein. A miRNA molecule or a mimic or an isomiR or an antagomir thereof may be used as such as a naked molecule, with or without chemical modifications, or encapsulated into a particle or conjugated to a moiety. A preferred composition comprises a miRNA molecule or a mimic or an isomiR or an antagomir thereof encapsulated into a nanoparticle or a liposomal structure. A miRNA molecule or a mimic or an isomiR or an antagomir thereof may be an aptamer-miRNA hybrid. An aptamer-miRNA is defined as a miRNA linked to an RNA (or DNA) oligonucleotide, the latter adopting a conformation that targets the aptamer-miRNA hybrid molecule to a cell-surface protein (e.g. cyclic RGD peptide (cyclic arginine(R)-glycine(G)-aspartic acid (D) peptide). The aptamer-tagged miRNA can be linked to e.g. polyethylene glycol, which increases the chimera's circulating half-life (Dassie, J. P., et al. 2009).

An activity of a given miRNA or an a mimic, isomiR or a corresponding source thereof or an activity of a given antagomir of a miRNA molecule or a mimic thereof or a corresponding source thereof all as defined herein is preferably the ability to exhibit a detectable promotion or induction of generation or regeneration of a neuronal cell. "Exhibiting a detectable promotion or induction of generation or regeneration of a neuronal cell" may be replaced by reverting, antagonizing, delaying, curing, and/or treating a neuronal deficiency or a disease or condition associated with a neuronal deficiency. "Exhibiting a detectable promotion or induction of generation or regeneration of a neuronal cell" is equivalent with at least one of:

inducing or promoting a detectable increase in the number of neuronal cells in a subject, inducing or promoting an improvement of an impaired function, activity and/or 3D aspect of a neuronal cell and inducing or promoting an increase of neuronal outgrowth, an increase of neuronal migration and/or an increase of neuronal connectivity or plasticity.

Each of these features is further defined below.

Exhibiting such a detectable promotion or induction of generation or regeneration of a neuronal cell is therefore crucial in the present invention in order to be able to prevent, delay, cure, revert and/or treat any neuronal deficiency or any disease or condition associated with neuronal deficiency.

Neuronal deficiency may be assessed and detected locally in a subject. In this context, "locally" may mean an organ, a tissue, cells and/or a given volume or area or place of the human body of said subject, such as in the optic nerve between the eye and brain, or in the brain and hippocampus. Such an organ, tissue, cells and/or volume or area or place of said body comprise or consist of neuronal cells. Such an organ, tissue, cells and/or volume or area or place of said body may comprise at least 30%, 40%, 50%, 60%, 70%, 80%, 90% or 100% of neuronal cells.

A neuronal cell is also known as a neuron or nerve cell. It is an electrically excitable cell that receives, processes, and transmits information through electrical and chemical signals. These signals between neuronal cells occur via specialized connections called synapses. Neuronal cells can connect to each other to form neural networks. Neurons are major components of the brain and spinal cord of the central nervous system, and of the autonomic ganglia of the peripheral nervous system. In optic nerve injury, the neural network in between the eyes and the brain is compromised, or sometimes even entirely disrupted.

Neuronal deficiency is intended to encompass either a quantitative neuronal deficiency and/or a qualitative neuronal deficiency.

A quantitative neuronal deficiency may mean a reduced number of neuronal cells locally in a subject. A reduced number of neuronal cells may be assessed by comparison to a corresponding number of neuronal cells in a control subject at the same or similar place or by comparison to a corresponding number of neuronal cells in the same subject but in a distinct place of its body. In this context, reduced may mean 1% less, 5% less, 10% less, 15% less, 20% less, 25% less, 30% less, 35% less, 40% less, 45% less, 50% less, 55% less, 60% less, 65% less, 70% less, 75% less, 80% less, 85% less, 90% less, 95% less, 100% less, 150% less, 200% less or less than 200% less. The assessment of the number of neuronal cells may be carried out by counting cells, for example (following transfection or in utero electroporation (IUE)) counting cells that express a specific reporter plasmid. A reporter plasmid can be tagged with, or co-introduced with a nucleic acid according to the invention, or can be in the same vector. Suitable reporters are GFP or RFP. Preferably, neuronal cells are transfected in vitro, or transfected using IUE for in vivo cells. Following transfection or IUE, cells or brain slices are fixed and immunostained for the specific tag that expresses a marker such as a fluroscent protein. Images can then be taken on a microscope and cells expressing the specific tag can be counted using image processing software that is known in the art. A control subject may be a healthy subject.

Exhibiting a detectable promotion or induction of generation or regeneration of a neuronal cell is preferably inducing or promoting a detectable increase in the number of neuronal cells in a subject. Alternatively, it means maintaining the same number of neuronal cells e.g. by stopping the decrease or the expected decrease in the number of healthy neuronal cells in a disease associated with neuronal deficiency, or by preventing healthy neuronal cells from degenerating. For example, reducing the amount of cells that exhibit abnormal and synchronous neuronal discharges within the brain will not lead to generation or regeneration of a neuronal cell, whereas is will reduce the symptoms of epilepsy. In other words, this preferred effect is the increase of the amount of cells that exhibit normal neuronal discharges within the brain.

A detectable increase in the number of neuronal cells in a subject may be assessed and detected locally in a subject. In this context, "locally" may mean an organ, a tissue, cells and/or a given volume or area or place of the human body of said subject, as defined above. Such an organ, tissue, cells and/or volume or area or place of said body comprise or consist of neuronal cells. Such an organ, tissue, cells and/or volume or area or place of said body may comprise at least 30%, 40%, 50%, 60%, 70%, 80%, 90% or 100% of neuronal cells.

A detectable increase in the number of neuronal cells may be assessed by comparison to a corresponding number of neuronal cells in a control subject at the same or similar place or by comparison to a corresponding number of neuronal cells in the same subject but in a distinct place of its body. In this context, increase may mean 1% more, 5% more, 10% more, 15% more, 20% more, 25% more, 30% more, 35% more, 40% more, 45% more, 50% more, 55% more, 60% more, 65% more, 70% more, 75% more, 80% more, 85% more, 90% more, 95% more, 100% more, 150% more, 200% more or more than 200%. The assessment of the number of neuronal cells may be carried out using the same technique identified for assessing a detectable decrease or reduction. A control subject may be a healthy subject.

A qualitative neuronal deficiency is meant to encompass that neuronal cells are impaired in terms of a function and/or activity and/or a 3 D aspect. A neuronal cell that is impaired in terms of a function and/or activity and/or 3D aspect may exhibit a deficit of neuronal outgrowth, a deficit of neuronal migration, a perturbation of neuronal connectivity or plasticity, and/or a deficit in neuronal (dis)charges. A molecule of the invention may therefore be considered to exhibit a detectable promotion or induction of generation or regeneration of a neuronal cell when it reverts, delays, prevents, treats, cures or stops a qualitative neuronal deficiency. A molecule of the invention is preferably considered to exhibit a detectable promotion or induction of generation or regeneration of a neuronal cell when it induces or promotes an improvement of an impaired function and/or activity, e.g. disfunctioal (dis)charging, and/or 3D aspect of a neuronal cell and/or when it induces or promotes an increase of neuronal outgrowth, an increase of neuronal migration and/or an increase of neuronal connectivity or plasticity. Neurite outgrowth may be defined as the induction or promotion of a detectable increase of the average neurite length in or from a subject.

An impaired neurite outgrowth or a deficient or a decreased neurite outgrowth may be present or detectable in neuronal deficiency or in a condition associated with neuronal deficiency. Such an impaired, deficient or decreased neurite outgrowth may be assessed and detected locally in a subject. In this context, "locally" may mean an organ, a tissue, cells and/or a given volume or area or place of the human body of said subject. Such an organ, tissue, cells and/or volume or area or place of said body comprise or consist of neuronal cells. Such an organ, tissue, cells and/or volume or area or place of said body may comprise at least 30%, 40%, 50%, 60%, 70%, 80%, 90% or 100% of neuronal cells. A preferred volume is that of the brain, preferably about 1050-1350 $cm^3$, more preferably about 1100-1300 $cm^3$. This volume is particularly relevant when the conditions to be treated or prevented is epilepsy. Such an impaired, deficient or decreased neurite outgrowth may be assessed by comparison to a corresponding neurite outgrowth capacity in a control subject at the same or similar place or by comparison to a corresponding neurite outgrowth capacity of neuronal cells in the same subject but in a distinct place of its body. Such an impaired, deficient or decreased neurite outgrowth may be assessed and detected on a neurite isolated from a subject. Preferably, impaired, deficient, or decreased neurite outgrowth can be assessed in vitro in primary neuronal cultures, for example by transfecting neurons in culture with miRNA mimics and assessing the effect of the mimics on neurite outgrowth by measuring longest neurite length post transfection, as performed by Van Spronsen et al., 2013 (PMID:24098357).

In this case, such an impaired, deficient or decreased neurite outgrowth may be assessed by comparison to a corresponding neurite outgrowth capacity in a control neurite from a control subject at the same or similar place or by comparison to a corresponding neurite outgrowth capacity of neuronal cells from the same subject but in a distinct place of its body. In this context, impaired, deficient or decreased may mean less or 1% less, 5% less, 10% less, 15% less, 20% less, 25% less, 30% less, 35% less, 40% less, 45% less, 50% less, 55% less, 60% less, 65% less, 70% less, 75% less, 80% less, 85% less, 90% less, 95% less, 100% less, 150% less, 200% less or less than 200% less. The assessment of neurite outgrowth may be carried out using techniques such as demonstrated in the Examples, for example through microscopic screening. A control subject may be a healthy subject.

A detectable increase of neurite outgrowth is preferably assessed as carried out in the experimental data (example 2) A detectable increase is preferably an increase of at least 1%, 5%, 10%, 15%, 20%, 25%, 30%, 35%, 40%, 45%, 50%, 55%, 60%, 65%, 70%, 75%, 80%, 85%, 90%, 95%, 100% or more, more preferably as assessed in the experimental data. Neurite outgrowth may be assessed locally in a subject. The meaning of "locally" has already been defined herein.

Neuronal migration may be defined as an impaired neuronal migration or a deficient or a decreased neuronal migration may be present or detectable in a condition associated with neuronal deficiency. In developing cortex, pyramidal neurons migrate from the ventricular zone (VZ) to the superficial cortical plate (CP) to differentiate and establish functional connections. Impaired or deficient neuronal migration is preferably defined as the inability of a neuronal cell to reach its target region. Optionally, this could be due to loss of function of a specific protein/pathway within the cell, or due to absence of external cues in the environment.

Such an impaired, deficient or decreased neuronal migration may be assessed and detected locally in a subject. In this context, "locally" may mean an organ, a tissue, cells and/or a given volume or area or place of the human body of said subject. Such an organ, tissue, cells and/or volume or area or place of said body comprise or consist of neuronal cells. Such an organ, tissue, cells and/or volume or area or place of said body may comprise at least 30%, 40%, 50%, 60%, 70%, 80%, 90% or 100% of neuronal cells Such an impaired, deficient or decreased neuronal migration may be assessed by comparison to a corresponding migration capacity in a control subject at the same or similar place or by comparison to a corresponding migration capacity of neuronal cells in the same subject but in a distinct place of its body. Such an impaired, deficient or decreased neuronal migration may be assessed and detected on a neuronal cell isolated from a subject. In this case, such an impaired, deficient or decreased neuronal migration may be assessed by comparison to a corresponding neuronal migration capacity in a control neuronal cell from a control subject at the same or similar place or by comparison to a corresponding neuronal migration capacity of neuronal cells from the same subject but in a distinct place of its body. In this context, impaired, deficient or decreased may mean 1% less, 5% less, 10% less, 15% less, 20% less, 25% less, 30% less, 35% less, 40% less, 45% less, 50% less, 55% less, 60% less, 65% less, 70% less, 75% less, 80% less, 85% less, 90% less, 95% less, 100% less, 150% less, 200% less or less than 200% less.

To assess an effect on neuronal migration in vivo, preferably neural progenitors of the brain area of interest can be transfected by plasmid DNA solution through microinjection into the lumen of the ventricular system, followed by manually directing electrical pulses to the relevant neurogenic tissue (dal Maschio et al., 2012. PMID:22805567). Alternately, the method described by van Erp et al., 2015. Dev. Cell. PMID:26651291 can be used, which employs IUE. In it, lateral ventricles of an embryo are injected with miRNAs or sources thereof, together with reporter plasmid pCAG-GFP (as a reporter to mark the cells taking up DNA). Motor cortices are preferably targeted by electroporation set to five unipolar pulses of 50 ms at 30 V (950 ms interval) using a platinum tweezer electrode holding the head (negative poles) and a third gold-plated electrode (positive pole) on top of the head. After electroporation embryos can be placed back into the abdomen, after which abdominal muscles and skin are sutured. Embryos are then preferably collected at defined age (for e.g., at E16.5—p10) and heads are fixed using formaldehyde, cryosections are made, and immunohistochemistry is performed for detecting cells that have taken up the miRNA, antagomir, or source thereof. Images can be acquired using conventional confocal microscopy. Migration of GFP-positive cells can then be analyzed and compared to other migration, or to similar migration in other subjects or control subjects. A control subject may be a healthy subject.

A detectable increase of neurite migration is preferably assessed as carried out in the experimental data (example 2) A detectable increase is preferably an increase of at least 5%, 10%, 15%, 20%, 25%, 30%, 35%, 40%, 45%, 50%, 55%, 60%, 65%, 70%, 75%, 80%, 85%, 90%, 95%, 100% or more, more preferably as assessed in the experimental data. Neurite migration may be assessed locally in a subject. The meaning of "locally" has already been defined herein.

Neuronal connectivity or plasticity may be defined as a comprehensive term that illustrates the brain's capacity to adapt, structurally and functionally, to environmental enhancement. Neuroplasticity is particularly important for cognitive abilities such as learning and memory formation An impaired or deficient or decreased neuronal connectivity or plasticity may be present or detectable in a condition associated with neuronal deficiency. Such an impaired, deficient or decreased neuronal connectivity or plasticity may be assessed and detected locally in a subject. In this context, "locally" may mean an organ, a tissue, cells and/or a given volume or area or place of the human body of said subject, as defined earlier herein. Such an organ, tissue, cells and/or volume or area or place of said body comprise or consist of neuronal cells. Such an organ, tissue, cells and/or volume or area or place of said body may comprise at least 30%, 40%, 50%, 60%, 70%, 80%, 90% or 100% of neuronal cells. Such an impaired, deficient or decreased neuronal connectivity or plasticity may be assessed by comparison to a corresponding neuronal connectivity or plasticity capacity in a control subject at the same or similar place or by comparison to a corresponding neuronal connectivity or plasticity capacity of neuronal cells in the same subject but in a distinct place of its body. In this context, impaired, deficient or decreased may mean 1% less, 5% less, 10% less, 15% less, 20% less, 25% less, 30% less, 35% less, 40% less, 45% less, 50% less, 55% less, 60% less, 65% less, 70% less, 75% less, 80% less, 85% less, 90% less, 95% less, 100% less, 150% less, 200% less or less than 200% less. The assessment of neuronal connectivity or plasticity may be carried out using techniques such as behavioural studies (for example memory function test, Morris water maze, novel object recognition) or electrophysiogical studies (for example long term potentiation (LTP) induction studies), or using combinations of such studies. A suitable method is described in Cole et al., 2012. (PMID:22885849). Another suitable method is described in Pavlopoulos et al., 2011. (PMID:22153079). A control subject may be a healthy subject.

A detectable increase of neuronal connectivity or plasticity is preferably assessed as the relative increase in connectivity or plasticity as compared to an untreated or mock treated sample or subject. A detectable increase is preferably an increase of at least 5%, 10%, 15%, 20%, 25%, 30%, 35%, 40%, 45%, 50%, 55%, 60%, 65%, 70%, 75%, 80%, 85%, 90%, 95%, 100% or more, more preferably as assessed in Example 2. Neuronal connectivity or plasticity may be assessed locally in a subject. The meaning of "locally" has already been defined herein.

A detectable increase of correct neuronal (dis) charge or a detectable decrease of incorrect neuronal (dis)charge is preferably assessed as the relative increase in a subject or in a sample previously obtained from a subject as compared to an untreated or mock treated subject or sample. A detectable increase is preferably an increase of at least 5%, 10%, 15%, 20%, 25%, 30%, 35%, 40%, 45%, 50%, 55%, 60%, 65%, 70%, 75%, 80%, 85%, 90%, 95%, 100% or more, more preferably as assessed in Example 3. Correct neuronal (dis)charge may be assessed locally in a subject. The meaning of "locally" has already been defined herein.

Krüppel-like factor 4 (KLF4, or gut-enriched Kruppel-like factor or GKLF) is a zinc-finger transcription factor. It is a known intrinsic inhibitor of axon growth and regeneration. KLF4 is highly expressed in non-dividing cells and its overexpression induces cell cycle arrest (Yoon H S and Yang V W (2004). J. Biol. Chem. 279 (6): 5035-41. doi:10.1074/jbc.M307631200). Knockdown of KLF4 in neurons enhances axon growth, leading process length and neuronal migration (Moore et al., 2009; Qin and Zhang, 2012). Knockout mice lacking KLF4 showed significantly enhanced retinal ganglion cell (RGC) axon regeneration following optic nerve injury (Moore et al., 2009; Qin et al., 2013) This effect of KLF4 requires downstream signalling via the Janus kinase (JAK)-signal transducer and activator of transcription 3 (STAT3) pathway (Qin et al., 2013), but upstream regulatory mechanisms of this pathway are unknown in the art. The inventors now found that miRNAs for use according to the invention can suppress expression of KLF4, promoting neuronal generation or regeneration or neural plasticity or neural connectivity.

In a disease or condition of the invention, a neuronal deficiency may be detectable before the onset of the disease or condition i.e. before the appearance of a symptom of said disease or condition. It is further encompassed by the present invention that a neuronal deficiency may be detectable during the development of said disease or condition, i.e. after the apparition of a symptom of said disease or condition. Neuronal deficiency may be assessed and detected in a subject before the onset of the treatment and/or after the onset of the treatment. Neuronal deficiency may be assessed and detected in a subject, preferably in an area of the body of said subject.

If a detectable promotion or induction of neuronal generation or regeneration is assessed using a miRNA molecule, isomiR, mimic, antagomir or source thereof as identified herein, such miRNA molecule, isomiR, mimic, antagomir or source thereof is said to be used as a medicament for treating, reverting, preventing, curing and/or delaying a neuronal deficiency or a disease or a condition associated with such neuronal deficiency.

The assessment of neuronal generation or regeneration may be carried out periodically, e.g. each week, each month. This assessment is preferably carried out at several time points for a given subject or at one or several time points for a given subject and a healthy control. The assessment may be carried out at regular time intervals, e.g. each week, each month. When one assessment of neuronal generation or regeneration has led to the finding of a detectable increase or promotion or induction of neuronal generation or regeneration, a miRNA molecule, a mimic, an isomiR thereof a or a source thereof or an antagomiR or a mimic or a source thereof is said is exhibit a detectable promotion of neuronal generation or regeneration.

A detectable increase or induction or promotion of neuronal generation or regeneration has been preferably detected when for at least one time point, a detectable increase or induction or promotion of neuronal generation or regeneration has been detected. Preferably, a detectable increase or induction or promotion of neuronal generation or regeneration has been detected for at least two, three, four, five time points.

The invention provides a combination of a miRNA-135a and/or a miRNA-135b and/or a miRNA-196a-5p molecule, mimics, isomiRs, antagomirs, or sources thereof and optionally a miRNA-124 molecule, mimic, isomiR, antagomir, or a source thereof or a composition comprising said miRNA-135a and/or miRNA-135b and/or miRNA-196a-5p molecule, mimic, isomiR, antagomir, or a source thereof and optionally a miRNA-124 molecule, mimic, isomiR, antagomir, or a source thereof, preferably for use as a medicament for treating, reverting, preventing, curing and/or delaying a neuronal deficiency or a disease or a condition associated with neuronal deficiency.

It has been surprisingly found that a miRNA-135 molecule or a mimic or isomiR thereof is able to exhibit a detectable promotion of neuronal generation or regeneration as demonstrated in example 2 described herein.

In particular, it has been surprisingly found that a miRNA-135a molecule or a mimic or isomiR thereof is able to exhibit a detectable promotion of neuronal generation or regeneration as demonstrated in example 2 described herein.

In particular, it has been surprisingly found that a miRNA-135b molecule or a mimic or isomiR thereof is able to exhibit a detectable promotion of neuronal generation or regeneration as demonstrated in example 2 described herein.

It has been surprisingly found that a miRNA-196a-5p molecule or a mimic or isomiR thereof is able to exhibit a detectable promotion of neuronal generation or regeneration as demonstrated in example 2 described herein.

It has been surprisingly found that a miRNA-135 molecule or a mimic or isomiR or antagomir thereof, preferably an antagomir thereof, is able to exhibit a detectable decrease in incorrect (dis)charge of neuronal cells as demonstrated in Example 3 described herein.

In particular, it has been surprisingly found that a miRNA-135a molecule or a mimic or isomiR or antagomir thereof, preferably an antagomir thereof, is able to exhibit a detectable decrease in incorrect (dis)charge of neuronal cells as demonstrated in Example 3 described herein.

In particular, it has been surprisingly found that a miRNA-135b molecule or a mimic or isomiR or antagomir thereof, preferably an antagomir thereof, is able to exhibit a detectable decrease in incorrect (dis)charge of neuronal cells as demonstrated in Example 3 described herein.

Preferably, a miRNA-135a, miRNA-135b, miRNA-196a-5p and/or miRNA-124 molecule or a mimic or an isomiR or an antagomir or a source thereof is able to prevent, treat, revert, cure and/or delay a neuronal deficiency or a disease or a condition associated with a neuronal deficiency when said molecule exhibits a detectable promotion of neuronal generation or regeneration.

A neuronal deficiency or a disease or condition wherein a neuronal deficiency is involved or associated is any disease or condition wherein a reduced number of neuronal cells and/or neuronal cells that are impaired in terms of a function or activity or 3 D aspect could be detected either before the onset of the disease or condition or during the development of said disease or condition. For example, a disease or condition may be any neurodegenerative disorder such as cerebrovascular accidents (CVA), Alzheimer's disease (AD), vascular-related dementia, Creutzfeldt-Jakob disease (CJD), bovine spongiform encephalopathy (BSE), Parkinson's disease (PD), brain trauma, (advanced) multiple sclerosis (MS), amyotrophic lateral sclerosis (ALS—Lou Gehrig's disease), enteric neurodegeneration, optic nerve injury, decreased cognitive function due to senescence, and Huntington's chorea. A disease or condition may be a lesion of the nervous system that have arisen from traumatic contusion, avulsion, compression, and/or transection or other physical injury, or from tissue damage either induced by, or resulting from, a surgical procedure, from vascular pharmacologic or other insults including hemorrhagic or ischemic damage, or other neurological diseases. A disease or condition may be glaucoma. A disease or condition may be epilepsy.

There are currently known medicaments that may be used for specifically treating, reverting, preventing, curing and/or delaying a neuronal deficiency or a disease or condition associated with neuronal deficiency in a subject. However, each of these treatments is likely to display a therapeutic activity which is not sufficient to be used in patients. This insufficiency may stem from toxicity, from poor pharmacokinetics leading to insufficient uptake or biodistribution, from inability to cross the blood brain barrier, or from general low efficacy. Such a therapeutic activity is not sufficient to be used in patients preferably when such known medicaments are not able to exhibit a detectable promotion of neuronal generation or regeneration. Each of these features has been defined earlier herein. The invention provides a new medicament which is expected not to have such drawbacks. The invention encompasses to use a miRNA-135a and/or miRNA-135b and/or miRNA-196a-5p, a mimic, an isomiR, an antagomir or a source thereof or a composition comprising said miRNA-135a and/or miRNA-135b molecule and/or miRNA-196a-5p, a mimic, an isomiR, an antagomir or a source thereof. This use includes increasing, preferably pharmacologically increasing an activity or the steady-state level of said miRNA-135a and/or miRNA-135b and/or miRNA-196a-5p, isomiR or of said source thereof in a subject, in a cell of said subject, in a tissue of said subject or in body fluid of said subject.

Within the context of the invention, "increasing an activity or the steady-state level of an antagomir or mimic thereof or of said source thereof" could be replaced by "decreasing an activity or the steady-state level of a miRNA molecule or or ismoR thereof". The same holds for other antagomir identified herein.

In this use, an activity or steady-state level of said miRNA-135a and/or miRNA-135b and/or miRNA-196a-5p, or an isomiR or source thereof is increased in order to exhibit a detectable promotion of neuronal generation or regeneration. The assessment of such detectable promotion of neuronal generation or regeneration in a subject had been earlier defined herein.

An activity or steady-state level of said miRNA-135a and/or miRNA-135b molecule and/or miRNA-196a-5p, isomiR or source thereof may be increased at the level of said miRNA molecule (or isomiR thereof) itself, e.g. by providing said miRNA molecule, mimic or isomiR, or source thereof to a subject, preferably to a cell of a subject, or to a tissue of said subject, or to an organ of said subject or to said subject, said miRNA molecule, mimic, isomiR or source thereof being from an exogenous source. For provision of a miRNA molecule or mimic or isomiR thereof from an exogenous source, said molecule may conveniently be produced by expression of a nucleic acid encoding said molecule or encoding a source of said molecule in a suitable host cell as described below or as completely synthetic molecule by chemical synthesis. An example of a nucleic acid molecule encoding a source of a miRNA-135a is a nucleic acid molecule that encodes a precursor of miRNA-135a. Said nucleic acid molecule is itself also a source of miRNA-135a.

A preferred cell of a subject is a brain cell or a spinal cord cell or a cell from the peripheral nervous system. Preferred nerve cells are efferent nerve cells and/or motor nerve cells.

Preferably, however, an activity or steady-state level of a miRNA molecule or isomiR thereof is increased or decreased by regulating the expression level of a nucleotide sequence encoding said miRNA molecule or isomiR thereof or encoding a source of said miRNA molecule or isomiR thereof. Preferably, the expression level of a nucleotide sequence is regulated in a cell of said subject or in a tissue of said subject or in the subject. The expression level of a miRNA molecule or isomiR thereof or a source of said miRNA molecule or isomiR thereof may be increased or decreased by introduction of a miRNA, isomiR, antagomir, mimic, or a source thereof, or an expression construct (or vector) into a cell, tissue, organ or body fluid of said subject, or in the subject whereby an expression vector comprises a nucleotide sequence comprising a miRNA molecule or mimic or isomiR or antagomir thereof or comprising a source of said miRNA molecule or mimic or isomiR or antagomir thereof, and whereby a nucleotide sequence is under control of a promoter capable of driving expression of a nucleotide sequence in said cell, tissue, organ, subject. Generally, expression can be increased by using a miRNA molecule, isomiR, mimic, or precursor thereof. Generally, expression can be decreased by using an antagomir or mimic thereof or a precursor thereof. The expression level of a miRNA molecule or mimic or isomiR or antagomir or source thereof may also be increased by introduction of an expression construct into a cell, tissue, organ, subject, whereby a construct comprises a nucleotide sequence encoding a factor capable of trans-activation of an endogenous nucleotide sequence encoding a miRNA molecule or mimic or isomiR or antagomir thereof.

A use of the invention preferably comprises the step of administering to a subject a therapeutically effective amount of a pharmaceutical composition comprising a nucleic acid construct for increasing the activity or steady state level of miRNA-135a and/or miRNA-135b and/or miRNA-196a-5p molecule or isomiR as defined herein, or for decreasing the activity or steady state level of miRNA-135a and/or miRNA-135b and/or miRNA 196a-5p molecule or isomiR as defined herein. Decrease can advantageously be effected using antagomirs or a source thereof. A nucleic acid construct may be an expression construct as further specified herein. Preferably, an expression construct is a viral gene therapy vector selected from gene therapy vectors based on an adenovirus, an adeno-associated virus (AAV), a herpes virus, a pox virus, an oncolytic virus vector and a retrovirus. A preferred viral gene therapy vector is adnoviral vector, an AAV vector, or a Lentiviral vector. A viral vector is a preferred source or precursor in the sense approach. In the antisense approach, use is made of a short hairpin blocker or antisense molecules to block the miRNA machinery. Alternatively, a use of the invention preferably comprises the step of administering to a subject a therapeutically effective amount of a pharmaceutical composition comprising a miRNA-135a and/or a miRNA-135b and/or a miRNA-196a-5p molecule, isomiR, mimic, antagomir or a source thereof as defined herein, or comprising a miRNA-135a and/or a miRNA-135b and/or a miRNA-196a-5p molecule, isomiR, mimic, antagomir, or a source thereof as defined herein.

In a use of the invention, a cell, a tissue, an organ or body fluid is preferably from a subject suspected to have a high risk of exhibiting neuronal deficiency or of having a disease or condition associated with neuronal deficiency due for example to its age or its genetic background. Alternatively, in another preferred embodiment, use of the invention is applied on a cell, tissue, organ or body fluid from a subject diagnosed as either having a predictive risk for developing later a disease or condition associated with neuronal deficiency. A diagnostic method used is preferably one of the inventions as described herein. Alternatively, a cell, a tissue or organ to be treated may be selected based on risk of progression of the disease or condition associated with neuronal deficiency. Such risk of progression may be assessed using classical clinic-pathological criteria or biomarker-based prognosis known to the skilled person. It is also encompassed by the invention to administer a miRNA-135 and/or miRNA-196a-5p molecule isomiR, mimic, antagomir, or a precursor thereof or a composition comprising said miRNA-135 and/or miRNA-196a-5p molecule isomiR, mimic, antagomir, or source thereof into a tissue or organ of said subject. The organ or tissue may correspond to the organ or tissue wherein neuronal deficiency or a disease or condition associated with neuronal deficiency had been diagnosed. In the invention, a preferred tissue is a tissue being associated with or comprising or containing or consisting of a neuronal tissue. In the invention, a preferred organ is any organ comprising or consisting of neuronal cells. Examples of preferred organs include the brain, the hippocampus, and the optic nerve. A tissue associated with neuronal cells may be located in the vicinity of such cells and may act on neuronal cells. An vicinity in this context may mean up to a few centimetres. In the invention, a preferred cell is a neuronal cell. In each case, a miRNA-135 and/or miRNA-196a-5p molecule, isomiR, mimic, antagomir, or source thereof is preferably administered to a neuronal cell present in said organ, tissue. Said miRNA-135 and/or miRNA-196a-5p molecule, isomiR, mimic, antagomir, or source thereof is preferably administered to a tissue comprising 30%, 40%, 50%, 60%, 70%, 80%, 90%, 100% neuronal cells. Said miRNA-135 and/or miRNA-196a-5p molecule, isomiR, mimic, antagomir, or source thereof may be targeted to neuronal cells. A treatment of a neuronal deficiency or of a disease or condition associated with neuronal deficiency may include a treatment that prevents neuronal deficiency in a tissue that contains neuronal or decreases neuronal deficiency around neuronal cells cell that has already been diagnosed as being neuronal deficient. Neuronal cells may be targeted by linking or conjugating said miRNA-135 and/or miRNA-196a-5p molecule, isomiR, mimic, antagomir, or source thereof to a targeting part or homing device. A preferred targeting part is any molecule known to recognize or bind a molecule which is expressed on neuronal cells. In the context of the invention, whenever a miRNA-135 or isomiR, mimic, antagomir, or source thereof is administered, reference is made to individual administration of a miRNA-135a or isomiR or mimic or antagomir or source thereof, individual administration of a miRNA-135b or isomiR or mimic or antagomir or source thereof, or combined administration of both a miRNA-135a and a miRNA-135b or isomiR or mimic or antagomir or source thereof.

In another use, the invention mentioned herein may be combined with standard treatments of a neuronal deficiency or of a disease or condition associated with neuronal deficiency such as memory training or use of known pharmaceuticals that act on the CNS.

Although gene therapy is a possibility for treating, reverting, preventing, and/or delaying a condition or a disease associated with neuronal deficiency, other possible treatments may also be envisaged. For example, treatment by "small molecule" drugs to steer certain molecular pathways in the desired direction, is also preferred. These small molecules are preferably identified by the screening method of the invention as defined later herein.

In the context of the invention, treating, reverting, preventing, curing and/or delaying a neuronal deficiency or a disease or condition associated with neuronal deficiency may mean that:

The severity of at least one symptom of this disease or condition has been reduced, and/or At least a parameter associated with this disease or condition has been improved: preferably such parameter is or is associated with neuronal deficiency and/or includes a number of neuronal cells and/or a function or activity or 3 D aspect of a neuronal cell all as described earlier herein.

A parameter may be the assessment of neuronal deficiency as explained earlier herein. In the context of the invention, treating, reverting, preventing, curing and/or delaying a neuronal deficiency or a disease or condition associated with neuronal deficiency may be replaced by achieving or promoting or inducing a neuronal generation or regeneration. Unless otherwise indicated, achieving or promoting or inducing a neuronal generation or regeneration is preferably assessed or detected after at least one week, two weeks, three weeks, fours weeks, one month, two months, three months, four months, five months, six months or more in a treated subject. Achieving or promoting or inducing a neuronal generation or regeneration is preferably identified in a subject as:

a prolongation of patient survival of at least one month, several months or more (compared to those not treated or treated with a control or compared with the subject at the onset of the treatment) and/or improvement of the quality of life and observed pain relief In the context of the invention, a patient may survive and/or may be considered as being disease free. Alternatively, the disease or condition may have been stopped or delayed. In the context of the invention, an improvement of quality of life and observed pain relief may mean that a patient may need less pain relief drugs than at the onset of the treatment. Alternatively or in combination with the consumption of less pain relief drugs, a patient may be less constipated than at the onset of the treatment. "Less" in this context may mean 5% less, 10% less, 20% less, 30% less, 40% less, 50% less, 60% less, 70% less, 80% less, 90% less. A patient may no longer need any pain relief drug. This improvement of quality of life and observed pain relief may be seen, detected or assessed after at least one week, two weeks, three weeks, fours weeks, one month, two months, three months, four months, five months, six months or more of treatment in a patient and compared to the quality of life and observed pain relief at the onset of the treatment of said patient.

Composition

In an aspect of the invention a composition comprising a miRNA, an antagomir, or a source thereof according to the invention is provided. Such a composition is preferably for use as defined above. Accordingly, preferred embodiments of this aspect provide a composition comprising a miRNA, an antagomir, or a source thereof according to the invention, for use according to the invention. Such a composition for use is referred to herein as a composition for use according to the invention. A preferred further ingredient of such a composition for use according to the invention is a pharmaceutically acceptable excipient.

In preferred embodiments, miRNA-135a, miRNA-135b, and miRNA-196a-5p or isomiRs, mimics, or sources of any of those, or an antagomir of said miRNAs are comprised in the composition. Accordingly, more preferred embodiments within this aspect provide a composition for use according to the invention, comprising:

i) a miRNA-135a molecule, or an isomiR, mimic, antagomir, or source thereof, and/or ii) a miRNA-135b molecule, or an isomiR, mimic, antagomir, or source thereof, and/or iii) a miRNA-196a-5p molecule, or an isomiR, mimic, antagomir or source thereof.

Further more preferred embodiments within this aspect provide:

a composition for use according to the invention, comprising a miRNA-135a molecule, or an isomiR, mimic, antagomir, or source thereof, preferably a miRNA molecule, or an isomiR, mimic, or source thereof.

a composition for use according to the invention, comprising a miRNA-135b molecule, or an isomiR, mimic, antagomir, or source thereof, preferably a miRNA molecule, or an isomiR, mimic, or source thereof.

a composition for use according to the invention, comprising a miRNA-196a-5p molecule, or an isomiR, mimic, antagomir, or source thereof, preferably a miRNA molecule, or an isomiR, mimic, or source thereof.

a composition for use according to the invention, comprising a miRNA-135a molecule, or an isomiR, mimic, antagomir, or source thereof, preferably a miRNA molecule, or an isomiR, mimic, or source thereof and a miRNA-135b molecule, or an isomiR, mimic, antagomir, or source thereof, preferably a miRNA molecule, or an isomiR, mimic, or source thereof.

a composition for use according to the invention, comprising a miRNA-135a molecule, or an isomiR, mimic, antagomir, or source thereof, preferably a miRNA molecule, or an isomiR, mimic, or source thereof and a miRNA-196a-5p molecule, or an isomiR, mimic, antagomir, or source thereof, preferably a miRNA molecule, or an isomiR, mimic, or source thereof.

a composition for use according to the invention, comprising a miRNA-135b molecule, or an isomiR, mimic, antagomir, or source thereof, preferably a miRNA molecule, or an isomiR, mimic, or source thereof and a miRNA-196a-5p molecule, or an isomiR, mimic, antagomir, or source thereof, preferably a miRNA molecule, or an isomiR, mimic, or source thereof.

a composition for use according to the invention, comprising a miRNA-135a molecule, or an isomiR, mimic, antagomir, or source thereof, preferably a miRNA molecule, or an isomiR, mimic, or source thereof and a miRNA-135b molecule, or an isomiR, mimic, antagomir, or source thereof, preferably a miRNA molecule, or an isomiR, mimic, or source thereof and a miRNA-196a-5p molecule, or an isomiR, mimic, antagomir, or source thereof, preferably a miRNA molecule, or an isomiR, mimic, or source thereof.

a composition for use according to the invention, comprising an antagomir of a miRNA-135a molecule, or a mimic thereof, or comprising a source thereof.

a composition for use according to the invention, comprising an antagomir of a miRNA-135b molecule, or a mimic thereof, or comprising a source thereof.

a composition for use according to the invention, comprising an antagomir of a miRNA-196a-5p molecule, or a mimic thereof, or comprising a source thereof.

a composition for use according to the invention, comprising an antagomir of a miRNA-135a molecule, or a mimic thereof, or comprising a source thereof, and comprising an antagomir of a miRNA-135b molecule, or a mimic thereof, or comprising a source thereof.

a composition for use according to the invention, comprising an antagomir of a miRNA-135a molecule, or a mimic thereof, or comprising a source thereof, and comprising an antagomir of a miRNA-196a-5p molecule, or a mimic thereof, or comprising a source thereof.

a composition for use according to the invention, comprising an antagomir of a miRNA-135b molecule, or a mimic thereof, or comprising a source thereof, and comprising an antagomir of a miRNA-196a-5p molecule, or a mimic thereof, or comprising a source thereof.

a composition for use according to the invention, comprising an antagomir of a miRNA-135a molecule, or a mimic thereof, or comprising a source thereof, and comprising an antagomir of a miRNA-135b molecule, or a mimic thereof, or comprising a source thereof, and comprising an antagomir of a miRNA-196a-5p molecule, or a mimic thereof, or comprising a source thereof.

All compositions described herein preferably also comprise a pharmaceutically acceptable excipient. Also encompassed by the invention are compositions as described herein, consisting essentially of the components that are described as comprised. Also encompassed by the invention are compositions as described herein, consisting of the components that are described as comprised.

In a further preferred embodiment there is provided a composition for use according to the invention, preferably as defined above, further comprising a miRNA-124 molecule, a miRNA-124 mimic, a miRNA-124 isomiR, a miRNA-124 antagomir, or a source thereof, preferably comprising a miRNA-124 molecule, mimic, isomiR, or a source thereof.

When the invention relates to a composition comprising more than one miRNA molecule, isomiR, mimic, antagomir, or source thereof or antagomir thereof it is encompassed that each miRNA molecule, isomiR, mimic, antagomir, or source thereof or antagomir thereof may be present each in a separate composition, each composition being sequentially or simultaneously administered to a subject. Alternatively, it is also encompassed that more than one miRNA molecules, isomiRs, mimics, or sources thereof or antagomir thereof is present in a composition as defined herein.

Therefore the invention further encompasses to additionally use a miRNA-124 molecule, an isomiR, mimic, antagomir, or a source thereof or a composition comprising said miRNA molecule or isomiR, mimic, antagomir, or a source thereof and/or an additional antagomir of a miRNA-124 molecule.

This preferred use includes increasing, preferably pharmacologically increasing an activity or the steady-state level of said miRNA-124 molecule, isomiR, or of said source thereof in a subject, in a cell of said subject, in a tissue of said subject or in body fluid of said subject.

In this preferred use an activity or steady-state level of a miRNA-124 molecule or isomiR or precursor as defined above may be increased in order to exhibit a detectable promotion of neuronal generation or regeneration.

Ways of increasing an activity or steady state level of an antagomir have already been defined earlier herein. The assessment of promotion of neuronal generation or regeneration in a subject had been earlier defined herein.

In a further aspect, there is provided the use of a miRNA-135a and/or miRNA-135b and/or a miRNA-196a-5p molecule, isomiR, mimic, antagomir, or a source thereof or a composition comprising said miRNA-135a and/or miRNA-135b and/or a miRNA-196a-5p molecule, isomiR, mimic, antagomir, or a source thereof preferably for the manufacture of a medicament for treating, reverting, preventing, curing and/or delaying a neuronal deficiency or a disease or a condition associated with neuronal deficiency. Each feature of this further aspect has already been described herein.

In a further aspect, there is provided a method for treating, reverting, preventing, curing and/or delaying a neuronal deficiency or a condition or disease associated with neuronal deficiency by administering a miRNA molecule, isomiR, mimic, or source thereof or an antagomir thereof or a composition as earlier defined herein to a subject in the need thereof. Each feature of this further aspect has already been described herein. The use according to the invention is preferably reduced to practice in a method for treating, curing, reverting, preventing, and/or delaying a neuronal deficiency or a condition or disease associated with neuronal deficiency. Accordingly, the invention provides a method for treating, curing, reverting, preventing and/or delaying a neuronal deficiency or a condition or disease associated with neuronal deficiency by administering a miRNA, an antagomir, or a source thereof according to the invention, or a composition according to the invention, to a subject in the need thereof. Additional features are described elsewhere herein.

In a further aspect, there is provided a method for diagnosing a neuronal deficiency or a disease or condition associated with neuronal deficiency in a subject, the method comprising the steps of:
(a) determining the expression level of a miRNA, isomiR, or a source thereof according to the invention, and optionally
(b) comparing the expression level of said miRNA, isomiR, or a source thereof according to the invention with a reference value for the expression level of said miRNA, isomiR, or a source thereof, the reference value preferably being the average value for the expression level of said miRNA, isomiR, or a source thereof in a healthy subject. In the context of the invention, diagnosis means either a predictive risk assessment of a subject for developing a neuronal deficiency or for developing a disease or a condition associated with neuronal deficiency. In the context of the invention, a subject may be an animal or a human being. Preferably, a subject is a human being. In the context of the invention, the reference value assessed in (b) and the expression level of a miRNA-135a and/or miRNA-135b and/or miRNA196a-5p molecule, isomiR, or a source thereof assessed in (a) are assessed in a corresponding or similar tissue of both subjects.

In preferred embodiments this aspect provides a method for diagnosing epilepsy or a disease or condition associated with epilepsy in a subject, the method comprising the steps of:
(a) determining the expression level of a miRNA or a source thereof as defined above, preferably a miRNA-135 molecule or a miRNA-135 isomiR, and optionally
(b) comparing the expression level of said miRNA or a source thereof with a reference value for the expression level of said miRNA or a source thereof, the reference value preferably being the average value for the expression level of said miRNA or a source thereof in a healthy subject.

Since the expression levels of these nucleotide sequences and/or amounts of corresponding miRNA molecule or isomiR or source thereof may be difficult to be measured in a subject, a sample from a subject is preferably used. According to another preferred embodiment, the expression level (of a nucleotide sequence or miRNA molecule or isomiR or source thereof) is determined ex vivo in a sample obtained from a subject. Therefor, in preferred embodiments the invention provides a method for diagnosing as described herein, wherein the expression level is determined ex vivo in a sample obtained from the subject. The sample may comprise a body fluid of a subject. A sample may be a tissue biopsy of a subject. A preferred tissue comprises or consists of or is associated with neuronal cells. A body fluid may comprise or be derived from blood, serum, sputum, plasma, CSF (Cerebrospinal Fluid), stool, urine. It is specifically contemplated that the invention can be used to evaluate or diagnose differences between stages of disease or condition associated with neuronal deficiency.

An increase or decrease of the expression level of a nucleotide sequence (or steady state level of the encoded miRNA molecule or isomi or source thereof) is preferably defined as being a detectable change of the expression level of a nucleotide (or steady state level of an encoded miRNA molecule or isomiR or source thereof or any detectable change in a biological activity of a miRNA molecule or isomiR or source thereof) using a method as defined earlier on as compared to the expression level of a corresponding nucleotide sequence (or steady state level of a corresponding encoded miRNA molecule or isomiR or source thereof) in a healthy subject. A preferred nucleotide sequence is a sequence encoding a precursor of a miRNA molecule or isomiR thereof. According to a preferred embodiment, an increase or decrease of a miRNA activity is quantified using a specific assay for a miRNA activity. A preferred assay is the assessment of neuronal deficiency or promotion of neuronal generation or regeneration as earlier defined herein.

Preferably, a decrease of the expression level of a nucleotide sequence means a decrease of at least 10% of the expression level of the nucleotide sequence using arrays. More preferably, a decrease of the expression level of a nucleotide sequence means an decrease of at least 15%, even more preferably at least 20%, at least 30%, at least 40%, at least 50%, at least 70%, at least 90%, or 100%. In this case, there is no detectable expression.

Preferably, a decrease of the expression level of a miRNA molecule or isomiR or source thereof means a decrease of at least 10% of the expression level of the miRNA using qPCR, microarrays or Northern blot analysis. Preferably qPCR is stem-loop RT qPCR. More preferably, a decrease of the expression level of a miRNA molecule or isomiR or source thereof means a decrease of at least 15%, even more preferably at least 20%, at least 30%, at least 40%, at least 50%, at least 70%, at least 90%, or 100%. In this case, there is no detectable expression.

Preferably, a decrease of a miRNA activity means a decrease of at least 5% of a miRNA activity using a suitable assay. More preferably, a decrease of a miRNA activity means a decrease of at least 10%, even more preferably at least 20%, at least 30%, at least 40%, at least 50%, at least 70%, at least 90%, or 100%. In this case, there is no detectable activity.

Preferably, an increase of the expression level of a nucleotide sequence means an increase of at least 10% of the expression level of the nucleotide sequence using any of the techniques mentioned herein. More preferably, an increase of the expression level of a nucleotide sequence means an increase of at least 15%, even more preferably at least 20%, at least 30%, at least 40%, at least 50%, at least 70%, at least 90%, at least 150% or more.

Preferably, an increase of the expression level of a miRNA molecule or isomiR or source thereof means an increase of at least 10% of the expression level of the miRNA molecule or isomiR or source thereof using RT-qPCR, preferably stem-loop RT qPCR. More preferably, an increase of the expression level of a miRNA molecule or isomiR or source thereof means an increase of at least 15%, even more preferably at least 20%, at least 30%, at least 40%, at least 50%, at least 70%, at least 90%, at least 150% or more.

Preferably, an increase of a miRNA activity means an increase of at least 5% of a miRNA activity using a suitable assay. More preferably, an increase of a miRNA activity means an increase of at least 10%, even more preferably at least 20%, at least 30%, at least 40%, at least 50%, at least 70%, at least 90%, at least 150% or more.

Preferably, an expression level is determined ex vivo in a sample obtained from a subject. More preferably, the sample is as earlier defined herein and wherein subsequently, a given nucleotide sequence and/or miRNA molecule or isomiR or source thereof is extracted and purified using known methods to the skilled person. More preferably, the sample is or comprises or is derived from a biopsy, blood, sputum, stool or urine.

In a diagnostic method of the invention preferably the expression level of more than one, more preferably of at least 1, 2, 3, 4, 5, 6, 7, 8, 9, 10, 11, 12, 13, 14, 15 miRNAs molecule or isomiR or source thereof and/or the steady state levels of the corresponding miRNAs molecule or isomiR or source thereof are determined.

Accordingly in a preferred method, in step (a) one determines the expression level of another miRNA molecule or isomiR or source thereof selected from:
i) a miRNA-124 molecule, a miRNA-124 isomiR, a miRNA-124 precursor, or of
ii) KLF4, or of
iii) both miRNA-135a and miRNA-135b, or isomiRs, or sources thereof, or of
iv) both miRNA-135a and miRNA-196a-5p, or isomiRs, or sources thereof, or of
v) both miRNA-135b and miRNA-196a-5p, or isomiRs, or sources thereof, or of
vi) each of miRNA-135a and miRNA-135b and miRNA-196a-5p, or isomiRs, or sources thereof.

In a further preferred method, in step (a) the expression level is determined of:
i) both miRNA-135a and miRNA-135b, or isomiRs, or sources thereof, or of
ii) Mef2a, or of
iii) Pre-miRNA-135a1, or of
iv) Pre-miRNA-135a2, or of
v) both pre-miRNA-135a1 and pre-miRNA-135a2.

Expression of Mef2a can be determined by determining the protein content, or by determining mRNA. Preferably, epilepsy is diagnosed when an increase in pre-miRNA-135a2 expression is found, more preferably for human subjects while no increase of pre-miRNA-135a1 is found. When a ratio between pre-miR-135a1 and pre-miR-135a2 is determined, the diagnosed epilepsy is preferably temporal lobe epilepsy. When a relative expression ratio between pre-miR-135a1 and pre-miR-135a2 is determined, epilepsy is preferably diagnosed when the relative expression of pre-miR-135a2 is at least 20, 30, 40, 50, 60, 70, 80, 90, 100, 110, 120, 130% or more higher than the relative expression of pre-miR-135a1, more preferably at least 60, 70, 80, 90, 100, 110, 120, 130% or more higher. Preferably, the relative expression of pre-miR-135a1 is at most 20, 15, 10, 5, or 0% higher than for a reference value such as a healthy subject or an average value for healthy subjects. In preferred embodiments, epilepsy is diagnosed when expression of pre-miR-135a1 is not increased as compared to a reference value or is increased by at most 15, 10, or 5%, while expression of pre-miR-135a2 is increased, or is increased by at least 30, 40, 50, 60, 70, 80, 90, or 100% or more as compared to a reference value. A preferred reference value is expression in a healthy subject or average expression in healthy subjects— in this context, expression levels are preferably normalized, such as normalized to GAPDH expression. Pre-miRs can be determined by known techniques, for example qPCR.

In a further preferred method, a neuronal deficiency or a disease or condition associated with neuronal deficiency is diagnosed when the comparison leads to the finding of a decrease of the expression level of said miRNA-135a and/or miRNA-135b and/or miRNA-196a-5p molecule, isomiR, or a source thereof. More preferably, epilepsy or a disease or condition associated with epilepsy is diagnosed when the comparison leads to the finding of an increase in the expression level of said miRNA molecule, isomiR, or a source thereof.

In a further preferred method, a neuronal deficiency or a disease or condition associated with neuronal deficiency is diagnosed when the comparison leads to the finding of a decrease of the expression level of said miRNA-135a and/or miRNA-135b and/or miRNA-196a-5p molecule, isomiR, or a source thereof and a decrease of the expression level of a miRNA-124 molecule, an isomiR, or a source thereof.

In a further preferred embodiment, a neuronal deficiency or a disease or condition associated with neuronal deficiency is diagnosed when the comparison leads to the finding of a decrease of the expression level of said miRNA molecule, isomiR, or a source thereof and/or a decrease of the expression level of a miRNA-124 molecule, isomiR, or a source thereof.

In a further aspect, there is provided a method for identification of a substance or a molecule capable of treating, reverting, preventing, curing and/or delaying a neuronal deficiency or a condition or disease associated with neuronal deficiency in a subject, the method comprising the steps of:
(a) providing a test cell population capable of expressing a miRNA-135a and/or miRNA-135b and/or a miRNA-196-5p molecule, isomiR, or source thereof, preferably the test population comprises neuronal cells such as SH-SY5Y, more preferably the test cell population comprises mammalian cells, even more preferably human cells;
(b) contacting or incubating the test cell population with the substance;
(c) determining the expression level of said miRNA-135a and/or miRNA-135b and/or miRNA-196-5p molecule, isomiR, or source thereof or an activity or steady state level of said miRNA-135a and/or miRNA-135b and/or miRNA-196a-5p molecule, isomiR, or source thereof in the test cell population contacted or incubated with the substance;
(d) comparing the expression, activity or steady state level determined in (c) with the expression, activity or steady state level of said miRNA-135a and/or miRNA-135b and/or miRNA-196a-5p molecule, isomiR, or source thereof in a test cell population that is not contacted with the substance; and,
(e) identifying a substance that produces a difference in expression level, activity or steady state level of said miRNA-135a and/or miRNA-135b and/or miRNA-196a-5p molecule, isomiR, or source thereof between the test cell population that is contacted with the substance and the test cell population that is not contacted with the substance.

A preferred test cell population is a test cell population capable of expressing a miRNA-135a and/or miRNA-135b; when such a test cell population is used, steps (c) and (d) and (e) only relate to miRNA-135a and/or miRNA-135b. Preferably, in step a), a test cell comprises a nucleic acid construct comprising a source or a precursor of a miRNA-135a and/or miRNA-135b and/or miRNA-196a-5p molecule or isomiR thereof or a precursor thereof as identified earlier herein. Preferably, in a method the expression levels, an activity or steady state levels of more than one nucleotide sequence or more than one miRNA molecule, isomiR, or source thereof are compared. Preferably, in a method, a test cell population comprises mammalian cells, more preferably human cells. More preferably, a test cell is a neuronal cell. A SH-SY5Y cell line may also be used. A preferred test cell population does not express a miRNA-135a and/or miRNA-135b and/or miRNA-196a-5p molecule or isomiR or source thereof or has a reduced expression compared to a normal counterpart. More preferably, a test cell population comprises a neuronal cell. More preferably, a test cell population comprises 20%, 30%, 40%, 50%, 60%, 70%, 80%, 90% or 100% of neuronal cells. Neuronal cells may be identified by their expression of markers. Alternatively or in addition to previous mentioned cells, in one aspect the invention also pertains to a substance that is identified in the aforementioned methods.

In a preferred method, the expression levels, activities or steady state levels of a miRNA-124 molecule or isomiR or source thereof is compared.

In a further aspect is provided an in vivo, in vitro, or ex vivo method for promoting neuronal generation or regeneration, at least comprising the step of contacting a cell with a miRNA, an antagomir, or a source thereof according to the invention, or with a composition according to the invention. Such a method may comprise steps of methods as described elsewhere herein. In the context of the invention, contacting a cell with a compound or a composition can comprise adding such a compound or composition to a medium in which a cell is cultured. Contacting a cell with a compound or a composition can also comprise adding such a compound or composition to a medium, buffer, or solution in which a cell is suspended, or which covers a cell. Other preferred methods of contacting a cell comprise injecting a cell with a compound or composition, or exposing a cell to a material comprising a compound or composition according to the invention. In an embodiment of this aspect, the method is an in vitro method. In a further embodiment of this aspect, the method is an ex vivo method. In a further embodiment of this aspect, the method is an in vivo method; in such a case, administration as defined elsewhere herein is a preferred mode of contacting a cell. In a preferred embodiment of this aspect, the method is an in vitro or an ex vivo method.

Within the embodiments of this aspect, the cell can be a cell from a sample obtained from a subject. Such a sample can be a sample that has been previously obtained from a subject. Within the embodiments of this aspect, samples can have been previously obtained from a human subject. Within the embodiments of this aspect, samples can have been obtained from a non-human subject. In a preferred embodiment of this aspect, obtaining the sample is not part of the method according to the invention. In preferred embodiments of methods or uses according to the invention, methods or uses according to the invention use products according to the invention.

General Definitions and General Technologies Referred to Herein

MicroRNA molecules ("miRNAs") are generally 21 to 22 nucleotides in length, though lengths of 17 and up to 25 nucleotides have been reported. Any length of 17, 18, 19, 20, 21, 22, 23, 24, 25 is therefore encompassed within the present invention. The miRNAs are each processed from a longer precursor RNA molecule ("precursor miRNA"). Precursor miRNAs are transcribed from non-protein-encoding genes. A precursor may have a length of at least 50, 70, 75, 80, 85, 100, 150, 200 nucleotides ore more. The precursor miRNAs have two regions of complementarity that enables them to form a stem-loop- or fold-back-like structure, which is cleaved by enzymes called Dicer and Drosha in animals. Dicer and Drosha are ribonuclease III-like nucleases. The processed miRNA is typically a portion of the stem.

The processed miRNA (also referred to as "mature miRNA") becomes part of a large complex, known as the RNA-Induced Silencing Complex (RISC) complex, to (down)-regulate a particular target gene. Examples of animal miRNAs include those that perfectly or imperfectly basepair with the mRNA target, resulting in either mRNA degradation or inhibition of translation respectively (Olsen et al, 1999; Seggerson et al, 2002). SiRNA molecules also are processed by Dicer, but from a long, double-stranded RNA molecule. SiRNAs are not naturally found in animal cells, but they can function in such cells in a RNA-induced silencing complex (RISC) to direct the sequence-specific cleavage of an mRNA target (Denli et al, 2003).

SIROCCO is a EU consortium which investigates silencing RNAs as organisers and coordinators of complexity in eukaryotic organisms (see for example the websites cordis.europa.eu/pub/lifescihealth/docs/sirocco.pdf and www.sirocco-project.eu). As a consortium, SIROCCO maintains a database of miRNA sequence information. Each miRNA entry listed in the SIROCCO database is based on observed and verified expression of said miRNA.

The study of endogenous miRNA molecules is described in U.S. Patent Application 60/575,743, which is hereby incorporated by reference in its entirety. A miRNA is apparently active in the cell when the mature, single-stranded RNA is bound by a protein complex that regulates the translation of mRNAs that hybridize to the miRNA. Introducing exogenous RNA molecules that affect cells in the same way as endogenously expressed miRNAs requires that a single-stranded RNA molecule of the same sequence as the endogenous mature miRNA be taken up by the protein complex that facilitates translational control. A variety of RNA molecule designs have been evaluated. Three general designs that maximize uptake of the desired single-stranded miRNA by the miRNA pathway have been identified. An RNA molecule with a miRNA sequence having at least one of the three designs may be referred to as a synthetic miRNA.

miRNA molecules of the invention can replace or supplement the gene silencing activity of an endogenous miRNA. An example of such molecules, preferred characteristics and modifications of such molecules and compositions comprising such molecules is described in WO2009/091982, which is hereby incorporated by reference in its entirety.

miRNA molecules of the invention or isomiRs or mimics or sources thereof comprise, in some embodiments, two RNA molecules wherein one RNA is identical to a naturally occurring, mature miRNA. The RNA molecule that is identical to a mature miRNA is referred to as the active strand. The second RNA molecule, referred to as the complementary strand or the passenger strand, is at least partially complementary to the active strand. The active and complementary strands are hybridized to create a double-stranded RNA, that is similar to the naturally occurring miRNA precursor that is bound by the protein complex immediately prior to miRNA activation in the cell. Maximizing activity of said miRNA requires maximizing uptake of the active strand and minimizing uptake of the complementary strand by the miRNA protein complex that regulates gene expression at the level of translation. The molecular designs that provide optimal miRNA activity involve modifications of the complementary strand.

Two designs incorporate chemical modifications of the complementary strand.

The first modification involves creating a complementary RNA with a group other than a phosphate or hydroxyl at its 5' terminus. The presence of the 5' modification apparently eliminates uptake of the complementary strand and subsequently favors uptake of the active strand by the miRNA protein complex. The 5' modification can be any of a variety of molecules including NH2, NHCOCH3, biotin, and others.

The second chemical modification strategy that significantly reduces uptake of the complementary strand by the miRNA pathway is incorporating nucleotides with sugar modifications in the first 2-6 nucleotides of the complementary strand. It should be noted that the sugar modifications consistent with the second design strategy can be coupled with 5' terminal modifications consistent with the first design strategy to further enhance miRNA activities.

The third miRNA design involves incorporating nucleotides in the 3' end of the complementary strand that are not complementary to the active strand.

Hybrids of the resulting active and complementary RNAs are very stable at the 3' end of the active strand but relatively unstable at the 5' end of the active strand. Studies with siRNAs indicate that 5' hybrid stability is a key indicator of RNA uptake by the protein complex that supports RNA interference, which is at least related to the miRNA pathway in cells. The inventors have found that the judicious use of mismatches in the complementary RNA strand significantly enhances the activity of said miRNA.

MiRNA Libraries

A key application for the miRNAs as identified herein is the assessment or diagnosis of the presence of one individual or groups of miRNAs in a sample. Cell populations with each of the different miRNAs can then be assayed to identify miRNAs whose presence affects a cellular phenotype (i.e.neuronal deficiency). The number of different miRNAs in the libraries is variable. It is contemplated that there may be, be at least, or be at most 1, 2, 3, 4, 5, 6, 7, 8, 9, 10, 11, 12, 13, 14, 15, 16, 17, 18, 19, 20 or more, or any range derivable therein, different miRNA-specific molecules in the library. In specific embodiments, libraries have 1 to 20 different miRNA-specific molecules, or 5 to 20 different miRNA-specific molecules. "Different" miRNA-specific molecules refers to nucleic acids that specifically encode miRNAs with different sequences.

miRNAs are contemplated to be made primarily of RNA, though in some embodiments, they may be RNA, nucleotide analogs, such as Locked nucleic acids (LNA) or Unlocked nucleic acids (UNA), DNA, or any combination of DNA, RNA, nucleotide analogs, and PNAs (Peptide Nucleic Acids). Accordingly, it is understood that the library contains one or more nucleic acids for these different miRNAs. In specific embodiments, the library is specific to human miRNAs, though libraries for multiple organisms are contemplated.

An RNA molecule of the invention has or comprises or consists of a miRNA region. In specific embodiments, a miRNA molecule or isomiR or mimic or antagomir or precursor thereof has a sequence that derives from any of SEQ ID NOs: 57-341. It is particularly contemplated that nucleic acid molecules of the invention may be derived from any of the mature miRNA sequences in SEQ ID NOs: 5-9.

A miRNA molecule or isomiR or mimic or precursor thereof will include a sequence that extends at least 1 to 5 nucleotides of coding sequence upstream and/or downstream of the predicted miRNA sequence. In some embodiments, molecules have up to 1, 2, 3, 4, 5, 6, 7, or more contiguous nucleotides, or any range derivable therein, that flank the sequence encoding the predominant processed miRNA on one or both sides (5' and/or 3' end).

Libraries of the invention can contain miRNA sequences from any organism having miRNAs, specifically including but not limited to, mammals such as humans, non human primates, rats and mice. Specifically contemplated are libraries having, having at least, or having at most 1, 2, 3, 4, 5, 6, 7, 8, 9, 10, 11, 12, 13, 14, 15, 16, 17, 18, 19, 20 or more different miRNAs (that is, miRNA-specific molecules having different sequences derived from different miRNA genes). Specifically contemplated are such libraries described in the previous sentence with respect to any of SEQ ID NOs: 1-4 or 10-13 or 147-241, particularly those corresponding to miRNA sequences (mature sequences).

Nucleic Acids

The present invention concerns nucleic acid molecules also called sources or precursors of miRNAs that can introduce miRNAs in cultured cells or into a subject. The nucleic acids may have been produced in cells or in vitro by purified enzymes though they are preferentially produced by chemical synthesis. They may be crude or purified. The term "miRNA," unless otherwise indicated, refers to the processed miRNA, after it has been cleaved from its precursor. Table 1 indicates which SEQ ID NO corresponds to a particular precursor sequence of a miRNA (SEQ ID NOs: 1-4) and Table 6 indicates which SEQ ID NO corresponds to the mature or mimic sequence of a miRNA (SEQ ID NOs: 147-241. Table 3 identifies the cloned DNA sequences into the lentiviral vector (SEQ ID NOs: 10-13) which were used in the functional screen as described in the examples. Tables 4 and 5 identify the preferred seed sequences (as SEQ ID NOs: 14-56) of each of the mature miRNAs of Table 2. The name of the miRNA is often abbreviated and referred to without the prefix and will be understood as such, depending on the context. Unless otherwise indicated, miRNAs referred to in the application are human sequences identified as mir-X or let-X, where X is a number and/or letter.

It is understood that a miRNA is derived from genomic sequences or a non-coding gene. In this respect, the term "gene" is used for simplicity to refer to the genomic sequence encoding the precursor miRNA for a given miRNA. However, embodiments of the invention may involve genomic sequences of a miRNA that are involved in its expression, such as a promoter or other regulatory sequences.

The term "recombinant" may be used and this generally refers to a molecule that has been manipulated in vitro or that is the replicated or expressed product of such a molecule.

The term "nucleic acid" is well known in the art. A "nucleic acid" as used herein will generally refer to a molecule (one or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

The term "miRNA" generally refers to a single-stranded molecule, but in specific embodiments, molecules implemented in the invention will also encompass a region or an additional strand that is partially (between 10 and 50% complementary across length of strand), substantially (greater than 50% but less than 100% complementary across length of strand) or fully complementary to another region of the same single-stranded molecule or to another nucleic acid. Thus, nucleic acids may encompass a molecule that comprises one or more complementary or self-complementary strand(s) or "complement(s)" of a particular sequence comprising a molecule. For example, precursor miRNA may have a self-complementary region, which is up to 100% complementary.

As used herein, "hybridization", "hybridizes" or "capable of hybridizing" is understood to mean the forming of a double or triple stranded molecule or a molecule with partial double or triple stranded nature using techniques known to the skilled person such as southern blotting procedures. The term "anneal" as used herein is synonymous with "hybridize." The term "hybridization", "hybridize(s)" or "capable of hybridizing" may mean "low", "medium" or "high" hybridization conditions as defined below.

Low to medium to high stringency conditions means prehybridization and hybridization at 42° C. in 5×SSPE, 0.3% SDS, 200 pg/ml sheared and denatured salmon sperm DNA, and either 25% 35% or 50% formamide for low to medium to high stringencies respectively. Subsequently, the hybridization reaction is washed three times for 30 minutes each using 2×SSC, 0.2% SDS and either 55° C., 65° C., or 75° C. for low to medium to high stringencies.

Nucleic acids or derivatives thereof of the invention will comprise, in some embodiments the miRNA sequence of any miRNA described in SEQ ID NOs: 1-4 or 147-341. It is contemplated that nucleic acids sequences of the invention derived from SEQ ID NO: 1-4 or 147-341 can have, have at least, or have at most 5, 6, 7, 8, 9, 10, 11, 12, 13, 14, 15, 16, 17, 18, 19, 20, 21, 22, 23, contiguous nucleotides from SEQ ID NOs: 1-4 or 147-341 (or any range derivable therein). In other embodiments, nucleic acids are, are at least, or are at most 80, 81, 82, 83, 84, 85, 86, 87, 88, 89, 90, 91, 92, 93, 94, 95, 96, 97, 98, 99, 100% identical to the miRNA sequence of SEQ ID NOs: 1-4 or 147-341.

Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in a manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moiety. Preferred alkyl (e.g., alkyl, caboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be comprised in a nucleoside or nucleotide, using any chemical or natural synthesis method described herein or known to one of ordinary skill in the art. Such nucleobase may be labeled or it may be part of a molecule that is labeled and contains the nucleobase.

Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

Nucleic Acid Analogs

A nucleic acid may comprise, or be composed entirely of, a derivative or analog of a nucleobase, a nucleobase linker moiety and/or backbone moiety that may be present in a naturally occurring nucleic acid. RNA with nucleic acid analogs may also be labeled according to methods of the invention. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in: U.S. Pat. No. 5,681,947, which describes oligonucleotides comprising purine derivatives that form triple helixes with and/or prevent expression of dsDNA; U.S. Pat. Nos. 5,652,099 and 5,763,167, which describe nucleic acids incorporating fluorescent analogs of nucleosides found in DNA or RNA, particularly for use as fluorescent nucleic acids probes; U.S. Pat. No. 5,614,617, which describes oligonucleotide analogs with substitutions on pyrimidine rings that possess enhanced nuclease stability; U.S. Pat. Nos. 5,670,663, 5,872,232 and 5,859,221, which describe oligonucleotide analogs with modified 5-carbon sugars (i.e., modified T-deoxyfuranosyl moieties) used in nucleic acid detection; U.S. Pat. No. 5,446,137, which describes oligonucleotides comprising at least one 5-carbon sugar moiety substituted at the 4' position with a substituent other than hydrogen that can be used in hybridization assays; U.S. Pat. No. 5,886,165, which describes oligonucleotides with both deoxyribonucleotides with 3'-5' internucleotide linkages and ribonucleotides with 2'-5' internucleotide linkages; U.S. Pat. No. 5,714,606, which describes a modified internucleotide linkage wherein a 3'-position oxygen of the internucleotide linkage is replaced by a carbon to enhance the nuclease resistance of nucleic acids; U.S. Pat. No. 5,672,697, which describes oligonucleotides containing one or more 5' methylene phosphonate internucleotide linkages that enhance nuclease resistance; U.S. Pat. Nos. 5,466,786 and 5,792,847, which describe the linkage of a substituent moiety which may comprise a drug or label to the 2' carbon of an oligonucleotide to provide enhanced nuclease stability and ability to deliver drugs or detection moieties; U.S. Pat. No. 5,223,618, which describes oligonucleotide analogs with a 2' or 3' carbon backbone linkage attaching the 4' position and 3' position of adjacent 5-carbon sugar moiety to enhanced cellular uptake, resistance to nucleases and hybridization to target RNA; U.S. Pat. No. 5,470,967, which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240, which describe oligonucleotides with three or four atom linker moiety replacing phosphodiester backbone moiety used for improved nuclease resistance, cellular uptake and regulating RNA expression; U.S. Pat. No. 5,858,988, which describes hydrophobic carrier agent attached to the 2'-0 position of oligonucleotides to enhanced their membrane permeability and stability; U.S. Pat. No. 5,214,136, which describes oligonucleotides conjugated to anthraquinone at the 5' terminus that possess enhanced hybridization to DNA or RNA; enhanced stability to nucleases; U.S. Pat. No. 5,700,922, which describes PNA-DNA-PNA chimeras wherein the DNA comprises 2'-deoxy-erythro-pentofuranosyl nucleotides for enhanced nuclease resistance, binding affinity, and ability to activate RNase H; and WO98/39352, WO99/14226, WO2003/95467 and WO2007/085485, which describe modified RNA nucleotides of which the ribose moiety is modified with an extra bridge connecting the 2' oxygen and 4' carbon. The locked ribose significantly increases the binding affinity and specificity; and WO2008/147824, which describes modified RNA nucleotides termed UNA (unlocked nucleic acid). UNA are acyclic analogues of RNA in which the bond between the C2' and C3' atoms has been cleaved, decreasing binding affinity towards a complementary strand. UNA are compatible with RNase H recognition and RNA cleavage and improves siRNA mediated gene silencing; WO2008/036127 which describes Morpholino nucleic acid analogues, which contain both uncharged and cationic intersubunit linkages; WO/2007/069092 and EP2075342 which describe Zip Nucleic Acids (ZNA), containing conjugating spermine derivatives as cationic moieties (Z units) to an oligonucleotide; U.S. Pat. No. 5,708,154, which describes RNA linked to a DNA to form a DNA-RNA hybrid; U.S. Pat. No. 5,728,525, which describes the labeling of nucleoside analogs with a universal fluorescent label.

Additional teachings for nucleoside analogs and nucleic acid analogs are U.S. Pat. No. 5,728,525, which describes nucleoside analogs that are end-labeled; U.S. Pat. Nos. 5,637,683, 6,251,666 (L-nucleotide substitutions), and U.S. Pat. No. 5,480,980 (7-deaza-2'-deoxyguanosine nucleotides and nucleic acid analogs thereof).

The use of other analogs is specifically contemplated for use in the context of the present invention. Such analogs may be used in synthetic nucleic acid molecules of the invention, both throughout the molecule or at selected nucleotides. They include, but are not limited to, 1) ribose modifications (such as 2'F, 2' NH2, 2'N3,4'thio, or 2' O—CH3) and 2) phosphate modifications (such as those found in phosphorothioates, methyl phosphonates, and phosphoroborates).

Such analogs have been created to confer stability on RNAs by reducing or eliminating their capacity to be cleaved by ribonucleases. When these nucleotide analogs are present in RNAs, they can have profoundly positive effects on the stability of the RNAs in animals. It is contemplated that the use of nucleotide analogs can be used alone or in conjunction with any of the design modifications of a synthetic miRNA for any nucleic acid of the invention.

Modified Nucleotides miRNAs of the invention specifically contemplate the use of nucleotides that are modified to enhance their activities. Such nucleotides include those that are at the 5' or 3' terminus of the RNA as well as those that are internal within the molecule. Modified nucleotides used in the complementary strands of said miRNAs either block the 5'OH or phosphate of the RNA or introduce internal sugar modifications that enhance uptake of the active strand of the miRNA. Modifications for the miRNAs include internal sugar modifications that enhance hybridization as well as stabilize the molecules in cells and terminal modifications that further stabilize the nucleic acids in cells. Further contemplated are modifications that can be detected by microscopy or other methods to identify cells that contain the synthetic miRNAs.

Preparation of Nucleic Acids

A nucleic acid may be made by any technique known to one of ordinary skill in the art, such as for example, chemical synthesis, enzymatic production or biological production. Though miRNAs according to the invention could be produced using recombinant methods, it is preferred to produce miRNAs by chemical synthesis or enzymatic production. miRNAs can be produced by a number of methods, including methods involving recombinant DNA technology.

Nucleic acid synthesis is performed according to standard methods. See, for example, Itakura and Riggs (1980). Additionally, U.S. Pat. Nos. 4,704,362, 5,221,619, and 5,583,013 each describe various methods of preparing nucleic acids. Non-limiting examples of a nucleic acid (e.g., a oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference.

Oligonucleotide synthesis is well known to those of skill in the art. Various different mechanisms of oligonucleotide synthesis have been disclosed in for example, U.S. Pat. Nos.

4,659,774, 4,816,571, 5,141,813, 5,264,566, 4,959,463, 5,428,148, 5,554,744, 5,574,146, 5,602,244, each of which is incorporated herein by reference.

Basically, chemical synthesis can be achieved by the diester method, the triester method polynucleotides phosphorylase method and by solid-phase chemistry. These methods are discussed in further detail below.

Diester Method

The diester method was the first to be developed to a usable state, primarily by Khorana and co-workers. (Khorana, 1979). The basic step is the joining of two suitably protected deoxynucleotides to form a dideoxynucleotide containing a phosphodiester bond. The diester method is well established and has been used to synthesize DNA molecules (Khorana, 1979).

Triester Method

The main difference between the diester and triester methods is the presence in the latter of an extra protecting group on the phosphate atoms of the reactants and products (Itakura et al., 1975). The phosphate protecting group is usually a chlorophenyl group, which renders the nucleotides and polynucleotide intermediates soluble in organic solvents. Therefore purifications are done in chloroform solutions. Other improvements in the method include (i) the block coupling of trimers and larger oligomers, (ii) the extensive use of high-performance liquid chromatography for the purification of both intermediate and final products, and (iii) solid-phase synthesis.

Polynucleotide Phosphorylase Method.

This is an enzymatic method of DNA synthesis that can be used to synthesize many useful oligonucleotides (Gillam et al., 1978; Gillam et al, 1979). Under controlled conditions, polynucleotide phosphorylase adds predominantly a single nucleotide to a short oligonucleotide.

Chromatographic purification allows the desired single adduct to be obtained. At least a trimer is required to start the procedure, and this primer must be obtained by some other method. The polynucleotide phosphorylase method works and has the advantage that the procedures involved are familiar to most biochemists.

Solid-Phase Methods.

Drawing on the technology developed for the solid-phase synthesis of polypeptides, it has been possible to attach the initial nucleotide to solid support material and proceed with the stepwise addition of nucleotides. All mixing and washing steps are simplified, and the procedure becomes amenable to automation. These syntheses are now routinely carried out using automatic nucleic acid synthesizers. Phosphoramidite chemistry (Beaucage and Lyer, 1992) has become by far the most widely used coupling chemistry for the synthesis of oligonucleotides. As is well known to those skilled in the art, phosphoramidite synthesis of oligonucleotides involves activation of nucleoside phosphoramidite monomer precursors by reaction with an activating agent to form activated intermediates, followed by sequential addition of the activated intermediates to the growing oligonucleotide chain (generally anchored at one end to a suitable solid support) to form the oligonucleotide product.

Recombinant Methods.

Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference. In certain embodiments, the present invention concerns nucleic acid molecules that are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

Design of miRNAs miRNAs typically comprise two strands, an active strand that is identical in sequence to the mature miRNA that is being studied and a complementary strand that is at least partially complementary to the active strand. The active strand is the biologically relevant molecule and should be preferentially taken up by the complex in cells that modulates translation either through mRNA degradation or translational control. Preferential uptake of the active strand has two profound results: (1) the observed activity of said miRNA increases dramatically and (2) non-intended effects induced by uptake and activation of the complementary strand are essentially eliminated. According to the invention, several miRNA designs can be used to ensure the preferential uptake of the active strand.

5' Blocking Agent.

The introduction of a stable moiety other than phosphate or hydroxyl at the 5' end of the complementary strand impairs its activity in the miRNA pathway. This ensures that only the active strand of the miRNA will be used to regulate translation in the cell. 5' modifications include, but are not limited to, NH2, biotin, an amine group, a lower alkylamine group, an acetyl group, 2' 0-Me, DMTO, fluoroscein, a thiol, or acridine or any other group with this type of functionality.

Other sense strand modifications. The introduction of nucleotide modifications like 2'-0 Me, 2'-deoxy, T-deoxy-2'-fluoro, 2'-O-methyl, 2'-O-methoxyethyl (2'-0-MOE), 2'-O-aminopropyl (2'-0-AP), 2'-O-dimethylaminoethyl (2'-0-DMAOE), 2'-O-dimethylaminopropyl (2'-O-DMAP), 2'-O-dimethylaminoethyloxyethyl (2'-0-DMAEOE), or 2'-O—N-methylacetamido (2'-0-NMA), NH2, biotin, an amine group, a lower alkylamine group, an acetyl group, DMTO, fluoroscein, a thiol, or acridine or any other group with this type of functionality in the complementary strand of the miRNA can eliminate the activity of the complementary strand and enhance uptake of the active strand of the miRNA.

Base mismatches in the sense strand. As with siRNAs (Schwarz 2003), the relative stability of the 5' and 3' ends of the active strand of the miRNA apparently determines the uptake and activation of the active by the miRNA pathway. Destabilizing the 5' end of the active strand of the miRNA by the strategic placement of base mismatches in the 3' end of the complementary strand of the synthetic miRNA enhances the activity of the active strand and essentially eliminates the activity of the complementary strand.

Host Cells and Target Cells

The cells wherein a miRNA or source thereof is introduced or wherein the presence of a miRNA is assessed may be derived from or contained in any organism. Preferably, the cell is a vertebrate cell.

More preferably, the cell is a mammalian cell. Even more preferably, the cell is a human cell.

A mammalian cell may be from the germ line or somatic, totipotent or pluripotent, dividing or non-dividing, epithelium, immortalized or transformed, or the like. The cell may be an undifferentiated cell, such as a stem cell, or a differentiated cell, such as from a cell of an organ or tissue. Alternatively, cells may be qualified as epithelial or endothelial cells, stromal cells, brain, breast, cervix, colon, gastrointestinal tract, heart, kidney, large intestine, liver, lung, ovary, pancreas, heart, prostate, bladder, small intestine, stomach, testes or uterus.

As used herein, the terms "cell," "cell line," and "cell culture" may be used interchangeably. All of these terms also include their progeny, which is any and all subsequent generations formed by cell division. It is understood that all progeny may not be identical due to deliberate or inadvertent mutations. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a small, interfering RNA or a template construct encoding a reporter gene has been introduced. Therefore, recombinant cells are distinguishable from naturally occurring cells that do not contain a recombinantly introduced nucleic acid.

A tissue may comprise a host cell or cells to be transformed or contacted with a nucleic acid delivery composition and/or an additional agent. The tissue may be part or separated from an organism. In certain embodiments, a tissue and its constituent cells may comprise, but is not limited to brain, cerebellum, spinal cord, brachial nerve, intercostal nerves, musculocultaneous nerve, subcostal nerve, lumbar plexus, sacral plexus, femoral nerve, pudental nerve, sciatic nerve, muscular brenches of femoral nerve, saphenous nerve, tibial nerve, radial nerve, median nerve, iliophypogastric nerve, genitofemoral nerve, obturator nerve, ulnar nerve, common peroneal nerve, deep pernneal nerve, superficial peroneal nerve, ganglion, optic nerve, nerve cells, stem cells.

In certain embodiments, the host cell or tissue may be comprised in at least one organism. In certain embodiments, the organism may be a mammal, a human, a primate or murine. One of skill in the art would further understand the conditions under which to incubate all of the above described host cells to maintain them and to permit their division to form progeny.

Delivery Methods

The present invention involves in some embodiments delivering a nucleic acid into a cell. This may be done as part of a screening method, or it may be related to a therapeutic or diagnostic application. RNA molecules may be encoded by a nucleic acid molecule comprised in a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, lentivirus, and plant viruses), and artificial chromosomes (e.g., YACs). One of skill in the art would be well equipped to construct a vector through standard recombinant techniques, which are described in Sambrook et al, 1989 and Ausubel et al, 1996, both incorporated herein by reference. In addition to encoding a modified polypeptide such as modified gelonin, a vector may encode non-modified polypeptide sequences such as a tag or targeting molecule. A targeting molecule is one that directs the desired nucleic acid to a particular organ, tissue, cell, or other location in a subject's body.

The term "expression vector" refers to a vector containing a nucleic acid sequence coding for at least part of a gene product capable of being transcribed. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). The expression vectors may contain an RNAi expression cassette comprising one promoter and one or more stem-loop structures separated by one or more spacer regions (WO2006/084209).

Another way of introducing expression vectors into cells, using avidin fusion proteins is described in U.S. Pat. No. 6,287,792.

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al, 1988) adeno-associated virus (AAV) (Ridgeway, 1988; Baichwal and Sugden, 1986; Hermonat and Muzycska, 1984), lentivirus (WO2008/071959, WO2004/054512), Hemaglutinating Virus of Japan (WO2004/035779), Baculovirus (WO2006/048662) and herpesviruses may be employed. They offer several attractive features for various mammalian cells (Friedmann, 1989; Ridgeway, 1988; Baichwal and Sugden, 1986; Coupar et al, 1988; Horwich et al, 1990).

Other suitable methods for nucleic acid delivery to affect expression of compositions of the present invention are believed to include virtually any method by which a nucleic acid (e.g., DNA, including viral and nonviral vectors) can be introduced into an organelle, a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al, 1987); by liposome mediated transfection (Nicolau and Sene, 1982; Fraley et al., 1979; Nicolau et al, 1987; Wong et al, 1980; Kaneda et al., 1989; Kato et al., 1991); by photochemical internalization (WO2008/007073); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464, 765, each incorporated herein by reference); by *Agrobacterium*-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985). Through the application of techniques such as these, organelle(s), cell(s), tissue(s) or organism(s) may be stably or transiently transformed.

A review provides several ways of formulating a RNA molecule in order to optimize its internalisation into a cell (Kim S S., et al, Trends Mol. Med., 2009, 15: 491-500). The following other publications discloses alternative ways of formulating a RNA molecule in order to improve its internalisation into a cell, each incorporated herein by reference: WO 2007/095152, describing the use of PTD-DRBD (Peptide transduction domains linked to double stranded binding domain) for delivery of oligonculeotides, WO 2009/086558, describing the use of SNALP (Stable Nucleic Acid Lipid Particles) particles, comprising a mixture of cationic and fusogenic lipids that enable the cellular uptake and endosomal release of the particle's nucleic acid payload, WO 2009/149418, describing neutral phospholipid-oil-RNAi emulsions, WO 2007/121947, describing the use of a delivery vehicle based on lipoplex, WO 2009/132131, describing the use of novel lipids and nucleic acid-lipid particles that provide efficient encapsulation and efficient delivery of the encapsulated nucleic aicd to cells, WO2004/091578 and WO2004/064805 describing cochleate technology of alternating layers of lipids that spiral around a nucleic acid molecule, WO2003/047494 and WO2003/047493 describing reverse micelles incorporating nucleic acids for oral and mucosal delivery, WO 2008/156702, describing bacteria and bacterial therapeutic particle (BTP), including oligonucleotides for as delivery vehicle to cells. Each of the formulations referred to or disclosed in these publications is encompassed by the present invention.

A variety of compounds have been attached to the ends of oligonucleotides to facilitate their transport across cell membranes. Short signal peptides found in the HIV TAT, HSV VP22, Drosphila antennapedia, and other proteins have been found to enable the rapid transfer of biomolecules across membranes (reviewed by Schwarze 2000). These signal peptides, referred to as Protein Transduction Domains (PTDs), have been attached to oligonucleotides to facilitate their delivery into cultured cells (Eguchi A, Dowdy S F, Trends Pharmacol Sci., 2009, 7:341-5). Cholesterols have been conjugated to oligonucleotides to improve their uptake into cells in animals (MacKellar 1992). The terminal cholesterol groups apparently interact with receptors or lipids on the surfaces of cells and facilitate the internalization of the modified oligonucleotides. Likewise, poly-L-lysine has been conjugated to oligonucleotides to decrease the net negative charge and improve uptake into cells (Leonetti 1990).

A variety of compounds have been developed that complex with nucleic acids, deliver them to surfaces of cells, and facilitate their uptake in and release from endosomes. Among these are: (1) a variety of lipids such as DOTAP (or other cationic lipid), DDAB, DHDEAB, and DOPE and (2) non-lipid-based polymers like polyethylenimine, polyamidoamine, and dendrimers of these and other polymers. In certain of these embodiments a combination of lipids is employed such as DOTAP and cholesterol or a cholesterol derivative (U.S. Pat. No. 6,770,291, which is hereby incorporated by reference). Several of these reagents have been shown to facilitate nucleic acid uptake in animals.

The cellular components involved in the miRNA pathway are becoming known. Proteins that stabilize and/or transport miRNAs within cells might enhance the stability and activity of miRNAs because they should protect and guide the bound miRNAs once they are in cells. Mixtures of miRNA-transporter proteins and miRNAs could enhance the efficacy of miRNA-based therapeutics. RNAs are hydrophilic molecules by virtue of their anionic phosphate and sugar backbone. Although the nucleobases are hydrophobic, hydrophilicity dominates owing to the extensive hydrogen bonding resulting from the phosphate and sugar residues. The hydrophilic character and anionic backbone reduces cellular permeation. Conjugation of lipophilic groups like cholesterol (Manoharan, 2002) and lauric and lithocholic acid derivatives with C32 functionality (Lorenz et al, 2004), have been shown to improve cellular uptake. Moreover binding of steroid conjugated oligonucleotides to different lipoproteins in the bloodstream, such as LDL, protect their integrity and govern their biodistribution (Rump et al, 2000). Cholesterol attached to anti-sense molecules (Bijsterbosch et al., 2001) and aptamers (Rusconi et al., 2004) has also been shown to stabilize oligonucleotides by allowing binding to lipoproteins. Cholesterol has been demonstrated to enhance uptake and serum stability of siRNAs in vitro (Lorenz et al., 2004) and in vivo (Soutschek et al., 2004). Additionally, a number of small molecules like SB-435495 (Blackie et al, (2002), Isradipine (Oravcova et al, 1994), amlodipine (Oravcova et al, 1994) and 2,2',4,4',5,5'-hexachlorobiphenyl (Borlakoglu et al, 1990) could enhance cellular uptake, and improve nuclease resistance by promoting lipoprotein association.

Screening with miRNA Libraries

As used in the patent application, screening is a process wherein multiple miRNA-specific reagents are delivered separately into individual cell populations or animals. At one or more designated times after delivery, the cell populations or animals are assayed for one or more phenotypes. Those cells or animals that have a significantly different phenotype than cells or animals in the negative control group are classified as positives. The miRNA that was being manipulated in the sample is defined as a hit. Hits represent targets for additional research and potential therapeutic development.

In some embodiments, there is a multi-step process for screening, in certain embodiments, there are four general steps:
(1) Develop Quantitative Assay to Monitor Cellular Process being Studied.

Assays that measure the intensity of a cellular phenotype range from microscopic assays that monitor cell size, cell cycle status, or antibody staining to enzymatic assays that assess the turnover of a specific substrate in a cell lysate to direct measurements of biomolecules or small molecules in lysates, on cells, or in medium.

Critical to the success of a screen is creating an assay that truly measures the cellular phenotype and maximizing the signal-to-noise ratio of the assay. Maximizing signal-to-noise involves testing variables like assay time, assay components, cell type, and length of time between transfection and assay. The greater the difference in the assay results between a positive phenotype and a negative control phenotype, the greater the spread will be in the screening results and the better the opportunity will be to identify interesting genes. Alternative screening methods exist using batch infection.

(2) Optimize Transfection Conditions for the Desired Cells.

The first step in this process is identifying a transfection reagent and plating conditions that maximize the uptake of synthetic miRNAs while maintaining high cell viability. We find it useful to test 2-5 different transfection reagents when using cell lines or 5-10 elelctroporation conditions when using primary or suspension cells. Transfection can be optimized for the reagent or electroporation condition that worked best among the conditions tested. Screening miRNA-specific libraries requires conditions for high-throughput transfection. In this type of screen, lentiviral introduction rather than transfection was used. This may require alternative optimization techniques.

(3) Screen

Once the assay and transfection process have been developed, a library of synthetic miRNAs or miRNAs expressed by viruses can be introduced sequentially into cells in a 24- or 96-well plate. Duplicate or Triplicate transfections for each reagent provide enough data for reasonable statistical analysis. MTS assay as carried out in the experimental part is an example of such a screen.

(4) Validate Hits

Validating a hit involves showing that the observed phenotype is due to the miRNA being targeted. Hits are typically confirmed by delivering a dilution series of the miRNA inhibitor or synthetic miRNA that registered as a hit into the cell that was originally assayed. Confirmation is slightly different from validation. Confirmation is a repeat of the miRNA-induced phenotype, whereas validation can also include reversal of the phenotype by antagonizing miRNA mediated phenotype.

Labeling and Labeling Techniques

In some embodiments, the present invention concerns miRNAs that are labeled, such as for screening assays to evaluate the therapeutic or diagnostic relevance of a particular miRNA species. It is contemplated that miRNA may first be isolated (either from a cell in which the miRNA is endogenous to the cell or from a cell in which miRNA is exogenous to the cell) and/or purified prior to labeling. This may achieve a reaction that more efficiently labels the miRNA, as opposed to other RNA in a sample in which the miRNA is not isolated or purified prior to labeling. In many embodiments of the invention, the label is non-radioactive. Generally, nucleic acids may be labeled by adding labeled nucleotides (one-step process) or adding nucleotides and labeling the added nucleotides (two-step process).

Moreover, miRNAs may be labeled as is described in U.S. Patent Application Ser. No. 60/649,584, which is hereby incorporated by reference. Such nucleotides include those that can be labeled with a dye, including a fluorescent dye, or with a molecule such as biotin. Labeled nucleotides are readily available; they can be acquired commercially or they can be synthesized by reactions known to those of skill in the art.

Nucleotides for Labeling

Nucleotides for labelling are not naturally occurring nucleotides, but instead, refer to prepared nucleotides that have a reactive moiety on them. Specific reactive functionalities of interest include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the other such chemical groups. In some embodiments, the reactive functionality may be bonded directly to a nucleotide, or it may be bonded to the nucleotide through a linking group. The functional moiety and any linker cannot substantially impair the ability of the nucleotide to be added to the miRNA or to be labeled. Representative linking groups include carbon containing linking groups, typically ranging from about 2 to 18, usually from about 2 to 8 carbon atoms, where the carbon containing linking groups may or may not include one or more heteroatoms, e.g. S, O, N etc., and may or may not include one or more sites of unsaturation. Of particular interest in many embodiments are alkyl linking groups, typically lower alkyl linking groups of 1 to 16, usually 1 to 4 carbon atoms, where the linking groups may include one or more sites of unsaturation. The functionalized nucleotides (or primers) used in the above methods of functionalized target generation may be fabricated using known protocols or purchased from commercial vendors, e.g., Sigma, Roche, Ambion, and IDT. Functional groups may be prepared according to ways known to those of skill in the art, including the representative information found in U.S. Pat. Nos. 4,404,289; 4,405,711; 4,337,063 and 5,268,486, and Br. Pat. No. 1,529,202, which are all incorporated by reference.

Amine-modified nucleotides are used in several embodiments of the invention. The amine-modified nucleotide is a nucleotide that has a reactive amine group for attachment of the label. It is contemplated that any ribonucleotide (G, A, U, or C) or deoxyribonucleotide (G, A, T, or C) can be modified for labeling. Examples include, but are not limited to, the following modified ribo- and deoxyribo-nucleotides: 5-(3-aminoallyl)-UTP; 8-[(4-amino)butyl]-amino-ATP and 8-[(6-amino)butyl]-amino-ATP; $N^6$-(4-amino)butyl-ATP, $N^6$-(6-amino)butyl-ATP, $N^4$[2,2-oxy-bis-(ethylamine)]-CTP; $N^6$-(6-Amino)hexyl-ATP; 8-[(6-Amino)hexyl]-amino-ATP; 5-propargylamino-CTP, 5-propargylamino-UTP; 5-(3-aminoallyl)-dUTP; 8-[(4-amino)butyl]-amino-dATP and 8-[(6-amino)butyl]-amino-dATP; N-(4-amino)butyl-dATP, $N^6$-(6-amino)butyl-dATP, $N^4$[2,2-oxy-to-(ethylamine)]-dCTP; $N^6$-(6-Amino)hexyl-dATP; 8-[(6-Amino)hexyl]-amino-dATP; 5-propargylamino-dCTP, and 5-propargylamino-dUTP. Such nucleotides can be prepared according to methods known to those of skill in the art. Moreover, a person of ordinary skill in the art could prepare other nucleotide entities with the same amine-modification, such as a 5-(3-aminoallyl)-CTP, GTP, ATP, dCTP, dGTP, dTTP, or dUTP in place of a 5-(3-aminoallyl)-UTP.

Labeling Techniques

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides is catalytically added to an miRNA, and the unlabeled nucleotide is modified with a chemical moiety that enables it to be subsequently labeled, in embodiments of the invention, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNAs is how to label the already existing molecule. To this end, we may use an enzyme capable of using a di- or tri-phosphate ribonucleotide or deoxyribonucleotide as a substrate for its addition to an miRNA, a small RNA molecule. Moreover, in specific embodiments, it involves using a modified di- or triphosphate ribonucleotide, which is added to the 3' end of an miRNA. The source of the enzyme is not limiting. Examples of sources for the enzymes include yeast, gram-negative bacteria such as E. coli, Lactococcus lactis, and sheep pox virus.

Enzymes capable of adding such nucleotides include, but are not limited to, poly(A) polymerase, terminal transferase, and polynucleotide phosphorylase. In specific embodiments of the invention, ligase is contemplated as NOT being the enzyme used to add the label, and instead, a non-ligase enzyme is employed.

Poly(A) polymerase has been cloned from a number of organisms from plants to humans. It has been shown to catalyze the addition of homopolymer tracts to RNA (Martin et al, RNA, 4(2):226-30, 1998).

Terminal transferase catalyzes the addition of nucleotides to the 3' terminus of a nucleic acid.

Polynucleotide phosphorylase can polymerize nucleotide diphosphates without the need for a primer.

Labels and Tags

In preferred embodiments of methods according to the invention, the expression level of a miRNA or source thereof is determined indirectly by quantifying the amount of the nucleotide sequence. Suitable quantification methods are described elsewhere herein. Alternately, miRNAs or miRNA probes may be labeled with a positron emitting (including radioactive), enzymatic, colorimetric (includes visible and UV spectrum, including fluorescent), luminescent or other label or tag for detection or isolation purposes. The label may be detected directly or indirectly. Radioactive labels include $^{125}$I, $^{32}$P, $^{33}$P, and $^{35}$S. Examples of enzymatic labels include alkaline phosphatase, luciferase, horseradish peroxidase, and β-galactosidase. Labels can also be proteins with luminescent properties, e.g., green fluorescent protein and phicoerythrin.

The colorimetric and fluorescent labels contemplated for use as conjugates include, but are not limited to, AMCA, Alexa Fluor dyes, BODIPY dyes, such as BODIPY FL, BODIPY 630/650, BODIPY 650/665, BODIP Y-R6G, BODIPY-TRX; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODEPY 530/550, BODEPY 558/568, BODIPY 564/570, BODDPY 576/589, BODIPY 581/591, BODEPY 630/650, BODIPY 650/655, BODIPY FL, BODIPY R6G, BODEPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODEPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP. Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODEPY FL-14-dUTP, Rhodamine Green-5-dUTP, Alexa Fluor 532-5-dUTP, BODEPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODEPY TR-14-dUTP, Alexa Fluor 594-5-dUTP, BODEPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP. It is contemplated that nucleic acids may be labeled with two different labels. Furthermore, fluorescence resonance energy transfer (FRET) may be employed in methods of the invention (e.g., Klostermeier et al., 2002; Emptage, 2001; Didenko, 2001, each incorporated by reference). Fluorescent energy transfer dyes, such as thiazole orange-ethidium heterodimer; and, TOTAB may be used.

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

Visualization Techniques

A number of techniques for visualizing or detecting labeled nucleic acids are readily available. The reference by Stanley T. Crooke, 2000 has a discussion of such techniques (Chapter 6), which is incorporated by reference. Such techniques include, microscopy, arrays, Fluorometry, Light cyclers or other real time PCR™ machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al, 1997, spectroscopy, capillary gel electrophoresis (Cummins et ah, 1996), spectroscopy; mass spectroscopy; radiological techniques; and mass balance techniques. Alternatively, nucleic acids may be labeled or tagged to allow for their efficient isolation. In other embodiments of the invention, nucleic acids are biotinylated.

When two or more differentially colored labels are employed, fluorescent resonance energy transfer (FRET) techniques may be employed to characterize the dsRNA. Furthermore, a person of ordinary skill in the art is well aware of ways of visualizing, identifying, and characterizing labeled nucleic acids, and accordingly, such protocols may be used as part of the invention. Examples of tools that may be used also include fluorescent microscopy, a BioAnalyzer, a plate reader, Storm (Molecular Dynamics), Array Scanner, FACS (fluorescent activated cell sorter), or any instrument that has the ability to excite and detect a fluorescent molecule (Acumen [TTP Labtech] plate cytometer for example.

Array Preparation

The present invention can be employed with miRNA arrays, which are ordered macroarrays or microarrays of nucleic acid molecules (probes) that are fully or nearly complementary or identical to a plurality of miRNA molecules or precursor miRNA molecules and that are positioned on a support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass and silicon Such arrays may vary in a number of different ways, including average probe length, sequence or types of probes, nature of bond between the probe and the array surface, e.g. covalent or non-covalent, and the like.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference. It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments, hi certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO03067217; WO 03066906; WO 03076928; WO 03093810; WO 03100448A1, all of which are specifically incorporated by reference.

Recently, alternative profiling methods have become available, based on solution hybridization and subsequent immobiliztion and identification e.g. Illumina platform.

Sample Preparation

It is contemplated that the miRNA of a wide variety of samples can be analyzed using assays described herein. While endogenous miRNA is contemplated for use with some embodiments, recombinant or synthetic miRNA—including nucleic acids that are identical to endogenous miRNA or precursor miRNA—can also be handled and analyzed as described herein. Samples may be biological samples, in which case, they can be from blood, CSF, tissue, organs, tumor, semen, sputum, stool, urine, saliva, tears, other bodily fluid, hair follicles, skin, or any sample containing or constituting biological cells. Alternatively, the sample may not be a biological sample, but be a chemical mixture, such as a cell-free reaction mixture (which may contain one or more biological enzymes).

Cell Assays to Identify miRNAs with Ties to Disease

Specifically contemplated applications include identifying miRNAs that contribute to the promotion of neuronal deficiency that are themselves parts of a disease or conditions or might otherwise be associated with a particular disease state. Additionally, a contemplated application includes the identification of miRNAs that are able to promote neuronal generation or regeneration. Also, miRNA functions may be compared between a sample believed to be susceptible to a particular disease or condition associated with neuronal deficiency and one believed to be not susceptible or resistant to that disease or condition. It is specifically contemplated that RNA molecules of the present invention can be used to treat any of the diseases or conditions discussed in the previous section or modulate any of the cellular pathways discussed in the previous section. Specifically contemplated applications include identifying miRNAs that contribute to neuronal deficiency cellular processes and/or induce a neuronal generation or regeneration that are themselves parts of a disease or might otherwise be associated with a particular disease state. Also, miRNA functions may be compared between a sample believed to be susceptible to a particular disease or condition associated with neuronal deficiency and one believed to be not susceptible or resistant to that disease or condition.

The efficacy of different therapeutic drugs may be altered by miRNAs as defined and used according to the present invention. MiRNA molecule, mimic, isomiR, antagomir, or source thereof that promote neuronal generation or regeneration may enhance susceptibility to other drugs.

Other Assays

In addition to the use of arrays and microarrays, it is contemplated that a number of difference assays could be employed to analyze miRNAs, their activities and their effects. Such assays include, but are not limited to, RT-PCR, in situ hybridization, hybridization protection assay (HPA) (GenProbe), branched DNA (bDNA) assay (Collins, M. L. et al. (1997). Nucleic Acids Research 25: 2979-2984), rolling circle amplification (RCA), single molecule hybridization detection (US Genomics), Invader assay (ThirdWave Technologies), and Bridge Litigation Assay (Qiagen). It is contemplated that such methods may be used in the context of arrays, as well as in the context of diagnostic assays.

Therapeutic and Diagnostic Applications miRNAs that affect phenotypic traits provide intervention points for therapeutic applications as well as diagnostic applications (by screening for the presence or absence of a particular miRNA). It is specifically contemplated that RNA molecules of the present invention can be used to treat any of the diseases or conditions discussed in the previous section. Moreover, any of the methods described above can also be employed with respect to therapeutic and diagnostic aspects of the invention. For example, methods with respect to detecting miRNAs or screening for them can also be employed in a diagnostic context. In therapeutic applications, an effective amount of the miRNAs of the present invention is administered to a cell, which may or may not be in an animal. In some embodiments, a therapeutically effective amount of the miRNAs of the present invention is administered to an individual for the treatment of disease or condition. The term "effective amount" as used herein is defined as the amount of the molecules of the present invention that are necessary to result in the desired physiological change in the cell or tissue to which it is administered. The term "therapeutically effective amount" as used herein is defined as the amount of the molecules of the present invention that achieves a desired effect with respect to a disease or condition associated with neo-angiogenesis as earlier defined herein. A skilled artisan readily recognizes that in many cases the molecules may not provide a cure but may provide a partial benefit, such as alleviation or improvement of at least one symptom. In some embodiments, a physiological change having some benefit is also considered therapeutically beneficial. Thus, in some embodiments, an amount of molecules that provides a physiological change is considered an "effective amount" or a "therapeutically effective amount."

In some embodiments the molecule has a sequence that corresponds to the miRNA sequence from that particular animal, as opposed to from another animal. Thus, in some embodiments, a human sequence is utilized in the RNA molecules of the present invention. In in vivo experiments, a miRNA sequence may differ in the test animal as compared to the human sequence. In that case, a miRNA that differs from the human sequence might be used to demonstrate therapeutic effect in the animal. Results obtained with this sequence tested in an animal may be extrapolated expected results in human with a corresponding miRNA molecule.

Modes of Administration and Formulations

The nucleic acid molecules of the invention may be administered to a subject alone or in the form of a pharmaceutical composition for the treatment of a condition or disease. Pharmaceutical compositions may be formulated in conventional manner using one or more physiologically acceptable carriers, diluents, excipients or auxiliaries which facilitate processing of the miRNA into preparations which can be used pharmaceutically. Proper formulation is dependent upon the route of administration chosen. For topical administration the miRNAs of the invention may be formulated as solutions, gels, ointments, creams, suspensions, etc. as are well-known in the art. Systemic formulations include those designed for administration by injection, e.g. subcutaneous, intravenous, intramuscular, intrathecal, intracerebroventricular, or intraperitoneal injection, as well as those designed for transdermal, transmucosal, inhalation, oral or pulmonary administration. For administration of antagomirs in the context of treating epilepsy, intracerebroventricular administration is highly preferred, especially intracerebroventricular injection. For injection, the nucleic acids of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the nucleic acid molecules may be in powder form for constitution with a suitable vehicle, e.g., sterile pyrogen-free water, before use. For transmucosal administration, penetrants appropriate to the barrier to be permeated are used in the formulation. Such penetrants are generally known in the art. For oral administration, the nucleic acids can be readily formulated by combining the molecules with pharmaceutically acceptable carriers well known in the art. Such carriers enable the nucleic acids of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. For oral liquid preparations such as, for example, suspensions, elixirs and solutions, suitable carriers, excipients or diluents include water, glycols, oils, alcohols, etc. Additionally, flavoring agents, preservatives, coloring agents and the like may be added. For buccal administration, the molecules may take the form of tablets, lozenges, etc. formulated in conventional manner. For administration by inhalation, the molecules for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the nucleic acids and a suitable powder base such as lactose or starch. The RNA molecules may also be formulated in rectal or vaginal compositions such as suppositories or retention enemas, e.g., containing conventional suppository bases such as cocoa butter or other glycerides.

In addition to the formulations described previously, the molecules may also be formulated as a depot preparation. Such long acting formulations may be administered by implantation (for example subcutaneously or intramuscularly) or by intramuscular injection. Thus, for example, the molecules may be formulated with suitable polymeric or hydrophobic materials (for example as an emulsion in an acceptable oil) or ion exchange resins, or as sparingly soluble derivatives, for example, as a sparingly soluble salt. Alternatively, other pharmaceutical delivery systems may be employed.

Liposomes and emulsions are well-known examples of delivery vehicles that may be used to deliver nucleic acids of the invention.

A nucleic acid of the invention may be administered in combination with a carrier or lipid to increase cellular uptake. For example, the oligonucleotide may be administered in combination with a cationic lipid. Examples of cationic lipids include, but are not limited to, lipofectin, DOTMA, DOPE, and DOTAP. The publication of WO0071096, which is specifically incorporated by reference, describes different formulations, such as a DOTAP; cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects. The nucleic acids may also be administered in combination with a cationic amine such as poly-L-lysine.

Nucleic acids may also be conjugated to a chemical moiety, such as transferrin and cholesteryls. In addition, oligonucleotides may be targeted to certain organs or tissues by linking specific chemical groups to the oligonucleotide. For example, linking the oligonucleotide to a suitable array of mannose residues will target the oligonucleotide to the liver. Other targeting ligands are described in Liu B., Brief Funct. Genomic Proteomic 6:112-119, 2007. Additional examples are carbohydrate sugars such as galactose, N-acetylgalactosamine, mannose; vitamins such as folates; small molecules including naproxen, ibuprofen or other known protein-binding molecules, cyclodextrin, which targets the transferrin receptor, also called transferring modified cyclodextrin (Hu-Lieskovan et al., 2005), PEI (RGD-targeted PEG-PEI, Schiffelers et al. 2004), anisamide, RGD-peptide or RGD mimics, poly-arginin, anti-TfR single chain antibody fragment/TfRscFv, Annexin A5 (targeting phophatidylserine exposing membranes, Gamier B. et al., bioconjugaet chem., 2009, 11:2114-22), WO 2009/126933 describing compositions and methods for site-specific delivery of nucleic acids by combining them with targeting ligands and endosomolytic components. Targeting ligands that are preferentially suitable are neuronal-associated cell surface proteins. Targeting of nucleic acids may also be accomplished by using aptamer technology as described in WO2005/111238. Moreover, additional lipid moieties, such as PEG-lipids, cholesterol, endosomolytic helper lipids or peptides (WO2009/046220) or the overall morphology of the generated nanoparticles (characterized by charge and particle size) to the above mentioned delivery vehicles may confer targeting specificity to either cancer cells and/or tumor vasculature.

Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

Alternatively, the molecules may be delivered using a coordination chemistry based delivery system as described in WO2007011217, which is specifically incorporated herein by reference.

In addition to the above, a molecule of the invention may be delivered using electroporation for local or targeted treatment. Electroporation methods are known to the skilled person and are for example described in Daud et al (2008) or Bodles-Brakhop (2009). Each of these publications is incorporated by reference.

Nucleic acids may be included in any of the above-described formulations as the free acids or bases or as pharmaceutically acceptable salts. Pharmaceutically acceptable salts are those salts that substantially retain the biological activity of the free bases and which are prepared by reaction with inorganic acids. Pharmaceutical salts tend to be more soluble in aqueous and other protic solvents than are the corresponding free base forms.

Pharmaceutical compositions of the present invention comprise an effective amount of one or more miRNA molecules dissolved or dispersed in a pharmaceutically acceptable carrier. The phrases "pharmaceutical or pharmacologically acceptable" refers to molecular entities and compositions that do not produce or produce acceptable adverse, allergic or other untoward reaction when administered to an animal, such as, for example, a human, as appropriate. Whether certain adverse effects are acceptable is determined based on the severity of the disease. The preparation of an pharmaceutical composition that contains at least one chimeric polypeptide or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The miRNAs may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal or a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise 2% to 75% of the weight of the unit, or 25% to 60%, for example, and any range derivable therein. In other non-limiting examples, a dose may also comprise less than 1 microgram/kg/body weight, or 1 microgram/kg/body weight, from 5 microgram/kg/body weight, 10 microgram/kg/body weight, 50 microgram/kg/body weight, 100 microgram/kg/body weight, 200 microgram/kg/body weight, 350 microgram/kg/body weight, 500 microgram/kg/body weight, 1 milligram/kg/body weight, 5 milligram/kg/body weight, 10 milligram/kg/body weight, 50 milligram/kg/body weight, 100 milligram/kg/body weight, 200 milligram/kg/body weight, 350 milligram/kg/body weight, or 500 milligram/kg/body weight, to 1000 mg/kg/body weight or more per administration, and any range derivable therein. In non-limiting examples of a derivable range from the numbers listed herein, a range of 5 mg/kg/body weight to 100 mg/kg/body weight, 5 microgram/kg/body weight to 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The molecules may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines. In certain embodiments, the molecules are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Any embodiment discussed above with respect to delivery or transport to cells can also be employed with respect to implementing delivery of medicinal compounds discussed in this section.

Effective Dosages

The molecules of the invention will generally be used in an amount effective to achieve the intended purpose. For use to treat or prevent a disease condition, the molecules of the invention, or pharmaceutical compositions thereof, are administered or applied in a therapeutically effective amount. A therapeutically effective amount is an amount effective to ameliorate or prevent the symptoms, or prolong the survival of the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the EC50 as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from 0.01 to 0.1 mg/kg/day, or from 0.1 to 5 mg/kg/day, preferably from 0.5 to 1 mg/kg/day or more. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs or treatment (including surgery).

Toxicity

Preferably, a therapeutically effective dose of the molecules described herein will provide therapeutic benefit without causing substantial toxicity. Toxicity of the molecules described herein can be determined by standard pharmaceutical procedures in cell cultures or experimental animals, e.g., by determining the LD50 (the dose lethal to 50% of the population) or the LD100 (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al, 1975, In: The Pharmacological Basis of Therapeutics, Ch. I, p. I).

Pendant Groups

A "pendant group" may be attached or conjugated to the nucleic acid. Pendant groups may increase cellular uptake of the nucleic acid. Pendant groups can be linked to any portion of the nucleic acid but are commonly linked to the end(s) of the oligonucleotide chain. Examples of pendant groups include, but are not limited to: acridine derivatives (i.e. 2-methoxy-6-chloro-9-aminoacridine); cross-linkers such as psoralen derivatives, azidophenacyl, proflavin, and azidoproflavin; artificial endonucleases; metal complexes such as EDTA-Fe(II), o-phenanthroline-Cu(I), and porphyrin-Fe(II); alkylating moieties; nucleases such as amino-1-hexanolstaphylococcal nuclease and alkaline phosphatase; terminal transferases; abzymes; cholesteryl moieties; lipophilic carriers; peptide conjugates; long chain alcohols; phosphate esters; amino; mercapto groups; radioactive markers; nonradioactive markers such as dyes; and polylysine or other polyamines. In one example, the nucleic acid is conjugated to a carbohydrate, sulfated carbohydrate, or glycan.

Kits

Any of the compositions described herein may be comprised in a kit. In a non-limiting example, individual miRNAs are included in a kit. The kit may further include one or more negative control synthetic miRNAs that can be used to control for the effects of synthetic miRNA delivery. The kit may further include water and hybridization buffer to facilitate hybridization of the two strands of the synthetic miRNAs. The kit may also include one or more transfection reagent(s) to facilitate delivery of the miRNA to cells.

In another non-limiting example, multiple synthetic miRNAs are included in a kit. The kit may further include one or more negative control synthetic miRNAs that can be used to control for the effects of synthetic miRNA delivery. The kit may also include one or more transfection reagents to facilitate delivery into cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent. The kits of the present invention will also typically include a means for containing the vials in close confinement for commercial sale, such as, e.g., injection and/or blow-molded plastic containers into which the desired vials are retained.

Such kits may also include components that preserve or maintain the miRNA or that protect against its degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented.

Kits of the invention may also include one or more of the following: miRNA, library of miRNAs, combination library of miRNA, negative control miRNA, nuclease-free water; RNase-free containers, such as 1.5 ml tubes; hybridization buffer; and transfection reagent(s).

It is contemplated that such reagents are embodiments of kits of the invention. Such kits, however, are not limited to the particular items identified above and may include any reagent used for the manipulation or characterization of miRNA.

Sequence Identity

"Sequence identity" is herein defined as a relationship between two or more nucleic acid (nucleotide, polynucleotide, RNA, DNA) sequences, as determined by comparing the sequences. In the art, "identity" also means the degree of sequence relatedness between nucleic acid sequences, as the case may be, as determined by the match between strings of such sequences. "Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988). In an embodiment, identity is assessed on a whole length of a given SEQ ID NO.

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1): 387 (1984)), BestFit, BLASTP, BLASTN, and FASTA (Altschul, S. F. et al., J. Mol. Biol. 215:403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215:403-410 (1990). The well-known Smith Waterman algorithm may also be used to determine identity.

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a miRNA, an isomiR, a mimic or a source or an antagomir thereof or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety. The following examples are offered for illustrative purposes only, and are not intended to limit the scope of the present invention in any way.

PREFERRED EMBODIMENTS OF THE INVENTION

1. A miRNA, an antagomir, or a source thereof, for treating, reverting, preventing, curing, and/or delaying a neuronal deficiency or a disease and/or condition associated with neuronal deficiency,
   wherein said miRNA or antagomir is a miRNA molecule, an isomiR, or a mimic thereof, and is an oligonucleotide with a seed sequence comprising at least 6 of the 7 nucleotides of the seed sequence represented by SEQ ID NOs: 14-56, or is an antagomir thereof, wherein said miRNA or antagomir is:
   a miRNA-135 or an isomiR thereof, or a mimic thereof, or an antagomir thereof, or
   a miRNA-196a-5p or an isomiR thereof, or a mimic thereof, or an antagomir thereof.

2. A miRNA, an antagomir, or a source thereof for use according to embodiment 1, wherein said miRNA or antagomir is a miRNA-135a molecule, a miRNA-135b molecule, a miRNA-196a-5p molecule, an isomiR of miRNA-135a, an isomiR of miRNA-135b, an isomiR of miRNA-196a-5p, an antagomir of miRNA-135a, an antagomir of miRNA-135b, an antagomir of miRNA-196a-5p, or a mimic thereof.

3. A miRNA, an antagomir, or a source thereof for use according to embodiment 1 or 2, wherein a source of a miRNA is a precursor of a miRNA and is an oligonucleotide of at least 50 nucleotides in length.

4. A miRNA, an antagomir, or a source thereof for use according to any one of embodiments 1-3, wherein said miRNA shares at least 70% sequence identity with any one of SEQ ID NOs: 147-241,
wherein said antagomir shares at least 70% sequence identity with any one of SEQ ID NOs: 242-341,
and/or wherein said miRNA or antagomir is from 15-30 nucleotides in length,
and/or wherein said source of a miRNA is a precursor of said miRNA and shares at least 70% sequence identity with any one of SEQ ID NOs: 1-4 or 10-13.

5. A miRNA, an antagomir, or a source thereof for use according to any one of embodiments 1-4 wherein said use is for suppressing expression of Kruppel-like factor 4 (KLF4).

6. A composition comprising a miRNA, an antagomir, or a source thereof as defined in any one of embodiments 1-5, for use according to any one of embodiments 1-5.

7. A composition for use according to embodiment 5, comprising:
   i) a miRNA-135a molecule, or an isomiR, mimic, antagomir, or source thereof, and/or
   ii) a miRNA-135b molecule, or an isomiR, mimic, antagomir, or source thereof, and/or
   iii) a miRNA-196a-5p molecule, or an isomiR, mimic, antagomir or source thereof.

8. A composition for use according to embodiment 6 or 7, further comprising a miRNA-124 molecule, a miRNA-124 mimic, a miRNA-124 isomiR, a miRNA-124 antagomir, or a source therefor.

9. A method for treating, curing, reverting and/or delaying a neuronal deficiency or a condition or disease associated with neuronal deficiency by administering a miRNA, an antagomir, or a source thereof as defined in any one of embodiments 1-5, or a composition as defined in any one of embodiments 6-8, to a subject in the need thereof.

10. A method for diagnosing a neuronal deficiency or a disease or condition associated with neuronal deficiency in a subject, the method comprising the steps of:
    (a) determining the expression level of a miRNA or a source thereof as defined in any one of embodiments 1-5, and optionally
    (b) comparing the expression level of said miRNA or a source thereof as defined in any one of embodiments 1-5 with a reference value for the expression level of said miRNA or a source thereof, the reference value preferably being the average value for the expression level of said miRNA or a source thereof in a healthy subject.

11. A method according to embodiment 10, comprising in step (a) determining the expression level of:
    i) a miRNA-124 molecule, a miRNA-124 isomiR, a miRNA-124 precursor, or of
    ii) KLF4, or of
    iii) both miRNA-135a and miRNA-135b, or isomiRs, or sources thereof, or of
    iv) both miRNA-135a and miRNA-196a-5p, or isomiRs, or sources thereof, or of
    v) both miRNA-135b and miRNA-196a-5p, or isomiRs, or sources thereof, or of
    vi) each of miRNA-135a and miRNA-135b and miRNA-196a-5p, or isomiRs, or sources thereof.

12. A method according to embodiment 10 or 11, wherein a neuronal deficiency or a disease or condition associated with neuronal deficiency is diagnosed when the comparison leads to the finding of a decrease of the expression level of said miRNA molecule, isomiR, or a source thereof and/or a decrease of the expression level of a miRNA-124 molecule, isomiR, or a source thereof.

13. A method according to any one of embodiments 9-12, wherein the expression level is determined ex vivo in a sample obtained from the subject.

14. A method for identification of a substance capable of treating, reverting, curing and/or delaying a neuronal deficiency or a condition or disease associated with neuronal deficiency in a subject, the method comprising the steps of:
    (a) providing a test cell population capable of expressing a miRNA-135a and/or miRNA-135b and/or a miRNA-196-5p molecule, isomiR, or source thereof, preferably the test population comprises neuronal cells such as SH-SY5Y, more preferably the test cell population comprises mammalian cells, even more preferably human cells;
    (b) contacting or incubating the test cell population with the substance;
    (c) determining the expression level of said miRNA-135a and/or miRNA-135b and/or miRNA-196-5p molecule, isomiR, or source thereof or an activity or steady state level of said miRNA-135a and/or miRNA-135b and/or miRNA-196a-5p molecule, isomiR, or source thereof in the test cell population contacted or incubated with the substance;
    (d) comparing the expression, activity or steady state level determined in (c) with the expression, activity or steady state level of said miRNA-135a and/or miRNA-135b and/or miRNA-196a-5p molecule, isomiR, or source thereof in a test cell population that is not contacted with the substance; and,
    (e) identifying a substance that produces a difference in expression level, activity or steady state level of said miRNA-135a and/or miRNA-135b and/or miRNA-196a-5p molecule, isomiR, or source thereof between the test cell population that is contacted with the substance and the test cell population that is not contacted with the substance.

15. An in vivo, in vitro, or ex vivo method for promoting neuronal generation or regeneration, at least comprising the step of contacting a cell with a miRNA, an antagomir, or a source thereof as defined in any one of embodiments 1-5, or with a composition as defined in any one of embodiments 6-8.

(A) Schematic representation of the Cellomics ArrayScan screen. SH-SY5Y cells were seeded and differentiated using retinoic acid. Viral library was added and after 3 days cells were fixed and immunostained. Images covering the entire surface of the well were taken using a Thermo Arrayscan automated microscope and analyzed using a Neuronal Profiling algorithm to assess the effect of miRNAs on general neuron-like features, such as the number of neurites, neurite length, and number of branch-points. The effect of a miRNA on each parameter was scored binarily (0 or 1). A positive score (1) was given when the effect on the parameter deviated more than 2 times the standard deviation of the median value for all miRNAs. Scores for each of the triplicate plates were combined, with the score for a certain parameter taken into account (effect is 'true') when the miRNA scored positive in a minimum of 2 out of 3 plates. This resulted in a final (cumulative) 'hitscore' which was used to rank the lentiviral clones for an effect on neuronal morphology. (B) Representative images of untreated SH-SY5Y cells (left panel) and SH-SY5Y cells treated with retinoic acid (middle panel). The right panel shows the result of tracings generated by the Neuronal Profiling algorithm. Scale bar: 100 μm. (C) Graph showing the cumulative score of all the parameters of the Neuronal Profiling algorithm for the top list of annotated miRNAs that have a positive effect on neuronal features of virus-transduced SH-SY5Y cells. (D) Graphs showing average total hitscore (left), hitscore based on parameters describing neurite length (middle), and hitscore based on parameters describing neurite branching (right) of SH-SY5Y cells electroporated with the indicated miRIDIAN miRNA mimics. Data are expressed as means±SEM. * $p<0.05$,  $p<0.01$, * $p<0.001$, **** $p<0.0001$, One-way ANOVA with Tukeys multiple comparison test. Scale bar: 200 μm.

Figure 2:
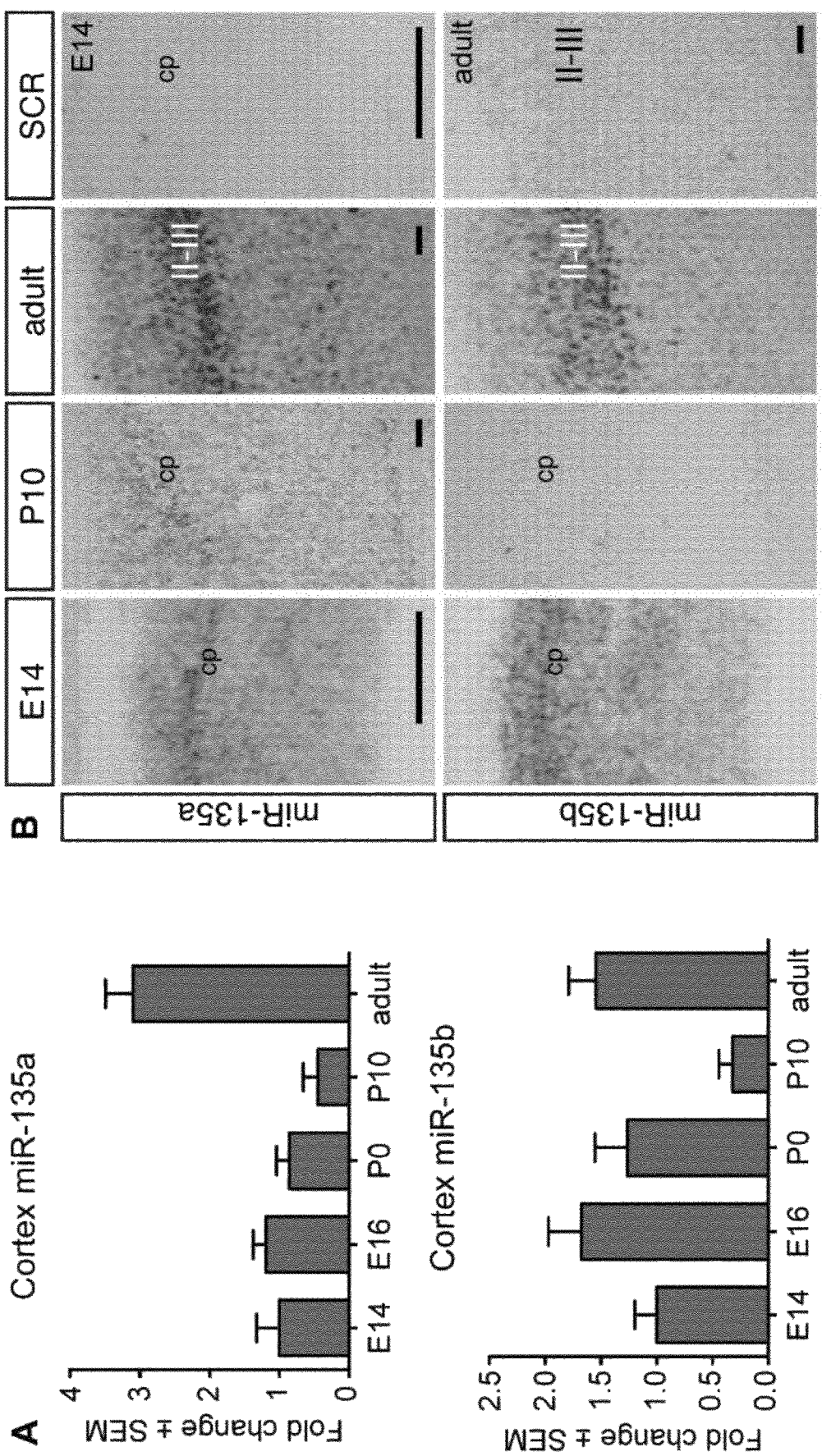
Figure 2:
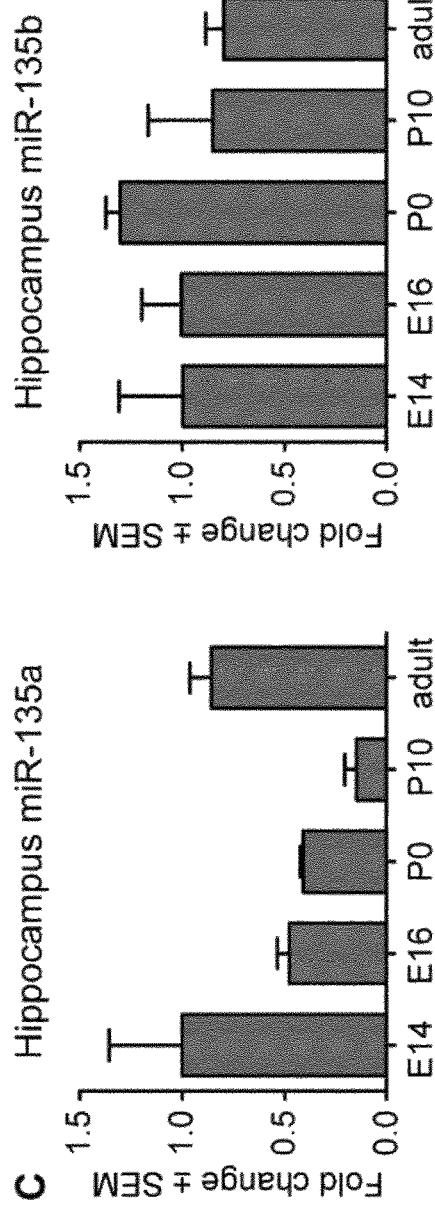
Figure 2:
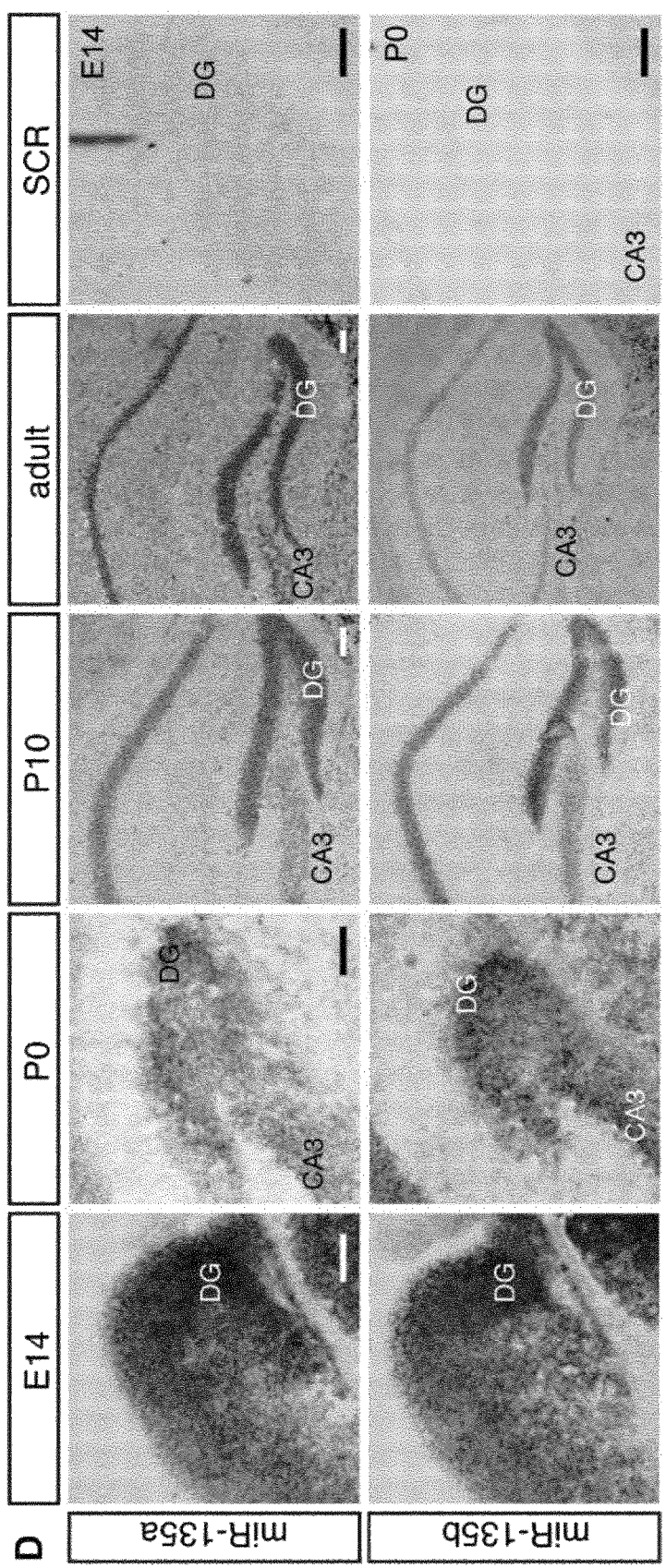

FIG. 2: Expression of miR-135a and miR-135b during neuronal development.

(A, C) Graphs show results of quantitative PCR experiments on RNA from isolated mouse cortex (A) or from hippocampus (C) from 5 different embryonic and post-natal stages. Tissue from three different mice from different litters was used for analysis. Samples were run in duplicate. Fold changes are relative to 5S housekeeping rRNA expression. Data are expressed as means±SEM. (B) Locked-nucleic acid (LNA) in situ hybridization shows miR-135a and miR-135b expression in the E14, P10 and adult cortex. miR-135a and miR-135b are expressed in the cortical plate (cp) and upper layers of the adult cortex. Sections treated with scrambled LNA-in situ probes were devoid of specific staining. Scale bars: 200 μm. (D) Locked-nucleic acid (LNA) in situ hybridization shows miR-135a and miR-135b expression in the E16, P0, P10 and adult hippocampus. In the hippocampus, the dentate gyrus (DG) and CA3 region specifically show strong miR-135a and miR-135b staining. Sections treated with scrambled LNA-in situ probes were devoid of specific staining. Scale bars: 200 μm.

Figure 3:
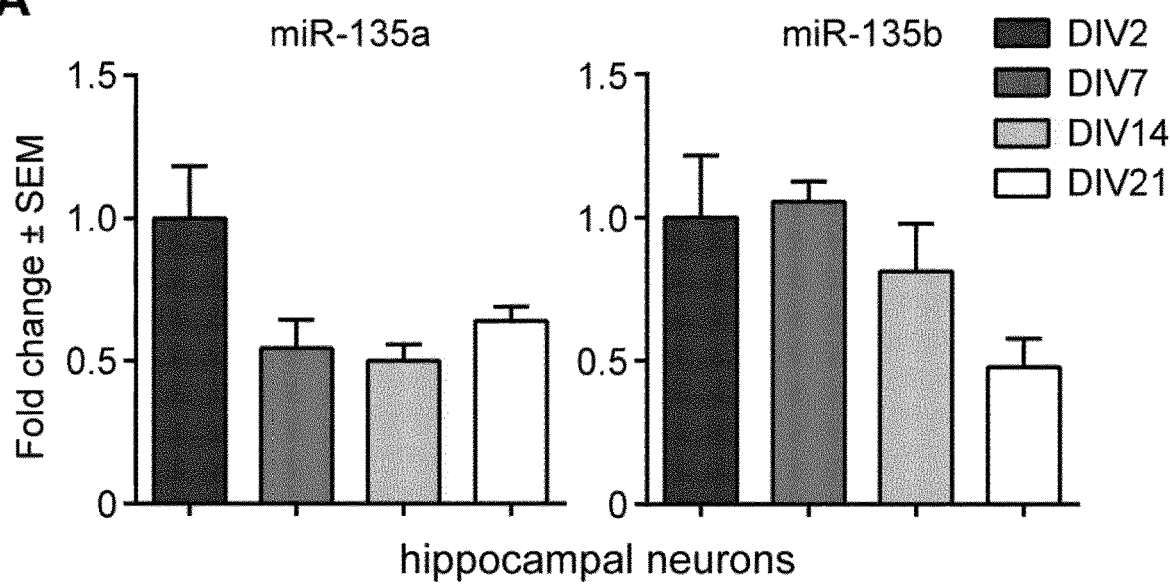
Figure 3:
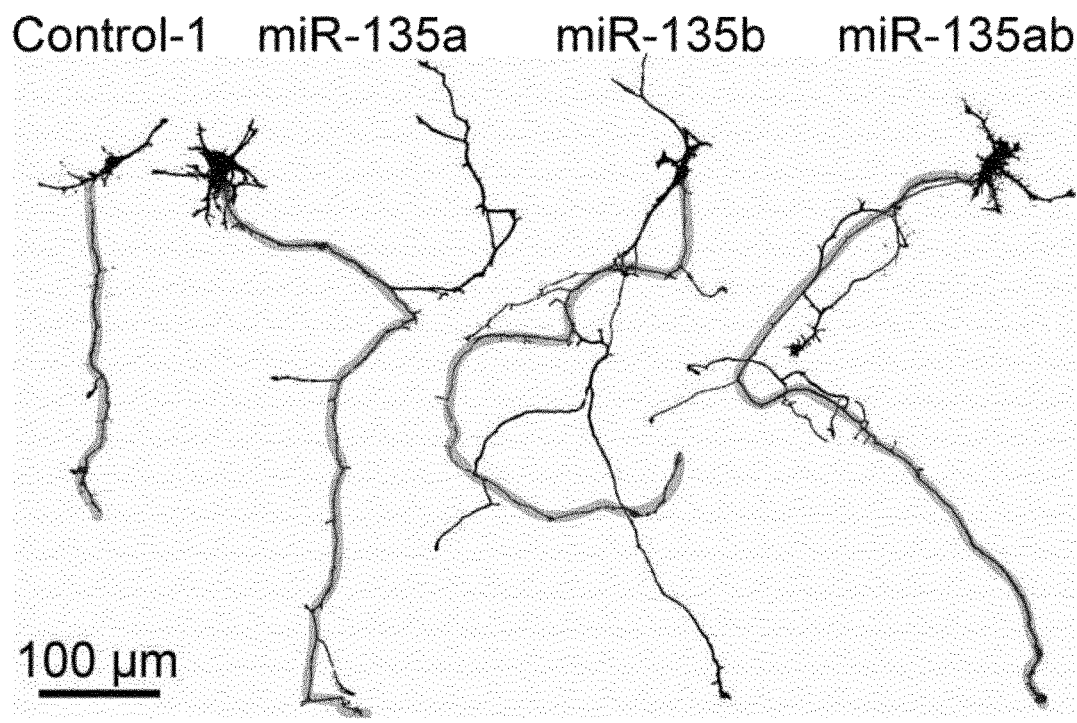
Figure 3:
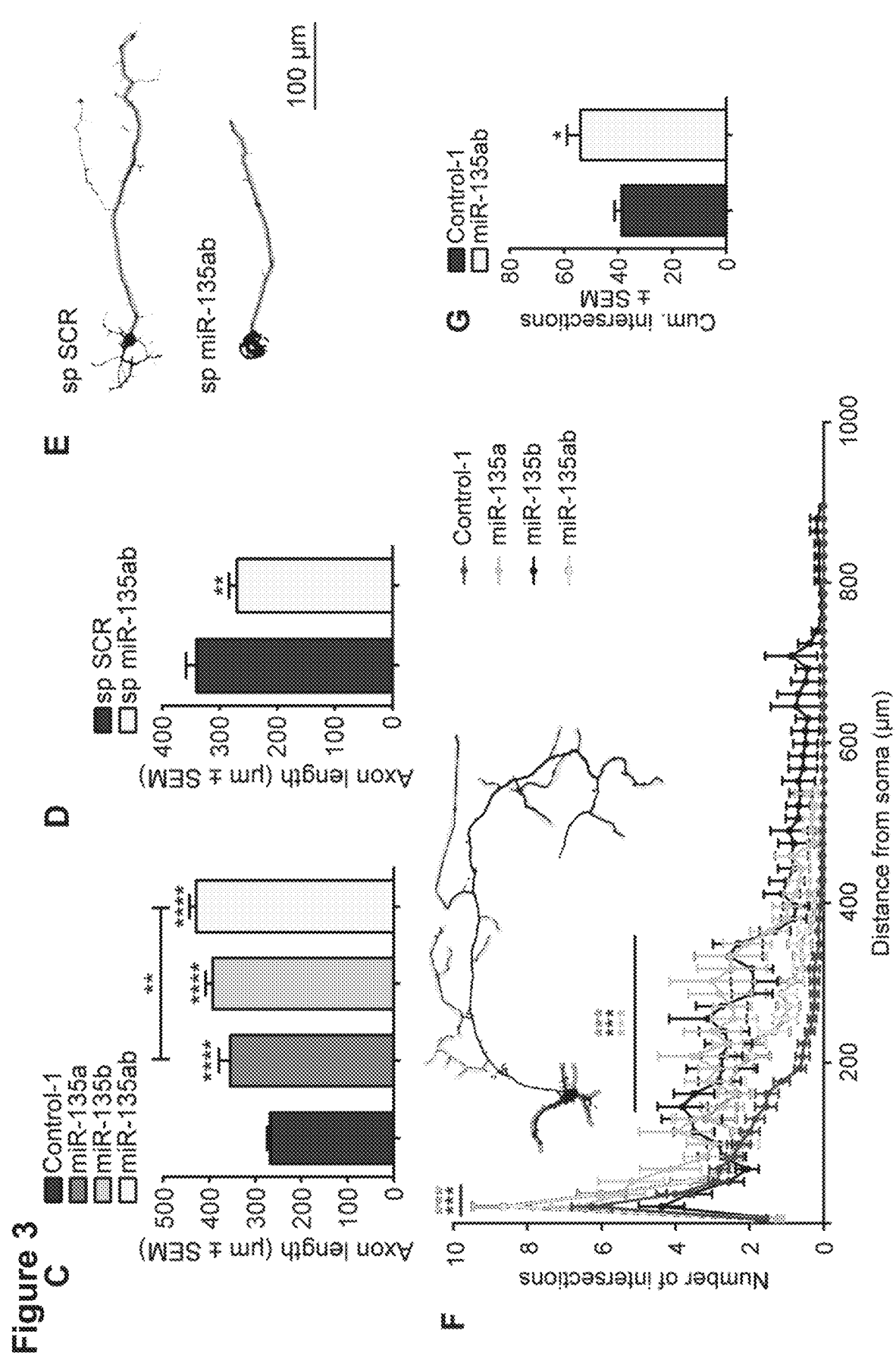

FIG. 3: miR-135a and miR-135b increase neurite outgrowth and branching.

(A) Graphs show results of quantitative PCR on primary hippocampal neurons at different days in vitro (DIV). RNA was collected from 3-4 coverslips of two different cultures. Samples were run in duplicate. Fold changes are relative to 5S housekeeping rRNA expression. Data are expressed as means±SEM. (B) Representative silhouettes of primary neurons at day in vitro (DIV) 4 following transfection with control-1, miR-135a, miR-135b and miR-135a/miR-135b mimics. Longest neurites are shaded in grey. (C) Graph shows results of tracing of the longest neurite of DIV4 hippocampal neurons in experiments as in A. At least 173 neurons were traced from 3 individual experiments. Data are expressed as means±SEM.  $p<0.01$,  $p<0.0001$, T-test. (D) Quantification of tracing of the longest neurite of DIV4 hippocampal neurons after transfection with scrambled or miR-135a and miR-135b H1-mCherry-sponge vectors. Sponges are labelled "sp" and are antagomiRs of their indicated miRNA. At least 100 neurons were traced from ≥3 individual experiments. Data are expressed as means±SEM.  $p<0.01$, T-test. (E) Representative silhouettes of primary neurons at DIV 4 following transfection with control sponge—or miR-135ab sponge vector. Longest neurites are shaded in grey. (F) Sholl analysis from 31 control-1 (dark grey), 15 miR-135a (light grey), 16 miR-135b (black) or 23 miR-135a and miR-135b (light grey with black outline) over-expressing neurons reveals increased branching in proximal neurites and in the distal axon. Data are expressed as means±SEM. ** $p<0.0001$, multiple T-tests. In the silhouette, proximal neurites originate from the main cellular corpus, and distal branches originate from the long neurite; both are shaded in grey. (G) Cumulative intersections of neurites from neurons transfected with control-1 or miR-135a and miR-135b mimics with the sholl-circles (as in D). Data are expressed as means±SEM.  $p<0.01$, T-test.

Figure 4:
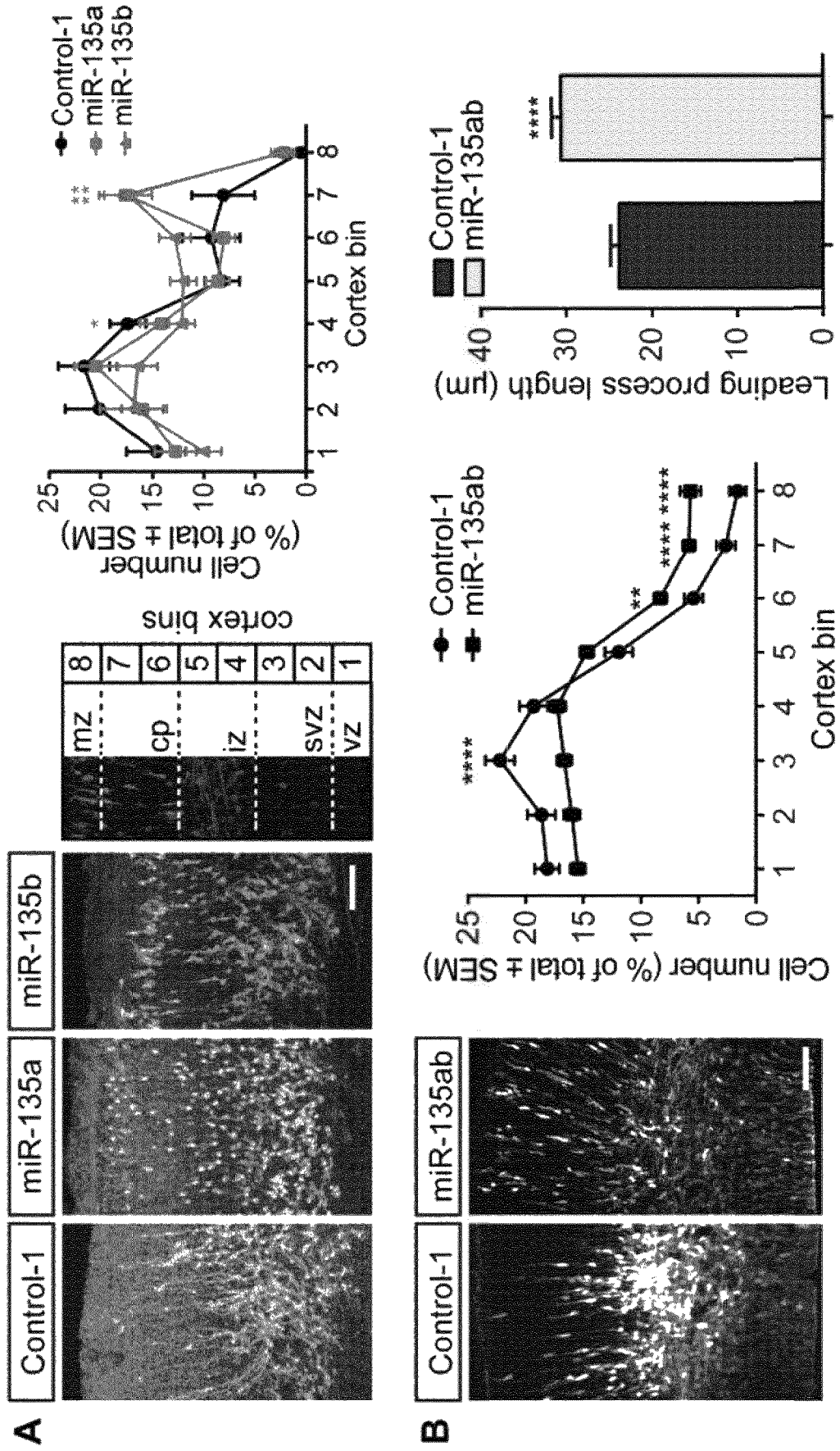
Figure 4:
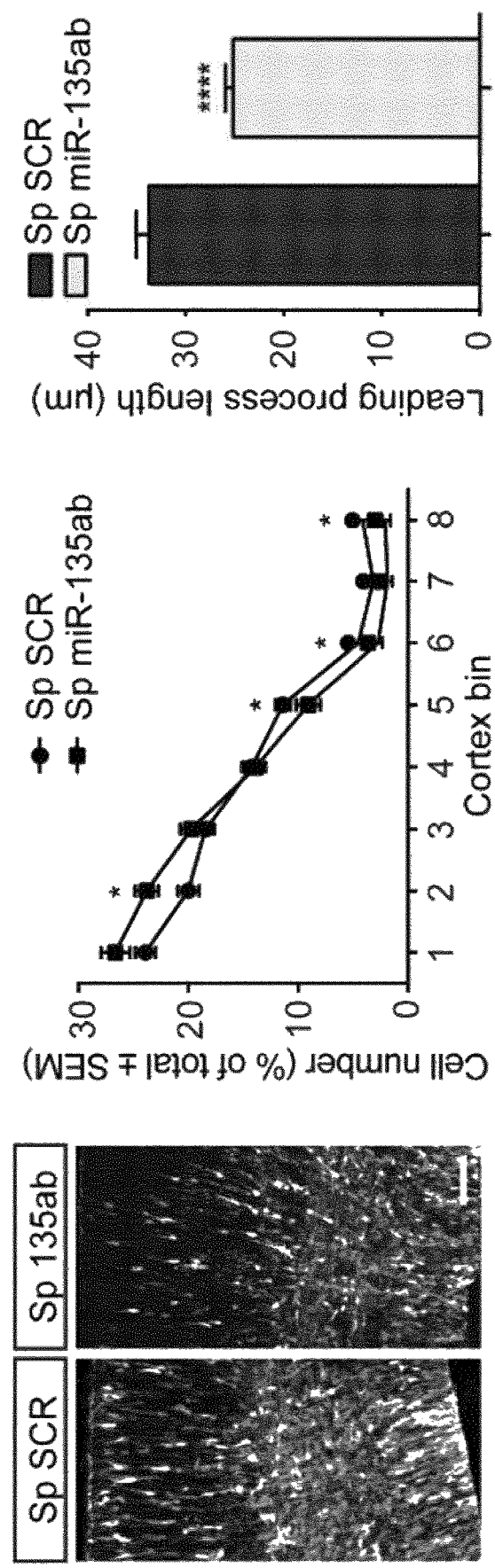
Figure 4:
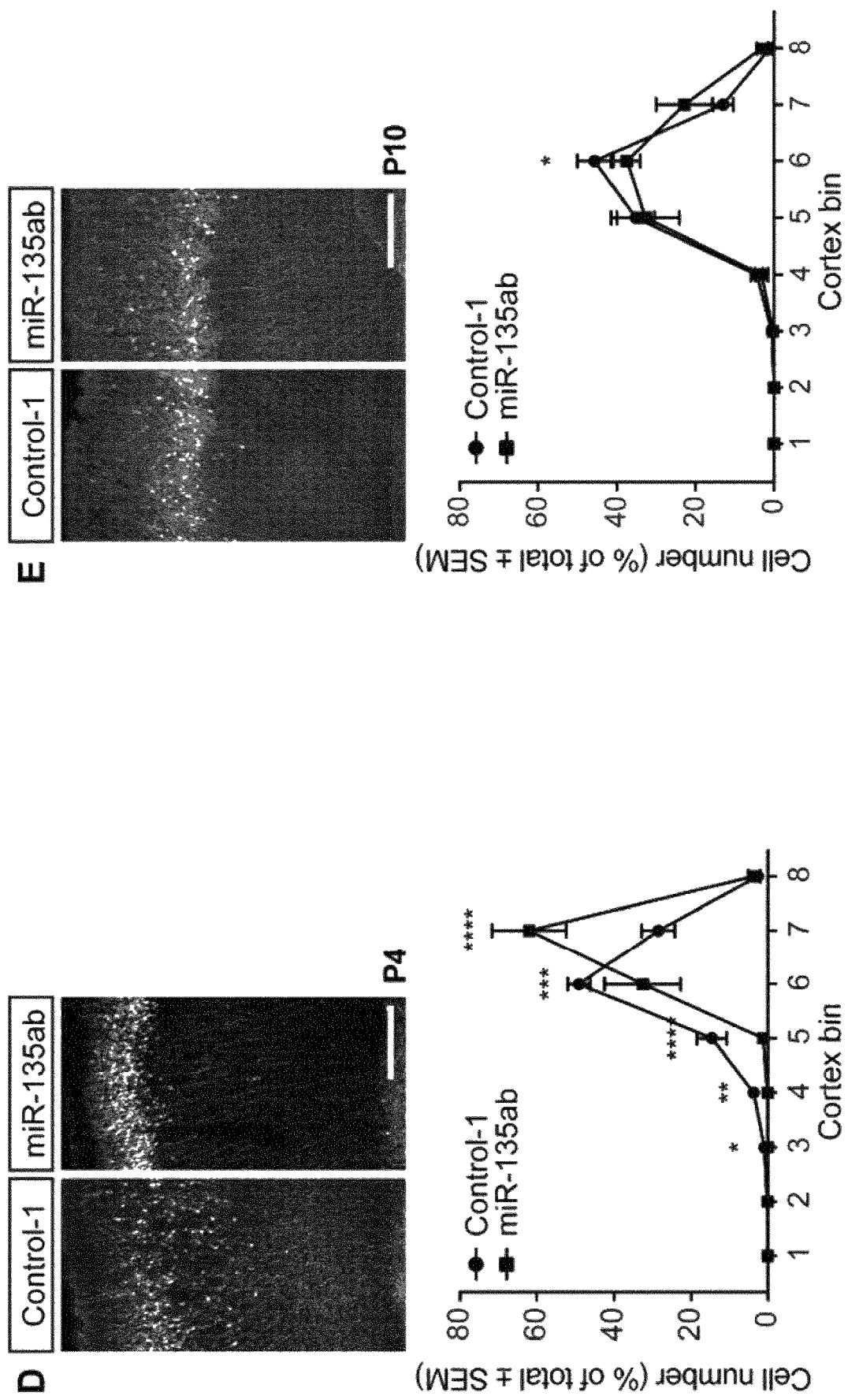

FIG. 4: miR-135s are required for cortical neuron migration.

(A) Representative images of cortices that were ex vivo electroporated with control-1, miR-135a, or miR-135b mimics. Neuron migration was quantified by placing a rectangle containing 8 square bins perpendicular on the cortex. Cells in each bin were counted and expressed as percentage of the total number of cells in the rectangle. The bins perfectly align with the layers of the cortex: ventricular zone (vz), subventricular zone (svz), intermediate zone (iz), cortical plate (cp), and marginal zone (mz). Cell-counts of two to three rectangles per section were used for comparison. At least two to three sections from 3 animals from different litters were used. Data are expressed as means±SEM. Red** bin7 control-1 vs. miR-135a: MWU=24, p=0.0042; blue* bin 4 control-1 vs. miR-135b: MWU=32, p=0.0195; blue** bin 7 control-1 vs. miR-135b: MWU=25, p=0.0051, Mann-Whitney U tests. Scale bar: 100 μm.

(B) Representative images and quantification of neuron migration and leading process length in in utero electroporated E16.5 cortices of mice embryos treated with either control-1 or miR-135a and miR-135b mimics. GFP signal in white. Neuron migration was quantified as described in (F). Data are expressed as means±SEM. Bin 3: MWU=198, p<0.0001; bin6 MWU=282, p<0.0053; bin 7: MWU=161, p<0.0001; bin 8: MWU=164, p<0.0001.  $p<0.01$,  $p<0.0001$, Mann-Whitney U tests, ** $p<0.0001$ T-test. Scale bar: 100 μm.

(C) Representative images and quantification of neuron migration and leading process length in in utero electroporated E16.5 cortices of mice embryos treated with either scrambled or miR-135a and miR-135b H1-mCherry-sponge vectors. mCherry signal in white. Neuron migration was quantified as described in (A). Data are expressed as means±SEM. Bin 2: MWU=70, p=0.018; bin 5: MWU=69, p=0.016; bin 6: MWU=75, p=0.030; bin 8: MWU=69, p=0.016, Mann-Whitney U tests, * $p<0.05$. **** $p<0.0001$ T-test. Scale bar: 100 μm.

(D) Representative images and quantification of neuron migration in in utero electroporated P4 cortices of mice pups electroporated with either control-1 or miR-135a and miR-135b mimics at E14.5. GFP signal in white. Neuron migration was quantified as described in (A). Data are expressed as means±SEM. Bin3: MWU=475, p=0.0114; bin 4: MWU=392.5, p=0.0016; bin 5: MWU=148, p<0.0001; bin 6: MWU=319.5, p=0.0004; bin 7: MWU=194.5, p<0.0001, Mann-Whitney U tests.* $p<0.05$,  $p<0.01$, * $p<0.001$, **** $p<0.0001$. Scale bar: 200 μm.

(E) Representative images and quantification of neuron migration in in utero electroporated P10 cortices of mice pups electroporated with either control-1 or miR-135a and miR-135b mimics at E14.5. GFP signal in white. Neuron migration was quantified as described in (A). Data are expressed as means±SEM. Bin 6: MWU 783.5, p=0.032, Mann-Whitney U test. * $p<0.05$. Scale bar: 200 μm.

Figure 5:
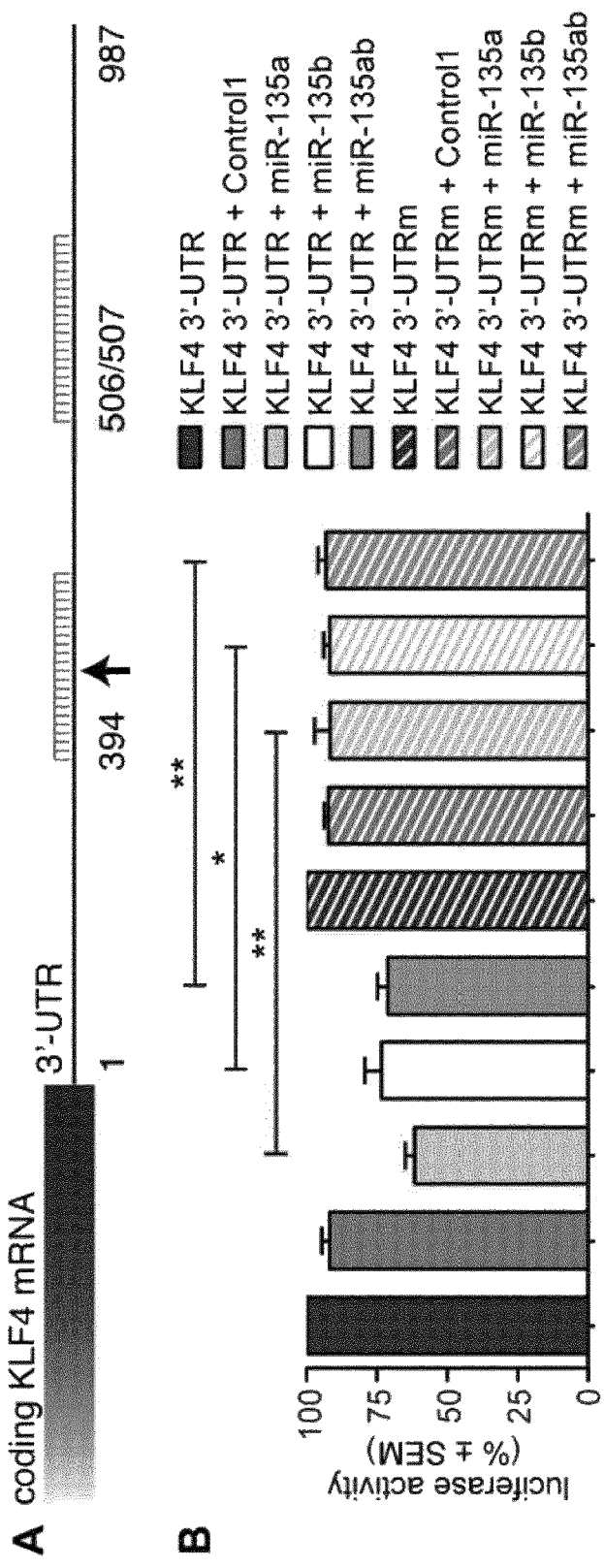
Figure 5:
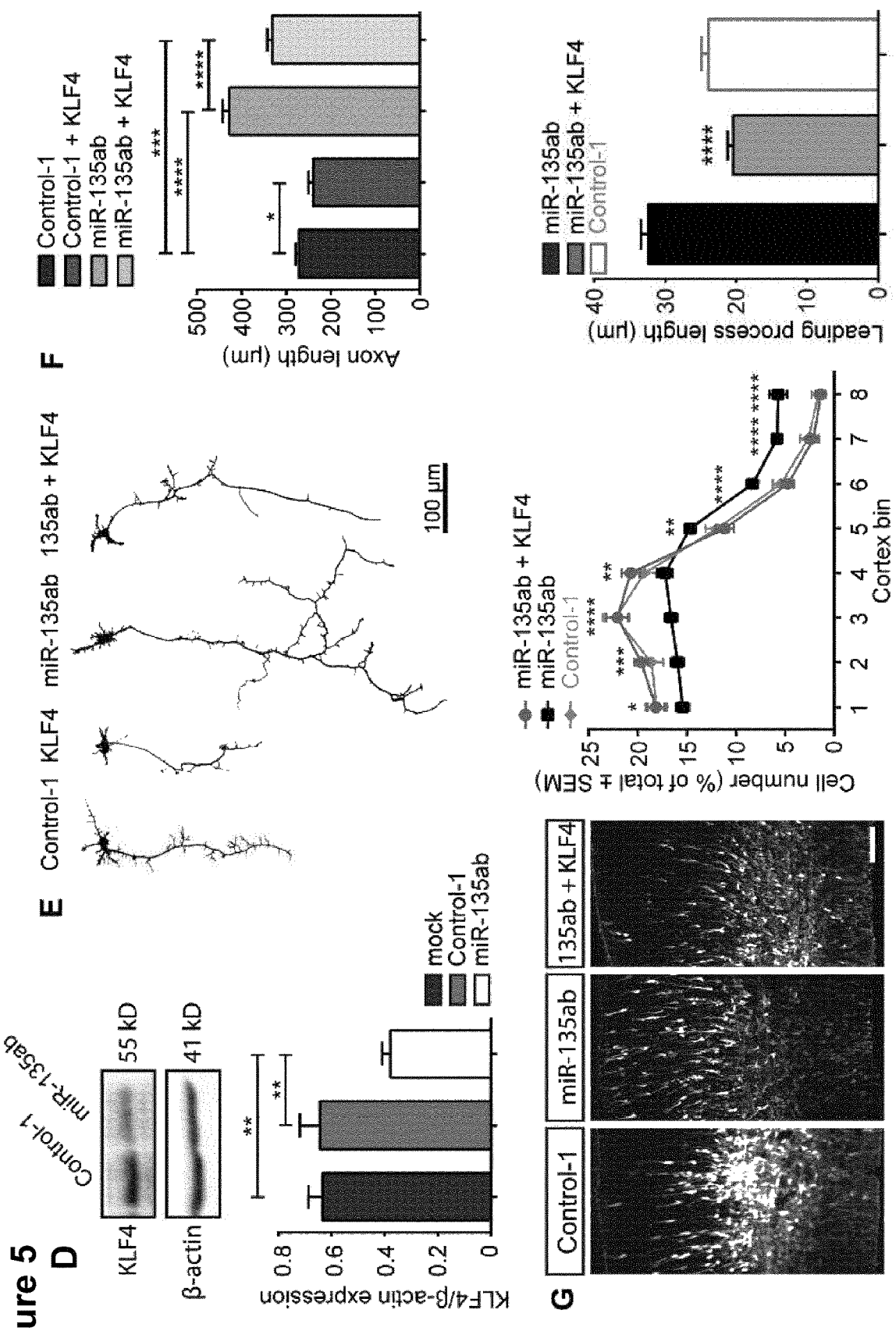

FIG. 5: Kruppel-like factor 4 (KLF4) is a functional target for miR-135a and miR-135b during axonal development and neuron migration. (A) Schematic representation of predicted miR-135a and miR-135b binding sites in the 3'-UTR of KLF4 mRNA. Site 394 is predicted to mediate strongest binding (marked by arrow). (B) The 3'-UTR of KLF4 was cloned into a psi-CHECK2 vector and used for a *Renilla*-luciferase assay with control-1 or miR-135a and miR-135b mimics. Subsequently, a psi-CHECK vector with the KLF4 3'-UTR in which 3 nucleotides within site 394 were mutated was used to confirm specificity of miRNA-135-KLF4 binding. Luciferase activity was normalized to the 3'-UTR only condition of either wild-type or mutated 3'-UTR (UTRm). The experiment was repeated 3 times. Data are expressed as means±SEM. ** $p<0.01$, * $p<0.05$, T-test. (C) Immunohistochemistry of KLF4 in sections of mouse cortex and hippocampus at E16.5 and adulthood. KLF4 is highly expressed in the cortical plate (cp), in axons running through the intermediate zone (iz) and in hippocampal granule cells in the dentate gyrus (DG) and in pyramidal cells of the CA3. Scale bars: 200 μm. (D) Western blot analysis of KLF4 protein levels after transfection of control-1 or miR-135a and miR-135b mimics in Neuro2A cells. Data are expressed as means±SEM. ** $p<0.01$, T-test. (E) Representative silhouettes of primary hippocampal neurons at 4 days in vitro (DIV 4) after transfection with control-1 mimics, control-1 mimics combined with a KLF4 cDNA insensitive for miRNA binding (CMV-KLF4-GFP), miR-135a and miR-135b mimics, and miR-135a and miR-135b mimics combined with CMV-KLF4-GFP. (F) Graph shows results of tracing of the longest neurite of DIV4 hippocampal neurons in experiments as in E. At least 182 neurons were traced from 3 individual experiments. Data are expressed as means±SEM. * $p<0.05$, * $p<0.001$, ** $p<0.0001$, T-test. (G) Representative images and quantification of neuron migration and leading process length in in utero electroporated E16.5 cortices of mice embryos treated with either miR-135a and miR-135b mimics, or miR-135a and miR-135b mimics combined with a pCAG-KLF4 vector which is insensitive to miR-135 regulation. Neuron migration was quantified as described in FIG. 4. Data are expressed as means±SEM. Bin1: MWU=422, p=0.0171, bin2: MWU=332, p=0.0005, bin3: MWU=293, p<0.0001, bin4: MWU=395, p=0.0068, bin5: MWU=357, p=0.0016, bin6: MWU=261, p<0.0001, bin7: MWU=219, p<0.0001 and bin8: MWU=211.5, p<0.0001. Mann-Whitney U tests. * $p<0.05$,  $p<0.01$, * $p<0.001$, **** $p<0.0001$. Control-1 condition is as described in FIG. 4B. Scale bar: 100 μm.

Figure 6:
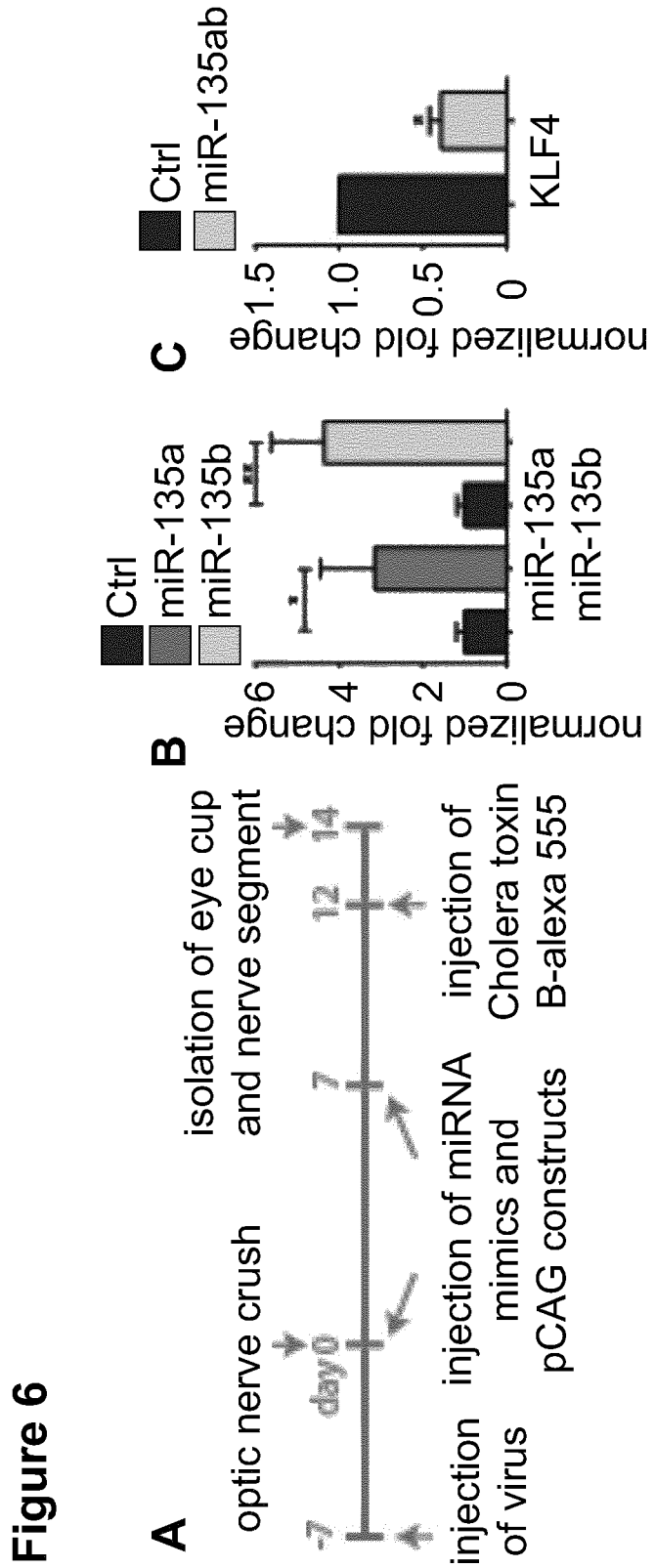
Figure 6:
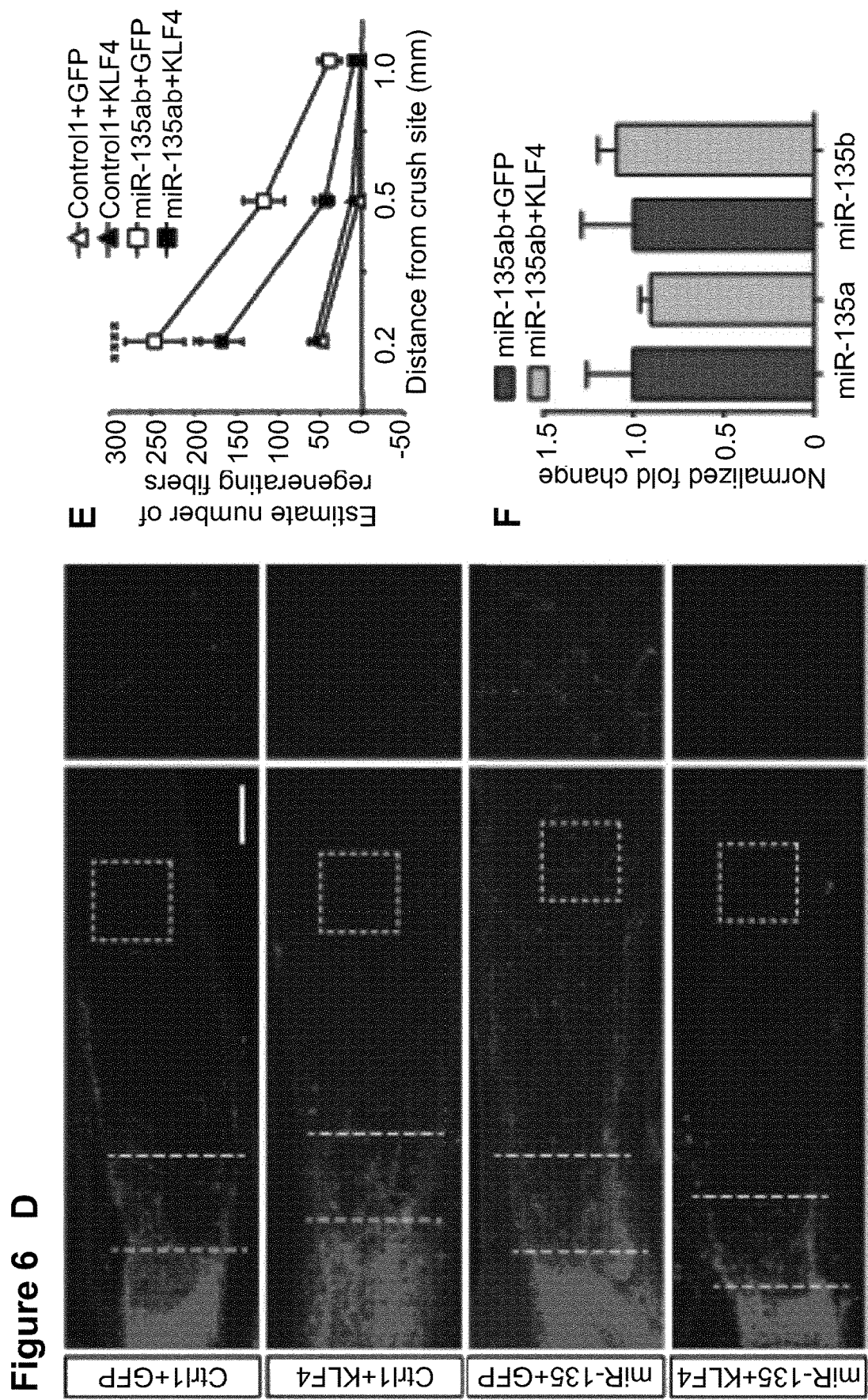
Figure 6:
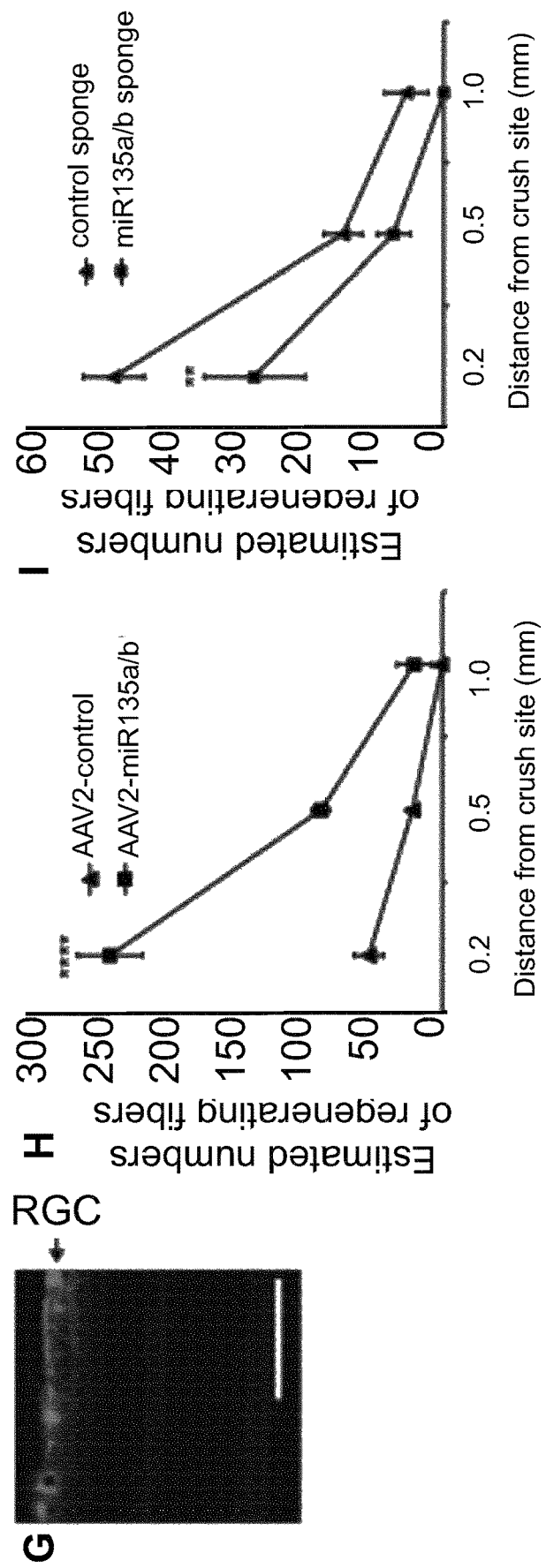

FIG. 6: Exogenous miR-135s enhance axon regeneration after optic nerve injury.

(A) Experimental setup of the optic nerve crush studies. (B, C) Graph shows results of quantitative PCR on eye tissue following injection of mimics. miR-135a and miR-135b levels are increased after two injections of miRNA-mimics, while KLF4 levels are decreased (C). Fold changes are relative to 5S housekeeping rRNA expression. Data are expressed as means±SEM. * $p<0.05$, ** $p<0.01$, T-test on delta Ct values. (D) Representative images of optic nerves stained for Cholera-toxin B conjugated to Alexa-555 14 days after optic nerve crush. Following injection of miR-135 mimics axons grow into and beyond the injury site (dotted lines indicate proximal and distal boundaries site of injury). Boxes indicate higher magnification images shown at the right. Scale bar: 100 μm. (E) Graph shows quantification of the number of regenerating axons relative to the distal end of the crush site at 14 days post-injury for the conditions represented in (D). n=9 mice per condition. * $p<0.05$; ** $p<0.0001$, ANOVA followed by Sidak's test. Data are presented as means±SEM. (F) Graph shows results of quantitative PCR on eye tissue following co-transfection of miR-135 mimics and GFP or KLF4 vector. No differences in miR-135a and miR-135b expression between the GFP or KLF4 transfected groups. Fold changes are relative to 5S housekeeping rRNA expression. Data are expressed as means±SEM. (G) AAV2-GFP virus was injected intravitreally. One week post-injection strong GFP signals are detected in RGCs but not in other cell types in the retina. Scale bar 100 μm. (H) Graph shows quantification of the number of regenerating axons relative to the distal end of the crush site at 14 days post-injury for experiments performed using intravitreal injection of AAV2 (at 7 days pot-lesion) expressing control miRNA or miR-135a and miR-135b (in addition to GFP). n=6 mice per condition.  p<0.0001, ANOVA followed by Sidak's test. Data are presented as means±SEM. (I) Graph shows quantification of the number of regenerating axons relative to the distal end of the crush site at 14 days post-injury for experiments performed using intravitreal injection of control or miR-135a and miR-135b sponge vectors. n=6 mice per condition.  p<0.01, ANOVA followed by Sidak's test. Data are presented as means±SEM.

Figure 7:
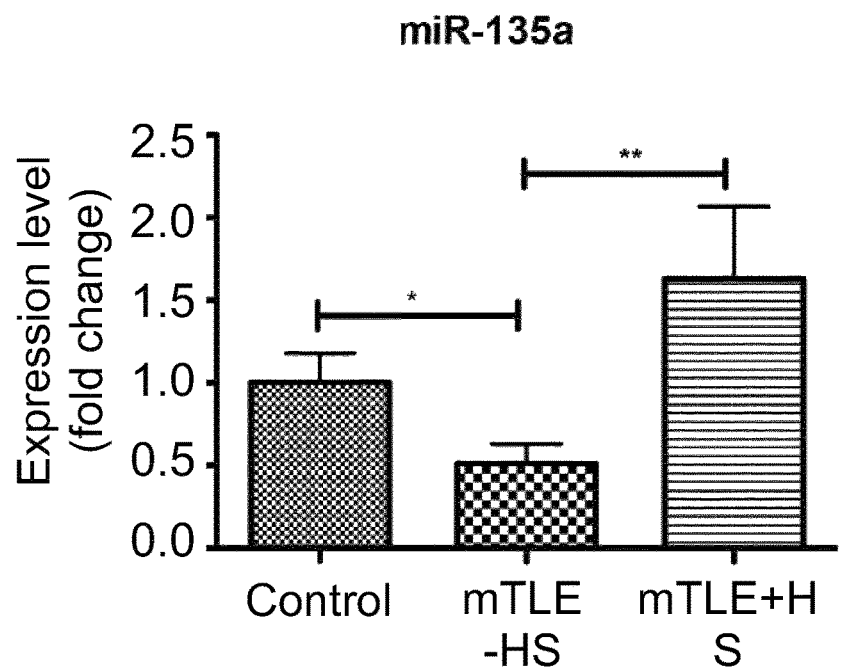
Figure 7:
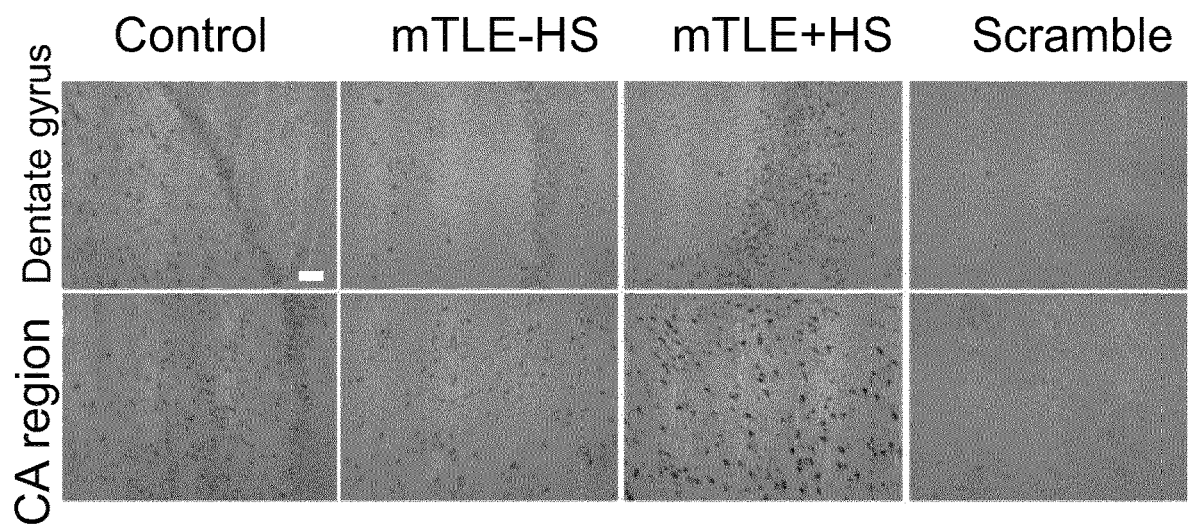

FIG. 7: Human data of miR-135a A) Expression levels of miR-135a in human TLE patients determined by quantitative PCR. C— controls, mTLE-HS, mTLE+HS. n=6 patients/group. Students tTest. Normalized to U6 and 5srRNA. Students Ttest, *p<0.05, **p<0.01.

B) Representative images of in situ localization of miR-135a among different groups. Scale bar, 200

Figure 8:
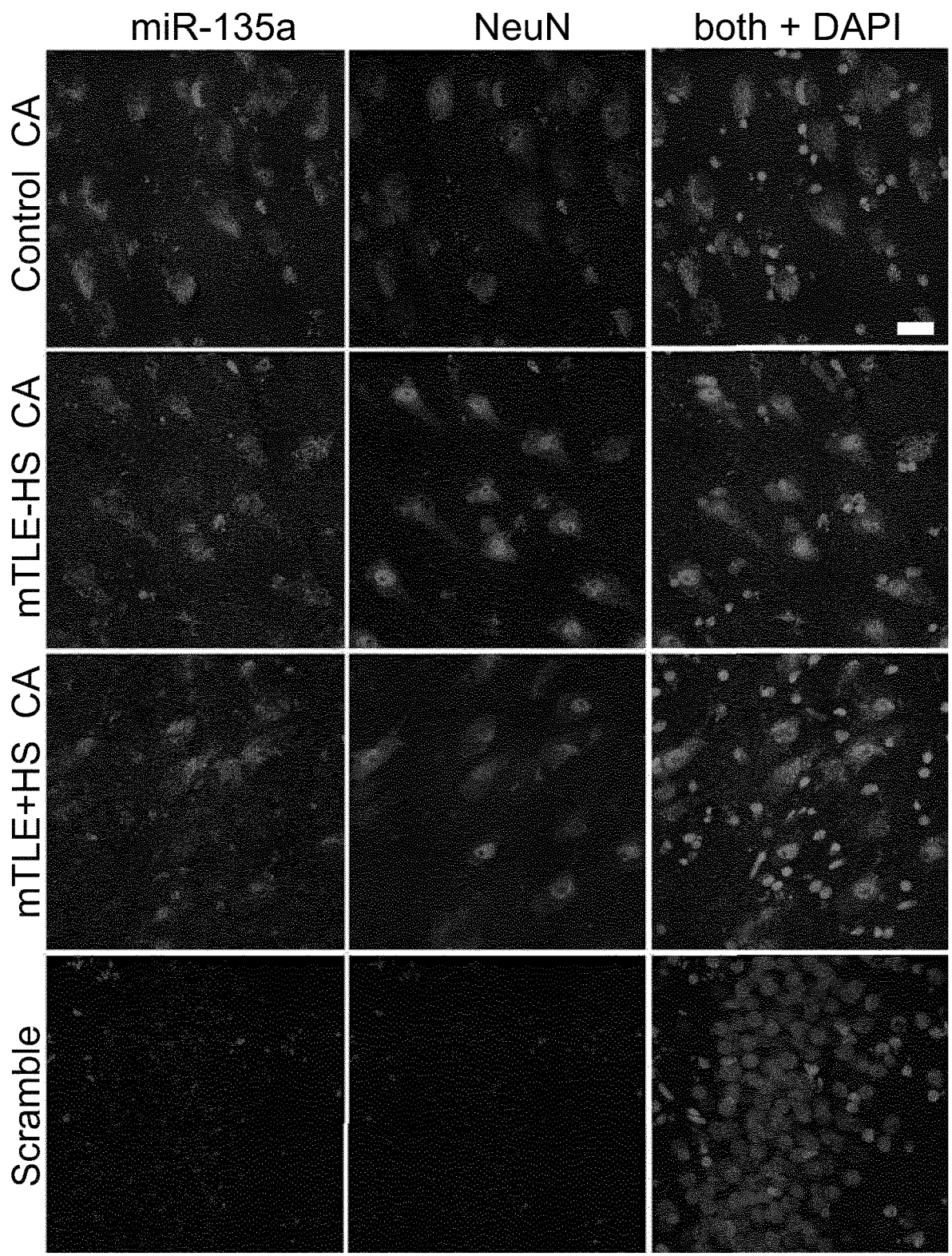

FIG. 8: Celltype specific localization of miR-135a. Co-localization with neuronal marker, NeuN. Specific localization of miR-135a was observed in neuronal soma co-stained with NeuN in the CA regions among different groups. Scale bar, 25 μm.

Figure 9:
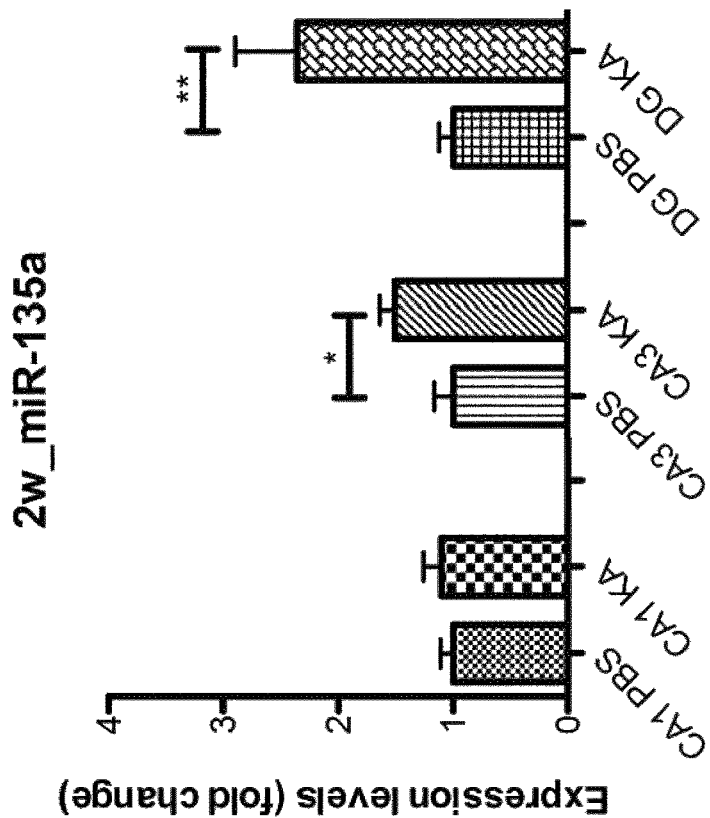
Figure 9:
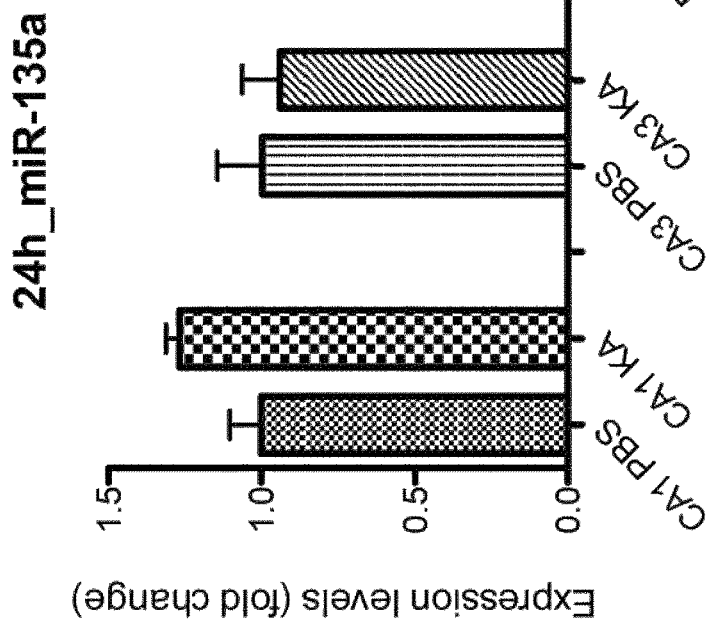
Figure 9:
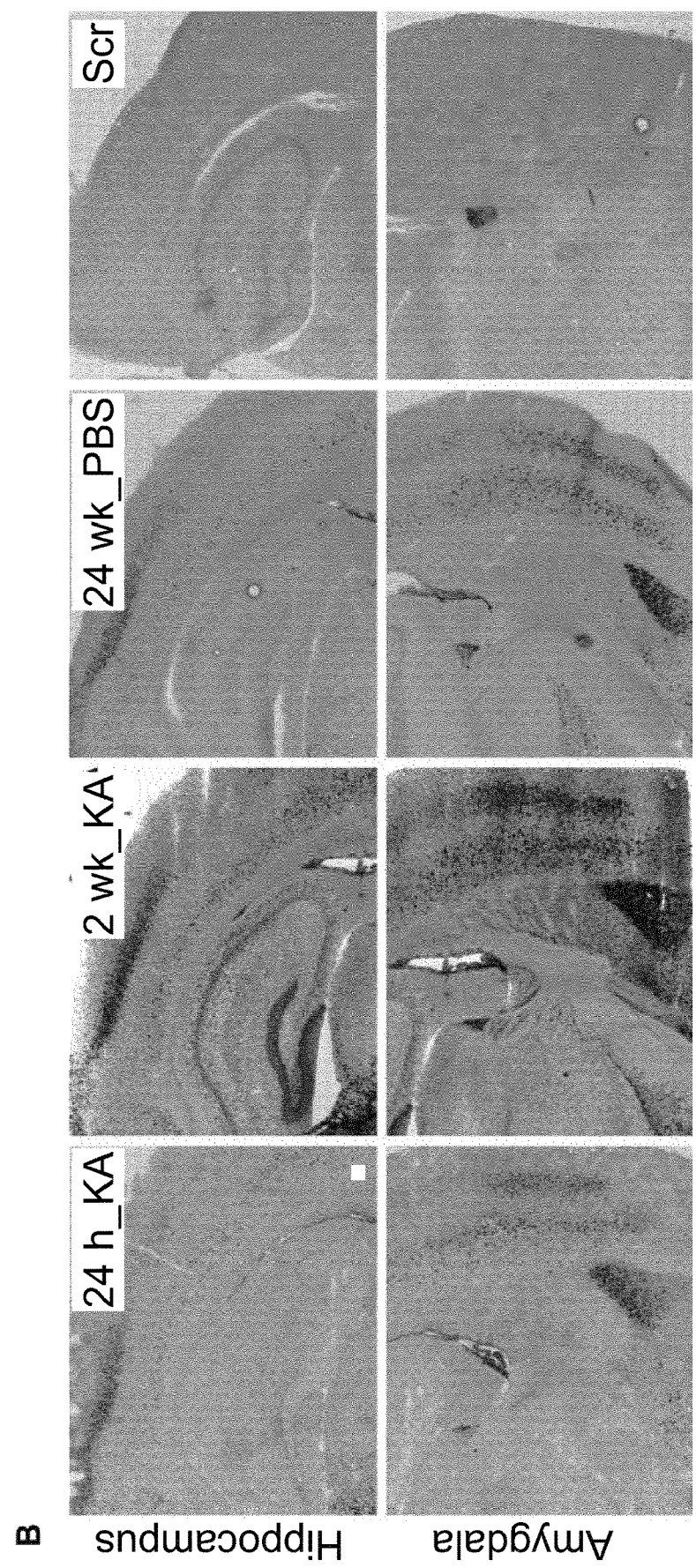
Figure 10:
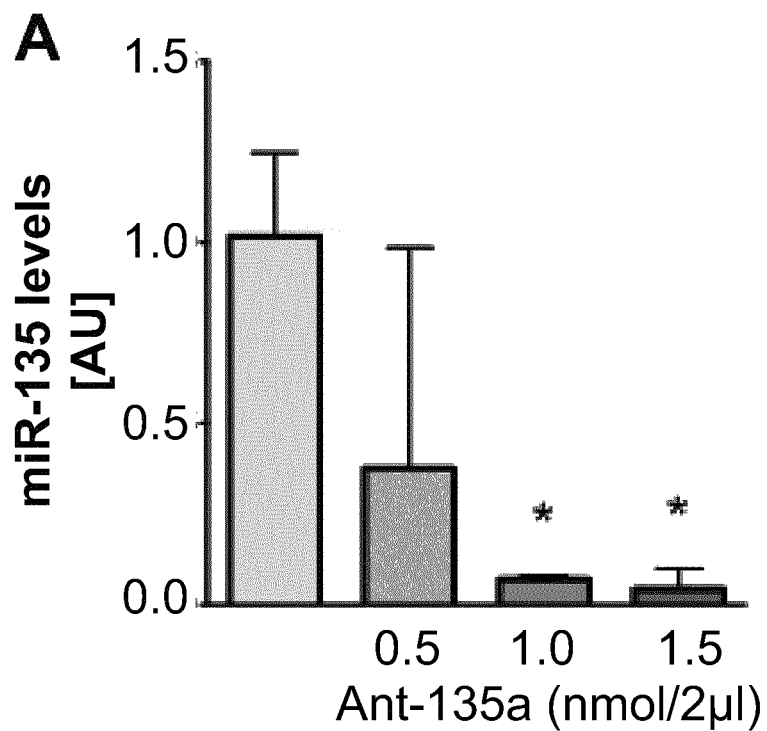
Figure 10:
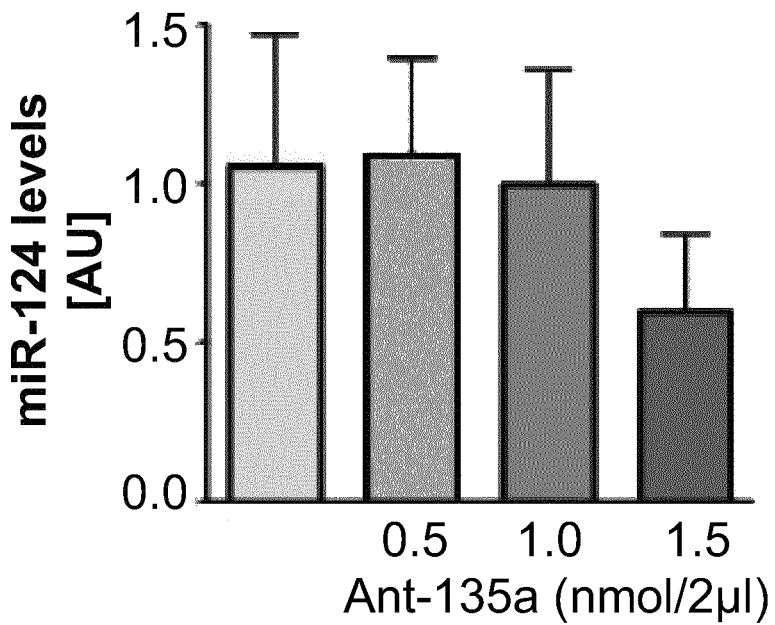
Figure 10:
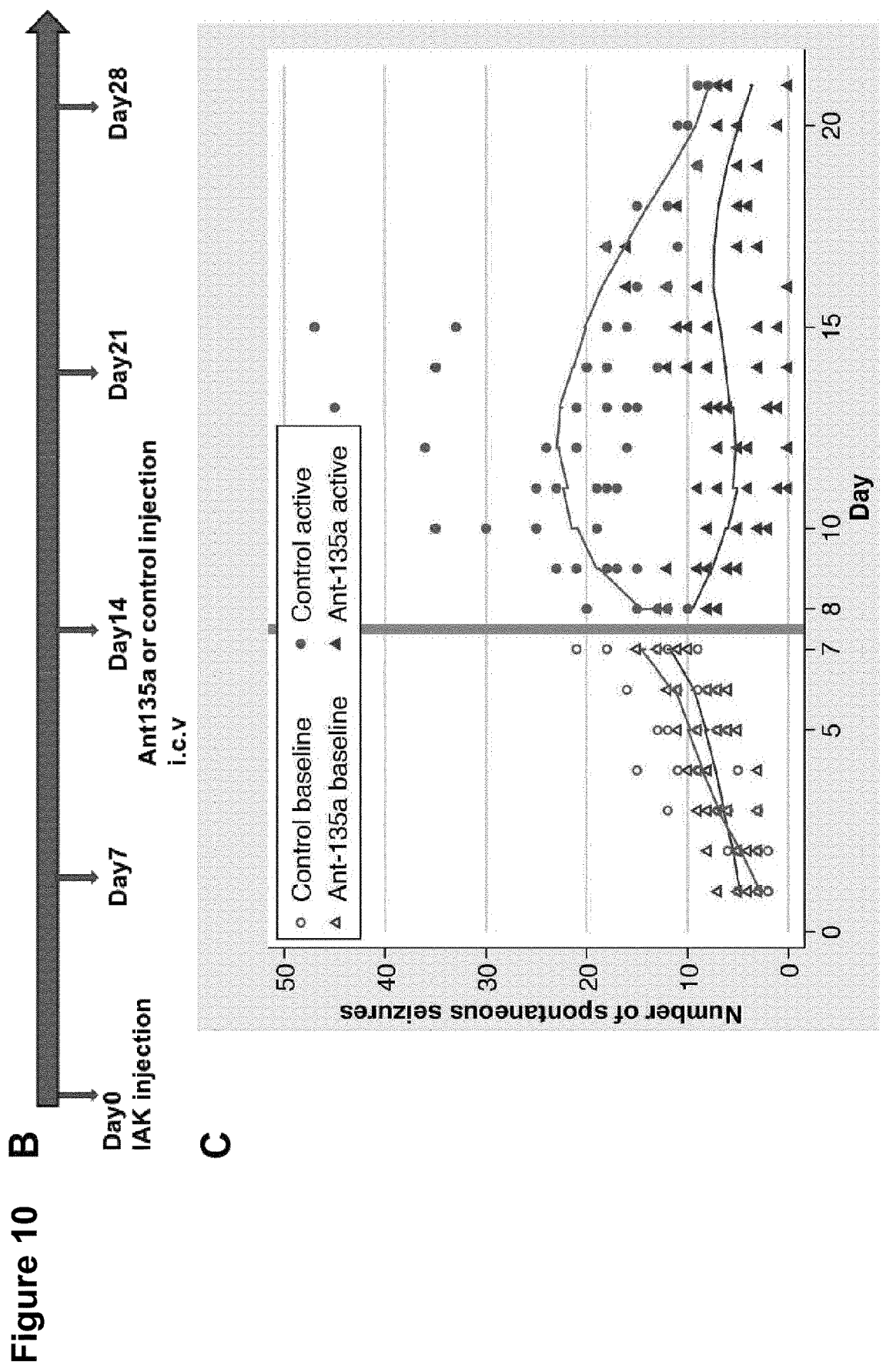

FIG. 9: miR-135a expression upregulated in Intraamygdala animal model. (A) Expression levels of miR-135a are found to be significantly upregulated at 2 weeks after status epilepticus. Normalized to 5srRNA, n=4 PBS injected, 3 KA injected mice. Students tTest. *p<0.05, **p<0.01. (B) ISH, representative images showing the upregulation of miR-135a at 2 weeks compared to 24 hr. Scale bar, 300 μm FIG. 10: In vivo data; antagomir administration and mice phenotype after kainate induction. A) miR-135a expression 24 h after antagomir administration, three doses were tested (0.5, 1.0, 1.5 nmol). 1 nmol of concentration was used further as it had maximum knockdown without any offtarget effects. miR-124 expression was unchanged at this concentration, n=3 mice/group. Normalized to RNU6B, One way ANOVA. *p<0.05. B) Schematic of the antagomir experiment plan. C) Graph showing number of spontaneous seizures recorded for 2 weeks after antagomir injections using EEG telemetry. There was no significant difference between treated and control animals in seizure frequency during the 7-day washout period (p=0.743). Following treatment, there was almost complete separation of the distributions of seizure frequencies in treated and control animals, with a Wilcoxon Mann-Whitney statistic of 0.90, 95% CI 0.65 to 0.97, indicating a 90% probability of a control animal having a higher seizure frequency than a treated animal (P<0.001). N=5 controls and 5 KA mice injected with Ant-135a. Epileptic seizures were significantly reduced in antagomir injected mice compared to controls.

FIG. 11: Increased miR-135a expression in human TLE. A) Expression levels of miR-135a in human TLE patients determined by quantitative PCR. Controls (n=8), mTLE+HS (n=7). Normalized to 5srRNA. Data is expressed as mean±SEM, **p<0.01. Mann Whitney U test. B) LNA in situ hybridization showing localization of miR-135a in control and mTLE+HS groups. Scale bar, 200 μm. C) Cell type specific localization of miR-135a. Co-localization with neuronal marker, NeuN. Specific localization of miR-135a was observed in neuronal soma in the CA regions. Arrows indicate co-labelled cells. No co-localization with astrocytic marker GFAP was observed. Scale bar, 25 µm.

FIG. 12: Increased miR-135a in mouse model of TLE. A) Increased miR-135a levels in the hippocampus of IAK mice 2 wk after SE. N=4 PBS and 3 KA mice. Normalized to 5srRNA. Data is expressed as mean±SEM. *p<0.05. t test. B) Representative images of the ISH showing strong miR-135a expression in hippocampus and amygdala regions at 2 wks after SE induction compared to 24 h and PBS injections. Scramble stained images were devoid of signal. Scale bar, 300 µm. C) FISH, co-labelling miR-135a with astrocytic marker GFAP with no specific co-localization observed. Dentate gyrus ML-molecular layer, GCL—granule cell layer, hilus, cornu ammonis regions CA2, CA3 and CA4. Scale bar, 100 µm. D) Increased levels of miR-135a-2 in mTLE+HS condition but no change of miR-135a-1. n=8 controls and 7 mTLE+HS samples. Data is expressed as mean±SEM, *p<0.05. t test. E) Both miR-135a-1 and miR-135a-2 levels are increased in KA mice compared to PBS injected controls. N=4 PBS and 3 KA mice. Data is expressed as mean±SEM, ***p<0.001, *p<0.05. t test.

FIG. 13: Ant-135a reduces seizure count in the mouse intra-amygdala kainite model of epilepsy. A) LNA ISH for miR-135a inhibitor probe in ant-135a injected mice. Strong signal for miR-135a.inh observed in ipsilateral (injected) hippocampus in images 1, 2 and the control was devoid of any signal. Scale bar, 200 µm. Ant-135a was taken up mainly by neuronal cells in hippocampal CA1, CA4 and DG regions. Scale bar, 50 µm. B) Male C57BL6 adult mice (~25 g) were implanted with DSI telemetry devices connected to cortical electrodes (both brain hemispheres) for EEG recordings. After appropriated surgical recovery mice were connected to the EEG, and underwent intra-amygdala kainic acid-induced status epilepticus (SE) on Day Zero (D0). Telemetry devices were turned off and reactivated on Day 7 (D07) to record a 7-days "Epileptic Baseline". On Day 14 (D14) mice were intracerebroventricularly (i.c.v) injected with Ant-135a or its scramble control, and continuously monitored for 6 days (D14 to D20; "after miR treatment period").

C) Epileptic baseline—There was no significant difference between treated and control animals in seizure frequency during the 7-day of epileptic baseline—prior the miR treatment (p=0.743). After miR treatment—Following treatment (on D14), there was an almost strong decrease in the number of seizures in treated and control animals starting from D15. D) Application of ant-135a at day 7 (dotted line) resulted in a significant decrease in seizure count with respect to time. N=5 for control and ant-135a. ***—mixed design repeated measures general linear model; day*treatment interaction; F statistic—5.834 ($F_{(20,60)}$=1.75 for $\alpha$=0.05); p<0.001. E) Average seizure duration: Epileptic baseline—There was no significant difference between treated and control animals in seizure duration during the 7-day of epileptic baseline—prior the miR treatment (p=0.4721). After miR treatment—Following treatment (on D14), Ant-135a-treated mice presented significantly shorter seizures than the control group, with a Student's t test analysis (P=0.0006). n=5 per group. F) Time spent in ictal activity: Epileptic baseline—There was no significant difference between treated and control animals in total time spent in seizures during the 7-day of epileptic baseline—prior the miR treatment (p=0.7546). After miR treatment—Following treatment (on D14), Ant-135a-treated mice significantly less time in seizures than the control group mice, with a Student's t test analysis (P=0.0021).

n=5/group. G) Representative EEG traces of spontaneous seizures 3 days after treatment with Ant-135a (bottom) or control (top). H) Total time spent in seizures—total time in seizures per day (seconds) per mouse.

FIG. 14: Target identification for miR-135a using biotinylated probes. A) Schematic of miRNA duplex design. The mature strand (SEQ ID NO: 5) is labelled with a biotin molecule at the 3' hydroxyl group via a C6 linker. B) Schematic showing the immunoprecipitation (IP) procedure. Neuro2A cells were transfected with biotin tagged probes, IP was performed using Streptavidin beads. Total RNA was extracted and deep RNA sequenced. N=3 biological replicates/group C) Representative WB showing Ago2 band in miR-135a and Scr IP samples. Beta-actin as loading control only present in the input samples. D) Heat maps of inputs and IPs showing differential gene expression. E) Principal component analysis (PCA) plots of inputs and IPs showing the clustering of samples basing on their differential gene expression F) PCA plots of inputs and IPs showing the clustering of samples basing on their differential gene expression.

FIG. 15: GeneOntology terms (A. Biological processes, B. Cellular compartments, C. Molecular function) for IPs showing the various processes that could be potentially regulated by miR-135a. The dotted line indicates p=0.05. D) Venn diagram showing the overlap of predicted seed sequence location (targeting site for miR-135a) in various segments of a transcript. E) Venn diagram showing the common (50.4%) and unique targets of miR-135a and miR135b. miR-135a and miR-135b contain same mature sequence with only one mis-match outside the seed region, so they essentially can target similar targets.

FIG. 16: Validation of Bio-IP targets. A) Few of the selected targets were tested by qPCR and found significantly enriched in the IP samples compared to inputs. Bargraphs and representative blot images showing GR (B-B1), PlxnA4 (C-C1) and Mef2a (D-D1) protein levels normalized to β-actin after miR-135a overexpression in N2A cells. All of the validated targets were significantly downregulated after miR-135a overexpression compared to scramble condition. Data is expressed as means, mean±SEM, *p<0.05. t test.

FIG. 17: Mef2a in TLE. A) Schematic of 3' UTR of Mef2a with miR-135a target site which is highly conserved. B) Target site of miR-135a were ligated into psiCheck2 vector multiple cloning site and tested for binding with *Renilla*-lucifearse assay. Luciferase assay in HeLa cells transfected with the constructs carrying miR-135a WT and mutant binding sites isolated from the 3' UTR of Mef2a, co-transfected with and without miR-135a mimic. N=3 independent transfections were performed with 4 wells/condition each time. Data is expressed as means mean±SEM, p<0.01. t test. C) Representative image showing secondary apical dendrites quantified for spine density. Dissociated neurons were transfected with miR-135a (with or without Mef2) or control vectors on div13 and fixed and analyzed on div17. D) Schematic showing the different types of spines quantified. E) Histogram showing the quantification, reduced spine density after miR-135a overexpression was observed and this effect was rescued by co-transfecting with Mef2. n=12-22 neurons were analyzed from three independent transfections. Data is expressed as means, mean±SEM. **p<0.0001, One way ANOVA multiple group comparison. F) Graph showing the percentage of different spine types. Increase in immature type of spines observed after miR-135a overexpression which was rescued after Mef2 co-expression. G) Representative WB image of Mef2a in control and IAK mice at 2 weeks after SE found to be strongly reduced. H) Quantification of total protein levels normalized to β-actin. N=5 controls, 4 KA mice hippocampi. Data is expressed as means, mean±SEM. *p<0.05. Mann-whitney test. I) Representative image of the Mef2a staining in IAK mice. Scale bar, 200 μm. J) Representative WB image of Mef2a in hippocampi of control and mTLE+HS patients. K) Quantification of total protein levels normalized to β-actin. N=6 controls, 4 mTLE+HS. Data is expressed as means mean±SEM. *p<0.05. Mann-whitney test. L) Representative image of the Mef2a staining in Controls and mTLE+HS dentate gyrus (DG) and CA regions. Scale 50 μm. M) Mef2a immunostaining in control and ant-135a injected mice. Scale bar, 100 μm.

EXAMPLES

Example 1. Generation of the Lentiviral Library Encoding miRNAs

Human miRNAs were selected from both the public miRNA repository (www.mirbase.org) and the proprietary small RNA deep sequencing database SIROCCO (see WO 2007/081204). The miRNA sequences were amplified from their genomic location with amplicons containing the full-length pre-miRNA hairpin and a flanking sequence on both sides of 50-150 basepairs. The primers for the amplicons were designed using a custom implementation of the Primer3 software (www.geneious.com). If the primer design program could not find appropriate primers in the designated sequences, the requirements for the flanking sequences were adjusted to 0-200 basepairs. The designed primers were complemented with a 5' GCGC overhang and a restriction site for directional cloning. As default the primer upstream of the miRNA was complemented with a BamHI restriction site (GGATCC) and the primer downstream of the miRNA was complemented with an EcoRI restriction site (GAATTC). Primers of amplicons with internal BamHI or EcoRI restriction sites (i.e. occurring in the genomic sequence) were complemented with either a BglII site (AGATCT) or a XbaI site (TCTAGA) respectively. The miRNAs were amplified using the abovementioned primers from human genomic DNA of a single individual in the following PCR reaction:

| constituent | concentration | volume | supplier/cat # |
|---|---|---|---|
| buffer | 10X | 1 μl | Stratagene/600159 |
| dNTPs | 10 mM each | 0.2 μl | GE Healthcare/27-18(58) 0-04 |
| fwd primer | 10 μM | 0.2 μl | Integrated DNA Technologies |
| rev primer | 10 μM | 0.2μl | Integrated DNA Technologie |
| gDNA | 100 ng/μl | 0.1 μl | private source |
| Pfu DNA pol | 2.5 U/μl | 0.1 μl | Stratagene/600159 |
| H$_2$O | 8.2 μl | | |

-continued

| temp (° C.) | time | cycles |
|---|---|---|
| 95 | 2 min | — |
| 95 | 15 s | 40 |
| 59* | 15 s | 40 |
| 72 | 90 s | 40 |
| 72 | 15 min | |
| 4 | ∞ | |

*–0.1° C./cycle

All miRNA loci were amplified in separate 10 μl PCR reactions. The products were purified using the Qiagen PCR Clean-Up buffer set and Whatman Unifilter GF/C filter plates (cat #7700-1101). DNA was eluted with 17 μl H$_2$O per well. The separate eluates were used in the following restriction reaction:

| Constituent | concentration | volume | supplier/cat # |
|---|---|---|---|
| buffer | E 10X | 2 μl | Promega/R005A |
| EcoRI* | 12 U/μl | 0.1 μl | Promega/R6017 |
| BamHI* | 10 U/μl | 0.1 μl | Promega/R6025 |
| eluate | N/A | 16 μl | N/A |
| H$_2$O | N/A | 1.8 μl | N/A |

*Amplicons with internal restriction sites for EcoRI or BamHI were cut with XbaI or BglII respectively instead. The EcoRI + BglII reaction was done with Promega buffer D. The BamHI + XbaI reaction was done with Promega buffer E.

| constituent | conc. | volume | supplier/cat # |
|---|---|---|---|
| buffer | 10X | 2 μl | Promega/C1263 |
| T4 DNA ligase | 1-3 U/μl | 0.2 μl | Promega/M1804 |
| restricted pCDH* | 1 ng/μl | 7.8 μl | System Biosciences/CD510B-1 |
| eluate | N/A | 10 μl | N/A |

Ligation overnight at 4° C.

*For directional cloning, pCDH was cut with both EcoRI and BamHI. An alternate construct called pCDH- was made with reversed EcoRI and BamHI restriction sites so that the amplicons with 5' BamHI and 3' EcoRI were cloned in the proper direction. The amplicons with an internal EcoRI site were cut with XbaI and ligated into a pCDH vector that was restricted with XbaI and BamHI.

The resulting ligates were transformed separately into bacteria (Promega Single Step (KRX) competent cells, cat #L3002). 50 μl competent cells was diluted with 950 μl transformation buffer II (10 mM MOPS, 75 mM CaCl$_2$, 10 mM RbCl, 15% glycerol, filter-sterilized). Per 20 μl ligate, 20 μl diluted competent cells was added. The mix was incubated for 15 minutes on ice, heat-shocked at 37° C. for 30 seconds, and put back on ice. After 2 minutes the transformed bacteria were reconstituted in 150 μl Luria broth (LB). The bacteria were allowed to recover for 20 minutes at 37° C. after which they were plated out separately on ampicillin-containing (50 μg/mL) LB-agar plates and grown overnight at 37° C.

Single colonies of each plate are picked and subcultured overnight in 400 μl ampicillin-containing (50 μg/mL) LB. 1 μl of subculture is lysed in 100 μl water for sequencing purposes. Bacterial lysate is used in the following PCR reaction:

| constituent | conc. | Volume | supplier/cat # |
|---|---|---|---|
| buffer | 5X | 1 μl | private source |
| dNTPs | 10 mM each | 0.1 μl | GE Healthcare/27-18(5-8)0-04 |
| pCDH-fwd | 10 uM | 0.1 μl | Integrated DANN Technologies |
| pCDH-rev | 10 uM | 0.1 μl | Integrated DANN Technologies |
| lysate | 1:100 | 1 μl | N/A |

| | | | |
|---|---|---|---|
| Taq DNA pol | unknown | 0.02 µl | private source |
| H₂O | N/A | 2.68 µl | N/A |

| temp (° C.) | time | cycles |
|---|---|---|
| 95 | 2 min | — |
| 95 | 15 s | 40 |
| 59* | 15 s | 40 |
| 72 | 90 s | 40 |
| 72 | 15 min | |
| 4 | ∞ | |

*−0.1° C./cycle pCDH-fwd
(SEQ ID No: 344)
CACGCTGTTTTGACCTCCATAGA pCDH-rev
(SEQ ID No: 345)
CACTGACGGGCACCGGAG The PCR products were diluted 25×. 1 µl of diluted PCR product was used in the following Sanger Sequencing reaction:

| Constituent | concentration | volume | supplier/cat # |
|---|---|---|---|
| buffer | N/A | 1.9 µl | private source |
| BigDye v3.1 | N/A | 0.1 µl | ABI/4336921 |
| pCDH-seq | 10 uM | 0.1 µl | Integrated DNA Technologies |
| PCR product | 1:25 | 1 µl | N/A |
| H₂O | N/A | 1.9 µl | N/A |

| temp (° C.) | time | cycles |
|---|---|---|
| 94 | 10 sec | — |
| 50 | 5 s | 40 |
| 60 | 2 min | 40 |
| 10 | ∞ | | pCDH-seq
(SEQ ID NO: 346)
GACCTCCATAGAAGATTCTAGAGCTAGC

30 µl precipitation mix (80% ethanol, 50 mM sodium acetate pH 5.5) was added to each of the sequencing reaction products. The mixes were vortexed for 10 seconds and spun down at 5000 rcf (relative centrifugal force) for 45 minutes at 4° C. Supernatant was aspirated and DNA pellets were washed with 30 µl ice cold 80% ethanol and spun at 5000 rcf for 5 minutes at 4° C. Supernatant was aspirated and the DNA pellet was dried on a heat block for 10 minutes. The dry DNA pellet was dissolved in 10 µl H₂O. The resulting DNA solution was sequenced on an ABI 3730XL DNA Analyzer. Sequences were compared to the expected genomic sequences. Correct clones were added to the library. For incorrect clones an additional 4 bacterial colonies were picked, and analyzed for insert sequence.

Library constructs were subcultured overnight in 50 mL ampicillin-containing (100 ug/mL) LB and isolated with the Qiagen QIAfilter Plasmid Midi Kit (cat #12245) supplemented with the Qiagen EndoFree Plasmid Buffer Set (cat #19048) according to the instructions of the manufacturer. DNA was dissolved in the supplied TE buffer and brought to a final concentration of 500 ng/µl.

We ordered constructs that we were not able to clone ourselves as minigenes from Integrated DNA Technologies. In these cases, the full-length hairpin plus 20 basepairs flanking each site were cloned into our vector as a service by IDT.

Packaging and virus production was performed by System Biosciences as described in the user manual of CD-500131-CD523-A1.

Example 2: An Image-Based miRNA Screen Identifies miRNA-135s as Regulators of CNS Axon Growth and Regeneration by Targeting Krüppel-Like Factor 4

Materials and Methods

Animals

All animal use and care was carried out in accordance with institutional guidelines and approved by the local ethical animal experimentation committee (DEC). C57Bl/6J mice (RRID:IMSR_JAX:000664, male and female) were obtained from Charles River. When timed-pregnant females were used, the morning on which a vaginal plug was detected was considered embryonic day 0.5 (E0.5). For pups the day of birth was considered postnatal day 0 (P0).

Lentiviral Human Whole miRnome Library High Content Screen and Hit Confirmation

SH-SY5Y cells, obtained from DSMZ (Acc 209, RRID: CVCL_0019), were grown in DMEM-F12 (Gibco)+10% FCS+L-Glutamine+penicillin/streptomycin and used between passage 12 and 21. Cells were seeded in 96-wells plates using an automated cell-seeder Multidrop Combi Reagent Dispenser (Thermo Scientific) at 6000 cells/well. One day after seeding, cells were treated with 60 µM retinoic acid and transduced with a lentiviral human genome-wide miRNA library at on average 7.34'10⁵ IFU/well (InteRNA Technologies). Each library plate was evaluated in triplicate. The lentiviral library contains 640 annotated human miRNA genes (miRBase 12) and 400 candidate miRNAs from deep-sequencing efforts and is based on the pCDH-CMV-MCS-EF1-Puro vector (No CD510B-1, System Biosciences) (Poell et al., 2011). Systems Bioscience performed the lentiviral packaging and the library had an average IFU/ml of 1.2210⁹. The library was stored in 14 96-wells plates. At 4 days in vitro (DIV), cells were fixed by addition of 1:1 8% paraformaldehyde in PBS and blocked in 0.4% Triton-X100, 5% Goat Serum, 1% BSA, 1% glycin, and 0.1% lysin in PBS. Cells were immunostained for βIII-tubulin (1:3000, mouse monoclonal T8660, Sigma, RRID: AB_477590) with an Alexa 488-conjugated secondary antibody (Invitrogen) and counterstained with DAPI. Cells were automatically washed thoroughly by two washing cycles with an AquaMax 2000 (Molecular Devices). Automated microscopy was carried out using a Thermo ArrayScan VTI HCS Reader (Thermo Scientific) and morphological features were extracted with the Cellomics Neuronal Profiling V3 Bioapplication algorithm. Raw data (.mdb files) were converted into Excel format using a custom script (courtesy of Ronald van Kesteren, Vrije Universiteit Amsterdam). All wells with a valid nucleus count below 100 were removed. Non-neuronal attributes and attributes dependent on cell number were trimmed from the dataset. For all other attributes the plate median was calculated. Each attribute of each well was scored binary (0 or 1), with a positive score (1) when deviating more than 2 times from the standard deviation of the control median. The median of all miRNAs was used as control, assuming that most miRNAs would not affect cell morphology. Triplicates of each plate were combined and a well attribute was taken as 'true' when a minimum of 2 out of 3 plates scored positive. This resulted in a final (cumulative) 'hitscore' which was used to rank the lentiviral clones with effects on neuronal morphology.

For hit confirmation, SH-SY5Y cells were harvested by trypsinization, washed with PBS and resuspended at $8*10^6$ cells/ml in INB buffer (135 mM KCl, 0.2 mM $CaCl_2$, 2 mM $MgCl_2$, 10 mM HEPES, 5 mM EGTA, pH 7.3). Then, cells were mixed with 20 pmol miRIDIAN mimic (always the human (hsa) isoform, Dharmacon, ThemnoScientific) and electroporated with 3 120V pulses of 900 μs and 2 s pulse interval in a 1 mm gap size cuvet in an ECM 830 square wave generator with PEP cuvette module (all BTX Harvard Apparatus). In this way, over 98% of the cells are electroporated. Each electroporation was divided and equally distributed over 4 wells of a 24-wells plate, leaving the outer left and right wells without cells to take into account possible edge-well effects. One day post-electroporation, cells were treated with 60 μM retinoic acid to induce the development of neuron-like features. Four days after electroporation, cells were fixed and immunostained as described above. Analysis of morphological cell features was performed using the Cellomics software outlined above.

Locked Nucleic Acid (LNA) In Situ Hybridization

E16.5 C57BL/6J mouse embryos were collected and decapitated. Brains were fixed in 4% PFA in PBS and cryoprotected in 30% sucrose in PBS. Twenty μm thick coronal brain cryosections were made. LNA in situ hybridization was performed as previously described (Kan et al., 2012). Briefly, sections were air-dried and post-fixed for 10 min in 4% PFA, acetylated (10 min RT), treated with proteinase K (5 μg/ml for 5 min at RT) and prehybridized (1 h at RT, 30 min at 55° C.) before incubation with 15 nM of LNA-containing, double DIG-labeled miR-135a, miR-135b or control in situ probes (Exiqon) (2 h, at 55° C.). After hybridization, slides were washed in 0.2×SSC for 1 h at 55° C. Slides were blocked 1 h with 10% FCS in PBS and incubated with anti-digoxigenin-AP Fab fragments (1:2500, Roche Diagnostics) in blocking buffer ON at 4° C. After PBS washes, slides were incubated with nitroblue and 5-bromo-4-chloro-3-indolyl phosphate (NBT/BCIP, Roche Diagnostics) substrates for 2-20 h at RT. Staining was terminated by washing of the slides in PBS. Slides were mounted in 90% glycerol in PBS. Sections stained with scrambled LNA-DIG probe were devoid of specific staining.

Quantitative PCR

E14.5 and E16.5 C57BL/6 embryos, P0 and P10 pups, and adult mice were decapitated and brains were removed. Hippocampi and cortices were dissected and frozen immediately on dry-ice. Total RNA was isolated from at least 3 animals from 3 different litters using the miRNeasy kit (Qiagen) according to manufacturer's protocol. In addition, total RNA was isolated from primary hippocampal neurons from 3-4 coverslips out of 2 different cultures at DIV 2, 7, 14, and 21. Furthermore, total RNA was isolated from retina 14 days after optic nerve crush experiments and intravitreal injection of miRNA mimics (see paragraph describing optic nerve injury experiments). RNA quantity was determined using Nanodrop (Thermo Scientific) and equal amounts of each sample were used for first strand cDNA synthesis using universal cDNA synthesis kit (Exiqon). Quantitive PCR reactions were run on Quantstudio 6 flex Real-Time PCR system (Applied Biosystems) using microRNA LNA™ PCR primer sets and SYBR Green master mix (Exiqon). All samples were run in duplicates. Ct values were determined using Quant studio real time per software v1.1. The expression levels of different miRNAs were estimated by normalization to 5S rRNA, and the statistical significance was analyzed with single factor ANOVA. $p<0.05$ was evaluated as significant.

Culturing and Transfection of Mouse Hippocampal and Cortical Neurons

Hippocampal and cortical cultures were generated as described previously (Van Battum et al., 2014). In brief, P0-P1 C57BL/6 mouse pups were decapitated and brains were rapidly removed in ice-cold dissection medium. Hippocampi or cortices were isolated, trypsinized and dissociated into single cells. They were cultured in neurobasal medium supplemented with B-27, L-glutamine, penicillin/streptomycin, and β-mercaptoethanol, on acid-washed, poly-D-lysin (PDL, 20 μg/ml) and laminin (40 μg/ml)-coated glass coverslips at 37° C.+5% $CO_2$ in 12-well plates. On DIV 1 neurons were co-transfected with 0.5 μg CAG-GFP vector and 50 pmol miRIDIAN mimics for miR-135a, miR-135b, or control-1 mimic (also known as Negative control-A, all obtained from Dharmacon) per well, or 0.5 μg miRNA H1-mCherry-sponge vectors per well for miR-135a or miR-135b (Tebu-bio) using Lipofectamine 2000 (Invitrogen). For rescue experiments, a pCMV-KLF4-EGFP vector (Origene) was used. On DIV4, neurons were fixed with 4% PFA and 4% sucrose in PBS. For immunocytochemistry, neurons were incubated with rabbit anti-GFP (1:1000, A-11122, Invitrogen, RRID:AB_221569) or rabbit-anti-RFP (1:1000, Rockland, RRID:AB_11182807) and mouse anti-8111 tubulin (1:3000, T8660, Sigma, RRID:AB_477590) dissolved in 3% normal horse serum, 0.1% BSA and 0.1% triton-X100 in PBS. Images were taken using an Axioskop 2 EPI fluorescent microscope (Zeiss). Longest neurites were traced semi-manually using the NeuronJ plugin (RRID: SCR_002074) of ImageJ and sholl analysis was performed using ImageJ software (RRID:SCR_003070). More than 100 transfected neurons from at least 3 independent experiments were traced. Non-paired parametric T-tests were performed in Prism6 (Graphpad software, RRID:SCR_002798) to statistically analyze the data.

miRNA Target Finding and Validation

The MiRecords database was used to search for shared mRNA targets of miR-135a and miR-135b, predicted by at least 6 target prediction programs (Xiao et al., 2009).

Predicted targets shared by miR-135a and miR-135b were post-selected on basis of potential involvement in neuronal development. For target validation, the entire 3'-UTR from KLF4 was retrieved from cDNA and cloned into the psi-CHECK2 vector (Promega). PCR-mediated mutagenesis of the KLF4 3'-UTR was performed to alter the binding site located at 394 nt of the KLF4 3'-UTR (FIG. 5A, arrow). HEK293 cells (RRID:CVCL_0045) were transfected using Lipofectamine with 250 ng vector and 20 pmol miRIDIAN miRNA mimic (Dharmacon). Cells were lysed 24 h post-transfection and examined with Dual-Luciferase reporter assay (E1960, Promega) on a spectrophotometer. T-tests were performed to compare luciferase activity in Prism6 (Graphad Software, RRID:SCR_002798).

For protein analysis, miRIDIAN miRNA mimics (Dharmacon) were transfected into Neuro2A cells (ATCC, RRID: CVCL_0470) using Lipofectamine 2000. After 24 h, cells were lysed in lysis buffer (20 mM Tris pH 8.0, 150 mM KCL, 1% Triton-X-100, protease inhibitor (Roche) in MQ). Samples were separated on 8% SDS-page gels and blotted onto nitrocellulose membrane. Non-specific binding was blocked with 5% milk in TBS-tween for 1 h at RT. After incubation with rabbit-anti-KLF4 (1:500, Santa-Cruz, RRID:AB_669567) and mouse-anti-$\beta$-actin (1:5000, Sigma, RRID:AB_476743) in 1% milk in TBS-tween, blots were stained with peroxidase-conjugated secondary antibodies (Abcam). Signals were detected using Pierce ECL Western Detection Reagent (Thermo Scientific), and images were made using FluorChem M Imaging system (Protein Simple). ImageJ was used to determine protein levels in the individual bands, and KLF4 expression was normalized to $\beta$-actin levels in the same sample. T-tests were performed to compare the relative KLF4 expression between conditions (Graphad Prism6 software, RRID:SCR_002798).

Immunohistochemistry

E16.5 C57BL/6J mouse embryos or adult mice were collected and decapitated. Brains were fixed in 4% PFA in PBS and cryoprotected in 30% sucrose in PBS. Twenty µm thick coronal brain cryosections were made. Sections were incubated with rabbit anti-KLF4 (Santa-Cruz, 1:500 (no longer available) or LabNed LN2023880 1:100, RRID: AB_2687557) diluted in 3% BSA and 0.1% Triton-X-100 in PBS, stained with Alexa Fluor-conjugated secondary antibody and counterstained with DAPI. Images were made using an AxioScope EPI-fluorescent microscope (Zeiss) and a confocal scanning microscope (Olympus).

Ex Vivo Electroporation

Ex vivo electroporation was performed as described previously (Yau et al., 2014). In brief, pregnant C57Bl/6 mice were sacrificed by cervical dislocation and E14.5 embryos were rapidly removed and decapitated. 30 µM miRIDIAN mimics (Dharmacon) for miR-135a, miR-135b or control-1 combined with 0.4 µg/µl pCAG-GFP vector were dissolved in 0.1% Fast Green in MQ, and 1.7 µl of this mixture was injected in the lateral ventricles using glass micro-pipettes (Harvard Apparatus) and a microinjector. Heads were subjected to three 100 ms pulses of 30 V with 100 ms pulse interval, using gold plated gene paddle electrodes and an 830 square wave generator (BTX Harvard Apparatus). Brains were then isolated, collected in cHBSS, embedded in 3% LMP-Agarose (Fisher Scientific) in cHBSS and sectioned coronally into 250 µm thick slices using a vibratome (Leica). Sections were collected on poly-D-lysin-laminin-coated culture membrane inserts (Falcon), placed on top of slice culture medium (70% v/v Basal Eagle Medium, 26% v/v cHBSS, 20 mM D-glucose, 1 mM L-glutamine, penicillin/streptomycin) and cultured for 4 days to assess the degree of migration. Cultures were fixed with 4% PFA, blocked in 3% BSA and 0.1% triton in PBS, and stained with rabbit anti-GFP (1:1000, A-11122, Invitrogen, RRID:AB_221569) and mouse anti-MAP2 SMI 52 (1:1000, Abcam, RRID: AB_776173) antibodies. Z-stack images were taken using confocal laser-scanning microscopy (Olympus). Migration of GFP-positive cells was analyzed as follows: using Adobe Photoshop, consistent rectangles divided in 8 equal bins were placed on top of the image, so that bin 1 includes the ventricular zone (vz) and bin 8 covers the marginal zone (mz, as shown schematically in FIG. 4A). Cells in each bin were counted and divided by the total amount of cells in the rectangle. The average of at least two rectangles of each image was used for comparison. For each condition, 12 cortical slices from at least 3 different experiments were used. Non-parametric Mann-Withney U tests were performed in Prism6 (Graphad software, RRID:SCR_002798) to compare migration between control and miRNA overexpression.

In Utero Electroporation

In utero electroporation was performed as described previously (van Erp et al., 2015). Pregnant C57131/6 mice at E14.5 were deeply anaesthetized with Isoflurane (induction: 3-4%, surgery: 1.5-2%), injected with 0.05 mg/kg buprenorfinhydrochloride in saline, and hereafter the abdominal cavity was opened under sterile surgical conditions. Uterine horns were exposed and 1.7 µl DNA mixture containing 0.4 µg/µl pCAG-GFP, and 15 µM miR-135a and 15 µM miR-135b mimic, or 30 pmol control-1 mimic, or 0.6 µg/µl scrambled sponge vector, or 0.3 µg/µl miR-135a sponge vector and 0.3 µg/µl miR-135b sponge vector (H1-mCherry vectors, Tebu-bio) dissolved in MQ with 0.05% Fast Green (Sigma) was injected in the lateral ventricles of the embryo's using glass micro-pipettes (Harvard Apparatus) and a PLI-100 Pico-injector (Harvard Apparatus). For rescue experiments, 0.2 µg/µl pCAG-GFP was combined with 0.2 µg/µl pCAG-KLF4, and 15 µM miR-135a and 15 µM miR-135b mimic. Brains were electroporated using an ECM 830 Electro-Square-Porator (Harvard Apparatus) set to five unipolar pulses at 30 V (50 ms pulse length interval and 950 ms pulse length). The motor cortex was targeted by holding the head with a platinum tweezer-electrode (negative pole) while a third a gold-plated Genepaddle (positive pole, Fisher Scientific) was placed on top of the head. Embryos were placed back into the abdomen, and abdominal muscles and skin were sutured separately. Release from isoflurane awakened the mother mice. Embryos were collected at E16.5 and pups at P4 or P10. Heads were fixed in 4% PFA in PBS and submerged in 30% sucrose. 20 µm thick coronal cryosections were made and immunohistochemistry and cortical migration analysis were performed as described for ex vivo electroporated slices. To measure neurite outgrowth in vivo, leading process length was traced using ImageJ. In the case of endogenous miR-135 down-regulation, where brains were electroporated with H1-mCherry sponge vectors (Tebu-bio), neuron migration and leading process length were analyzed upon staining with rabbit-anti-RFP (1:1000, Rockland, RRID:AB_11182807). Control and miRNA test conditions were always equally distributed among the embryos in the uterus. Analysis was always performed on the slice in which the corpus callosum was first complete and in 1 or 2 consecutive slices. At least 5 embryos from at least 2 separate experiments were used for comparison.

Optic Nerve Injury and In Vivo Gene Transfection 3-week-old C57BL/6J mice were obtained from SLC company (Hamamatsu, Japan). Optic nerve injury was performed as previously described in detail (van Erp et al., 2015). The left optic nerve was crushed with fine forceps for 10 sec approximately 1 mm posterior to the optic disc. 50 pmol/µl miR-135a and 50 pmol/µl miR-135b or 100 pmol/µl control-1 mimic were injected intravitreally (with lipofectamine) immediately following injury and on day 7 post-axotomy. In vivo gene transfection was performed as described previously (van Erp et al., 2015). Briefly, pCAG-GFP or pCAG-KLF4 was mixed with miRNA mimics and Lipofectamine 2000. 2 µl of the complexes were injected intravitreally immediately following injury and on day 7 post-axotomy. Nine mice were used for each group. Similarly, 4 ug of sponge vectors specifically targeting miR-135a and miR-135b or control sponge (Tebu-bio) were injected intravitreally (with lipofectamine). Six mice per group were used. AAV2 virus (AAV-miR-GFP-Blank Control virus, Cat. No: Am00102, GFP mmu-miR-135a-5p AAV miRNA Virus, Cat. No: Amm1006802, GFP mmu-miR-135b-5p AAV miRNA Virus, Cat. No: Amm1007002, abm) was injected at 7 days before optic nerve crush injury. To visualize RGC axons, 1 µl of cholera toxin β subunits conjugated to Alexa Fluor 555 (2 µg/µL, Invitrogen) was injected into the vitreous with a glass needle 12 days after the injury. On day 14 post-axotomy, animals were perfused with 4% PFA. The eye cups with the nerve segment attached were post-fixed, and immersed in 30% sucrose overnight at 4° C. Tissues were embedded in Tissue Tek and serial cross-sections (16 µm) were prepared using cryostat and collected on MAS-coated glass slides (Matsunami, Osaka, Japan). Axonal regeneration was quantified by counting the number of CTB-labeled fibers extending 0.2, 0.5, and 1.0 mm from the distal end of the lesion site in 5 sections. The cross-sectional width of the optic nerve was measured at the point at which the counts were taken and was used to calculate the number of axons per millimeter of nerve width. The number of axons per millimeter was then averaged over the 5 sections. $\Sigma ad$, the total number of axons extending distance d in a nerve having a radius of r, was estimated by summing all the sections having a thickness t (16 µm): $\Sigma ad = \pi r^2 \times [\text{average axons/mm}]/t$. Statistical analyses were performed using one-way ANOVAs. $p<0.05$ was considered significant.

Experimental Design and Statistical Analysis

In this study, female and male C57Bl/6J mice were used regardless of their sex. For statistical analyses, Prism 6 software (Graphpad) was used. Generally unpaired T-tests were used to compare the means of two groups, with the exception of neuron migration analyses (non-parametric Mann-Whitney U tests) and q-PCR analyses (single factor ANOVA). For all statistical tests, significance was set at $p<0.05$. Exact p values, t-values and degrees of freedom are provided in the results, and Ns are provided in the figure legends.

Figure 1:
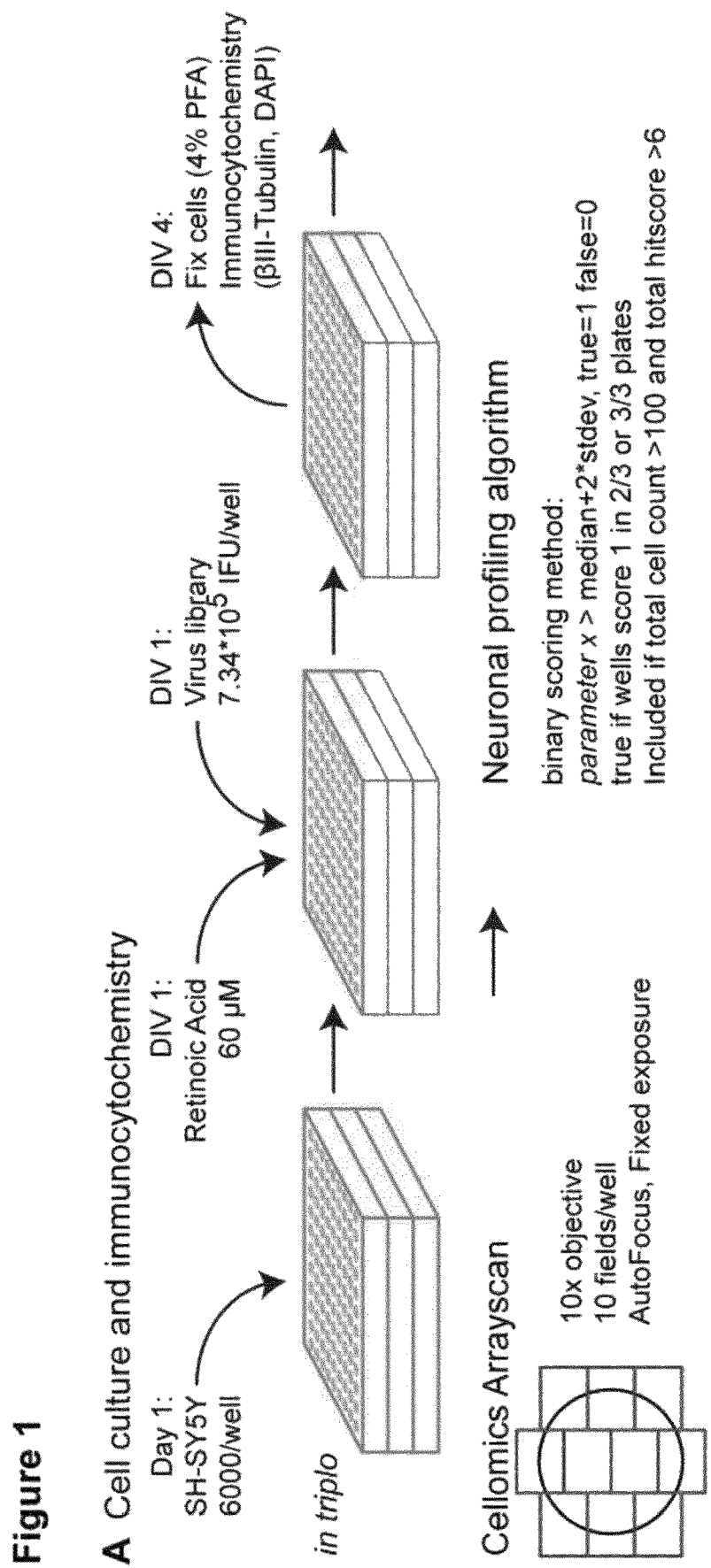
FIG. 1: Image-based high content screen identifies miRNAs involved in neurite growth.
Figure 1:
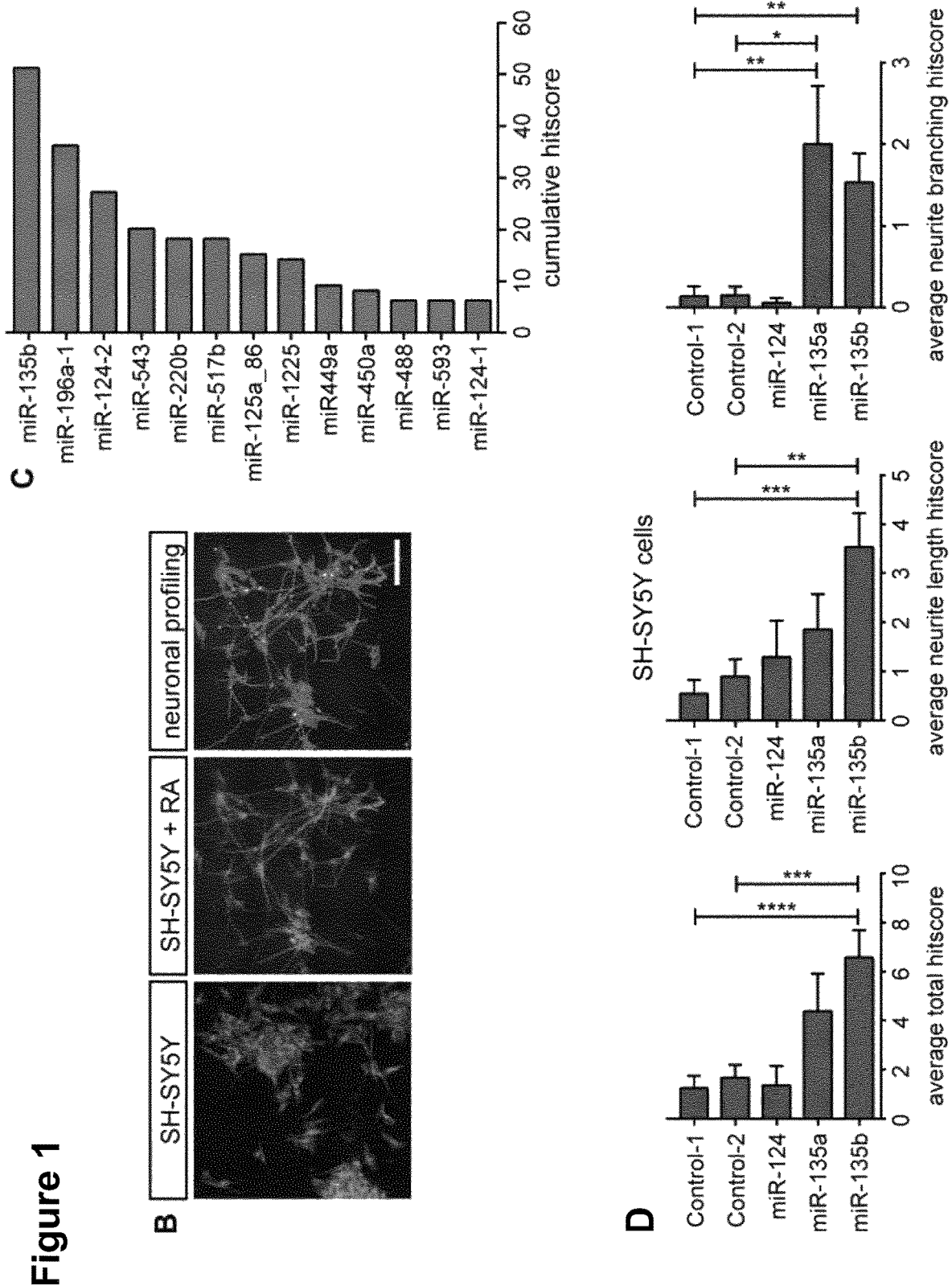

At the start of this study an automated morphological cellomics screen of retinoic acid-treated SH-SY5Y cells that were transduced with a lentiviral library containing 1140 unique human miRNAs (Poell et al, 2011) was performed to identify miRNAs that (positively) influence neuronal features (FIG. 1A). The screen was conducted in triplo, and morphological parameters were scored with a neuroprofiling algorithm. To confirm the effect of the most robust miRNAs, the cellomics analysis was repeated on SH-SY5Y cells that were electroprated with miRNA mimics for a selection of hits. This experiment was performed three times in quadruplo (i.e., three times four coverslips, FIG. 1D), and statistically analyzed using Student T-tests.

Expression of miR-135a and miR-135b in the mouse brain at different ages was tested by LNA in situ hybridization and q-PCR experiments (in tissue of at least 3 different mice per age (FIG. 2)). Expression of miR-135a and miR-135b was also determined in cultured primary hippocampal neurons (FIG. 3A). Q-PCR experiments were statistically analyzed using single factor ANOVAs.

Next, the effect of miR-135a and miR-135b overexpression and down-regulation was examined in primary neuron cultures. Lipofectamine-based transfections were replicated at least 3 times in triplo (i.e., 3 times 3 coverslips). miRNA mimics were co-transfected with GFP vector and in case of sponge-vectors internal RFP was exploited to trace neurite length using the NeuronJ plugin of ImageJ (FIG. 3B-F). Student T-tests were performed to compare the means of each group with the control condition.

To assess the endogenous effects of miR-135a and miR-135b during neuronal development, ex vivo electroporation of miRNA mimics combined with a GFP vector and subsequent organotypic slice cultures of mouse embryonic cortex were performed (E14, FIG. 4A). Embryos of one mother were divided among the three conditions to compare littermates, and the experiment was repeated three times. Similar cortical slices of at least 6 embryos from 3 different mothers were used for comparison. Next, in utero electroporation experiments were performed in E14 mice embryos to overexpress and down-regulate miR-135a and miR-135b in vivo. For embryonic analysis, the three conditions were divided over the embryos that were present in the uterus to always compare littermates. In utero electroporation dedicated to the isolation of postnatal tissue was performed one condition per mother. For analysis of migration and neurite outgrowth of electroporated cortical neurons three consecutive cryo-sections showing the corpus callosum were used and taken from at least 9 pups derived from at least 3 different mothers. For both ex vivo and in utero electroporation analyses we performed Mann-Whitney U-tests to compare the distribution of the migrating cells. These were manually counted in 2-3 rasters containing 8 cortical 'bins' per slice placed exactly perpendicular to the direction of migration, with the bottom of bin 1 touching the border of the ventricle (for embryonic brains) or the axons of the anterior commissure (for postnatal brains) and the top of bin 8 reaching the cortical surface (FIG. 4A).

Next, possible mRNA targets of miR-135a and miR-135b were identified using the bio-informatic tool miRecords (Xiao et al 2009). KLF4 was selected based on its reported effects on neurite outgrowth and neuronal migration. The strongest predicted binding site of miR-135a and miR-135b in the KLF4 3'-UTR was selected and used for a luciferase assay performed three times in HEK293 cells to confirm direct target binding (FIG. 5A, B). Immunohistochemistry was then used to assess whether KLF4 and miR-135a and b are expressed in similar brain areas (FIG. 5C). Next, we tested whether endogenous KLF4 expression in N2A cells was down-regulated upon miR-135a and miR-135b administration. To determine an endogenous role for miR-135-KLF4 signaling, rescue experiments were performed in primary hippocampal neuron cultures and in utero electroporation using KLF4 cDNA (insensitive to miRNA regulation) using the same experimental procedures and repetitions as described before.

Since KLF4 is one of the most important signals counteracting axon regeneration, we investigated whether miR-135a and miR-135b could be used to decrease KLF4 expression in poorly regenerating neurons in a specific and cell-autonomous fashion. We first injected miRNA mimics intravitreally (on day 0 and day 7) to learn whether this was sufficient to deliver miRNAs to the optic nerve and down-regulate KLF4 expression. Q-PCR was performed on 3 optic nerves per condition, 14 days after the first injection of mimics. Then, mimics were combined with GFP vector and/or KLF4 cDNA to determine axon regeneration 14 days after optic nerve injury. This was repeated in 9 mice per condition. Q-PCR experiments revealed no differences in transfection efficiency between conditions. AAV2 virus containing miR-135a, miR-135b, or control miRNA was injected to transduce RGCs only in 6 mice 7 days before the optic nerve crush and to assess the cell-autonomous nature of the effect observed with mimic injections. Finally, we determined whether miR-135a and miR-135b had an endogenous role in optic nerve regeneration measured 14 days after the optic nerve crush by injecting sponge vectors at day 0 and day 7 in 6 mice. Axon regeneration was statistically tested by ANOVAs followed by Sidak post-hoc tests.

Results miRNome-Wide Screen for miRNAs that Regulate Neurite Growth

To identify miRNAs that can promote neurite growth, an image-based miRNA screen was performed in neuronal SH-SY5Y cells, a cell line regularly used for cellular screening. Neuronal differentiation of SH-SY5Y cells was induced by retinoic acid treatment followed by transduction of a lentiviral library containing 1140 unique human miRNAs (Poell et al., 2011)(FIG. 1A, B). Using a Cellomics Array-Scan platform, thousands of cells in each condition were analyzed for parameters related to neuronal morphology. This multiparametric analysis resulted in a cumulative hitscore that was based on parameters such as neurite length and branching. To identify hits, scores for each individual miRNA were compared to the median score of all miRNAs. This approach assumes that the majority of miRNAs do not affect neuronal morphology. This approach identified 13 annotated miRNAs with pronounced effects on specific morphological properties of differentiated SH-SY5Y cells (e.g. neurite length). Of these miRNAs, miR-135b had the largest effect (FIG. 1C). miRNA-135a was later shown to perform similarly—in this screen it in the corner of the plate and suffered from edge-well artefacts.

To confirm the effect of miR-135b, retinoic acid-treated SH-SY5Y cells were electroporated with miR-135b mimics to simulate over-expression. miR-135a, a close homolog of miR-135b (Table 7) was also included since it shares many mRNA targets with miR-135b and because we suspected that miR-135a was not identified in the initial screen because of technical problems (edge-well effects in the culture plates). miR-124, a well-known brain-enriched miRNA that was identified in the screen, was also included (FIG. 1D), as well as two control miRNA mimics (both originating from C. elegans and proven to not target specific mammalian mRNAs (Dharmacon, own observations)). In line with the results of the screen, miR-135b mimics affected the general morphology of SH-SY5Y cells (6.58±1.11 vs. 1.24±0.50, t(188)=4.64, p<0.0001 (control-1), or vs. 1.67±0.52, t(188)=4.19, p<0.0001 (control-2), one-way ANOVA, Sidak post-hoc test; FIG. 1D, left panel). Furthermore, miR-135b enhanced neurite outgrowth (3.53±0.69, t(189)=4.46, p<0.0001 vs. 0.55±0.28 (control-1), or vs. 0.90±0.35 t(189)=3.87, p=0.0006 (control-2), one-way ANOVAs, Sidak post-hoc tests; FIG. 1D, middle panel). Total hitscore and hitscore related to neurite length appeared to be affected by miR-135a, but these effects did not reach statistical significance. Neurite branching was significantly increased by miR-135a (2.00±0.71, t(189)=3.62, p=0.0015 vs. control-1 and t(189)=3.54; p=0.0020 vs. control-2) and miR-135b (1.53±0.36, t(189)=3.11, p=0.0085 vs. control-1 and t(189)=3.03, p=0.011 vs. control-2, one-way ANOVAs, Sidak post-hoc tests) mimics compared to control mimics (0.14±0.12 (control-1), or 0.15±0.11 (control-2); FIG. 1D, right panel). Together, these data confirm that miR-135b and miR-135a increase neurite growth and complexity.

Expression of miR-135a and miR-135b in the Developing Mouse and Hippocampus miR-135a and miR-135b sequences are preserved across species and detected in mouse brain tissue (Lagos-Quintana et al., 2002; Sempere et al., 2004; Ziats and Rennert, 2014; Caronia-Brown et al., 2016), but the precise spatiotemporal pattern of expression and functional role of these miRNAs in neurons remained poorly understood. We analyzed the expression of miR-135a and miR-135b by quantitative PCR (qPCR) in the developing (at E14, E16, P0 and P10 during which neurite growth and branching occur) and in adult mouse cortex and hippocampus. qPCR analysis detected miR-135a and miR-135b in embryonic and postnatal cortex and hippocampus. Expression of both miRNAs declined as cortical development progressed, and increased in adult. In contrast, while hippocampal miR-135a expression decreased towards P10 and increased in adult, miR-135b levels remained unchanged (FIG. 2A, C). Locked nucleic acid (LNA)-based in situ hybridization supported these results by revealing miR-135a and miR-135b expression in the cortex (at E14, P10 and adult, FIG. 2B) and hippocampus (at E14, P0, P10 and adult, FIG. 2D). Specific signals were observed in the dentate gyrus (DG) and CA3 pyramidal cell layers of the hippocampus and in the cortical plate of the developing cortex. Furthermore, both miRNAs were expressed abundantly in the adult mouse brain (FIG. 2B, D). Thus, miR-135a and miR-135b display specific spatiotemporal patterns of expression in the developing mouse brain.

miR-135s Control Axon Growth and Branching

Both miR-135a and miR-135b displayed prominent hippocampal expression and therefore, to investigate their functional role in neurons, hippocampal neurons were dissociated, transfected with miRNA mimics, and analyzed for axon growth at 4 days in vitro (DIV). First, qPCR was used to confirm endogenous expression of miR-135a and miR-135b in primary hippocampal cultures (FIG. 3A). At DIV4, the longest neurite, confirmed to be the axon, was significantly longer in neurons transfected with miR-135a (354.9±24.41 µm) or miR-135b (392.8±15.24 µm) mimics as compared to control (271.7±7.18 µm, t(776)=4.443 (Control-1 vs. miR-135a), t(900)=8.181 (Control-1 vs. miR-135b), both p<0.0001, unpaired T-tests; FIGS. 3B and C). Co-transfection of both miR-135a and miR-135b further increased axon length (428.7±14.97 µm, vs. Control-1 t(1022)=10.36, p<0.0001; vs. miR-135a t(590)=2.628, p=0.0088, unpaired T-tests). To assess the endogenous roles of miR-135a and miR-135b specific miRNA sponges designed to sequester miR-135a and miR-135b were co-transfected into hippocampal neurons. Decreased availability of the miRNAs resulted in a significant decrease in axon length (270.1±13.63 µm) compared to scrambled control sponge transfection (340.1±18.09 µm, t(211)=3.053, p=0.0026, unpaired T-test; FIG. 3D). Since the initial screen in SH-SY5Y cells showed effects on both neurite growth and branching, Sholl analysis was performed on primary hippocampal neurons transfected with miR-135a, miR-135b and the combination of the two mimics. Over-expression of both miRNAs alone and combined resulted in a marked increase in neurite branching in more distal regions (FIG. 3E). Interestingly, combined over-expression of miR-135a and miR-135b or of miR-135b alone also resulted in increased branching in the area close to the cell body. These data suggest an increase in the number of (branches of-) primary neurites and increased branching of the axon (control-1 vs. miR-135a: t(12800) ranges from 3.728 to 8.52, control-1 vs. miR-135b: t(13144) ranges from 3.735 to 6.426; control-1 vs. miR-135ab: t(12164) ranges from 3.84 to 7.496; p<0.001 for all; unpaired T-tests). The number of cumulative intersections of neurites with the Sholl circles was also higher in miR-135ab treated neurons (53.9±4.91) as compared to control (38.69±2.67, t(37)=2.414, p=0.021, unpaired T-test; FIG. 3F). Together, these experiments show that miR-135s (miRNA-135a and miR-135b) regulate axon growth and branching.

Cortical Neuron Migration Requires miR-135a and miR-135b miR-135a and miR-135b are expressed in hippocampal and cortical neurons as they migrate in the developing nervous system and extend neurites (FIG. 2) and manipulation of these miRNAs affects neuronal morphology in cultured hippocampal but also cortical neurons (FIG. 3; data not shown). To next assess the role of miR-135a and miR-135b in neurons in the complex environment of the embryonic brain, we performed ex vivo and in utero electroporation (van Erp et al., 2015). Ex vivo electroporation of mouse cortex with miR-135a and miR-135b mimics was performed at E14.5, brains were sliced and cultured, and analyzed at DIV4. Electroporation of miR-135a or miR-135b mimics induced a marked increase in the migration of cortical neurons from the ventricular zone (VZ) to the cortical plate (CP), exemplified by a larger number of electroporated GFP-positive neurons in the CP and fewer cells in the intermediate zone (IZ), as compared to control mimic conditions (FIG. 4A, see figure legend for statistical results). To confirm these effects in vivo, we delivered miRNA mimics or sponges to the E14.5 cortex by in utero electroporation and analyzed migrating neurons at E16.5. Mimics for miR-135a and miR-135b were combined to elicit significant phenotypes in a short time period. In line with the ex vivo electroporation data, delivery of miR-135ab mimics to the cortex enhanced neuronal migration towards the pial surface and induced a concomitant depletion in deeper layers such as the SVZ (FIG. 4B, see figure legend for statistical results). Electroporation of miR-135a and miR-135b sponges had a small, but opposite effect, i.e. delayed migration of cortical neurons, confirming an endogenous requirement for miR-135a and miR-135b in cortical neuron migration (FIG. 4C, see figure legend for statistical results). As a measure for in vivo neurite outgrowth, we quantified the length of the leading process of migrating neurons following in utero electroporation. While miR-135a and miR-135b mimics induced an increase in leading process length ($30.65 \pm 1.09$ vs. $23.91 \pm 1.01$, $t(364)=4.497$, $p<0.0001$, unpaired T-test; FIG. 4B), leading processes were shorter after application of miR-135 sponges ($25.23 \pm 0.80$ vs. $33.78 \pm 1.28$, $t(325)=5.712$, $p<0.0001$, unpaired T-test; FIG. 4C). To assess the long-term effect of miR-135 over-expression in vivo, we isolated the brains from embryos in utero electroporated at E14.5 at P4 (FIG. 4D) and P10 (FIG. 4E). Interestingly, at P4 electroporation of miR-135a and miR-135b significantly enhanced neuron migration resulting in a larger number of neurons in upper cortical areas (FIG. 4D, see figure legend for statistical results). At P10, a small but significant difference in the distribution of cells in the upper cortical layers remained between embryos electroporated with control or miR135 mimics (FIG. 4E, see figure legend for statistical results). Overall, these data suggest that, in line with their effects in cultured neurons, miR-135a and miR-135b control neurite length and neuron migration in vivo.

miRNA-135s Control Axon Growth and Neuronal Migration Through KLF4

How do miR-135s (both miR-135a and miR-135b) control neuronal morphology and migration? Based on high sequence similarity and comparable biological effects in neurons, we hypothesized that miRNA-135s (miRNA-135a and miRNA-135b) may share many of their mRNA targets. To identify those targets, we performed target prediction analysis using miRecords (Xiao et al., 2009). By combining data from at least 6 databases in miRecords, 57 overlapping targets were found for miR-135a and miR-135b. Several of these targets had confirmed roles in neurite growth and neuronal morphology. However, for many of these targets (e.g. PTK2, TAF4) knockdown had been reported to reduce neurite growth or neuron migration (data not shown). KLF4 was particularly interesting as knockdown of KLF4 in neurons, similar to overexpression of miR-135s, enhances axon growth, leading process length and neuronal migration (Moore et al., 2009; Qin and Zhang, 2012). Furthermore, recent work in vascular smooth muscle and hepatocellular carcinoma cells links miRNA-135a to KLF4 (Lin et al., 2016; Yao et al., 2016). Finally, KLF4 contains predicted binding sites for several miRNAs in the top list of our initial screen (miR-124, miR-449, miR-488, miR-499; FIG. 1C). The 3'-UTR of KLF4 harbours two predicted miR-135 binding sites (FIG. 5A) and to confirm that KLF4 is a bona fide target for miR-135s we first performed dual-luciferase reporter assays by co-transfecting psiCHECK2-KLF4 3'-UTR and miR-135a and miR-135b mimics into HEK293 cells. miR-135a and miR-135b mimics significantly decreased luciferase activity both when transfected alone or when combined (FIG. 5B). To confirm direct and specific binding, the miRNA-135 binding site that was predicted to have the strongest association (according to www.microRNA.org) was mutated (site 394; FIG. 5A). This mutation completely abolished miR-135-mediated effects on luciferase activity, suggesting that site 394 is the main miR-135 binding site in KLF4 (KLF4 WT miR-135a vs. KLF4 mutated miR-135a, $t(4)=4.715$, $p=0.0092$; KLF WT miR-135b vs. KLF4 mutated miR-135b, $t(4)=2.933$, $p=0.0427$; KLF4 WT miR-135ab vs. KLF4 mutated miR-135ab, $t(4)=4.735$, $p=0.0091$, Unpaired T-test) (FIG. 5B). Next, we performed immunohistochemistry for KLF4 to assess whether miR-135s and KLF4 are expressed in the same brain regions. Indeed, in line with our in situ hybridization data for miR-135a and miR-135b, prominent KLF4 expression was detected in neurons in the CP of the E16.5 and adult cortex and in the developing and adult hippocampus (FIG. 5C). To further validate the relation between miR-135 and KLF4, endogenous KLF4 protein levels were analyzed in transfected Neuro2A cells by Western blot. Reduced KLF4 expression was observed after transfection with miR-135a and miR-135b mimics as compared to control mimic transfection (miR-135ab vs. Control-1: $0.378 \pm 0.032$ vs. $0.643 \pm 0.01$, $t(10)=3.170$, $p=0.010$, Unpaired T-test; FIG. 5D). Together, these data indicate that KLF4 is a target for miR-135a and miR-135b.

Next, we assessed whether the effects of miR-135s (miR-135a and miR-135b) on axon growth and neuronal migration require KLF4. In primary hippocampal neurons, co-transfection of KLF4 cDNA lacking the 3'-UTR (KLF4A3'-UTR), and therefore miR-135 binding sites, markedly reduced the increase in axon growth by transfection of miR-135 mimics (FIG. 5E, Control-1 vs. Control-1+KLF4: $271.1 \pm 7.178$ vs. $239.9 + 9.701$, $t(785)=2.250$, $p=0.025$; Control-1 vs. miR-135ab+KLF4: $271.1 \pm 7.178$ vs. $331.7 \pm 10.92$, $t(980)=4.787$, $p<0.0001$; miR-135ab+KLF4 vs. miR-135ab: $331.7 \pm 10.92$ vs. $428.7 \pm 14.97$, $t(794)=5.139$, $p<0.0001$, Unpaired T-test). FIG. 5F). Similarly, the positive effect of miR-135a and miR-135b over-expression on cortical neuron migration and leading process length was normalized by co-electroporation of KLF4A3'-UTR (see figure legend for statistical results of neuronal migration, for leading process length: miR-135ab: $32.34 \pm 1.084$, miR-135ab+KLF4: $20.42 \pm 0.79$, $t(240)=8.851$, $p<0.0001$. Unpaired T-test. FIG. 5G). Together, these experiments indicate that miRNA-135s enhance axon growth and neuronal migration by repressing KLF4 protein expression.

Exogenous miR-135 Application Promotes Optic Nerve Regeneration Through KLF4

Lowering neuronal KLF4 expression not only promotes axon growth in developing neurons but is also one of the few experimental treatments that facilitates regenerative axon growth following CNS injury. Knockout mice lacking KLF4 showed significantly enhanced retinal ganglion cell (RGC) axon regeneration following optic nerve injury (Moore et al., 2009; Qin et al., 2013) This effect of KLF4 requires downstream signalling via the Janus kinase (JAK)-signal transducer and activator of transcription 3 (STAT3) pathway (Qin et al., 2013), but upstream regulatory mechanisms of this pathway remain unknown. Because of these results and our data showing that miR-135 mimics can promote axon growth by reducing KLF4 expression, we next asked whether application of miR-135 mimics can facilitate regenerative axon growth in the CNS. To test this hypothesis, we used the optic nerve crush model. siRNAs and miRNA mimics can be efficiently targeted to adult RGCs and optic nerve regeneration can be reliably quantified (Dickendesher et al., 2012; van Erp et al., 2015). Further, both KLF4 and miR-135s are expressed in adult mouse RGCs and reducing KLF4 expression enhances optic nerve regeneration (Moore et al., 2009; Qin et al., 2013). First, we confirmed that intravitreal injection of miR-135 mimics leads to an elevation of miR-135a and miR-135b levels (FIG. 6A, B). Although endogenous expression of miR-135s was detected, intravitreal injection of mimics markedly increased miR-135a and miR-135b expression, as compared to injections with scrambled controls (Ctrl1 vs. miR-135a: t(4)=2.462, p=0.0348; Ctrl1 vs. miR-135b: t(4)=4.309, p=0.0063, Unpaired T-test). In line with our data identifying KLF4 as a miR-135 target (FIG. 5), injection of miR-135 mimics in the eye led to a decrease in KLF4 expression (Ctrl1 vs. miR-135ab: t(3)=2.901, p=0.0312, Unpaired T-test. FIG. 6C). Next we assessed the effect of miR-135 injection on optic nerve regeneration. Following administration of scrambled control mimics, most CTB-labeled RGC axons stopped abruptly at the crush site and only few fibers crossed the lesion into the distal nerve (FIG. 6D, E). In contrast, miR-135 mimics induced significant regeneration (0.2 mm, Control-1+GFP vs. miR-135ab+GFP: 46.89±6.816 vs. 208.4±35.11, t(96)=7.374, p<0.0001. one-way ANOVA with Sidak post-hoc test) beyond the lesion site and more pronounced sprouting in the distal segment of the nerve (FIG. 6D, E). To examine whether this effect was caused by the ability of miR-135s to reduce KLF4 expression, we combined intravitreal injection of miR-135 mimics with co-transfection of vectors expressing GFP (pCAG-GFP) or a KLF4 cDNA which is not targeted by miR-135s (pCAG-KLF4) (van Erp et al., 2015). Overexpression of KLF4 did not affect RGC axon regeneration, but partly normalized the regeneration promoting effect of miR-135 mimic injection following ONI (0.2 mm, Control-1+GFP vs. miR-135ab+KLF4: 46.89±6.816 vs. 115.4±24.63, t(96)=3.128, p=0.028, one-way ANOVA with Sidak post-hoc test) (FIG. 6D, E). Importantly, this effect of KLF4 was not due to its ability to regulate miR-135 expression as miR-135a and miR-135b levels in the retina were similar following miR-135ab+GFP and miR-135ab+KLF4 administration (FIG. 6F).

Intravitreal injection may target miRNA mimics to different cell types in the mouse retina. To ensure that miR-135a and miR-135b can have a positive, cell autonomous effect in RGCs on axon regeneration, overexpression of both miRNAs was induced by intravitreal injection of AAV2, a viral serotype known to specifically target RGCs (FIG. 6A, G) (Weitz et al., 2013). Indeed, targeting miR-135s to RGCs induced RGC axon regeneration at a level comparable to that observed following mimic injection (0.2 mm, AAV2-Control vs. AAV2-miR-135ab: 53.76±10.62 vs. 243.6±23.59, t(30)=10.98, p<0.0001. one-way ANOVA with Sidak post-hoc test) (FIG. 6H). Finally, to assess a potential endogenous role of miR-135a and miR-135b in regenerating RGC axons specific miRNA sponges designed to sequester miR-135a and miR-135b were injected intravitreally. Decreased availability of the miRNAs resulted in a small but significant decrease in the number of regenerating axons close to the injury site compared to scrambled control sponge transfection (0.2 mm, Control sponge vs. miR-135a/b sponge: 49.6±4.566 vs. 28.46±7.593, t(18)=3.589, p=0.0063. one-way ANOVA with Sidak post-hoc test) (FIG. 6I). Together, these results indicate that overexpression of miR-135 promotes CNS axon regeneration in part by reducing KLF4 expression, while decreasing functional miR-135 levels further reduces the regenerative potential of adult RGCs.

During embryonic development, axons extend over long distances to establish functional connections. In contrast, axon regeneration in the adult mammalian central nervous system (CNS) is limited, in part by a reduced intrinsic capacity for axon growth. Therefore, insight into the intrinsic control of axon growth may provide new avenues for enhancing CNS regeneration. Here, we performed one of the first miRNome-wide functional miRNA screens to identify microRNAs (miRNAs) with robust effects on axon growth. High-content screening identified the miRNA-135s (miR-135a and miR-135b) as potent stimulators of axon growth and cortical neuron migration in vitro and in vivo in male and female mice. Intriguingly, both these developmental effects of miR-135s relied, in part, on silencing of KLF4, an intrinsic inhibitor of axon growth and regeneration. These results prompted us to test the effect of miR-135s on axon regeneration following injury. Our study shows that intravitreal application of miR-135s facilitates retinal ganglion cell (RGC) axon regeneration following optic nerve injury (ONI) in adult mice in part by repressing KLF4. In contrast, depletion of miR-135s further reduced RGC axon regeneration. Together, these data identify a novel neuronal role for miR-135s and the miR-135-KLF-4 pathway, and highlight the potential of miRNAs as tools for enhancing CNS axon regeneration.

Example 3: The Role of miR-135a in Temporal Lobe Epilepsy

Epilepsy is a chronic neurological disorder that effects 65 million people worldwide, is a major socioeconomic burden (Moshe et al., 2015). It is characterized by recurrent unprovoked seizures, caused due to abnormal and synchronous neuronal discharges with in the brain (Chang and Lowenstein, 2003). In some cases, epilepsy is caused by single gene mutations mainly of genes encoding ion channels, but the reason for most epilepsies is unknown. Temporal lobe Epilepsy (TLE) is a subclass of epilepsy, accounts for about one third of all patients with epilepsy (Engel, 2001). It consists of several subgroups of which Mesial Temporal Lobe Epilepsy with Hippocampal Sclerosis (MTLE-HS) is the most severe one. MTLE-HS presents with a typical set of diagnostics, clinical and pathological characteristics (neuron loss, gliosis and axonal sprouting) and is known to be most resistant to pharmacological treatment (Wieser and Epilepsy, 2004). For many patients, surgical removal of the hippocampus is the only alternative to achieve seizure control (Semah et al., 1998). The pathological mechanisms underlying TLE are largely unknown. Anticonvulsant and anti-epileptic drugs are used to treat these patients. But, unfortunately these only reduce the occurrence of seizures but do not treat the underlying pathophysiology. Hence there is an urgent need to develop novel treatment strategies for this disabling condition. A need for developing disease-modifying drugs is increasingly recognized by research community and in clinical practice (Loscher et al., 2013).

The pathological mechanisms underlying MTLE are still largely unknown. Animal models of epilepsy and human tissue studies suggest that epileptogenesis involves a cascade of molecular, cellular and neuronal network alterations (Rakhade and Jensen, 2009). Approaches starting from the transcriptome have revealed that patterns of gene expression are significantly altered in human MTLE (van Gassen et al., 2008) and during epileptogenesis in animal models for TLE (Gorter et al., 2006; Pitkanen and Lukasiuk, 2009; Rakhade and Jensen, 2009). This dysregulation effects entire gene regulatory networks that normally control gene expression that regulate pathways involving inflammation, gliosis, synaptic structure and neuronal function. Insight into whether or how these mechanisms are altered may not only provide important new insights into the pathogenesis of TLE, but could also yield novel targets for therapy.

During the past several years, microRNAs (miRNAs) have emerged as important post-transcriptional regulators of gene expression, providing a completely new level of control of large groups of genes. miRNAs are small, non-coding RNAs (18-25 nucleotides long) that are generated by a series of cleavage events from longer RNA precursors transcribed from the genome. miRNAs recognize partially complementary target sequences in cognate mRNAs and inhibit protein expression by either destabilizing their mRNA targets or by inhibiting protein translation (Kosik, 2006). A single miRNA can have many different targets, it can regulate several genes in multiple pathways or single genes in multiple pathways (Ebert and Sharp, 2012). Deletion of miR-128, a brain expressed miRNA led to upregulation of more than thousand transcripts, from which 154 were direct targets of miR-128 and 25 were from extracellular signal kinase regulated kinase ½ (ERK1/2) network (Tan et al., 2013). This property of multi-targeting is of advantage as it can target genes and disrupt multiple pathways but at the same time disadvantageous due to the potential of unwanted side effects of miRNA-based therapy (Henshall et al., 2016). Overall miRNAs can control different aspects of cellular physiology and are considered as novel targets for therapy (Czech, 2006).

Deregulation of miRNAs has been linked to several pathological mechanisms observed in TLE (Gorter et al., 2014; Jimenez-Mateos et al., 2012; Jimenez-Mateos and Henshall, 2013; Kan et al., 2012). Studies in mice show that miR-134 inhibition after status epilepticus suppressed the development of spontaneous seizures (Jimenez-Mateos et al., 2012) and complete loss of miR-128 leads to fatal epilepsy (Tan et al., 2013). Similarly, miR-324-5p was found to inhibit Kv4.2 expression in epilepsy (a major mediator of hyperpolarizing A-type currents in brain, which is a crucial regulator of neuronal excitability), and antagonizing miR-324 is seizure suppressive and neuroprotective (Gross et al., 2016). Not just these few, but the function of more miRNAs has been investigated using miRNA inhibitors (called antagomirs: miRNA-targeting antisense oligonucleotides) and mimics (agomirs) in various animal models of epilepsy (reviewed in (Henshall et al., 2016)). Of those miRNAs (12 out of 14) that are functionally validated have been found to have beneficial effects on electroencephalogram (EEG), seizures or histopathology level. Hence miRNAs could be a flexible and broad class of targets for treatment of seizures (Henshall et al., 2016).

Materials and Methods

RNA Isolation and Quantitative PCR

Two patient groups (six each) mTLE-HS (without hippocampal sclerosis), mTLE+HS (with hippocampal sclerosis) and six post-mortem controls were used. Patient tissue representing all hippocampal regions was selected following nissl stainning. Approximately 20 mg of tissue was collected by slicing 25 µm thick sections on a cryostat and stored at −80° C. Total RNA was isolated using miRNeasy kit (Qiagen), according to manufacturer's instructions. RNA quantity was determined using Nanodrop (Thermo Scientific), first strand cDNA synthesis was performed using a universal cDNA synthesis kit (Exiqon). Quantitive PCR reactions were run on Quantstudio 6 flex Real-Time PCR system (Applied Biosystems) using microRNA LNA™ PCR primer sets and SYBR Green master mix (Exiqon). All samples were run in duplicates. Ct values were determined using Quant studio real time per software v1.1. The expression levels of different miRNAs were estimated by normalizing to 5s rRNA, and the statistical significance was analyzed with single factor ANOVA and $p<0.05$ was considered as significant.

Non-Radioactive In Situ Hybridisation

Non-radioactive in situ hybridization was performed as described previously (Obernosterer et al., 2007). Three patients from each patient group (Control, mTLE-HS and mTLE+HS) with two to three sections per patient were used for performing the in situ. Briefly, 16 µm thick sections from fresh frozen human hippocampal tissue were collected on glass slides and stored at −80° C. until use. On day of in situ sections were fixed (4% PFA for 10 min at room temperature (RT)), acetylated (10 min at RT) and treated with proteinase K (5 µg/ml for 5 m at RT). Pre-hybridisation was performed for 1 h at RT. Hybridisation was performed with 10 nM of double-DIG (3' and 5')—labeled locked nucleic acid (LNA) probe for human-miR-135a-5p (Exiqon) or LNA-DIG Scramble probe overnight at 50° C. Slides were washed at 55° C. in 0.2×SSC for 1 h, followed by blocking with 10% fetal calf serum (FCS) in B1 buffer (0.1 M Tris pH 7.5/0.15 M NaCl) for 1 h at RT. Sections were incubated with anti-digoxigenin-AP Fab fragments (1:2,500, Roche Diagnostics) in 10% FCS in B1 buffer overnight at 4° C. Slides were treated with 5-bromo-4-chloro-3-indolyl phosphate (BCIP) and nitrobluetetrazolium (NBT) substrates (NBT/BCIP stock solution, Roche Diagnostics) in B3 (0.1 M Tris pH 9.5/0.1 M NaCl/50 mM MgCl2) for 5-20 h at RT. Staining was stopped by washing in PBS and slides were mounted using vectashield (VectorLabs). No staining was observed in sections hybridized with scramble probe. Images were acquired with brightfiled microscope and processed on ImageJ.

FISH

Similar protocol was used for FISH except hybridization was done at 55° C. and washes at 60° C., to reduce background staining. After blocking slides were co-incubated with anti-Digoxigenin-POD (1;500, Roche Diagnostics) and NeuN (1;400, Millipore) or GFAP (1;1000, Dako Cytomation) antibody overnight at 4° C. Signal was amplified using ISA™ Cyanine 3 System (1;50 in amplification diluent, PerkinElmer) for 10 min at RT. After washes with PBS, slides were incubated with secondary antibody (Alexafluor 488, Invitrogen) specific against the primary antibody for 1.5 h at RT. Nuclei were stained with DAPI (10 min at RT) and slides were mounted using ProLong Gold (Life Technologies). Images were acquired using Confocal laser scanning microscope (LSM880, Zeiss).

Intra Amygdala Kainate Mice

Status epilepticus (SE) induction, EEG recording and analysis was done as in previous studies (Jimenez-Mateos et al., 2012; Mouri et al., 2008). Briefly, mice were implanted with telemetric EEG transmitters (Data Systems International). Two days after surgery, SE was induced for 40 min by administration of kainic acid (0.3 ug in 0.2 ul in PBS). Control animals received the same volume of PBS. Forty minutes after microinjection, mice received an intravenous injection of lorazepam (6 mg/kg) to stop SE. Mice were EEG monitored for 1 hr after injection to make sure that all the seizure activity is reduced. From day 7 after SE induction, baseline EEG was recorded.

Intra Cerebro Ventricular (i.c.v) Injections

For antagomirs, i.c.v injections were performed streotractically. On day 14 after SE mice received an infusion of 1.0 nmol/2 ul of Antagomir-135a LNA modified and 3'-cholesterol-modified oligonucleotides (Exiqon) in PBS. Controls received same volume of PBS. During this period mice were continuously EEG and video monitored for another 2 weeks. EEG data analysis was performed using LabChart 8 software (ADInstruments Ltd). The antagomir used in this experiment is available from Exiqon A/S, Denmark (Product Number 199900 Batch Number 182482—Exiqon is a Qiagen company) and consisted of an oligonucleotide featuring phosphorothioate backbone linkages instead of phosphodiester backbone linkages, and having a sequence represented by CACATAGGAATAAAAAGCCAT (SEQ ID NO: 261). The antagomir was 3'-modified with a tetraethyleneglycol-linked cholesterol.

Results

Increased Expression of miR-135a in Human and Mouse Model of TLE

Increased expression of miR-135a was observed in human TLE using a microRNA array (Kan et al., 2012). Upon validating the expression of miR-135a by quantitative PCR in human TLE tissue comparing expression in two patient groups (mTLE+HS, mTLE−HS) to controls, a significant reduction in miR-135a levels was observed in mTLE-HS condition whereas the expression of miR-135a was increased in mTLE+HS condition (FIG. 7A). By in situ hybridisation (ISH) the localization of miR-135a was checked and found a stronger signal in mTLE+HS condition (FIG. 7B). To confirm the cell type specific localization fluorescent ISH was performed and found miR-135a co-localized mainly with the neuronal marker NeuN (FIG. 8).

Next, we checked if seizure induction (status epilepticus) in an experimental model of TLE by intraamygdala microinjection of glutamate receptor agonist kainic acid (Mouri et al., 2008), will mimic the increased levels of miR-135a found in human patient tissue. By qPCR, a significant increase in miR-135a levels were observed at 2 weeks after SE induction specifically in the CA3 and DG regions of the hippocampus (FIG. 9A). Similarly, a stronger signal for miR-135a was detected in the soma of pyramidal neurons in the hippocampus, and also in neuronal cells of cortex, thalamic and amygdala regions by ISH at 2 weeks after SE, and no change in expression at 24 h (FIG. 9B).

Reduction of Spontaneous Seizures Upon Silencing miR-135a

To further understand the in vivo effect of miR-135a increased expression in TLE and check if it contributes to the recurrence of spontaneous seizures, we targeted it by antagomirs. Antagomirs targeting miR-135a were administered to reduce the increased levels of miR-135a after 2 weeks after SE. SE induced mice were injected with anti-miRs for miR-135a or PBS (intra-cerebro-ventricularly) at 2 weeks after SE and continuously EEG monitored for two weeks after injection (FIG. 10B). There was no significant difference between treated and control animals in seizure frequency from day 7-day 14 (p=0.743) after SE, baseline recording. Following treatment with miR-135a on day 14, there was an almost complete separation of the distributions of seizure frequencies in treated and control animals, with a Wilcoxon Mann-Whitney statistic of 0.90, 95% CI 0.65 to 0.97, indicating a 90% probability of a control animal having a higher seizure frequency than a treated animal (P<0.001). Silencing of miR-135a expression protected mice from spontaneous epileptic seizures compared to PBS injected. The number of spontaneous epileptic seizures were significantly reduced, total time spent during seizures was reduced but no difference was observed in the severity of seizures (FIG. 10C). These data suggest that miR-135a increased expression at 2 weeks after SE contributes to increased seizure activity, and this can be rescued by in vivo depletion of miR-135a. Further histological analysis is to be performed in the antimiR injected brains to assess if pathological hallmarks of TLE (neuron loss, gliosis, rearrangement of mossy fibers) are rescued. No off-target effects of the anti-miR were observed, ant-135a was specifically targeting miR-135a as the levels of miR-124 were unaltered at 1 nmol (FIG. 10A).

Summary

In this study, we found increased miR-135a levels in intra-amygdala kainate mice (2 weeks after SE), and silencing miR-135a expression using antagomirs protected mice from spontaneous epileptic seizures. This is the first time that silencing miR-135a in already established epilepsy after epileptogenesis, can significantly reduce recurrence of spontaneous seizures. To identify new targets that are mediating miR-135a function in TLE we performed immunoprecipitation using biotin-tagged miRNA mimics and found several interesting targets (data not shown), for example MEF2 as a potential target. MEF2 proteins are a family of transcription factors which mediate activity-dependent synaptic development. MEF proteins are activated by neurotrophin stimulation and calcium influx resulting from increased neurotransmitter release at synapses (Flavell et al., 2008). MEF2 negatively regulates excitatory synapses (Flavell et al., 2006), and loss of MEF2 in mTLE could lead to abnormal spine formation and contribute to aberrant firing pattern and cell death observed in epilepsy.

TABLE 1

Precursor sequences of miRNAs identified in screening or referred to
List of miRNA precursor sequences (5' to 3' direction). All sequences
were obtained from miRBase (release 21: June 2014; www.mirbase.org) and
checked for consistency with SIROCCO. In case of discrepancy, SIROCCO
data was used.

| SEQ ID No | Precursor of: | Precursor sequence |
|---|---|---|
| 1 | hsa-mir-135a-1 | AGGCCUCGCUGUUCUCUAUGGCUUUUUAUUCCUAUGUG AUUCUACUGCUCACUCAUAUAGGGAUUGGAGCCGUGGC GCACGGCGGGGACA |
| 2 | hsa-mir-135a-2 | AGAUAAAUUCACUCUAGUGCUUUAUGGCUUUUUAUUCCU AUGUGAUAGUAAUAAAGUCUCAUGUAGGGAUGGAAGCC AUGAAAUACAUUGUGAAAAAUCAUCAAC |
| 3 | hsa-mir-135b | CCCCUCCACUCUGCUGUGGCCUAUGGCUUUUCAUUCCU AUGUGAUUGCUGUCCCAAACUCAUGUAGGGCUAAAAGC CAUGGGCUACAGUGAGGGGCGAGCUCC |
| 4 | hsa-mir-196a-1 | GAACUGCUGAGUGAAUUAGGUAGUUUCAUGUUGUUGGG CCUGGGUUUCUGAACACAACAACAUUAAACCACCCGAUU CAC |

TABLE 2

Mature and mimic sequences of canonical miRNAs identified in screening
or referred to
List of mature miRNA sequences (5' to 3' direction). All sequences were
obtained from miRBase (release 21: June 2014; www.mirbase.org) and
checked for consistency with SIROCCO. In case of discrepancy, SIROCCO
data was used.

| miRNA precursor | Mature miRNA | SEQ ID No | SEQ mature miRNA |
|---|---|---|---|
| hsa-mir-135a-1 hsa-mir-135a-2 | hsa-miR-135a-5p | 5 | UAUGGCUUUUUAUUCCUAUGUGA |
| hsa-mir-135a-1 | hsa-miR-135a-3p | 6 | UAUAGGGAUUGGAGCCGUGGCG |
| hsa-mir-135b | hsa-miR-135b-5p | 7 | UAUGGCUUUUCAUUCCUAUGUGA |
| hsa-mir-135b | hsa-miR-135b-3p | 8 | AUGUAGGGCUAAAAGCCAUGGG |
| hsa-mir-196a-1 | hsa-miR-196a-5p | 9 | UAGGUAGUUUCAUGUUGUUGGG |

TABLE 3

DNA sequences of miRNAs identified in screening

| SEQ ID No | miRNA | Cloned sequence in lentiviral vector |
|---|---|---|
| 10 | hsa-miR-135a-1 | TCCACACCCTCAGGGAGGAGGGGAGGGTTGGGGTGGAAGAAGT GCCTGCAAGAGCAGCCCCAGGCCTCGCTGTTCTCTATGGCTTTT TATTCCTATGTGATTCTACTGCTCACTCATATAGGGATTGGAGCC GTGGCGCACGGCGGGGACAGCCAGCGGAGGGTTCTGACACTG AGCAAGGGGGCTCAAAAGGAGGCAGGACAGTGGCACCTCCCTC |
| 11 | hsa-miR-135a-2 | GCTTTGAAATGGTTGTGAAGTCATGTGAAGAAAATAAGTTTTGCA TCCGACCAAGATAAATTCACTCTAGTGCTTTATGGCTTTTTATTCC TATGTGATAGTAATAAAGTCTCATGTAGGGATGGAAGCCATGAAA TACATTGTGAAAAATCATCAACTAAGAAGGGGCCATCAGTATAGA GAACGTTAGCCTGTGGAGCTGTG |
| 12 | hsa-miR-135b | CTCGCTTCCCTATGAGATTCCTGCCGCTGGACCCCTCCACTCTG CTGTGGCCTATGGCTTTTCATTCCTATGTGATTGCTGTCCCAAAC TCATGTAGGGCTAAAAGCCATGGGCTACAGTGAGGGGCGAGCT CCTTCTCCTGCGCAGCTGCACCTCCCATGGGACCAGGTTCGGA GCCAGCCACCAAGGGGCACCAGAAGGAGGCTTTG |

TABLE 3-continued

DNA sequences of miRNAs identified in screening

| SEQ ID No | miRNA | Cloned sequence in lentiviral vector |
|---|---|---|
| 13 | hsa-miR-196a-1 | CCCCCAGTGAGCTCTTGACCTAGAGCTTGAATTGGAACTGCTGAGTGAATTAGGTAGTTTCATGTTGTTGGGCCTGGGTTTCTGAACACAACAACATTAAACCACCCGATTCACGGCAGTTACTGCTCCTCGCTTAGCTGGAGGAGTTGGGG |

TABLE 4

Seed sequences of canonical miRNAs

List of miRNA seed sequences (5 to 3' direction). Seed sequence is defined as nucleotide 2-8 (5' to 3' direction) of the mature miRNA sequence processed from miRNA precursor hairpins. All sequence designations were obtained from miRBase (release 21: June 2014; www.mirbase.org). The seed sequences of the mature miRNAs listed in Table 2 are enclosed in this Table.

| miRNA precursor | Mature miRNA | SEQ ID No | Seed sequence mature miRNA |
|---|---|---|---|
| hsa-mir-135a-1<br>hsa-mir-135a-2 | hsa-miR-135a-5p | 14 | AUGGCUU |
| hsa-mir-135a-1 | hsa-miR-135a-3p | 15 | AUAGGGA |
| hsa-mir-135b | hsa-miR-135b-5p | 16 | AUGGCUU |
| hsa-mir-135b | hsa-miR-135b-3p | 17 | UGUAGGG |
| hsa-mir-196a-1 | hsa-miR-196a-5p | 18 | AGGUAGU |

TABLE 5

IsomiRs and seed sequences of miRNAs identified in screening (see Table 1) or referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
|---|---|---|
| hsa-miR-135a-5p | AUGGCUU (19)<br>UGGCUUU (20)<br>GGCUUUU (21)<br>GCUUUUU (22)<br>CUUUUUA (23)<br>UUUUUAU (24)<br>UUUUAUU (25)<br>UUUAUUC (26)<br>UUAUUCC (27) | UAUGGCUUUUUAUUCCUAUGUGAUAG (57)<br>UAUGGCUUUUUAUUCCUAUGUGAUUC (58)<br>UAUGGCUUUUUAUUCCUAUGUGAUA (59)<br>UAUGGCUUUUUAUUCCUAUGUGAU (60)<br>UAUGGCUUUUUAUUCCUAUGUG (61)<br>UAUGGCUUUUUAUUCCUAUGU (62)<br>UAUGGCUUUUUAUUCCUAUG (63)<br>UAUGGCUUUUUAUUCCUAU (64)<br>UAUGGCUUUUUAUUCCUA (65)<br>UAUGGCUUUUUAUUC (66)<br>UAUGGCUUUUUAUUCC (67)<br>AUGGCUUUUUAUUCCUAUGUGAU (68)<br>AUGGCUUUUUAUUCCUAUGUGA (69)<br>AUGGCUUUUUAUUCCUAUGUG (70)<br>AUGGCUUUUUAUUCCUAUGU (71)<br>UGGCUUUUUAUUCCUAUGUGAU (72)<br>UGGCUUUUUAUUCCUAUGUGA (73)<br>UGGCUUUUUAUUCCUAUGUG (74)<br>GGCUUUUUAUUCCUAUGUGA (75)<br>GCUUUUUAUUCCUAUGUGA (76)<br>GCUUUUUAUUCCUAUGUG (77)<br>GCUUUUUAUUCCUAUGU (78)<br>CUUUUUAUUCCUAUGUGA (79)<br>CUUUUUAUUCCUAUGUG (80)<br>CUUUUUAUUCCUAUG (81)<br>CUUUUUAUUCCUAUGU (82)<br>UUUUUAUUCCUAUGUGA (83)<br>UUUUUAUUCCUAUGU (84)<br>UUUUUAUUCCUAUGUG (85)<br>UUUUAUUCCUAUGUGA (86)<br>UUUUAUUCCUAUGUG (87)<br>UUUAUUCCUAUGUGA (88) |

TABLE 5-continued

IsomiRs and seed sequences of miRNAs identified in screening (see Table 1) or referred to in the application. These isomiR sequences have been derived from small RNA high-throughput deep sequencing analyses, and were obtained after combining the data of 87 human tissue samples.

| Mature miRNA | Seed (SEQ ID NO) | IsomiR sequence (SEQ ID NO) |
| --- | --- | --- |
| hsa-miR-135a-3p | AUAGGGA (28) | UAUAGGGAUUGGAGCCGUGGC (89) |
| | UAUAGGG (29) | UAUAGGGAUUGGAGCCGUGG (90) |
| | AUAUAGG (30) | AUAUAGGGAUUGGAGCCGUGGC (91) |
| | UAGGGAU (31) | AUAUAGGGAUUGGAGCCGUGG (92) |
| | | AUAUAGGGAUUGGAGCCGUG (93) |
| | | CAUAUAGGGAUUGGAGCCGUGGCG (94) |
| | | AUAGGGAUUGGAGCCGUGGC (95) |
| hsa-miR-135b-5p | AUGGCUU (32) | UAUGGCUUUUCAUUCCUAUG (96) |
| | UGGCUUU (33) | UAUGGCUUUUCAUUCCUAU (97) |
| | GGCUUUU (34) | UAUGGCUUUUCAUUCCUA (98) |
| | CUUUUCA (35) | AUGGCUUUUCAUUCCUAUGUGAU (99) |
| | UUUUCAU (36) | AUGGCUUUUCAUUCCUAUGUGA (100) |
| | UUUCAUU (37) | AUGGCUUUUCAUUCCUAUGUG (101) |
| | UUCAUUC (38) | AUGGCUUUUCAUUCCUAUGU (102) |
| | UAUGGCU (39) | UGGCUUUUCAUUCCUAUGUGA (103) |
| | | GCUUUUCAUUCCUAUGUGA (104) |
| | | CUUUUCAUUCCUAUGUGA (105) |
| | | CUUUUCAUUCCUAUGU (106) |
| | | CUUUUCAUUCCUAUGUG (107) |
| | | CUUUUCAUUCCUAUG (108) |
| | | UUUUCAUUCCUAUGUGA (109) |
| | | UUUUCAUUCCUAUGU (110) |
| | | UUUUCAUUCCUAUGUG (111) |
| | | UUUCAUUCCUAUGUGA (112) |
| | | UUUCAUUCCUAUGUG (113) |
| | | CUAUGGCUUUUCAUUCCUAUGU (114) |
| hsa-miR-135b-3p | UGUAGGG (40) | AUGUAGGGCUAAAAGCCAUGGGC (115) |
| | GUAGGGC (41) | AUGUAGGGCUAAAAGCCAUGG (116) |
| | GGCUAAA (42) | AUGUAGGGCUAAAAG (117) |
| | | UGUAGGGCUAAAAGCCAUGGGCU (118) |
| | | UGUAGGGCUAAAAGCCAUGGGC (119) |
| | | GGGCUAAAAGCCAUGGG (120) |
| hsa-miR-196a-5p | AGGUAGU (43) | UAGGUAGUUUCAUGUUGUUGGGCC (121) |
| | GGUAGUU (44) | UAGGUAGUUUCAUGUUGUUGGGC (122) |
| | GUAGUUU (45) | UAGGUAGUUUCAUGUUGUUGG (123) |
| | UAGUUUC (46) | UAGGUAGUUUCAUGUUGUUG (124) |
| | AGUUUCA (47) | UAGGUAGUUUCAUGUUGUU (125) |
| | GUUUCAU (48) | UAGGUAGUUUCAUGUUGU (126) |
| | UUCAUGU (49) | UAGGUAGUUUCAUGUUG (127) |
| | UUAGGUA (50) | UAGGUAGUUUCAUGUU (128) |
| | UAGGUAG (51) | UAGGUAGUUUCAUGU (129) |
| | | AGGUAGUUUCAUGUUGUUGGGCC (130) |
| | | AGGUAGUUUCAUGUUGUUGGGC (131) |
| | | AGGUAGUUUCAUGUUGUUGG (132) |
| | | AGGUAGUUUCAUGUUGUUGG (133) |
| | | GGUAGUUUCAUGUUGUUGGG (134) |
| | | GGUAGUUUCAUGUUGUUGG (135) |
| | | GUAGUUUCAUGUUGUUGGG (136) |
| | | GUAGUUUCAUGUUGUUGG (137) |
| | | UAGUUUCAUGUUGUUGGG (138) |
| | | UAGUUUCAUGUUGUUGG (139) |
| | | AGUUUCAUGUUGUUGGG (140) |
| | | AGUUUCAUGUUGUUGG (141) |
| | | UUUCAUGUUGUUGGGC (142) |
| | | UUUCAUGUUGUUGGG (143) |
| | | AUUAGGUAGUUUCAUGUUGUUG (144) |
| | | UUAGGUAGUUUCAUGUUGUUGGG (145) |
| | | UUAGGUAGUUUCAUGUUGUUGG (146) |

TABLE 6

Sequences of antagomirs (Anti-miRNAs, 5' to 3' direction) based on mature miRNA sequences and on miRNA isomiR sequences (5' to 3' direction) obtained from miRBase (release 21: June 2014; www.mirbase.org) or from SIROCCO. In case of discrepancy, SIROCCO data was used. Numbers in between parentheses that follow a sequence refer to the corresponding SEQ ID NO.

| Mature miRNA | Seed (SEQ ID NO) | SEQ anti-miRNA (5'-3') (SEQ ID NO) |
| --- | --- | --- |
| hsa-miR-135a-5p | AUGGCUU (52) | TCACATAGGAATAAAAAGCCATA (242) |
| hsa-miR-135a-3p | AUAGGGA (53) | CGCCACGGCTCCAATCCCTATA (243) |
| hsa-miR-135b-5p | AUGGCUU (54) | TCACATAGGAATGAAAAGCCATA (244) |
| hsa-miR-135b-3p | UGUAGGG (55) | CCCATGGCTTTTAGCCCTACAT (245) |
| hsa-miR-196a-5p | AGGUAGU (56) | CCCAACAACATGAAACTACCTA (246) |

| Mature miRNA | miRNA/isomiR sequence (SEQ ID NO) | SEQ anti-miRNA (5'-3') (SEQ ID NO) |
| --- | --- | --- |
| hsa-miR-135a-5p | UAUGGCUUUUUAUUCCUAUGUGA (147) | TCACATAGGAATAAAAAGCCATA (247) |
| | UAUGGCUUUUUAUUCCUAUGUGAUAG (148) | CTATCACATAGGAATAAAAAGCCATA (248) |
| | UAUGGCUUUUUAUUCCUAUGUGAUUC (149) | GAATCACATAGGAATAAAAAGCCATA (249) |
| | UAUGGCUUUUUAUUCCUAUGUGAUA (150) | TATCACATAGGAATAAAAAGCCATA (250) |
| | UAUGGCUUUUUAUUCCUAUGUGAU (151) | ATCACATAGGAATAAAAAGCCATA (251) |
| | UAUGGCUUUUUAUUCCUAUGUG (152) | CACATAGGAATAAAAAGCCATA (252) |
| | UAUGGCUUUUUAUUCCUAUGU (153) | ACATAGGAATAAAAAGCCATA (253) |
| | UAUGGCUUUUUAUUCCUAUG (154) | CATAGGAATAAAAAGCCATA (254) |
| | UAUGGCUUUUUAUUCCUAU (155) | ATAGGAATAAAAAGCCATA (255) |
| | UAUGGCUUUUUAUUCCUA (156) | TAGGAATAAAAAGCCATA (256) |
| | UAUGGCUUUUUAUUCCU (157) | AGGAATAAAAAGCCATA (257) |
| | UAUGGCUUUUUAUUC (158) | GAATAAAAAGCCATA (258) |
| | AUGGCUUUUUAUUCCUAUGUGAU (159) | ATCACATAGGAATAAAAAGCCAT (259) |
| | AUGGCUUUUUAUUCCUAUGUGA (160) | TCACATAGGAATAAAAAGCCAT (260) |
| | AUGGCUUUUUAUUCCUAUGUG (161) | CACATAGGAATAAAAAGCCAT (261) |
| | AUGGCUUUUUAUUCCUAUGU (162) | ACATAGGAATAAAAAGCCAT (262) |
| | UGGCUUUUUAUUCCUAUGUGAU (163) | ATCACATAGGAATAAAAAGCCA (263) |
| | UGGCUUUUUAUUCCUAUGUGA (164) | TCACATAGGAATAAAAAGCCA (264) |
| | UGGCUUUUUAUUCCUAUGUG (165) | CACATAGGAATAAAAAGCCA (265) |
| | GGCUUUUUAUUCCUAUGUGA (166) | TCACATAGGAATAAAAAGCC (266) |
| | GCUUUUUAUUCCUAUGUGA (167) | TCACATAGGAATAAAAAGC (267) |
| | GCUUUUUAUUCCUAUGUG (168) | CACATAGGAATAAAAAGC (268) |
| | GCUUUUUAUUCCUAUGU (169) | ACATAGGAATAAAAAGC (269) |
| | CUUUUUAUUCCUAUGUGA (170) | TCACATAGGAATAAAAAG (270) |
| | CUUUUUAUUCCUAUGUG (171) | CACATAGGAATAAAAAG (271) |
| | CUUUUUAUUCCUAUG (172) | CATAGGAATAAAAAG (272) |
| | CUUUUUAUUCCUAUGU (173) | ACATAGGAATAAAAAG (273) |
| | UUUUUAUUCCUAUGUGA (174) | TCACATAGGAATAAAAA (274) |
| | UUUUUAUUCCUAUGU (175) | ACATAGGAATAAAAA (275) |
| | UUUUUAUUCCUAUGUG (176) | CACATAGGAATAAAAA (276) |
| | UUUUUAUUCCUAUGUGA (177) | TCACATAGGAATAAAA (277) |
| | UUUUAUUCCUAUGUG (178) | CACATAGGAATAAAA (278) |
| | UUUAUUCCUAUGUGA (179) | TCACATAGGAATAAA (279) |
| hsa-miR-135a-3p | UAUAGGGAUUGGAGCCGUGGCG (180) | CGCCACGGCTCCAATCCCTATA (280) |
| | UAUAGGGAUUGGAGCCGUGGC (181) | GCCACGGCTCCAATCCCTATA (281) |
| | UAUAGGGAUUGGAGCCGUGG (182) | CCACGGCTCCAATCCCTATA (282) |
| | AUAUAGGGAUUGGAGCCGUGGC (183) | GCCACGGCTCCAATCCCTATAT (283) |
| | AUAUAGGGAUUGGAGCCGUGG (184) | CCACGGCTCCAATCCCTATAT (284) |
| | AUAUAGGGAUUGGAGCCGUG (185) | CACGGCTCCAATCCCTATAT (285) |
| | CAUAUAGGGAUUGGAGCCGUGGCG (186) | CGCCACGGCTCCAATCCCTATATG (286) |
| | AUAGGGAUUGGAGCCGUGGC (187) | GCCACGGCTCCAATCCCTAT (287) |
| hsa-miR-135b-5p | UAUGGCUUUUCAUUCCUAUGUGA (188) | TCACATAGGAATGAAAAGCCATA (288) |
| | UAUGGCUUUUCAUUCCUAUG (189) | CATAGGAATGAAAAGCCATA (289) |
| | UAUGGCUUUUCAUUCCUAU (190) | ATAGGAATGAAAAGCCATA (290) |
| | UAUGGCUUUUCAUUCCUA (191) | TAGGAATGAAAAGCCATA (291) |
| | AUGGCUUUUCAUUCCUAUGUGAU (192) | ATCACATAGGAATGAAAAGCCAT (292) |
| | AUGGCUUUUCAUUCCUAUGUGA (193) | TCACATAGGAATGAAAAGCCAT (293) |
| | AUGGCUUUUCAUUCCUAUGUG (194) | |
| | AUGGCUUUUCAUUCCUAUGU (195) | |

TABLE 6-continued

Sequences of antagomirs (Anti-miRNAs, 5' to 3' direction) based on mature miRNA sequences and on miRNA isomiR sequences (5' to 3' direction) obtained from miRBase (release 21: June 2014; www.mirbase.org) or from SIROCCO. In case of discrepancy, SIROCCO data was used. Numbers in between parentheses that follow a sequence refer to the corresponding SEQ ID NO.

|  |  |  |
|---|---|---|
|  | UGGCUUUUCAUUCCUAUGUGA (196) | CACATAGGAATGAAAAGCCAT (294) |
|  | GCUUUUCAUUCCUAUGUGA (197) | ACATAGGAATGAAAAGCCAT (295) |
|  | CUUUUCAUUCCUAUGUGA (198) | TCACATAGGAATGAAAAGCCA (296) |
|  | CUUUUCAUUCCUAUGU (199) | TCACATAGGAATGAAAAGC (297) |
|  | CUUUUCAUUCCUAUGUG (200) | TCACATAGGAATGAAAAG (298) |
|  | CUUUUCAUUCCUAUG (201) | ACATAGGAATGAAAAG (299) |
|  | UUUUCAUUCCUAUGUGA (202) | CACATAGGAATGAAAAG (300) |
|  | UUUUCAUUCCUAUGU (203) | CATAGGAATGAAAAG (301) |
|  | UUUUCAUUCCUAUGUG (204) | TCACATAGGAATGAAAA (302) |
|  | UUUCAUUCCUAUGUGA (205) | ACATAGGAATGAAAA (303) |
|  | UUUCAUUCCUAUGUG (206) | CACATAGGAATGAAAA (304) |
|  | CUAUGGCUUUUCAUUCCUAUGU (207) | TCACATAGGAATGAAA (305) |
|  |  | CACATAGGAATGAAA (306) |
|  |  | ACATAGGAATGAAAAGCCATAG (307) |
| hsa-miR-135b-3p | AUGUAGGGCUAAAAGCCAUGGG (208) | CCCATGGCTTTTAGCCCTACAT (308) |
|  | AUGUAGGGCUAAAAGCCAUGGGC (209) | GCCCATGGCTTTTAGCCCTACAT (309) |
|  | AUGUAGGGCUAAAAGCCAUGG (210) | CCATGGCTTTTAGCCCTACAT (310) |
|  | AUGUAGGGCUAAAAG (211) | CTTTTAGCCCTACAT (311) |
|  | UGUAGGGCUAAAAGCCAUGGGCU (212) | AGCCCATGGCTTTTAGCCCTACA (312) |
|  | UGUAGGGCUAAAAGCCAUGGGC (213) | GCCCATGGCTTTTAGCCCTACA (313) |
|  | GGGCUAAAAGCCAUGGG (214) | CCCATGGCTTTTAGCCC (314) |
| hsa-miR-196a-5p | UAGGUAGUUUCAUGUUGUUGGG (215) | CCCAACAACATGAAACTACCTA (315) |
|  | GGUAGUUUCAUGUUGUUGGGCC (216) | GGCCCAACAACATGAAACTACC (316) |
|  | UAGGUAGUUUCAUGUUGUUGGGC (217) | GCCCAACAACATGAAACTACCTA (317) |
|  | UAGGUAGUUUCAUGUUGUUGG (218) | CCAACAACATGAAACTACCTA (318) |
|  | UAGGUAGUUUCAUGUUGUUG (219) | CAACAACATGAAACTACCTA (319) |
|  | UAGGUAGUUUCAUGUUGUU (220) | AACAACATGAAACTACCTA (320) |
|  | UAGGUAGUUUCAUGUUGU (221) | ACAACATGAAACTACCTA (321) |
|  | UAGGUAGUUUCAUGUUG (222) | CAACATGAAACTACCTA (322) |
|  | UAGGUAGUUUCAUGUU (223) | AACATGAAACTACCTA (323) |
|  | UAGGUAGUUUCAUGU (224) | ACATGAAACTACCTA (324) |
|  | AGGUAGUUUCAUGUUGUUGGGCC (225) | GGCCCAACAACATGAAACTACCT (325) |
|  | AGGUAGUUUCAUGUUGUUGGGC (226) | GCCCAACAACATGAAACTACCT (326) |
|  | AGGUAGUUUCAUGUUGUUGGG (227) | CCCAACAACATGAAACTACCT (327) |
|  | AGGUAGUUUCAUGUUGUUGG (228) | CCAACAACATGAAACTACCT (328) |
|  | GGUAGUUUCAUGUUGUUGGG (229) | CCCAACAACATGAAACTACC (329) |
|  | GGUAGUUUCAUGUUGUUGG (230) | CCAACAACATGAAACTACC (330) |
|  | GUAGUUUCAUGUUGUUGGG (231) | CCCAACAACATGAAACTAC (331) |
|  | GUAGUUUCAUGUUGUUGG (232) | CCAACAACATGAAACTAC (332) |
|  | UAGUUUCAUGUUGUUGGG (233) | CCCAACAACATGAAACTA (333) |
|  | UAGUUUCAUGUUGUUGG (234) | CCAACAACATGAAACTA (334) |
|  | AGUUUCAUGUUGUUGGG (235) | CCCAACAACATGAAACT (335) |
|  | AGUUUCAUGUUGUUGG (236) | CCAACAACATGAAACT (336) |
|  | UUUCAUGUUGUUGGGC (237) | GCCCAACAACATGAAA (337) |
|  | UUUCAUGUUGUUGGG (238) | CCCAACAACATGAAA (338) |
|  | AUUAGGUAGUUUCAUGUUGUUG (239) | CAACAACATGAAACTACCTAAT (339) |
|  | UUAGGUAGUUUCAUGUUGUUGGG (240) | CCCAACAACATGAAACTACCTAA (340) |
|  | UUAGGUAGUUUCAUGUUGUUGG (241) | CCAACAACATGAAACTACCTAA (341) |

TABLE 7

Sequence and genomic location of miRNA-135s being miRNA-135a and miRNA-135b.
The mature sequence of miRNA-135a and miRNA-135b differs by only one nucleotide (underlined) which is outside the seed region (in bold).
Numbers in between parentheses that follow a sequence refer to the corresponding SEQ ID NO.

| | |
|---|---|
| miRNA-135b | UAUGGCUUUU<u>C</u>AUUCCUAUGUGA (342) |
| | chr1:205448302-205448398 |
| miRNA-135a | UAUGGCUUUU<u>U</u>AUUCCUAUGUGA (343) |
| mir-135a-1 | chr3:52294219-52294308 |
| mir-135a-2 | chr12:97563812-97563911 |

Example 4: miRNA-135a Reduces MEF2a Expression

Methods:

Animals: C57bl6J mice (male and female) were obtained from Charles Rivers Laboratories.

Target Validation: Western Blot and Luciferase Assay

HEK293 (RRID:CVCL_0045) and N2A (RRID: CVCL_0470) cells were cultured according to the guidelines provided by ATCC. Luciferase assay was performed in HEK293 cells and target validations by western blot were performed in N2A cells.

For luciferase assays, miRNA recognition elements (MRE) for miR-135a present on the 3' UTR of Mef2a were identified in RNAseq data and also predicted by Targetscan. Oliogonucleotides with these sites were cloned into the psi-Check2 vector (Promega). Oligonucleotides with WT (MEF2A-135a-fw: TCG AGA GCA GAA CCT TGG AAA AAA AAA GCC ATG GC (SEQ ID NO: 351), Rv-GGC CGC CAT GGC TTT TTT TTT CCA AGG TTC TGC TC (SEQ ID NO: 352)) and MUT (MEF2A-135aM-fw: TCG AGA GCA GAA CCT TGG AAA AAA AAA GGC TTG GC (SEQ ID NO: 353); Rv-GGC CGC CAA GCC TTT TTT TTT CCA AGG TTC TGC TC (SEQ ID NO: 354)) miR-135a binding sites on Mef2a 3' UTR were phosphorylated, annealed and ligated into NotI and XhoI sites of the multiple cloning site. Cells ($8 \times 10^4$) were transfected using Lipofectamine 2000 (Invitrogen) with 250 ng of reporter construct together with 25 pmol of miRIDIAN miRNA mimic or Scramble control (NC-1, Dharmacon). Cells were harvested after 24 h and luciferase assay was performed using the dual-luciferase assay system (E1960, Promega) on a Luminometer. Normalizing against Renilla luciferase activity was used to determine relative luciferase activity.

For protein analysis, western blotting was performed. N2A cells were transfected with miRIDIAN mimics for miR-135a or a scrambled control using Lipofectamine 2000. After 48 h cells were harvested and lysed in RIPA buffer (50 mM Tris pH.7.5, 150 mM Nacl, 0.5% NP-40, 0.5% NaDoc, 1% Triton, Protease inhibitor (Roche) in MilliQ (MQ)). Equal amounts of protein samples were separated on SDS-PAGE gels (8%) and transferred onto nitrocellulose blotting membranes (GE Healthcare Lifesciences), following blots were blocked for 1 hr at RT in 5% milk powder in 1×TBS-Tween. Blots were incubated overnight at 4° C. with rabbit-anti-NR3C1 (GR) (1;1000, Santa-cruz Biotechnology, RRID:AB_2155786), rabbit-anti-PlxnA4 (1;250, Abcam, RRID:AB_944890), mouse-anti-β actin (1;2000, Sigma-Aldrich, RRID:AB_476743). Blots were stained with peroxidase-conjugated secondary antibodies for 1 hr at RT and signal was detected by incubating blots with Pierce ECL substrate (Thermo Fischer Scientific). Images were acquired using a FluorChem M imaging system (Protein Simple). Using ImageJ, individual band intensities for each sample were measured and normalized to corresponding β-actin levels. Relative expression between conditions of each protein was estimated by t test (GraphPad Prism version 6 software, RRID:SCR_002798). Except for Mef2a, blots were blocked in Supermix blocking solution (Tris 50 mM, Nacl 154 mM, 0.25% Gelatin, 0.5% Triton-x-100 in MQ, pH-7.4) for 10 min at RT and inclubated overnight at 4° C. with rabbit-anti-Mef2a (1;50,000, Abcam, RRID: AB_10862656) and mouse-anti-β actin (1;2000, Sigma-Aldrich, RRID:AB_476743). Blots were washed in 1×TBS-Tween and incubated with secondary antibodies coupled with IR dyes (anti-rabbit-IRdye 800 1;5000 and anti-mouse-IRdye700 1;2000 in 1×TBS-Tween) for 1 hr at RT. Finally, blots were washed in 1×TBS-Tween and scanned on Odyssey Clx imaging system (LI-COR biosciences, Westburg) using Li-COR Image studio v3.1 software (RRID: SCR_015795) and band intensities were measured and relative expression between conditions was estimated by t test (GraphPad Prism version 6 software, RRID:SCR_002798).

Culturing and Transfection of Primary Mouse Hippocampal Neurons

Dissociated hippocampal neurons were cultured. Briefly, C57bl6J (P0-1) mouse pups were decapitated and brains were quickly isolated in ice cold dissection medium (Leibovitz's L-15 supplemented with 7 mM HEPES (Thermo scientific)). Hippocampus was isolated, trypsinized in 0.25% trypsin in L15-HEPES medium for 20 min at 37° C., followed by trituration using fire polished Pasteur pipettes in growth medium (Neurobasal medium supplemented with B27, Penicillin/streptomycin L-glutamine and β-mercaptoethanol). Dissociated cells were plated onto glass coverslips coated with PDL (20 µgml$^{-1}$) and Laminin (40 µgml$^{-1}$) in growth medium and incubated at 37° C. with 5% $CO_2$. Half of the growth medium was refreshed twice a week. On day in vitro (DIV)14 neurons were transfected with 0.5 µg of pre-miR-135a1 (cloned into pJEBB vector with CMV promoter, contains GFP reporter) or pJEBB vector only. For rescue experiments, pJEBB-pre-miR-135a1 and the constitutively active mutant Mef2-vp16 (Fiore et al., 2009) were co-transfected. Transfected neurons were fixed on DIV16 with 4% PFA and 4% sucrose in PBS for 20 min. Immunocytochemistry was performed by blocking neurons in blocking buffer (4% NGS, 0.1% BSA, 0.1% Triton-X-100 in 1×PBS (pH-7.4)) for 1 hr at RT followed by incubation with primary antibody chicken-anti-GFP (1;1000, Abcam, RRID: AB_300798) diluted in blocking buffer. The next day washes in 1×PBS were performed followed by incubation with appropriate secondary antibodies in blocking buffer for 1 hr at RT. Sections were mounted using ProLong Gold (Thermo Fischer Scientific). High resolution images were acquired using an oil immersion 63× objective of a confocal laser scanning microscope (LSM880, Zeiss). 6-7 Z stack images of each apical dendrites close to the soma were captured. Using ImageJ software (RRID:SCR_003070) with cell counter plugin, different types of spines categorized as immature to mature: filopodium, thin, stubby, mushroom and cupshaped on secondary dendrite were identified and counted. Spine density was determined by dividing the number of spines on a branch with the length of the branch.

RNA Isolation and Quantitative PCR

Samples from seven patients with mTLE+HS (with hippocampal sclerosis) and eight post-mortem control samples were used (for patient details see Table 8). Patient tissue representing all hippocampal regions was selected using Nissl staining. Approximately 20 mg of tissue was collected by slicing 25 μm thick sections on a cryostat. For intraamygdala kainate (IAK) mice, hippocampus was dissected, frozen and stored at −80° C. Total RNA was isolated using the miRNeasy kit (Qiagen), according to the manufacturer's instructions. RNA quantity was determined using Nanodrop (Thermo Scientific). For miRNA quantitative PCR (qPCR), first strand cDNA synthesis was performed using a universal cDNA synthesis kit (Exiqon) according to the manufacturer's recommendation. QPCR reactions were run in a Quantstudio 6 flex Real-Time PCR system (Applied Biosystems) using microRNA LNA™ PCR primer sets (miR-135a, miR-124) and SYBR Green master mix (Exiqon). For pre-miRNA qPCR, primer sequences (pre-miR-135a1 and a2) were designed using Primer3 software. Primers sequences for each target are provided in Table 11. 100 ng of RNA was reverse transcribed using Superscript III first strand synthesis kit (Thermo fischer scientific). Similarly, for validation of bio-IP targets equal amount of input and IP RNA was reverse transcribed as above. Primers sequences for each target are provided in Table 11. QPCR reactions were run on Quantstudio 6 flex Real-Time PCR system (Applied Biosystems) using Fast start universal SYBR Green master mix (Roche). All samples were run in duplicates. Ct values were determined using Quant studio real time PCR software v1.1. For miRNA, expression levels were estimated by normalizing to 5s rRNA. Pre-miRs were normalized to GAPDH (human) and beta-actin (mouse). For Bio-ip fold enrichment of target gene in the IP sample was estimated after normalizing to input deltaCt. DeltaCt and fold changes were calculated and the statistical significance was analyzed by Mann Whitney U test and Students t test. $P<0.05$ was considered as significant.

Non-Radioactive In Situ Hybridisation

Non-radioactive in situ hybridization was performed as described previously (Kan et al., 2012). Three patients from each group (control and mTLE+HS) were used for in situ hybridization. Similarly, for IAK mice sections three mice per group were used. Briefly, 16 μm thick sections from fresh frozen hippocampal tissue were collected on glass slides and stored at −80° C. until use. Sections were fixed (4% PFA for 10 min at RT), acetylated (10 min at RT) and treated with proteinase K (5 μg/ml for 5 min at RT). Pre-hybridisation was performed for 1 h at RT. Hybridisation was performed with 10 nM of double-DIG (3' and 5')-labeled locked nucleic acid (LNA) probe for human-miR-135a-5p (Exiqon) or LNA-DIG Scramble probe overnight at 50° C. Slides were washed at 55° C. in 0.2×SSC for 1 h, followed by blocking with 10% fetal calf serum (FCS) in B1 buffer (0.1 M Tris pH 7.5/0.15 M NaCl) for 1 h at RT. Sections were incubated with anti-digoxigenin-AP Fab fragments (1;2,500, Roche Diagnostics) in 10% FCS in B1 buffer overnight at 4° C. Slides were treated with 5-bromo-4-chloro-3-indolyl phosphate (BCIP) and nitrobluetetrazolium (NBT) substrates (NBT/BCIP stock solution, Roche Diagnostics) in B3 (0.1 M Tris pH 9.5/0.1 M NaCl/50 mM $MgCl_2$) for 5-20 h at RT. Staining was stopped by washes in PBS and slides were mounted using vectashield (VectorLabs). No staining was observed in sections hybridized with scramble probe. Images were acquired with brightfield microscope and processed using ImageJ.

A similar protocol was used for FISH except that hybridization was performed at 55° C. and washes at 60° C. After blocking, slides were co-incubated with anti-Digoxigenin-POD (1;500, Roche Diagnostics) and mouse-anti-NeuN (1;400, Millipore, RRID:AB_2298772) or rabbit-anti-GFAP (1;1000, Dako Cytomation, RRID:AB_10013482) antibodies overnight at 4° C. Signal was amplified using the ISA™ Cyanine 3 System (1;50 in amplification diluent, PerkinElmer) for 10 min at RT. After washes with PBS, slides were incubated with secondary antibodies (Alexafluor 488, Invitrogen) against the primary antibody for 1.5 h at RT. Nuclei were stained with DAPI (10 min at RT) and slides were mounted using ProLong Gold (Life Technologies). Images were acquired using a confocal laser scanning microscope (LSM880, Zeiss).

RNA Immunoprecipitation with Biotinylated miRIDIAN Mimics

N2A cells were cultured in Dulbecco's modified Eagle's medium (DMEM) low glucose supplemented with L-glutamine, pencillin/streptomycin (100 U/ml and 100 mg/ml, respectively) and 10% FCS (Invitrogen) at 37° C. with 5% $CO_2$. For each condition (miR-135a, scrambled and no transfection) three 10 cm dishes with $2\times10^6$ cells/dish were plated and transfected with 37.5 nM of 3' biotinylated miRNA mimics (miR-135a and Scramble: Dharmacon) using HighPerfect Transfection reagent (Qiagen). RNA immunoprecipitation was performed as described previously (Wani and Cloonan, 2014) with some modifications. Briefly, 24 h after transfection cells were collected and lysed in lysis buffer (10 mM Tris-Cl pH 7.5, 10 mM KCl, 1.5 mM Mgcl2, 5 mM DTT, 0.5% NP-40, 60 U/ml SUPERase-in RNase inhibitor (Invitrogen), protease inhibitor tablet (Roche) in MQ) and the cleared cell lysates were incubated with Dynabeads M-280 Streptavidin beads (Invitrogen) for 30 min at RT. Beads were washed three times in wash buffer (lysis buffer containing 1 M NaCl) and stored in Qiazol at −80° C. Total RNA was extracted using miRNeasy kit (Qiagen). One part of the beads was incubated with 4× Nu-PAGE sample buffer (with 10% β-mercaptoethanol in MQ) for 10 min at 70° C. to extract bound proteins. Proteins were then separated on 8% SDS-PAGE gel and the subsequent proteins transferred blot was incubated with rabbit-anti-Ago2 antibody (1;1000, Cell-signalling, RRID: AB_2096291) and mouse-anti-β actin (1;2000, Sigma-Aldrich, RRID:AB_476743) in blocking solution (5% Milk in 1×TBS-T) overnight at 4° C., finally signal was detected as above.

Library Preparation and Total RNA Sequencing

For input samples, libraries for total RNA sequencing were prepared using the TruSeq Stranded Total RNA (w/ RiboZero Gold) sample prep kit (Illumina). The starting material (100 ng) of total RNA was depleted of rRNAs using Ribo-Zero Gold (removes both cytoplasmic and mitochondrial rRNA) magnetic bead-based capture-probe system (Illumina). The remaining RNA, including mRNAs, lincRNAs and other RNA species, was subsequently purified (RNAcleanXP) and enzymatically fragmentated. For IP samples, libraries were prepared using the TruSeq stranded mRNA sample prep kit (Illumina) according to the manufacturer's instructions with some modifications: the starting material (37.5-50.0 ng) of total RNA was not mRNA-enriched nor fragmented prior to library synthesis. First strand synthesis and second strand synthesis were performed and double stranded cDNA was purified (Agencourt AMPure XP, Beckman Coulter). The cDNA was end repaired, 3' adenylated and Illumina sequencing adaptors were ligated onto the fragments ends, and the library was purified (Agencourt AMPure XP). The polyA+ RNA stranded libraries were pre-amplified with PCR and purified (Agencourt AMPure XP). Library size distribution was validated and quality inspected using the 2100 Bioanalyzer (high sensitivity DNA chip, Agilent). High quality libraries were quantified using the Qubit Fluorometer (Life Technologies). Single-end sequencing was performed using the NextSeq500 instrument according to the manufacturer's instructions (Illumina).

Read Mapping and Differential Expression Analysis

Following trimming of low-quality bases and adapter sequences with FASTQ-MCF (version 0.0.13), processed reads were mapped to the GRCm38.p6 reference mouse genome (Ensembl) with TopHat2 (version 2.0.13) (Kim et al., 2013). 'fr-secondstrand' option was chosen for the alignments of the total RNA sequencing data. Mapped counts were summarised for each gene using the python script htseq-count (Anders et al., 2015).

For differential expression analysis, count data for genes and transcripts were analysed for differential expression in R using the Bioconductor package EdgeR version 3.12.1 (Robinson et al., 2010) with the trimmed mean of M-values (TMM) normalisation method (Robinson and Oshlack, 2010). Gene expression levels were corrected for batch effects by including the series of sequencing rounds. Adjusted P values for multiple testing were calculated using the Benjamini-Hochberg false discovery rate (FDR) and only genes with an FDR<0.05 were considered significantly differentially expressed. Data visualisation was performed in R using the ggplot2 library. Gene expression heatmaps with hierarchical clustering of expression profiles were created in R with the Bioconductor pheatmap package. Enrichment analysis was performed using the R package goseq (Young et al., 2010) to correct for bias due to transcript length.

In Silico Prediction of miRNAs Binding Sites miRanda software version 3.3a was used to predict microRNA signatures. The following parameters were used in this study: match with a minimum threshold score of 150; target mRNA duplex with minimum folding free energy threshold −7 kcal/mol; gap opening penalty −8; gap extension penalty −2; scaling parameter 4 for complementary nucleotide match score.

Immunohistochemistry and Western Blotting for Mef2a

Mef2a immunostainings were performed on resected human hippocampal sections and 2 wk IAK mouse tissue. 16 µm sections were blocked in 10% NGS, 0.4% Triton in 1×PBS (pH 7.4) for 1 hr at RT followed by incubation in anti-Mef2a antibody (1;150, Abcam) and anti-NeuN antibody (1;400, Millipore) in blocking solution overnight at 4° C. Sections were washed and incubated with corresponding Alexa-fluor conjugated (Thermofischer scientific) secondary antibodies for 1.5 hr at RT, followed by washes in 1×PBS and stained for nuclei with DAPI (4',6-diamidino-2-phenylindole) and mounted using ProLong gold (Thermofischer scientific). High resolution images were acquired using confocal microscope (LSM880, Zeiss) and processed using ImageJ.

For analyzing Mef2a protein levels in human TLE and IAK mice hippocampal tissue. Protein lysates were prepared in RIPA buffer and equal amounts of proteins were separated on SDS-PAGE gels (8% gel for mice samples amd 10% gel for human samples), and transferred onto nitrocellulose membranes, blocked and incubated overnight at 4° C. with rabbit-anti-Mef2a (for human—1;20,000, for mice—1;50, 000, Abcam, RRID:AB_10862656) and mouse-anti-β actin (1;2000, Sigma-Aldrich, RRID:AB_476743). Blots were stained, developed and quantified as described above.

Intraamygdala Kainate Mice

Status epilepticus (SE) induction, EEG recording and analysis was done as previously described (Jimenez-Mateos et al., 2012) (Mouri et al., 2008). Briefly, mice were implanted with telemetric EEG transmitters (Data Systems International). Two days after surgery, SE was induced for 40 min by administration of kainic acid (0.3 µg in 0.2 µl in PBS). Control animals received the same volume of scrambled mimics or PBS. Forty minutes after microinjection, mice received an intravenous injection of lorazepam (6 mg/kg) to stop SE. Mice were EEG monitored for 1 hr after injection to make sure that all the seizure activity was reduced.

Intracerebroventricular Injections

For antagomirs, intracerebroventricular (i.c.v) injections were performed as described (Jimenez-Mateos et al., 2012) (Reschke et al., 2017). From day 7 after SE induction, baseline EEG was recorded. At day 14 (D14) mice received an infusion of 1.0 nmol/2 µl of antagomir-135a LNA modified and 3'-cholesterol-modified oligonucleotides (Exiqon) in PBS. Controls received same volume of PBS. During this period mice were continuously EEG and video monitored for another 2 weeks. EEG data analysis was performed using LabChart 8 software (ADInstruments Ltd).

Statistical Analysis

Statistical analysis was performed using GraphPad Prism and a p value<0.05 was considered as significant. Seizure frequencies before (baseline) and after Ant-135a were analyzed using paired t test, the number of seizures per day using F statistics mixed design repeated measures general linear model. Seizure duration and total time spent in seizures were analyzed using t test. Differences between two groups were tested using either two tailed student t test or Mann whitney test. For comparing more than two groups one way ANOVA was used.

TABLE 8

Control and mTLE patient group details. Details of mediation used for TLE patients. LTG lamotrigine, PHT phenytoin, CBZ carbamazepine, LEV levetiracetam, OXC oxcarbazepine, CLO clobazam, DZP diazepam, LZP lorazepam, SER Seroquel, PGB pregabaline, RES restoril.

| # | Sample | Age | Sex | PMD | Age of onset | Years of epilepsy | AED's |
|---|--------|-----|-----|-----|--------------|-------------------|-------|
| 1 | Control | 58 | M | 7 hr | NA | NA | NA |
| 2 | Control | 73 | F | 6.5 hr | NA | NA | NA |
| 3 | Control | 71 | M | 9 hr | NA | NA | NA |
| 4 | Control | 62 | M | 7 hr | NA | NA | NA |
| 5 | Control | 64 | F | 4.5 hr | NA | NA | NA |
| 6 | Control | 74 | M | 8 hr | NA | NA | NA |
| 7 | Control | 94 | F | 4 hr | NA | NA | NA |
| 8 | Control | 70 | M | 20.5 hr | NA | NA | NA |
| 9 | Control | 82 | M | 4 hr | NA | NA | NA |
| 10 | Control | 94 | M | 5 hr | NA | NA | NA |

TABLE 8-continued

Control and mTLE patient group details. Details of mediation used
for TLE patients. LTG lamotrigine, PHT phenytoin, CBZ carbamazepine,
LEV levetiracetam, OXC oxcarbazepine, CLO clobazam, DZP diazepam,
LZP lorazepam, SER Seroquel, PGB pregabaline, RES restoril.

| # | Sample | Age | Sex | PMD | Age of onset | Years of epilepsy | AED's |
|---|--------|-----|-----|-----|--------------|-------------------|-------|
| 11 | Control | 78 | F | 7 hr | NA | NA | NA |
| 12 | Control | 93 | M | 7.5 hr | NA | NA | NA |
| 13 | Control | 72 | F | 7 hr | NA | NA | NA |
| 14 | Control | 75 | F | 9 hr | NA | NA | NA |
| 1 | TLE + HS | 41 | M | NA | 1 | 40 | CBZ |
| 2 | TLE + HS | 36 | F | NA | 14 | 22 | OXC, LZP |
| 3 | TLE + HS | 42 | M | NA | 0.45 | 41 | LEV, LTG |
| 4 | TLE + HS | 52 | F | NA | 20 | 32 | CBZ, CLO, DZP |
| 5 | TLE + HS | 50 | M | NA | 2.5 | 47 | LTG, CBZ, CLO |
| 6 | TLE + HS | 41 | M | NA | 10 | 31 | PHT, CLO, CBZ, LTG |
| 7 | TLE + HS | 49 | F | NA | 12 | 37 | OXC, CLO, SER |
| 8 | TLE + HS | 58 | F | NA | 36 | 22 | LEV, LTG |
| 9 | TLE + HS | 23 | F | NA | 14 | 9 | LTG |
| 10 | TLE + HS | 60 | F | NA | 15 | 45 | LTG, CBZ, LEV |
| 11 | TLE + HS | 41 | M | NA | 16 | 25 | PGB, RES, CBZ |

Results

Increased Expression of miR-135a in Human and Experimental TLE

Figure 11A:
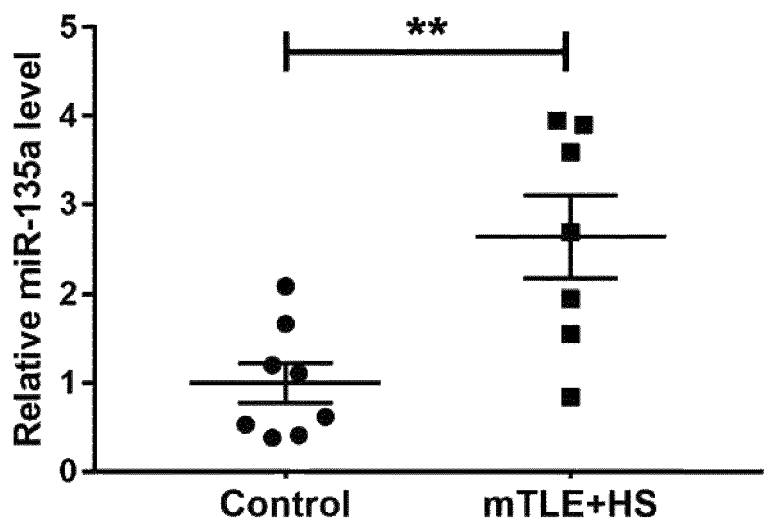
Figure 11B:
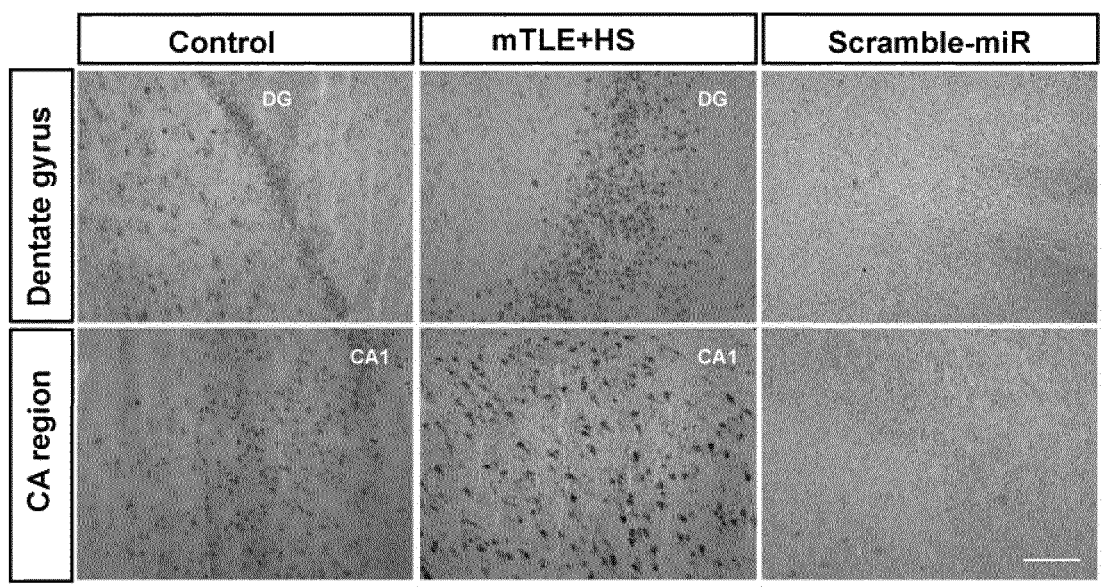
Figure 11C:
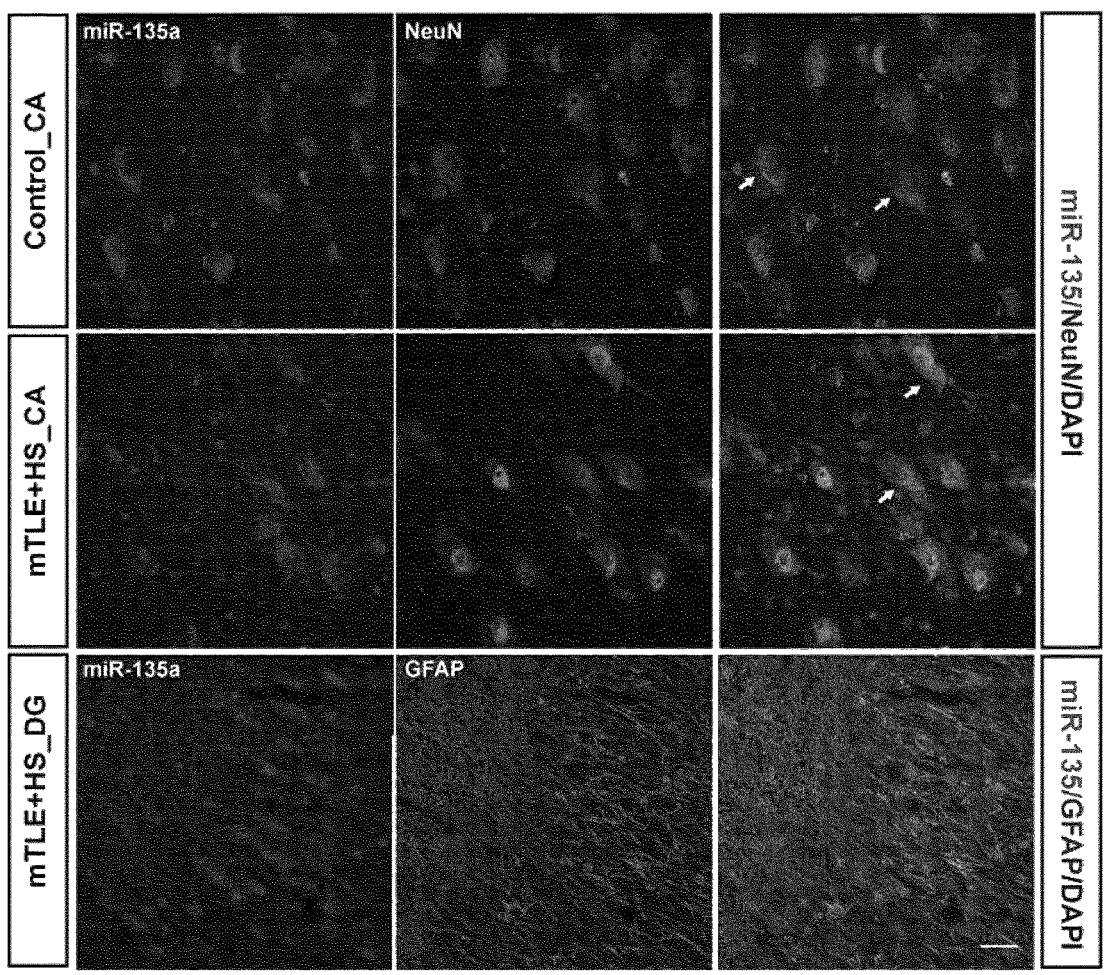

To begin to characterize a potential role for miR-135a in the pathophysiology of TLE, miR-135a expression was assessed in human TLE hippocampus (mTLE+HS) and controls. miR-135a expression levels were increased in mTLE hippocampus as compared to control (FIG. 11A). To verify the spatial distribution of miR-135a in human hippocampal tissue we performed in situ hybridization (ISH). In line with the qPCR data stronger signals for miR-135a were observed in mTLE+HS hippocampus as compared to control. Signals were mainly confined to neurons in the CA and DG regions (FIG. 11B). To confirm this cell type-specific localization, fluorescent ISH (FISH) was performed in combination with immunohistochemistry for NeuN (neurons) or GFAP (astrocytes). MiR-135a specifically co-localized with NeuN but not GFAP (FIG. 11C).

Figure 12A:
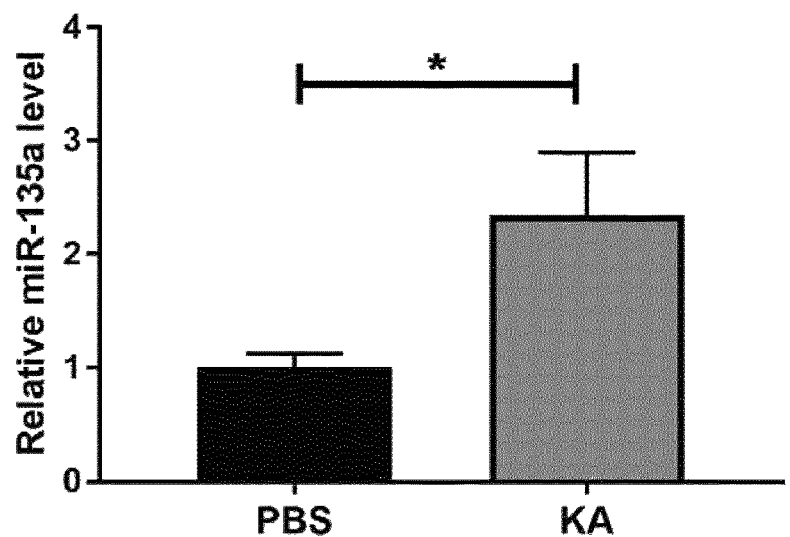
Figure 12B:
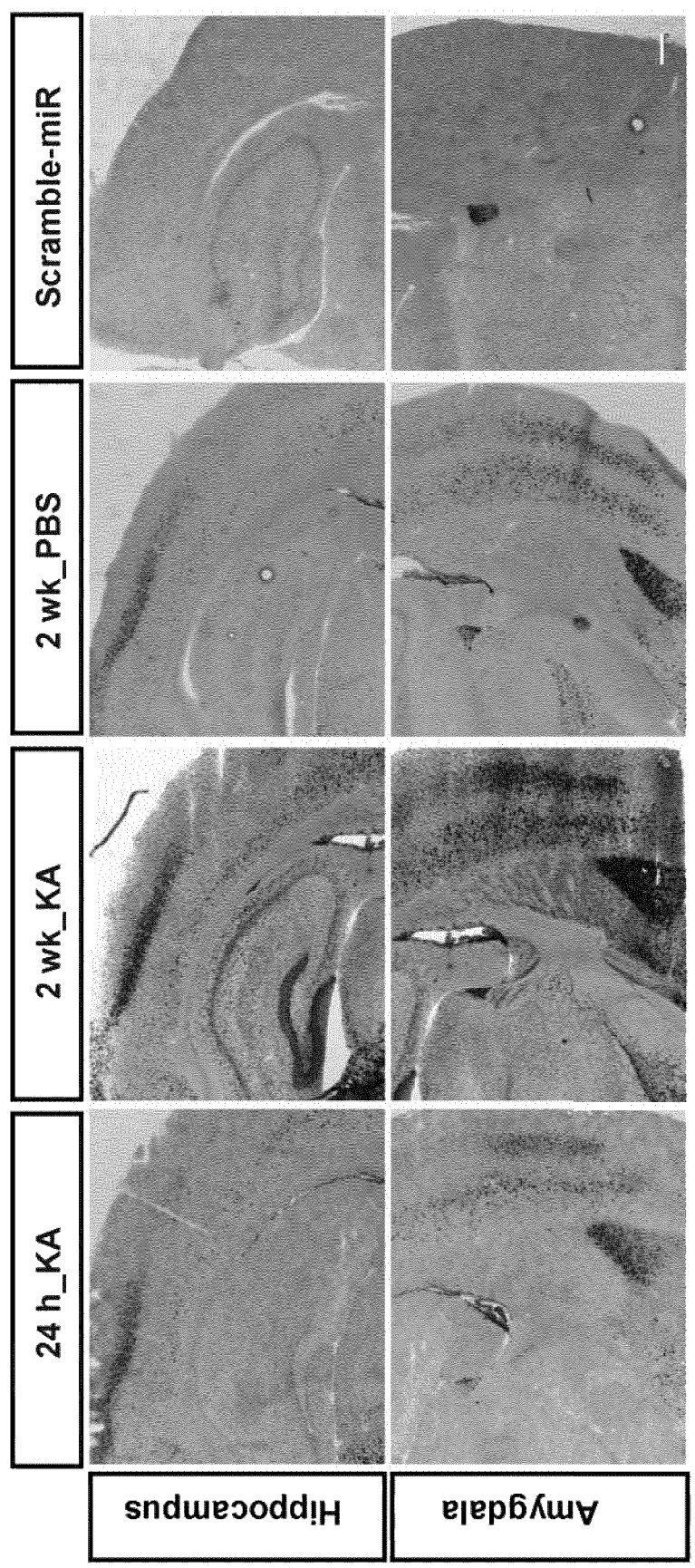
Figure 12C:
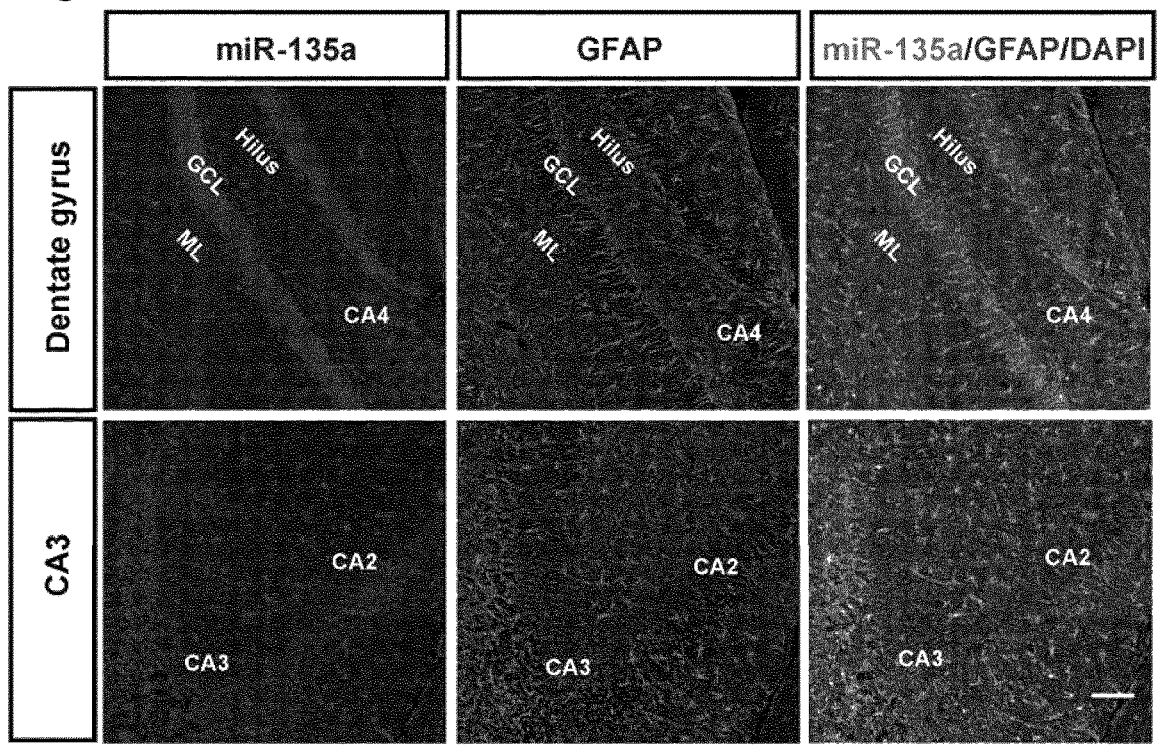
Figure 12D:
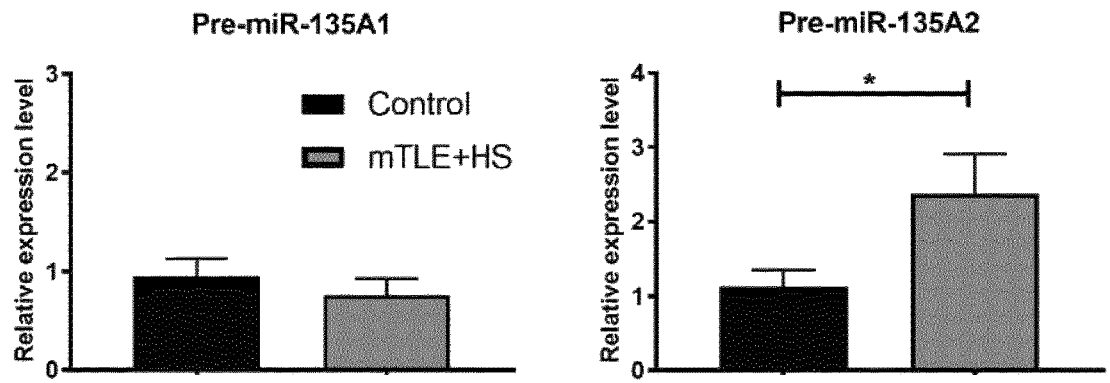
Figure 12E:
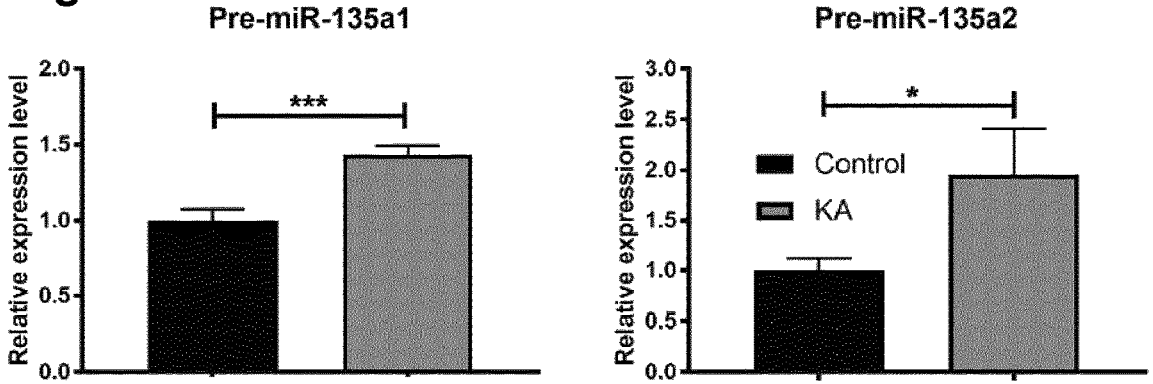

Next, we checked whether seizure induction (status epilepticus, SE) in an experimental model of TLE by intra-amygdala microinjection of glutamate receptor agonist kainic acid (Mouri et al., 2008) would also lead to increased levels of miR-135a. Indeed, we observed a strong increase in miR-135a expression at day 14 (D14) after SE by qPCR and/or ISH (FIG. 12A, 12B). ISH revealed a strong signal for miR-135a in the soma of pyramidal neurons in the hippocampus, and also in neurons in the cortex, thalamus and amygdala at D14 (FIG. 12B). Similar to our observations in the human mTLE hippocampus, miR-135a was mainly localized in neurons and not in astrocytes (FIG. 12C). The mature form of miR-135a, miR-135a-5p, is spliced from two different pre-transcripts in both human and mice that arise from different loci on the chromosomes (Table 9). To examine whether a specific locus was responsible for the increase in miR-135a expression in TLE, pre-miR levels were studied in human and mouse. Pre-miR-135A2 was significantly increased in human TLE (FIG. 12D), whereas in mice both pre-miR-135a1 and pre-miR-135a2 were significantly increased (FIG. 12E). In all, we found increased expression of miR-135a in TLE and the increased miRNA is localized mainly to neuronal cells.

TABLE 9

Genomic location and sequence of miR-135a in human and mice.
Mature miR-135a-5p is spliced from two pre-sequences in mice
and human.

| Species | Pre-miR | Chromosome | Location |
|---------|---------|------------|----------|
| Human | miR-135A-1 | 3 | 52,294,219-52,295,308 |
| | miR-135A-2 | 12 | 97,563,812-97,563,911 |
| Mouse | miR-135a-1 | 9 | 106,154,124-106,154,213 |
| | miR-135a-2 | 10 | 92,072,086-92,072,185 |
| Sequence | miR-135a-5p: | UAUGGCUUUUUAUUCCUAUGUGA (SEQ ID NO: 5) | |

Silencing of miR-135a Rescues Mice from Spontaneous Recurrent Seizures

Figure 13A:
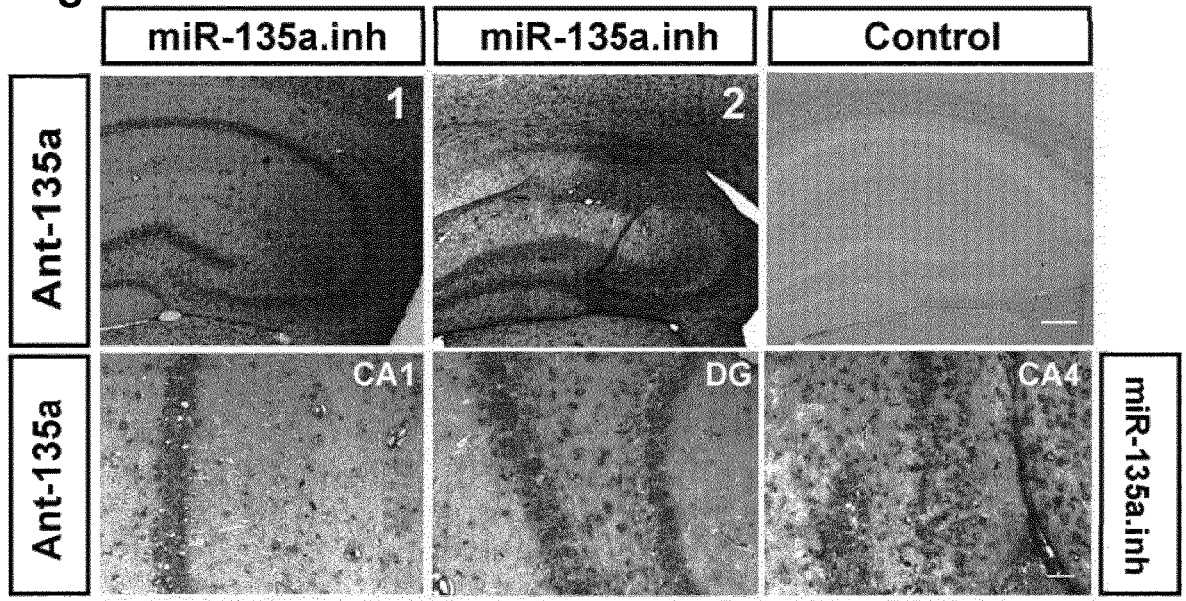

Our data show that miR-135a levels are high at the time recurrent spontaneous seizures are detected. To link increased miR-135a expression to spontaneous seizures, this miRNA was targeted by antagomirs (in this case locked nucleic acid (LNA) 3' cholesterol-conjugated oligonucleotides (Exiqon)). Several studies have shown that antagomirs can effectively reduce spontaneous seizures when administered either before status epilepticus (Jimenez-Mateos et al., 2012) (Gross et al., 2016) or immediately after SE (Reschke et al., 2017). However, it remained unknown whether administering of antagomirs in the spontaneous recurrent seizure phase can impact on seizure propagation. Antagomirs were administered (intracerebroventricularly, i.c.v) in different concentrations to test for their specific effect on miR-135a. Twenty four hours after injection, miR-135a levels were significantly reduced at 1.0 nmol of antagomir, whereas expression of another, unrelated miRNA, miR-124, was not affected. Injection of 1.5 nmol had a small but non-significant effect on miR124 expression (data not shown). On basis of these data we decided to use injections of 1.0 nmol in subsequent experiments. However, first ISH was used to detect endogenous miR-135a and ant-miR-135a following antagomir or control injection. This analysis showed that ant-miR-135a is taken up primarily by hippocampal neuronal cells in the CA and DG regions (FIG. 13A).

Figure 13B:
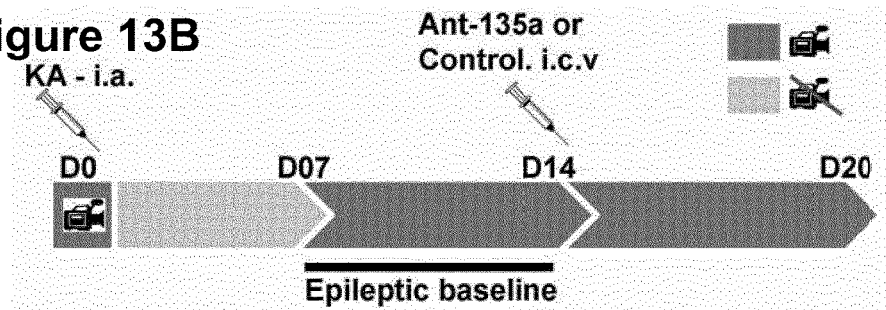
Figure 13C:
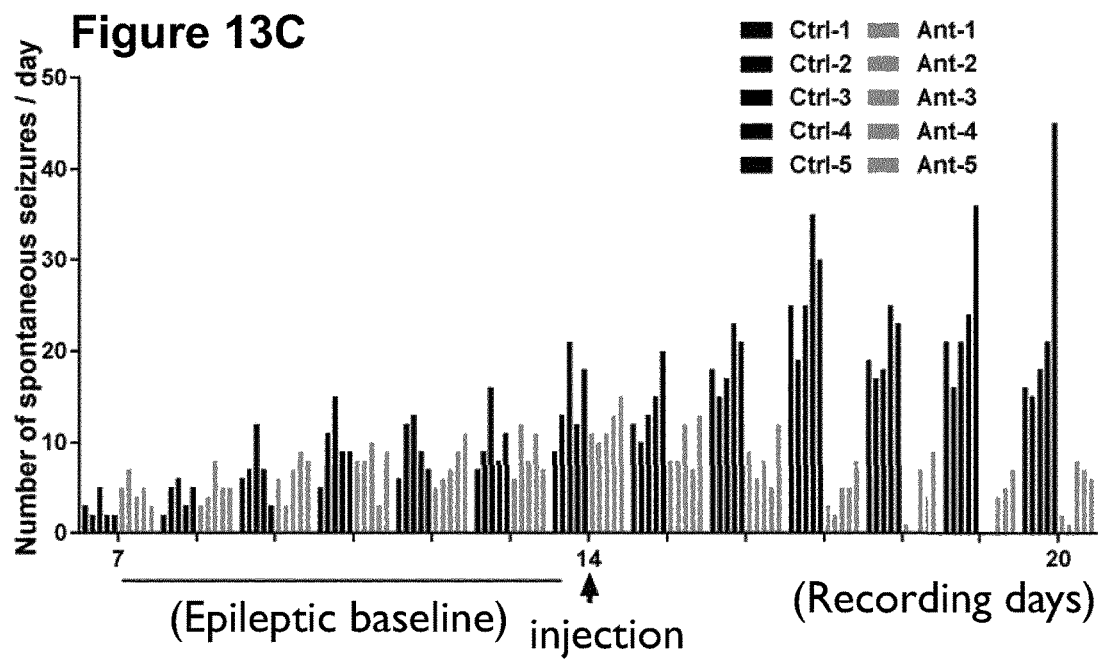
Figure 13D:
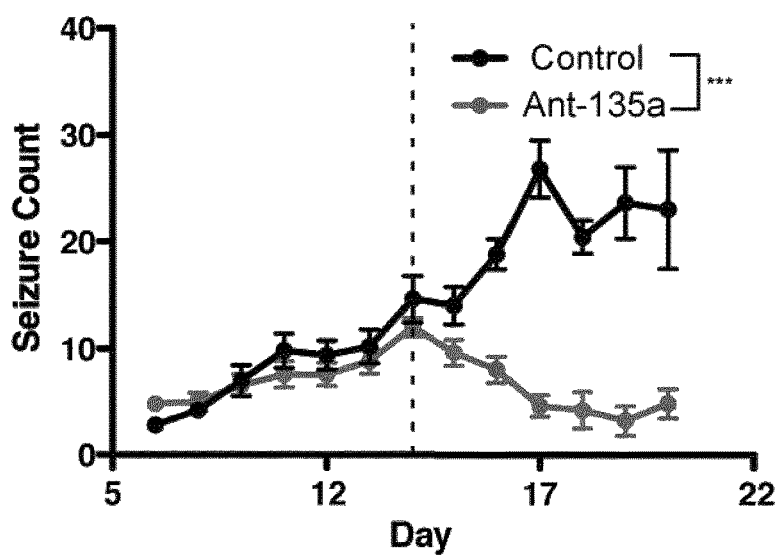
Figure 13E:
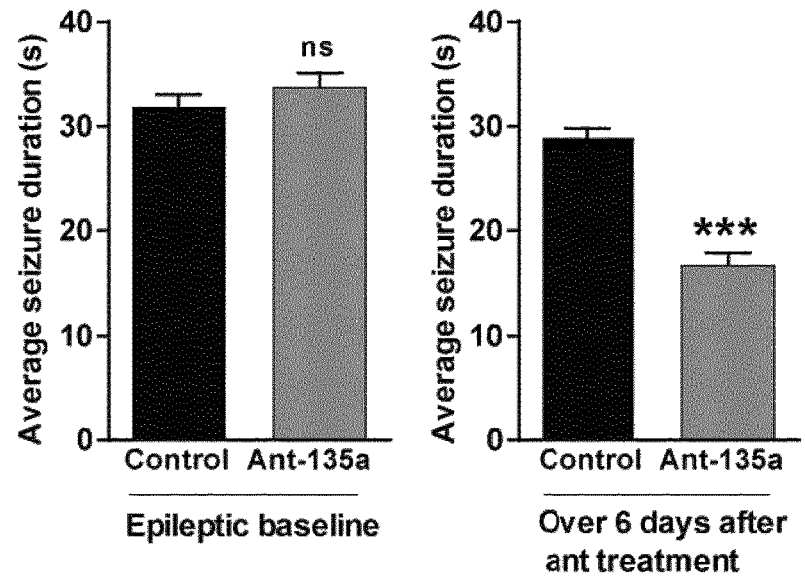
Figure 13F:
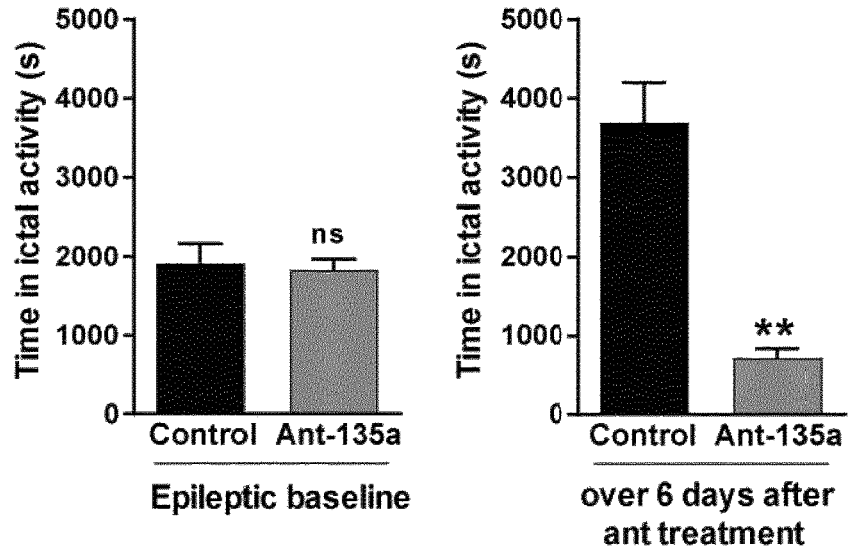
Figure 13G:
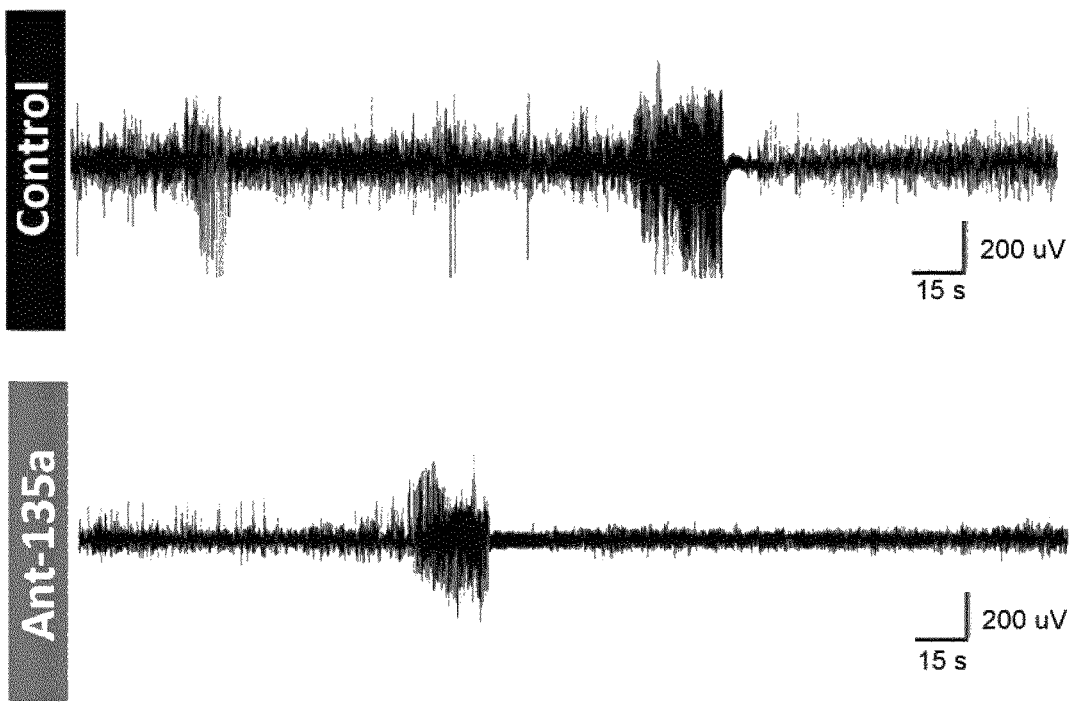
Figure 13H:
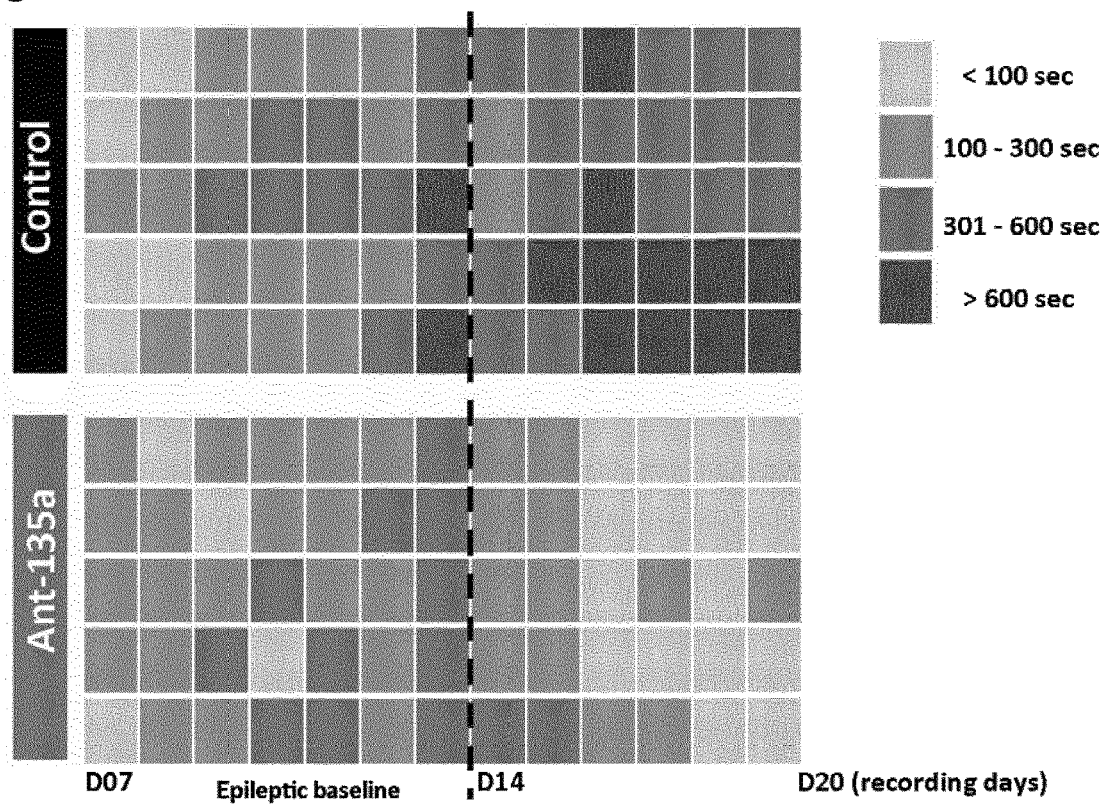

To assess the effect of blocking miR-135 on the occurrence of spontaneous seizures, SE-induced mice were injected with antagomirs for miR-135a or control at D14 and continuously monitored by EEG for 6 days after injection (FIG. 13B). One-week prior injections (D7-D14 after SE) baseline EEG recordings were performed and no significant difference in seizure frequency between treated and control animals was observed (FIG. 13C-13D). We verified in an independent experiment that injecting PBS or a modified Scramble (same as antagomir) yielded similar seizure pattern after SE (data not shown). Following injection of anti-miR-135a at D14, a significant decrease in the number of seizures per day was detected (FIG. 13C). A significantly different and strong reduction in seizure count was observed in ant-miR-135a as compared to control mice (FIG. 13D (n=5 control and ant-miR-135a injected; mixed design repeated measures general linear model; F statistic—5.834 ($F_{(20,60)}$=1.75 for $\alpha$=0.05); P<0.001). The average seizure duration was not different between the groups, before ant-135a injection (p=0.4721), whereas it was significantly lower (P=0.0006, Student's t test) after injection (FIG. 13E). Similarly, the total amount of time spent during seizures reduced in the first 6 days following ant-miR-135a injection (P=0.0021, Student's t test) (FIG. 13F). On average, ant-135a injected mice spent less time (<300 sec) in seizures per day, as compared to control injected mice (>300 sec) (FIG. 13H). Together, these data show that blocking elevated expression of miR-135a during the period of recurrent spontaneous seizures has an acute and seizure suppressive effect.

Figure 14A:
Figure 14B:
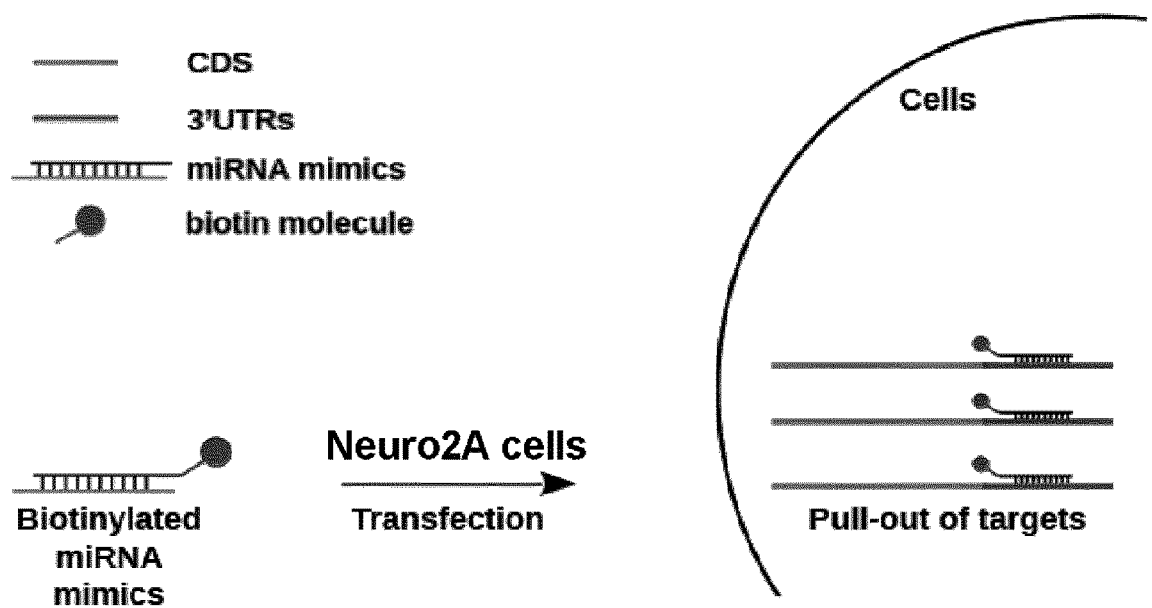
Figure 14C:
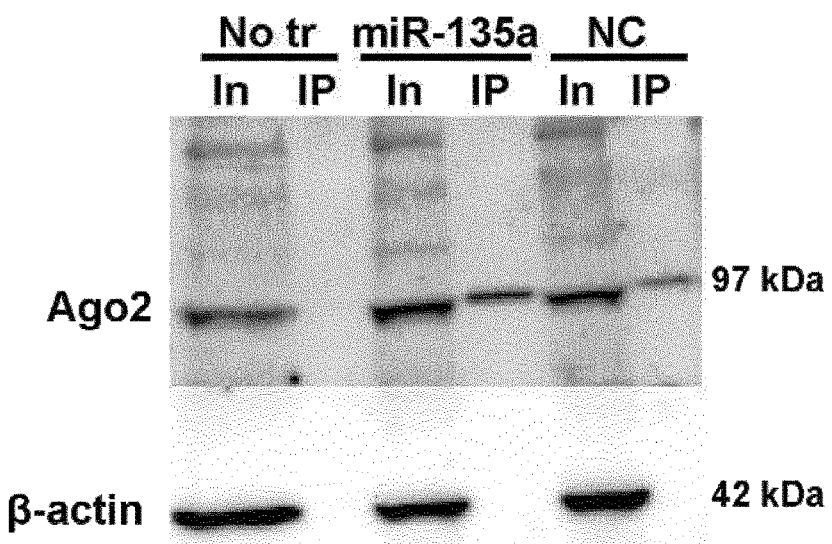

Identification of miR-135a Targets miR-135a can affect axon growth and regeneration by controlling KLF4 expression. However, the acute nature of the effects of ant-miR-135a injection on seizure activity in vivo hints at interference with cellular processes that regulate neuronal activity such as intracellular signaling, synaptic transmission or synaptic morphology. miRNAs function by binding specific sequences known as miRNA recognition elements (MRE) in the 3' untranslated regions (UTR) of target transcripts. Upon binding, miRNAs repress translation or induce target RNA degradation. Prediction tools are available that predict targets based on few empirical rules derived experimentally (Brennecke et al., 2005) (Lewis et al., 2005), but many of these computational prediction tools perform poorly in experimental validation due to high false positive rates (Krek et al., 2005). To identify targets that are physically interacting with miR-135a, we performed miRNA immunoprecipitation in neuronal mouse Neuro2A cells using biotin-tagged mimics. miR-135a and scrambled mimics were tagged with a biotin molecule at their 3' end (FIG. 14A, 14B) as 3' molecule tagging was reported to not interfere with seed recognition and miRNA binding (Wani and Cloonan, 2014). Although applying previously reported protocols for bio-miR IP (Wani and Cloonan, 2014), we confirmed the IP procedure by immunoblotting for Ago2 (the main component of RISC complex) following IP of miR-135 and scrambled mimics. Ago2 was detected in both input and IP samples, whereas the cytoskeletal protein $\beta$-actin was detected only in input samples (FIG. 14C). The presence of Ago2 confirms that the bio-miRNA mimic has been immunoprecipitated with the RISC complex, and presumably bound RNA targets. The sequence of the scr control is based on *Caenorhabditis elegans* microRNAs with minimal sequence identity with human, mice and rat. The presence of Ago2 in the scr IP sample can most likely be explained by the fact that Argonaute proteins are very conserved among species (Hack and Meister, 2008).

Figure 14D:
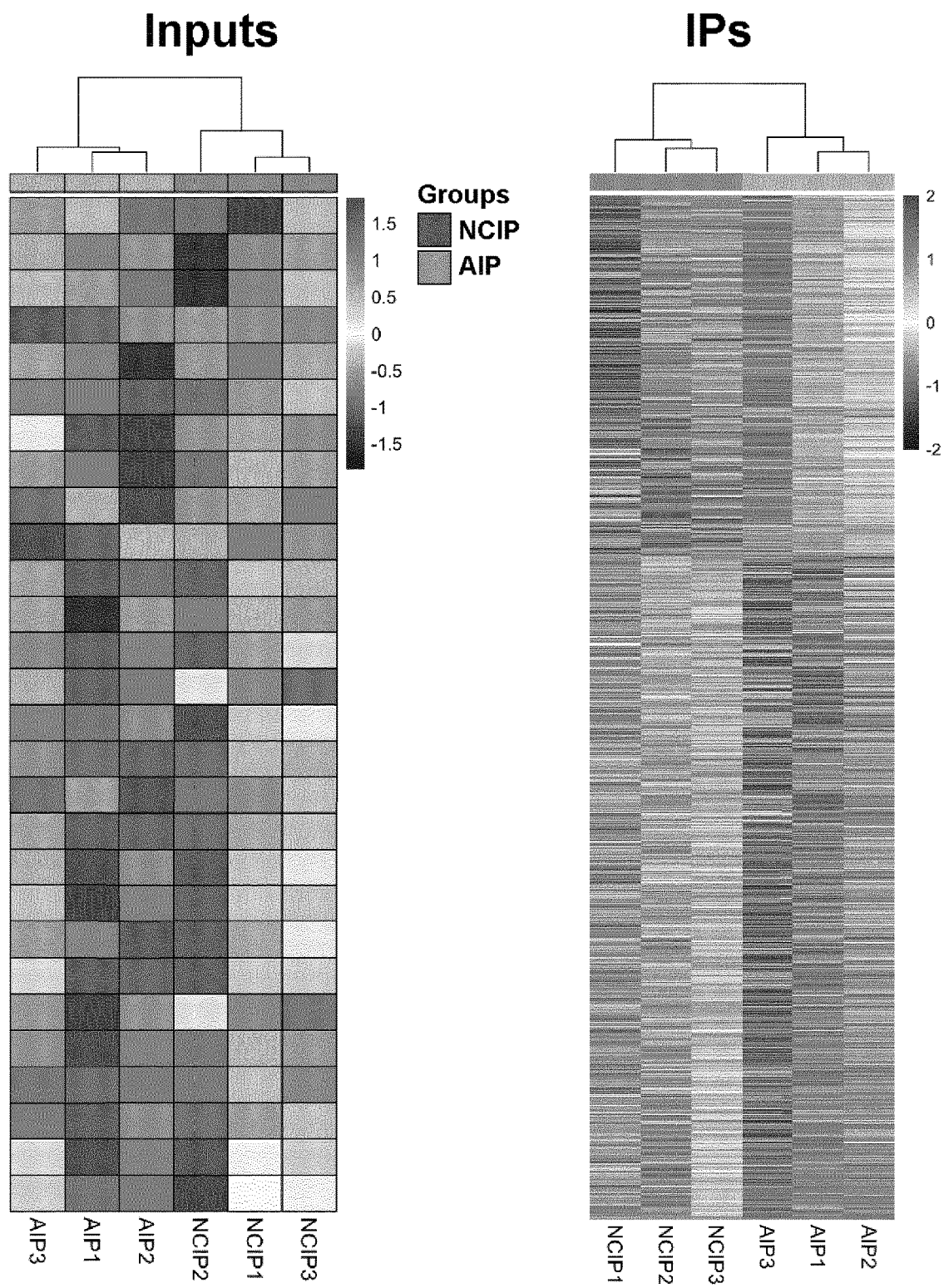
Figure 14E:
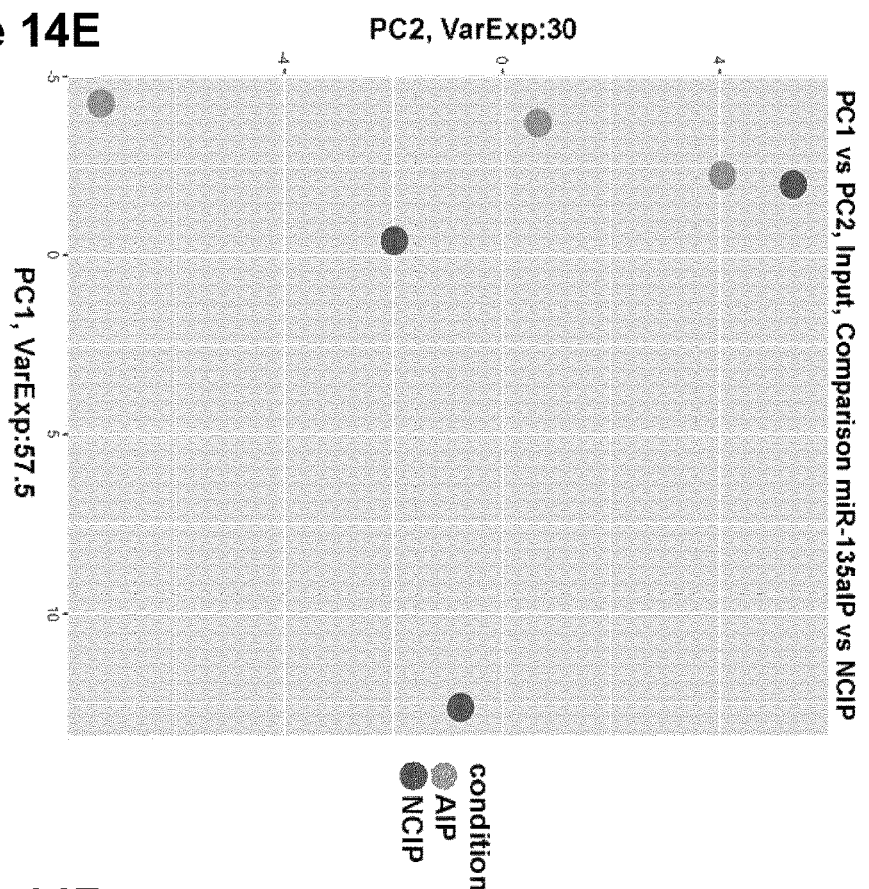
Figure 14F:
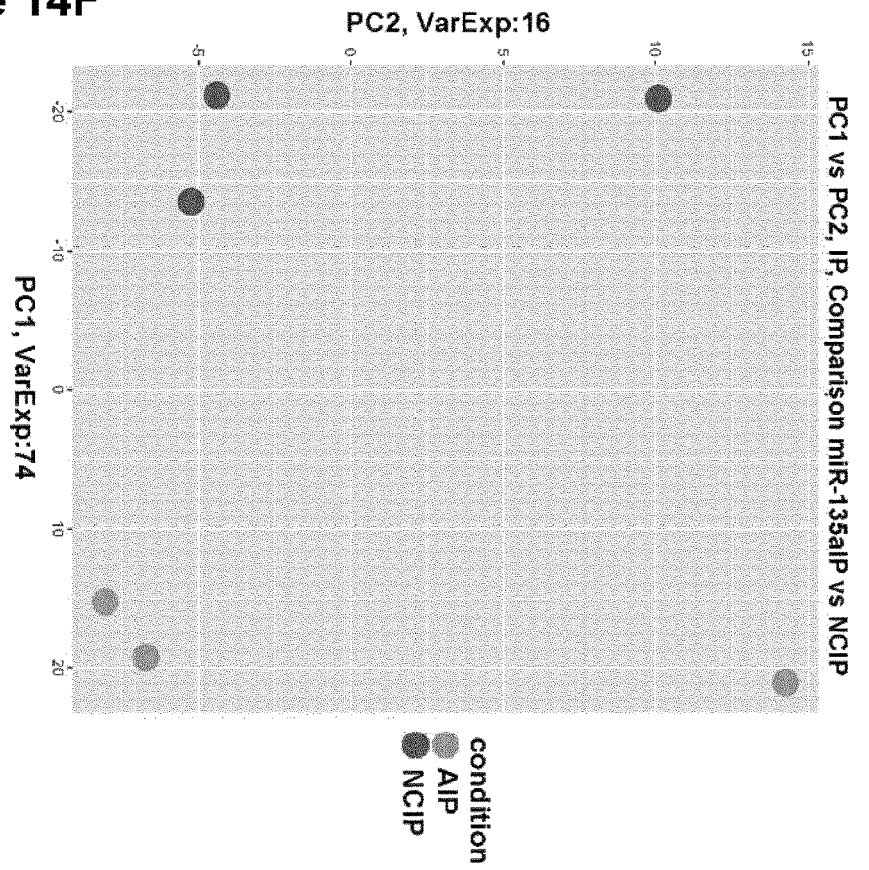
Figure 15A:
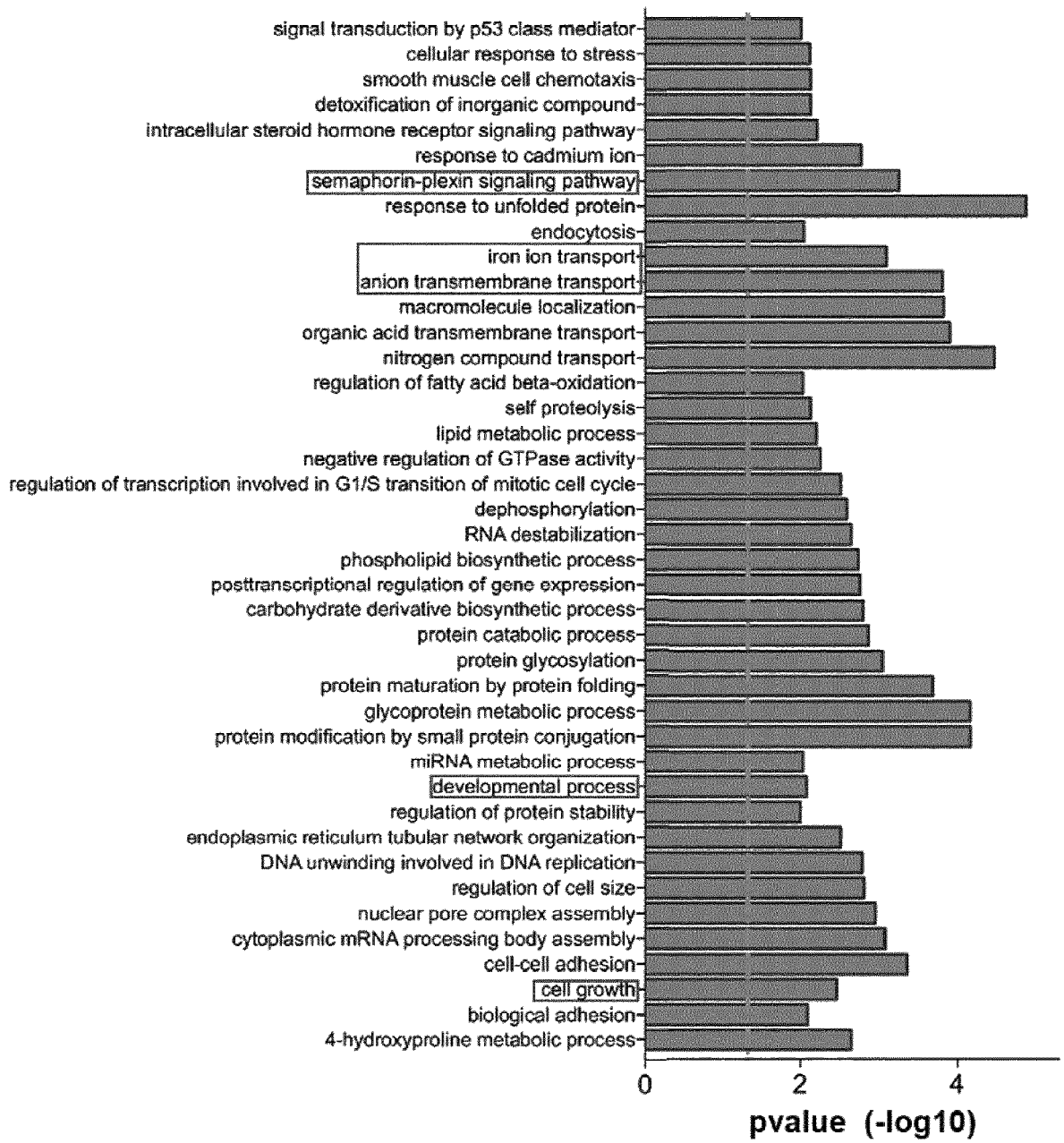
Figure 15B:
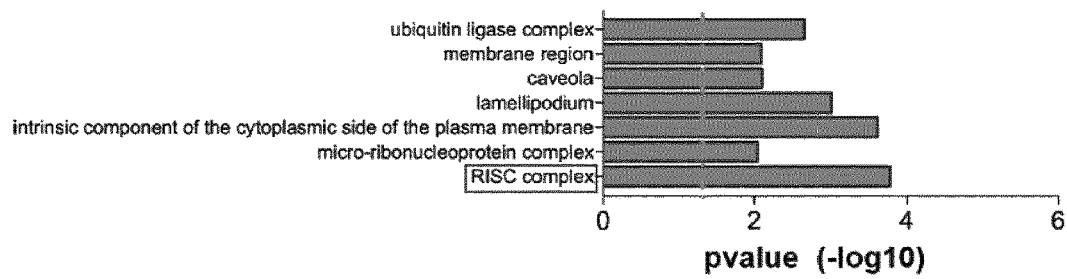
Figure 15C:
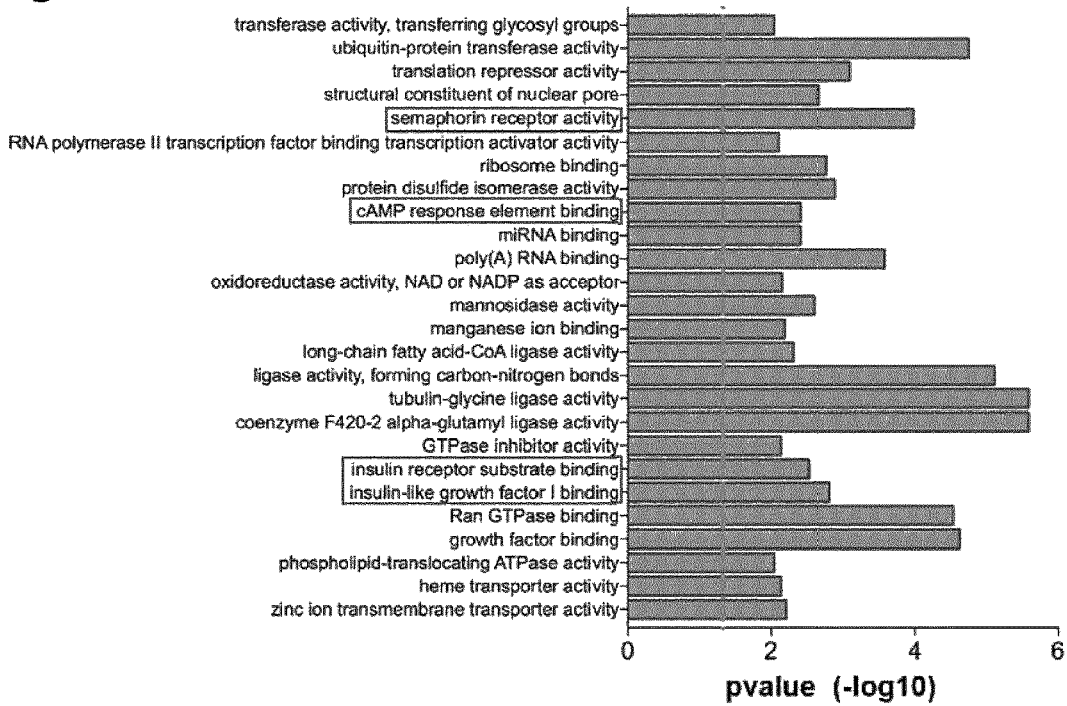
Figure 15D:
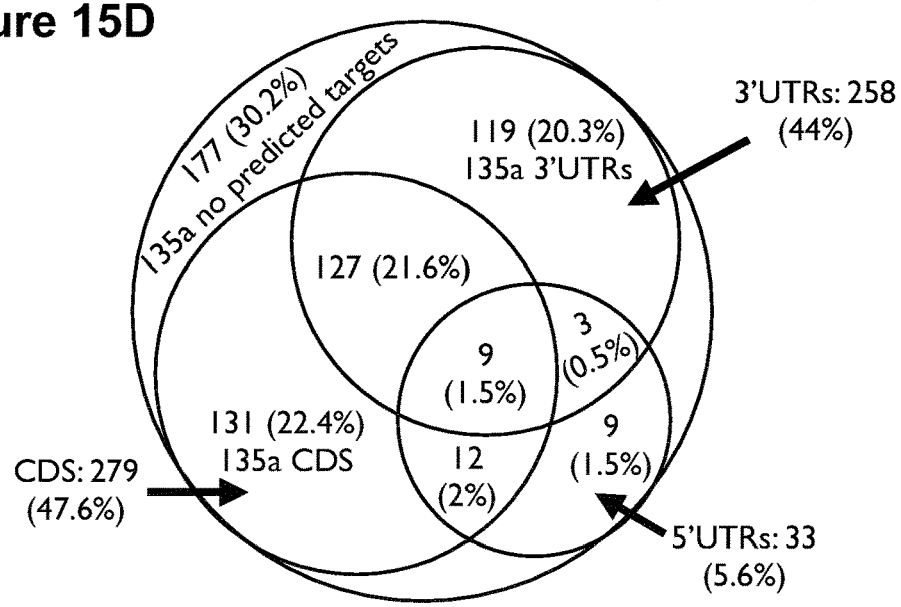
Figure 15E:
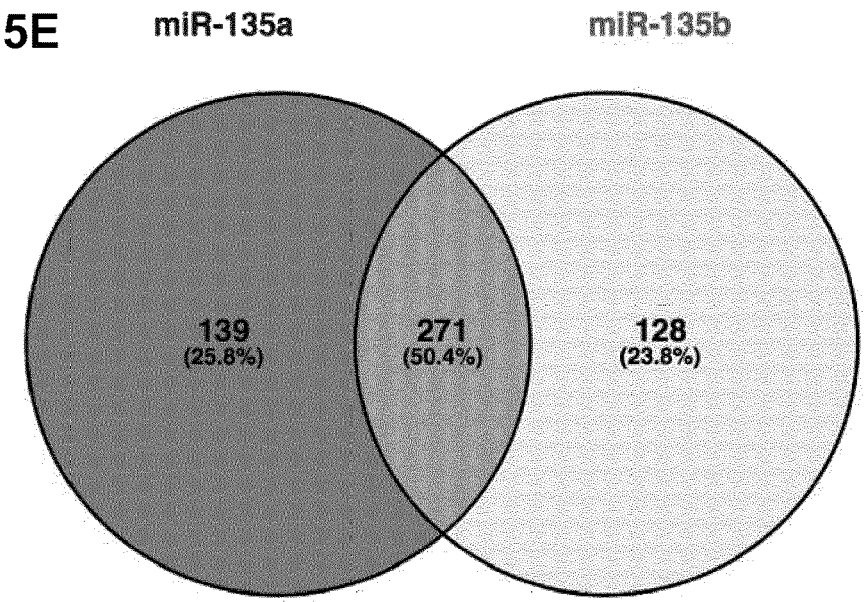

Following IP, total RNA sequencing was performed. For input samples, on average 58.5 million and for IP samples 48.7 million high quality reads were obtained. For input samples, most of these reads could be aligned with the mouse reference genome, but for IP samples 39.7% of reads could be aligned with the reference genome. As no polyA+ enrichment or ribosomal RNA depletion was performed, a large part of the aligned sequences derived from ribosomal RNA. For each sample, gene-level read counts and KPKM-values (K-mers Per Kilobase of exon per Million reads) were generated with Sailfish (Patro et al., 2014). Analysis of input samples revealed only few significantly changed transcripts including validated miR-135a targets such as Complexins (Cplx1 and Cplx2) (Hu et al., 2014). In IP samples, levels of 587 transcripts were significantly altered (using a cutoff of FDR<0.05 and P<0.01) (FIG. 14D). These observations were supported by principal component analyses (PCA) which showed clear segregation of gene expression profiles for IP samples (Scr vs miR-135a IP), but no clear segregation for inputs (FIG. 14E, F). Furthermore, IP samples contained many previously reported miR-135a targets such as Metastasis suppressor protein (Mtss)1 (Zhou et al., 2012), Cyclin-dependent kinase (Cdk)4 (Dang et al., 2014), proteoglycan Versican (Vcan) (Zhao et al., 2017), Zinc finger protein (Zfp) 217 (Xiang et al., 2017). Gene ontology (GO) analysis demonstrated that differentially expressed transcripts found in IP samples are involved in neuron-related functions as semaphorin-plexin signaling, semaphorin receptor activity, ion transport, and cAMP response element binding (FIG. 15A-C). As a first step to identify targets of miR-135a relevant for the observed effect of ant-miR-135a treatment in vivo, we selected transcripts from the IP samples with predicted miR-135a MREs, using miRanda software. MREs were found to be present not only in the 3'UTR (258), but also in the 5' UTR (33) and the coding sequence (CDS) (279) of the 578 transcripts. 177 putative targets had no predicted target site (FIG. 15D). miR-135a and miR-135b are highly similar and have an identical seed region, so in principle these miRNAs should target a similar set of mRNAs. Comparison of targets in IP samples of miR-135a and miR-135b (not shown) revealed 50% overlap while 25.8% of targets were unique for miR-135a) and 23.8% for miR-135b (FIG. 15E).

Figure 16A:
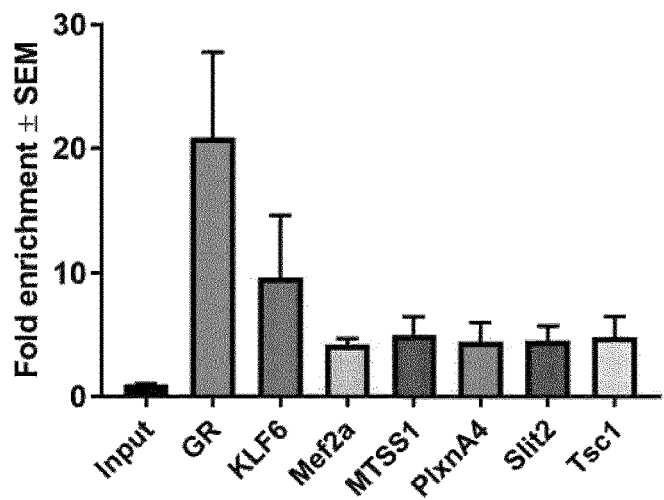
Figure 16B:
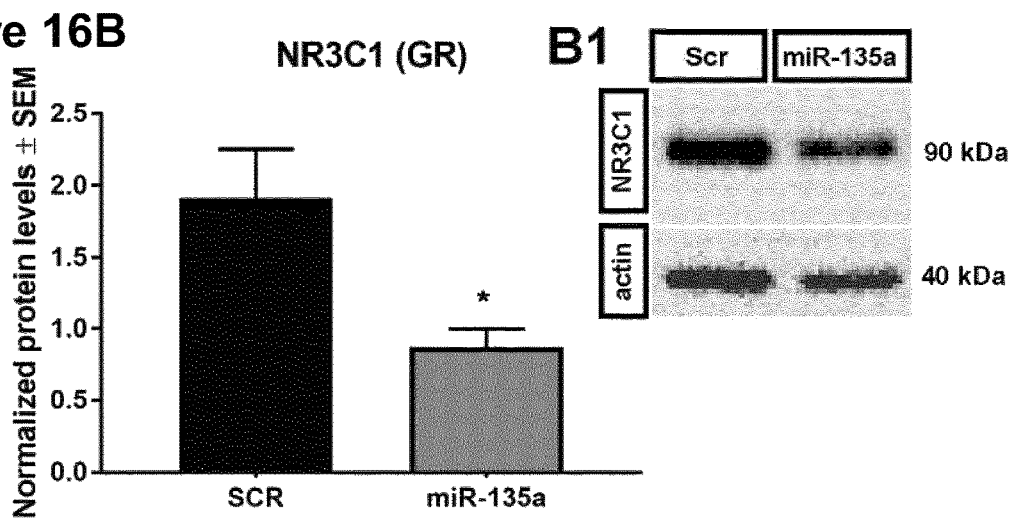
Figure 16C:
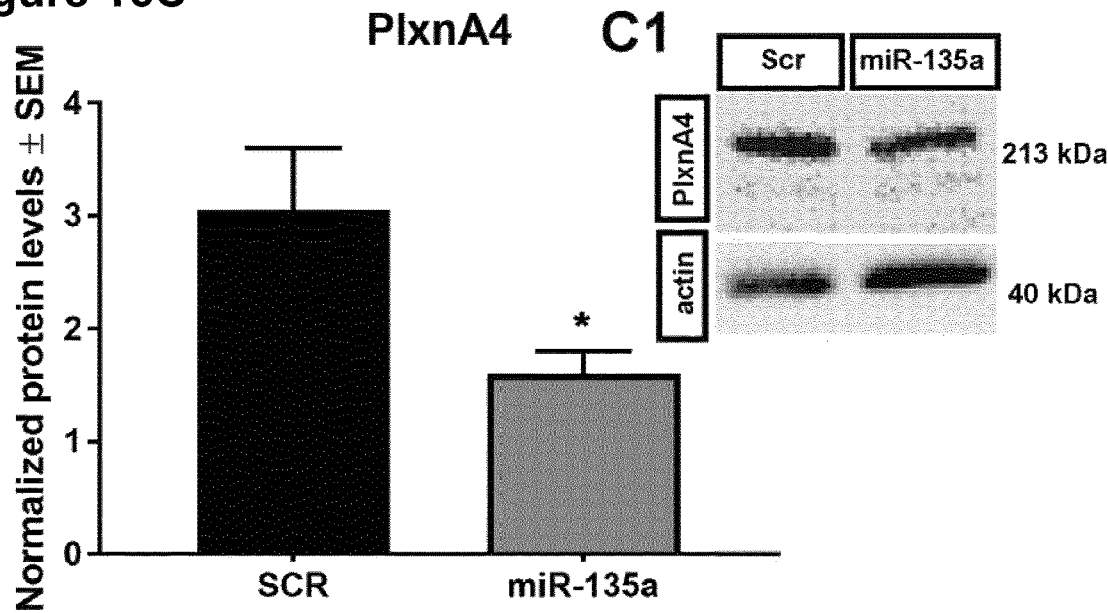
Figure 16D:
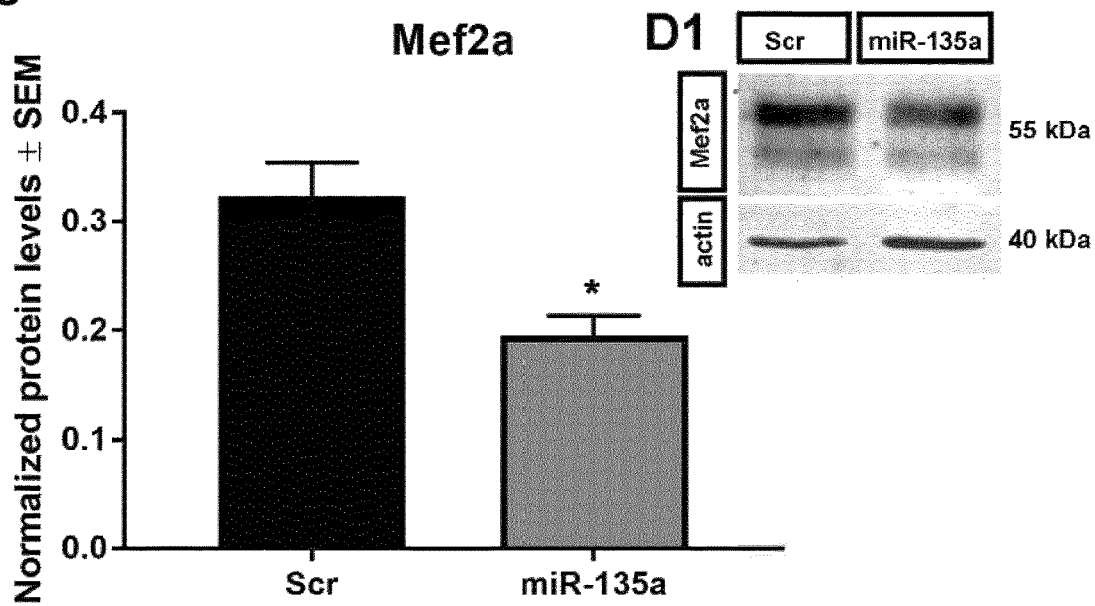

Using the approach outlined above, we identified several new targets of miR-135a with reported roles in the regulation of neuronal development and function (Table 10). For further validation, 7 targets were selected on basis of their function in neurons and/or implication in epilepsy (Tuberous sclerosis complex (TSC)1, Calcium channel (Cacnacic)). All targets tested were enriched in IP as compared to input samples (FIG. 16A). The effect of overexpression of miR-135a mimics in N2A cells on the expression of a few of the selected targets was tested and showed a significant down-regulation of NR3C1 (GR), PlxnA4 and Mef2a protein expression (FIG. 16B-D). This experiment confirms that targets identified by IP can be regulated by miR-135a.

TABLE 10

Gene list of selected targets for validation of Bio-IP.

| Gene | Function involved | Log FC | P-value | FDR |
| --- | --- | --- | --- | --- |
| Nr3c1 (GR) | Glucocorticoid receptor | 3.378650362 | 8.86E−16 | 2.17E−13 |
| Tsc1 | Tuberous sclerosis complex | 1.502705494 | 0.000161564 | 0.002630348 |
| Nrp1 | AG, MFS | 1.367505695 | 7.45E−06 | 0.000172036 |
| Tgfbr1 | Tgf beta signaling | 1.35700473 | 1.27E−06 | 3.73E−05 |
| Mtss1 | Spine density | 1.327584297 | 0.002385165 | 0.020182166 |
| PlxnA4 | AG, MFS | 1.207035618 | 0.000125568 | 0.00190651 |
| Cacna1c | Calcium channel | 1.1901732 | 0.000761925 | 0.008197154 |
| Ncam 1 | Neurite outgrowth | 1.052455671 | 5.18E−05 | 0.000926565 |
| Slit2 | AG, MFS | 1.044428042 | 0.000332578 | 0.004183416 |
| Mef2a | Spine density | 0.983455004 | 0.002032665 | 0.01769962 |
| Creb1 | Transcription factor | 0.909096844 | 0.00363345 | 0.028097983 |

AG—axon guidance, MFS—mossy fiber sprouting.

The miR-135 Target Mef2a is Regulated in TLE

Figure 17A:
Figure 17B:
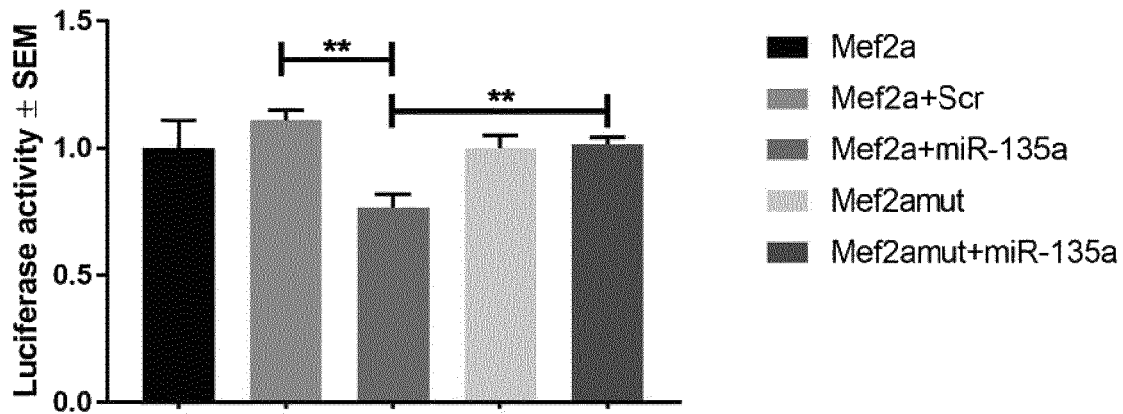
Figure 17C:
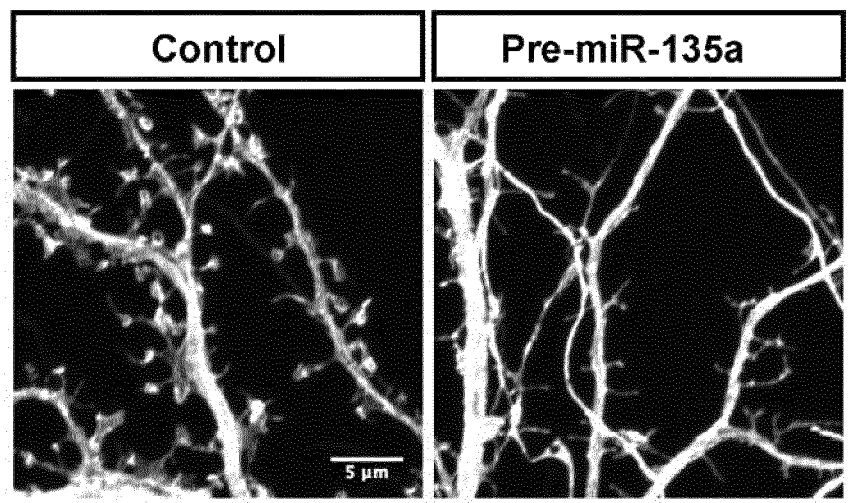

MEF2 proteins (MEF2A-D) form a family of transcription factors that are spatially and temporally expressed in the brain (Lyons et al., 1995), with most prominent expression for MEF2A, 2C and 2D. MEF2s mediate activity-dependent synaptic development, and are activated by neurotrophin stimulation and calcium influx resulting from increased neurotransmitter release at synapses (Flavell et al., 2008). Mutations in MEF2C were described in patients with severe mental retardation and epilepsy (Bienvenu et al., 2013) (Nowakowska et al., 2010). In addition, Mef2a is deregulated in temporal cortex of human and experimental TLE (Huang et al., 2016). Based on the ant-miR-135a experiments (FIG. 13) and its specific enrichment by miR-135a IP, we focused subsequent experiments on Mef2a. Mef2a 3'UTR contains one specific conserved binding site for miR-135a (seed sequence from 1024-1030 nt) (FIG. 17A). This site is targeted by miR-135a as shown by luciferase assay. Co-expression of miR-135a mimics with the miR-135a binding site in a luciferase reporter vector led to reduced luciferase activity. Mutation of the site abolished the effect of miR-135a (FIG. 17B).

Figure 17D:
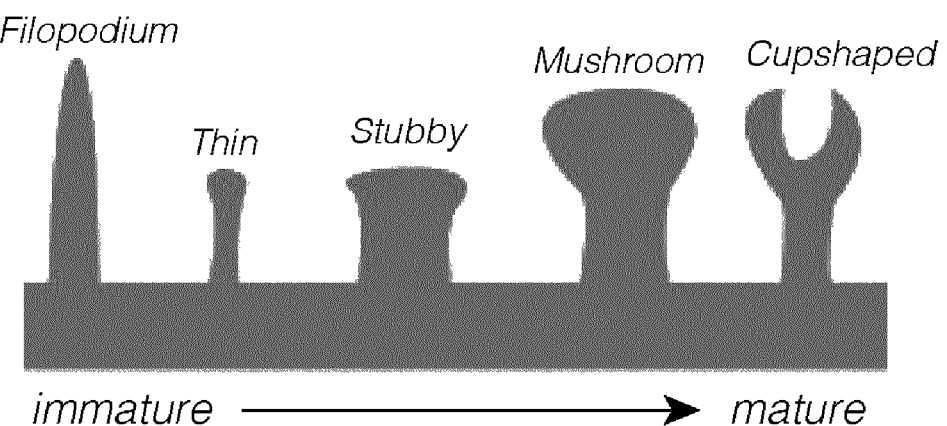
Figure 17E:
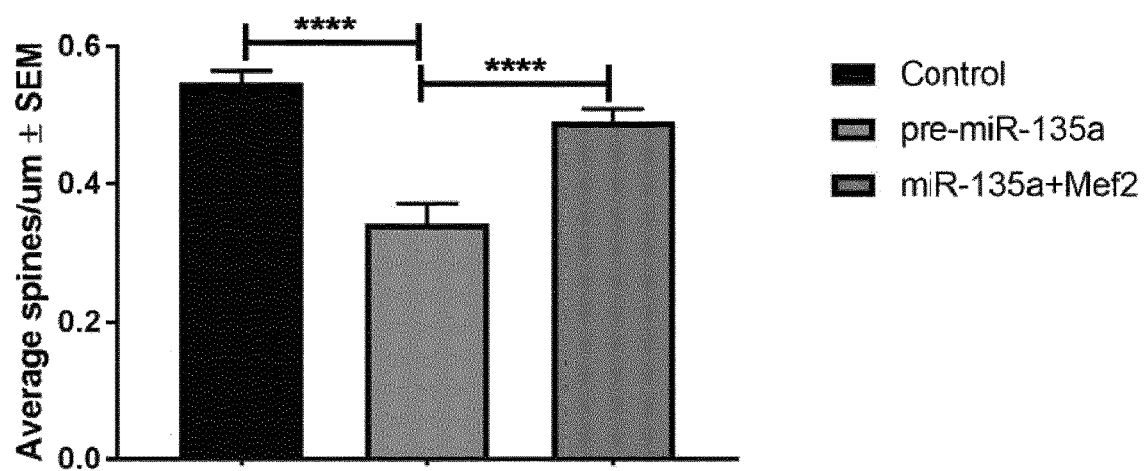
Figure 17F:
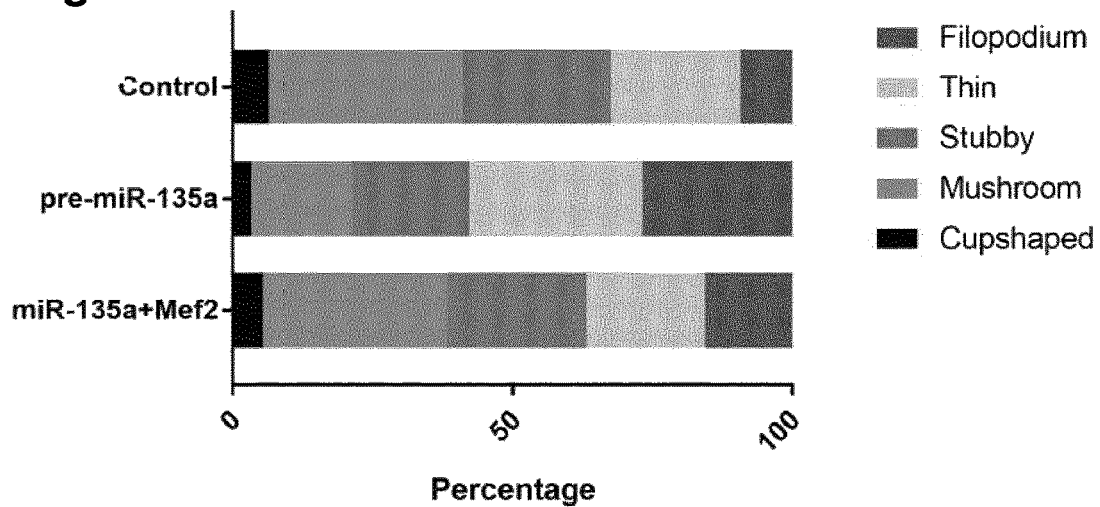
Figure 17G:
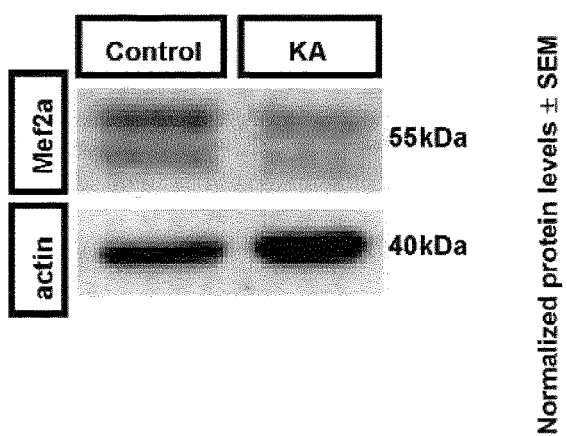
Figure 17H:
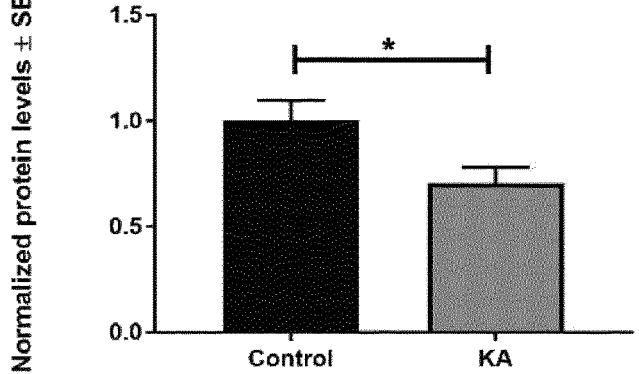

To verify if miR-135a also regulates spine number, miR-135a was overexpressed in mouse primary hippocampal neurons. Spine density was measured at a distance of 100 um from the 1$^{st}$ secondary dendritic branch on the apical dendrite (FIG. 17C) and 5 different spine types (cupshaped, mushroom, stubby, thin and filopodium) were counted (FIG. 17D). Overexpression of miR-135a led to a significant reduction in the number of spines (0.34±0.13 spines/um) compared to the control (0.55±0.06 spines/um). Overexpression of miR-135a in vitro resembled pathological neuronal cell observed in vivo in TLE, and so increased miR-135a in epileptic brain could be directly or indirectly contributing to the neuronal spine loss observed, though the exact mechanisms are not clear. This effect was rescued to control levels when Mef2 vector lacking the 3' UTR was co-expressed with miR-135a (0.49±0.08 spines/um) (FIG. 17E). Interestingly, miR-135a overexpression led to a specific reduction in the number of mature spines: cupshaped (3.32%), mushroom (18.05%), stubby (20.81%), but led to increase in immature type of spines thin (31.00%) and filopodium (26.82%) compared to control (cupshaped: 6.60%, mushroom: 34.51%, stubby: 26.53%, thin: 23.16%, filopodium: 9.2%). The reduction in mature spines and increase in immature spine type due to miR-135a overexpression was normalized to control levels when miR-135a was co-expressed with Mef2 (cupshaped: 5.49%, mushroom: 32.77%, stubby: 25.00%, thin: 21.12%, filopodium: 15.63%) (FIG. 17F). Thus, increased expression of miR-135a leads to a MEF2-dependent increase in spine number and type.

Figure 17I:
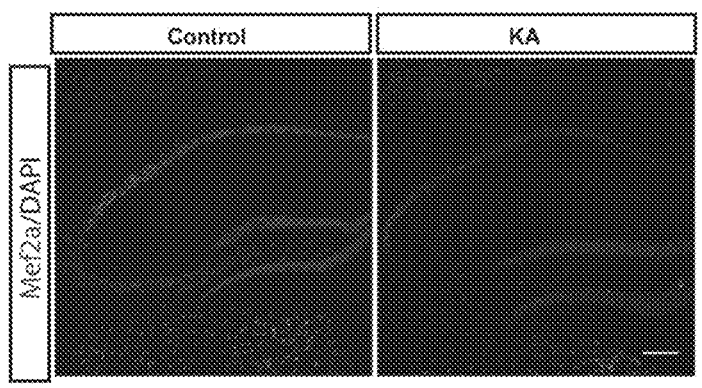
Figure 17J:
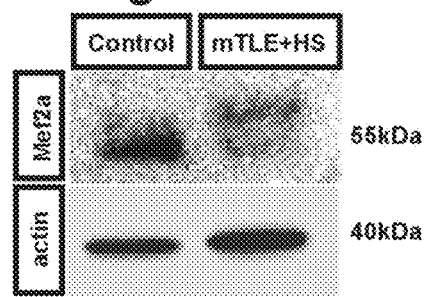
Figure 17K:
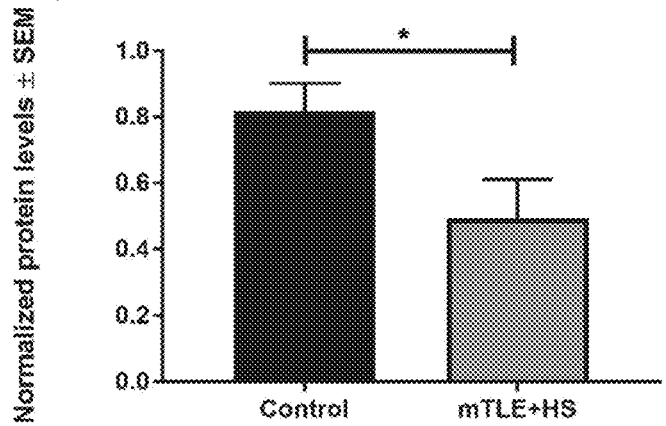
Figure 17M:
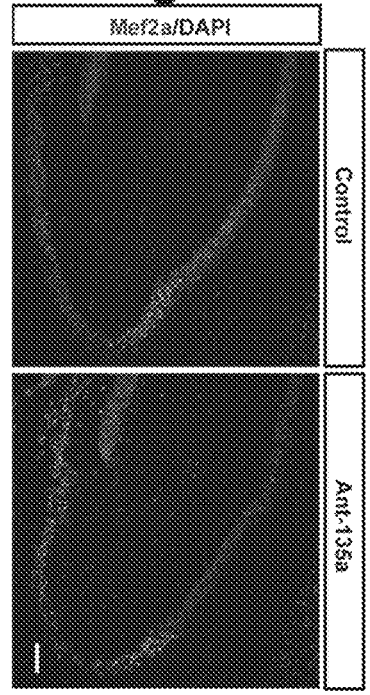
Figure 17L:
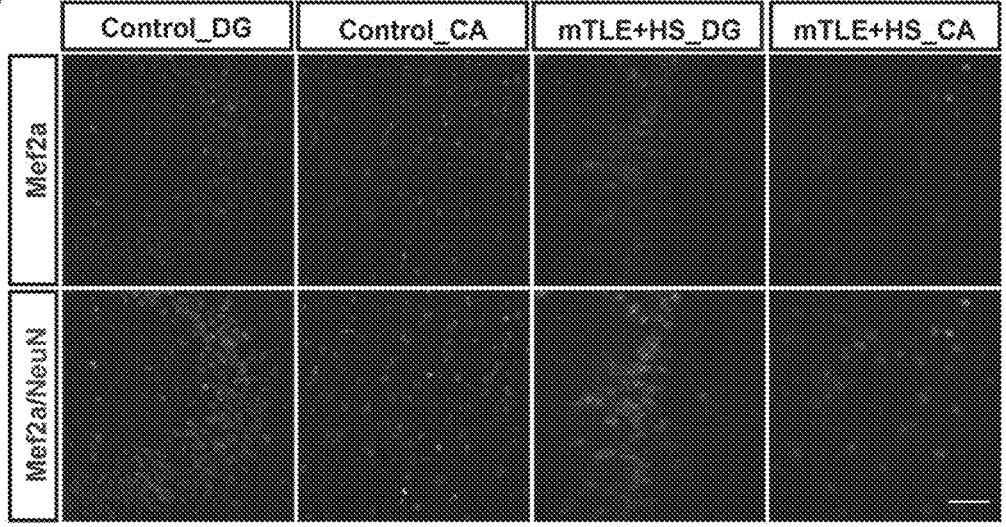

To examine whether miR-135a could interact in TLE we tested Mef2a expression in mouse and human TLE hippocampus. In line with our model, Mef2a protein expression was significantly reduced in the hippocampus of D14 IAK mice (FIG. 17G-H) and a weaker immunosignals were observed (FIG. 17I). Similarly, in patients with mTLE, MEF2A expression was strongly reduced in mTLE+HS hippocampal samples compared to controls (FIG. 17J-K), and weaker immunostaining was observed in mTLE+HS condition compared to controls in the dentate gyrus and CA region (FIG. 17L). Finally, blocking miR-135a in vivo using antagomirs resulted in increased Mef2a expression, as detected by immunohistochemistry (FIG. 17M). Together, these results show that the increased expression of miR-135a in hippocampal neurons in mTLE leads to decreased MEF2A levels. Loss of MEF2 in mTLE leads to abnormal spine formation and thereby contributes to aberrant firing patterns and cell death observed in epilepsy.

TABLE 11 pre-miRNA qPCR primer sequences (pre-miR-135a1 and a2) were designed with Primer3 software. Similarly, for validation of bio-IP targets primer sequences per target are shown below.

| Pre-mir primers | | | | |
| --- | --- | --- | --- | --- |
| Gene | Species | | Sequence | SEQ ID NO |
| Pre-miR-135a1 | Human | Forward | TCGCTGTTCTCTATGGCTTTT | 355 |
|  |  | Reverse | CGGCTCCAATCCCTATATGA | 356 |
| Pre-miR-135a2 | Human | Forward | TGCTTTATGGCTTTTTATTCCT | 357 |
|  |  | Reverse | TGGCTTCCATCCCTACATGA | 358 |

TABLE 11-continued pre-miRNA qPCR primer sequences (pre-miR-135a1 and a2) were designed with Primer3 software. Similarly, for validation of bio-IP targets primer sequences per target are shown below.

| | | | | |
|---|---|---|---|---|
| Pre-miR-135a1 | Mice | Forward | GCCTCACTGTTCTCTATGGCTTT | 359 |
| | | Reverse | CCACGGCTCCAATCCCTATATGA | 360 |
| Pre-miR-135a2 | Mice | Forward | TGCTTTATGGCTTTTTATTC | 361 |
| | | Reverse | CATCCCTACATGAGACTTTATT | 362 |
| GAPDH | Human | Forward | TGGAAGGACTCATGACCACA | 363 |
| | | Reverse | GGGATGATGTTCTGGAGAGC | 364 |
| Beta-actin | Mice | Forward | AGCCATGTACGTAGCCATCC | 365 |
| | | Reverse | CTCTCAGCTGTGGTGGTGAA | 366 |

Bio-IP targets mouse primers

| Gene | | Sequence | SEQ ID NO |
|---|---|---|---|
| GR | Forward | GGGGAAGCGTGATGGACTTG | 367 |
| | Reverse | CAGCAGCCACTGAGGGTGAA | 368 |
| KLF6 | Forward | GAGTTCCTCCGTCATTTCCA | 369 |
| | Reverse | GTCGCCATTACCCTTGTCAC | 370 |
| Mef2a | Forward | AGCAGCACCATCTAGGACAA | 371 |
| | Reverse | CTGCTGTTGGAAGCCTGATG | 372 |
| Mtss1 | Forward | ACAGCACCCAGACCACCACC | 373 |
| | Reverse | TGCCTCCTGGTCGCCACTTA | 374 |
| PlxnA4 | Forward | TCTCAGTACAACGTGCTG | 375 |
| | Reverse | TAGCACTGGATCTGATTGC | 376 |
| Slit2 | Forward | CAGTCATTCATGGCTCCCTC | 377 |
| | Reverse | TTCCCTCGGCAGTCTACAAT | 378 |
| Tsc1 | Forward | CAGGAGTTACAGACAAAGCTGG | 379 |
| | Reverse | AGCTTCTGAGAGACCTGGCT | 380 |

REFERENCE LIST

Adams R. H. and Alitalo K. Nat Rev Mol Cell Biol 8(6): 464-478, 2007.
Aksoy-Aksel A, Zampa F, Schratt G (2014) Philos Trans R Soc Lond B Biol Sci 369:20130515-20130515—rstb.royalsocietypublishing.org/cgi/doi/10.1098/rstb.2013.0515
Anand S., Majeti B. K., Acevedo L. M., et al., Nat Med 16(8):909-914, 2010.
Apara A, Goldberg J L (2014) Neural Regen Res 9:1418-1421 Available at: www.nrronline.org/text.asp?2014/9/15/1418/139454
Aravin, A. & Tuschl, T. FEBS Lett 579:5830-40, 2005.
Asahara T., Masuda H., Takahashi T., Kalka C., Pastore C., Silver M., Kearne M., Magner M. and Isner J. M. Circ Res 85(3):221-228, 1999.
Baldwin K T, Giger R J (2015) Front Mol Neurosci 8:23 Available at: www.ncbi.nlm.nih.gov/pubmed/26113809
van Battum E Y, Gunput R-AF, Lemstra S, et al., (2014) Nat Commun 5:4317 Available at: www.ncbi.nlm.nih.gov/pubmed/25007825
Baudet M-L, Bellon A, Holt C E (2013) Semin Cell Dev Biol 24:146-155 Available at: www.ncbi.nlm.nih.gov/pubmed/23219835
Beijnum, J. R., Rousch, M., Castermans, K., van der Linden, E & Griffioen, A W. Nature Protocols 3(6):1085-1091, 2008.
Berezikov, E., Cuppen, E., and Plasterk, R. H. Nat Genet 38 Suppl, S2-7, 2006.
Berezikov, E., Liu, N., Flynt, A. S., Hodges, E., Rooks, M., Hannon, G. J., and Lai, E. C. Nat Genet 42:6-9; author reply 9-10, 2010.
Berezikov, E. et al. Genome Res 21:203-215, 2011.
Blackmore M G, Moore D L, et al., (2010) Mol Cell Neurosci 44:43-54 Available at: linkinghub.elsevier.com/retrieve/pii/S1044743110000254
Bodles-Brakhop A M, Heller R and Draghia-Akli R. Current Clinical Developments. Molecular Therapy vol. 17 no. 4:585-592, apr. 2009
Bonnet, E., Wuyts, J., Rouze, P. and Van De, P. e. Y. Bioinformatics 20:2911-2917, 2004.
Carmeliet P. Nature 438(7070):932-936, 2005.
Carmeliet P. Nat Med 6(4):389-395, 2000.
Carmeliet P. and Jain R. K. Nature 407(6801):249-257, 2000.
Caronia-Brown G, Anderegg A, Awatramani R (2016) Neural Dev 11:9 Available at: neuraldevelopment.biomedcentral.com/articles/10.1186/s13064-016-0065-y
Chang, B. S., and Lowenstein, D. H. (2003). Epilepsy. N. Engl. J. Med. 349, 1257-1266.
Chang T. C. and Mendell J. T. Annu Rev Genomics Hum Genet 8:215-239, 2007.
Chen C. Z., Li L., Lodish H. F. and Bartel D. P. Science 303(5654):83-86, 2004.
Creighton, C J., et al., Briefings in Bioinformatics. VOL 10. NO 5:490-497, 2009.
Czech, M. P. (2006). N. Engl. J. Med. 354, 1194-1195.
Daud, A. I. et al., Journal of clinical oncology 26(36):5896-903, 2008.

Dickendesher T L, Baldwin K T, et al., (2012) Nat Neurosci 15:703-712 Available at: www.pubmedcentral.nih.gov/articlerenderfcgi?artid=3337880&tool=pmcentrez&rendertype=abstract Ebert, M. S., and Sharp, P. A. (2012). Cell 149, 515-524.

Enciu, A et al., BMC Neurology, 2011, 11:75, DOI: 10.1186/1471-2377-11-75

Engel, J., Jr. (2001). Epilepsia 42 Suppl 6, 3.

van Erp S, van den Heuvel D M A, et al., (2015) Dev Cell 35:537-552 Available at: www.ncbi.nlm.nih.gov/pubmed/26651291

Fang J, Shaw P X, Wang Y, Goldberg J L (2016) eNeuro 3 Available at: www.ncbi.nlm.nih.gov/pubmed/27022622

Fish J. E., Santoro M. M., Morton S. U., Yu S., Yeh R. F., Wythe J. D., Ivey K. N., Bruneau B. G., Stainier D. Y. and Srivastava D. Dev Cell 15(2):272-284, 2008.

Flavell, S. W., Cowan, C. W., Kim, T. K., Greer, P. L., Lin, Y., Paradis, S., Griffith, E. C., Hu, L. S., Chen, C., and Greenberg, M. E. (2006). Science 311, 1008-1012.

Flavell, S. W., Kim, T. K., et al., (2008). Neuron 60, 1022-1038.

Folkman J. N Engl J Med. 285, 21:1182-1186, 1971.

Folkman J. Nat Med 1(1):27-31, 1995.

Folkman J. Nat Rev Drug Discov 6(4):273-286, 2007.

Folkman J. Semin Oncol 29(6 Suppl 16):15-18, 2002.

Gamier B. et al., bioconj. chem., 2009, 11:2114-22 van Gassen, K. L., de Wit, M., Koerkamp, M. J., Rensen, M. G., van Rijen, P. C., Holstege, F. C., Lindhout, D., and de Graan, P. N. (2008). Epilepsia 49, 1055-1065.

Gaudet A D, Mandrekar-Colucci S, Hall J C E, et al., (2016) J Neurosci 36:8516-8532 Available at: www.ncbi.nlm.nih.gov/pubmed/27511021

Gorter, J. A., Iyer, A., White, I., et al., (2014). Neurobiol Dis 62, 508-520.

Gorter, J. A., van Vliet, E. A., et al., (2006). J Neurosci 26, 11083-11110.

Griffioen A. W. and Molema G. Pharmacol Rev 52(2):237-268, 2000.

Gross, C., Yao, X., Engel, T., et al., (2016). Cell Rep 17, 37-45.

Hanahan D. and Folkman J. Cell 86(3):353-364, 1996.

Hancock M L, Preitner N, Quan J, Flanagan J G (2014) J Neurosci 34:66-78 Available at: www.jneurosci.org/cgi/doi/10.1523/JNEUROSCI.3371-13.2014

Harris T. A., Yamakuchi M., et al., Proc Natl Acad Sci USA 105(5):1516-1521, 2008.

He Z, Jin Y (2016) Neuron 90:437-451 Available at: www.ncbi.nlm.nih.gov/pubmed/27151637

Helisch A. and Schaper W. Microcirculation 10(1):83-97, 2003.

Henshall, D. C., Hamer, H. M., et al., (2016). Lancet Neurol. 15, 1368-1376.

Heusschen R. et al., iochim Biophys Acta. 1805, 1:87-96, 2010

Hofacker, I. L. Nucleic Acids Res 31:3429-31, 2003.

Kuehbacher A., Urbich, C., Zeiher A. M. and Dimmeler S. Circ Res 101(1):59-68, 2007.

Hu Y-W, Jiang J-J, Yan-Gao, Wang R-Y, Tu G-J (2016) Neurosci Lett 622:61-66 Available at: www.ncbi.nlm.nih.gov/pubmed/27102143

Hu Z, Yu D, Gu Q, Yang Y, Tu K, Zhu J, Li Z (2014) Nat Commun 5:3263 Available at: www.nature.com/doifinder/ncomms4263

Issler O, Haramati S, Paul E D, et al., (2014) Neuron 83:344-360 Available at: linkinghub.elsevier.com/retrieve/pii/S0896627314004863

Jiang J-J, Liu C-M, Zhang B-Y, Wang X-W, et al., (2015) Cell Death Dis 6:e1865 Available at: www.ncbi.nlm.nih.gov/pubmed/26313916

Jimenez-Mateos, E. M., Engel, T., et al., (2012). Nat Med 18, 1087-1094.

Jimenez-Mateos, E. M., and Henshall, D. C. (2013). Neuroscience 238, 218-229.

Kan A A, van Erp S, Derijck A A H A, de Wit M, et al., (2012) Cell Mol Life Sci 69:3127-3145 Available at: www.ncbi.nlm.nih.gov/pubmed/22535415

Khatri R, Subramanian S (2013) Front Oncol 3:268 Available at: journal.frontiersin.org/article/10.3389/fonc.2013.00268/abstract Kosik, K. S. (2006). Nat. Rev. Neurosci. 7, 911-920.

Kraev et al, PLoS ONE, 10 Aug. 2011, Vol 6, Issue 8, DOI: 10.1371/journal.pone.0023433

Lagos-Quintana M, Rauhut R, Lendeckel W, Tuschl T (2001) Science (80-) 294:853-858 Available at: www.ncbi.nlm.nih.gov/pubmed/11679670

Lagos-Quintana M, Rauhut R, Yalcin A, Meyer J, Lendeckel W, Tuschl T (2002) Curr Biol 12:735-739 Available at: www.ncbi.nlm.nih.gov/pubmed/12007417

Li P, Teng Z-Q, Liu C-M (2016) Neural Plast 2016:1-11 Available at: www.ncbi.nlm.nih.gov/pubmed/27818801

Lin C-W, Chang Y-L, Chang Y-C, et al., (2013) Nat Commun 4:1877 Available at: www.nature.com/doifinder/10.1038/ncomms2876

Lin L, et al., (2016) Curr Vasc Pharmacol 14:211-218 www.ncbi.nlm.nih.gov/pubmed/26202084.

Linsen, SEV., de Wit, E., de Bruijn, E.& Cuppen, E. BMC Genomics 11:249, 2010.

Loscher, W., Klitgaard, H., et al., (2013). Nat. Rev. Drug Discov. 12, 757-776.

Martirosyan N L, Carotenuto A, Patel A A, et al., (2016) Front Surg 3:56 Available at: www.ncbi.nlm.nih.gov/pubmed/27878119

Miki K., Miki A., et al., Ophthalmology 116(9):1748-1754, September 2009.

Moore D L, Blackmore M G, et al., (2009) Science 326: 298-301 Available at: www.sciencernag.org/cgi/doi/10.1126/science.1175737

Moritoki Y, Hayashi Y, Mizuno K, et al., (2014) J Urol 191:1174-1180 Available at: linkinghub.elsevier.com/retrieve/pii/S002253471305876X Moshe, S. L., Perucca, E., Ryvlin, P., and Tomson, T. (2015). Lancet 385, 884-898.

Mouri, G., et al., (2008). Brain Res 1213, 140-151.

Nagel R, le Sage C, et al., (2008) Cancer Res 68:5795-5802 Available at: cancerres.aacrjournals.org/cgi/doi/10.1158/0008-5472.CAN-08-0951

Obad, S., dos Santos, C. O. et al. Nature Genetics 43,371-378, 2011.

Obernosterer, G., Martinez, J., and Alenius, M. (2007). Nat. Protoc. 2, 1508-1514.

Phay M, Kim H H, Yoo S (2015) Sciatic Nerve Di Giovanni S, ed. PLoS One 10:e0137461 Available at: www.ncbi.nlm.nih.gov/pubmed/26331719

Pitkanen, A., and Lukasiuk, K. (2009). Epilepsy Behav. 14 Suppl 1, 16-25.

Podolska et al., PLoS One. 2011 Jan. 6;6(1):e14494, doi: 10.1371/journal.pone.0014494

Poell J B, van Haastert R J, Cerisoli F, et al., (2011) BMC Genomics 12:546 Available at: bmcgenomics.biomedcentral.com/articles/10.1186/1471-2164-12-546

Poliseno L., Tuccoli A., Mariani L., Evangelista M., Citti L., Woods K., Mercatanti A., Hammond S. and Rainaldi G. Blood 108(9):3068-3071, 2006.

Poy M. N., Eliasson L., Krutzfeldt J., Kuwajima S., Ma X., Macdonald P. E., Pfeffer S., Tuschl T., Rajewsky N., Rorsman P. and Stoffel M. Nature 432(7014):226-230, 2004.

Qin S, Liu M, Niu W, Zhang C-L (2011) Proc Natl Acad Sci 108:21117-21121 Available at: www.ncbi.nlm.nih.gov/pubmed/22160720

Qin S, Zhang C-L (2012) Mol Cell Biol 32:4297-4305 Available at: mcb.asm.org/cgi/doi/10.1128/MCB.00838-12

Qin S, Zou Y, Zhang C-L (2013) Nat Commun 4:2633 Available at: www.ncbi.nlm.nih.gov/pubmed/24129709

Rakhade, S. N., and Jensen, F. E. (2009). Nat. Rev. Neurol. 5, 380-391.

Ren J-W, Li Z-J, Tu C (2015) Int J Clin Exp Pathol 8:6356-6366 Available at: www.ncbi.nlm.nih.gov/pubmed/26261511

Ribatti D., Vacca A. and Presta M. Gen Pharmacol 35(5): 227-231, 2000.

van Rooij E., et al., Science 316(5824):575-579, 2007.

Rossi M, Kilpinen H, Muona M, et al., (2014) Eur J Hum Genet 22:840-843 Available at: www.nature.com/doifinder/10.1038/ejhg.2013.246 le Sage C. et al. EMBO J 26(15):3699-3708, 2007.

Semah, F., Picot, M. C., et al., (1998). Neurology 51, 1256-1262.

Sempere L F, Freemantle S, et al., (2004) Genome Biol 5:R13 Available at: genomebiology.biomedcentral.com/articles/10.1186/gb-2004-5-3-r13

Shen et al. Gene therapy 13:225-234, 2006.

Shi H, Ji Y, Zhang D, Liu Y, Fang P (2015) Biochem Biophys Res Commun 465:125-130 Available at: linkinghub.elsevier.com/retrieve/pii/S0006291X15303466

Song Y, Ori-McKenney K M, Zheng Y, Han C, Jan L Y, Jan Y N (2012) Genes Dev 26:1612-1625 Available at: www.ncbi.nlm.nih.gov/pubmed/22759636

Steffen P., Voss B., Rehmsmeier M., Reeder J., Giegerich R. Bioinformatics, 22:500-503, 2006

Steketee M B, Oboudiyat C, Daneman R, et al., (2014) Investig Opthalmology Vis Sci 55:4369 Available at: iovs.arvojournals.org/article.aspx?doi=10.1167/iovs.14-13882

Suarez Y., Fernandez-Hernando C., et al., Circ Res 100(8): 1164-1173, 2007.

Tan, C. L., Plotkin, J. L., Veno, M. T., et al. (2013). Science 342, 1254-1258.

Vader P, van der Meel R, Symons M H, et al., Angiogenesis. 2011 December; 14(4):457-66, 2011.

Valeri N et al. (2014) Cancer Cell 25:469-483 Available at: linkinghub.elsevier.com/retrieve/pii/S1535610814001159

Wang S. et al., Dev Cell 15(2):261-271, 2008.

Weitz A C, Behrend M R, et al., (2013) J Neurophysiol 109:1979-1988 Available at: www.ncbi.nlm.nih.gov/pubmed/23343890

Wieser, H. G., and Epilepsy, I. C. o. N. o. (2004). Epilepsia 45, 695-714.

de Wit, E., Linsen, S. E., Cuppen, E., and Berezikov, E. Genome Res 19:2064-2074, 2009.

Wu C W, Ng S C, Dong Y, Tian L, Ng S S M, et al., (2014) lClin Cancer Res 20:2994-3002 Available at: www.ncbi.nlm.nih.gov/pubmed/24691020

Wu D, Raafat A, Pak E, Clemens S, Murashov A K (2012) Exp Neurol 233:555-565 Available at: linkinghub.elsevier.com/retrieve/pii/S0014488611004456

Xiao F, Zuo Z, Cai G, Kang S, Gao X, Li T (2009) Nucleic Acids Res 37:D105-10 Available at: academic.oup.com/nadarticle-lookup/doi/10.1093/nar/gkn851

Yang X, Wang X, Nie F, Liu T, Yu X, Wang H, Li Q, Peng R, Mao Z, Zhou Q, Li G (2015) Int J Mol Med Available at: www.spandidos-publications.com/10.3892/ijmrn.2015.2259

Yao S, et al., (2016) Oncotarget 7:42566-42578 Available at: www.oncotarget.com/abstract/9934

Yau K W, van Beuningen S F B, Cunha-Ferreira I, et al., (2014) Neuron 82:1058-1073 Available at: linkinghub.elsevier.com/retrieve/pii/S089662731400333X Yoon H S and Yang V W (2004). J. Biol. Chem. 279 (6): 5035-41. doi:10.1074/jbc.M307631200

Zhang Y K, Sun B, Sui G (2016) Genet Mol Res 15 www.ncbi.nlm.nih.gov/pubmed/27525941

Ziats M N, Rennert O M (2014) Mol Psychiatry 19 www.nature.com/doifinder/10.1038/mp.2013.93

Zou Y, et al., (2013) Science (80-) 340:372-376 www.ncbi.nlm.nih.gov/pubmed/23599497

Aliashkevich, A. F. et al., Acta Neuropathol. 106, 99-106. https://doi.org/10.1007/s00401-003-0707-0

Anders, S., et al., 2015. Bioinformatics 31, 166-169. https://doi.org/10.1093/bioinformatics/btu638

Bienvenu, T. et al., 2013. Neurogenetics 14, 71-75. https://doi.org/10.1007/s10048-012-0344-7

Brennecke, J. et al., 2005. PLoS Biol. 3, 0404-0418. https://doi.org/10.1371/journal.pbio.0030085

Dang, Z., et al., 2014. Int. J. Biol. Sci. 10, 733-745. https://doi.org/10.7150/ijbs.8097

Fiore, R., et al., 2009. EMBO J. 28, 697-710. https://doi.org/10.1038/emboj.2009.10

Flavell, S. W., et al., 2006. Science 311, 1008-1012. https://doi.org/10.1126/science.1122511

Gibbs, S., Chattopadhyaya, B., Desgent, S., et al., 2011. Neurobiol. Dis. 43, 312-321. https://doi.org/10.1016/j.nbd.2011.02.013

Guo, D., Arnspiger, S., Rensing, N. R., Wong, M., 2012. Neurobiol. Dis. 45, 348-355. https://doi.org/10.1016/j.nbd.2011.08.020

Höck, J., Meister, G., 2008. The Argonaute protein family. Genome Biol. 9. https://doi.org/10.1186/gb-2008-9-2-210

Huang, Y., Wu, X., Guo, J., Yuan, J., 2016. Int. J. Neurosci. 126, 786-796. https://doi.org/10.3109/00207454.2015.1062003

Isokawa, M., 1998. Neurosci. Lett. 258, 73-76. https://doi.org/10.1016/S0304-3940(98)00848-9

Jimenez-Mateos, E. M., et al., 2012. Nat. Med. 18, 1087-1094. https://doi.org/10.1038/nm.2834

Kim, D., et al., 2013. Genome Biol. https://doi.org/10.1186/gb-2013-14-4-r36

Krek, A., et al., 2005. Nat. Genet. 37, 495-500. https://doi.org/10.1038/ng1536

Lewis, B. P., et al., 2005. Cell 120, 15-20. https://doi.org/10.1016/j.cell.2004.12.035

Lyons, G. E., et al., 1995. J. Neurosci. 15, 5727-38.

Multani, P., et al., 1994. Epilepsia. https://doi.org/10.1111/j.1528-1157.1994.tb02503.x Nowakowska, B. A., et al., 2010. Am. J. Med. Genet. Part B Neuropsychiatr. Genet. 153, 1042-1051. https://doi.org/10.1002/ajmg.b.31071

Patro, R., Mount, S. M., Kingsford, C., 2014. Nat. Biotechnol. https://doi.org/10.1038/nbt.2862

Reschke, C. R., Silva, L. F. A., et al., 2017. Mol. Ther.—Nucleic Acids 6, 45-56. https://doi.org/10.1016/j.omtn.2016.11.002

Robinson, M., McCarthy, D., Smyth, G., 2010. https://doi.org/10.1093/bioinformatics/btp616

Robinson, M. D., Oshlack, A., 2010. Genome Biol. https://doi.org/10.1186/gb-2010-11-3-r25

Wani, S., Cloonan, N., 2014. bioRxiv 0-11. https://doi.org/10.1101/005439

Xiang, H., et al., 2017. Int. J. Mol. Sci. 18, 1-17. https://doi.org/10.3390/ijrns18071367

Young, M. D., et al., 2010 Genome Biol. https://doi.org/10.1186/gb-2010-11-2-r14

Zhao, X., et al., 2017 Cancer Biomarkers. https://doi.org/10.3233/CBM-170566

Zhou, W., et al. 2012. Acta Biochim Biophys Sin https://doi.org/10.1093/abbs/gms071.Original

The invention claimed is:

1. A method for treating, reverting, preventing, curing, and/or delaying epilepsy comprising administering to a subject in need thereof a therapeutically effective amount of an antagomir of a miRNA-135, or a source of such an antagomir or a pharmaceutical composition comprising an antagomir of a miRNA-135, or a source of such an antagomir,
wherein said miRNA-135 is a miRNA-135 molecule or a miRNA-135 isomiR, and is an oligonucleotide with a seed sequence comprising at least 6 of the 7 nucleotides of the seed sequence represented by SEQ ID NOs: 14-17, 19-42, 52-55, or is a source thereof.

2. The method according to claim 1, wherein said miRNA-135 is a miRNA-135a molecule, a miRNA-135b molecule, an isomiR of miRNA-135a, or an isomiR of miRNA-135b.

3. The method according to claim 1, wherein a source of a miRNA is a precursor of a miRNA and is an oligonucleotide of at least 50 nucleotides in length.

4. The method according to claim 1,
wherein said miRNA-135 shares at least 70% sequence identity with any one of SEQ ID NOs: 147-214, and/or
wherein said antagomir shares at least 70% sequence identity with any one of SEQ ID NOs: 242-245, 247-314,
and/or wherein said miRNA or antagomir is from 15-30 nucleotides in length,
and/or wherein said source of a miRNA is a precursor of said miRNA and shares at least 70% sequence identity with any one of SEQ ID NOs: 1-3 or 10-12.

5. The method according to claim 1,
wherein the amount of antagomir administered is effective to restore expression of myocyte-specific enhancer factor 2A (Mef2a).

6. The method according to claim 1,
wherein the amount of antagomir administered is effective to reduce seizure count and/or seizure duration.

7. The method according to claim 1,
wherein the amount of antagomir administered is effective to prevent, delay, or revert abnormal neuronal spine formation.

8. The method according to claim 1, wherein the subject is a human with mesial temporal lobe epilepsy with hippocampal sclerosis.

9. A method for reducing spontaneous seizures in a subject with epilepsy comprising administering to the subject a therapeutically effective amount of an antagomir of a miRNA-135, or a source of such an antagomir or a pharmaceutical composition comprising an antagomir of a miRNA-135, or a source of such an antagomir,
wherein said miRNA-135 is a miRNA-135 molecule or a miRNA-135 isomiR, and is an oligonucleotide with a seed sequence comprising at least 6 of the 7 nucleotides of the seed sequence represented by SEQ ID NOs: 14-17, 19-42, 52-55, or is a source thereof.

* * * * *

SEQUENCE LISTING

```
<160> NUMBER OF SEQ ID NOS: 380

<210> SEQ ID NO 1
<211> LENGTH: 90
<212> TYPE: RNA
<213> ORGANISM: Homo sapiens

<400> SEQUENCE: 1
aggccucgcu guucucuaug gcuuuuauu ccuaugugau ucuacugcuc acucauauag      60
ggauuggagc cguggcgcac ggcggggaca                                     90

<210> SEQ ID NO 2
<211> LENGTH: 105
<212> TYPE: RNA
<213> ORGANISM: Homo sapiens

<400> SEQUENCE: 2
agauaaauuc acucuagugc uuuauggcuu uuuauuccua ugugauagua auaaagucuc     60
auguagggau ggaagccaug aaauacauug ugaaaaauca ucaac                    105

<210> SEQ ID NO 3
<211> LENGTH: 103
<212> TYPE: RNA
<213> ORGANISM: Homo sapiens

<400> SEQUENCE: 3 cccccuccacu cugcuguggc cuauggcuuu ucauuccuau gugauugcug ucccaaacuc    60
auguagggcu aaaagccaug ggcuacagug aggggcgagc ucc                      103

<210> SEQ ID NO 4
<211> LENGTH: 80
<212> TYPE: RNA
<213> ORGANISM: Homo sapiens

<400> SEQUENCE: 4
gaacugcuga gugaauuagg uaguuucaug uuguugggcc ugggguucug aacacaacaa     60
cauuaaacca cccgauucac                                                80

<210> SEQ ID NO 5
<211> LENGTH: 23
<212> TYPE: RNA
<213> ORGANISM: Artificial Sequence
<220> FEATURE:
<223> OTHER INFORMATION: hsa-miR-135a-5p

<400> SEQUENCE: 5
uauggcuuuu uauuccuaug uga                                            23

<210> SEQ ID NO 6
<211> LENGTH: 22
<212> TYPE: RNA
```

```
<213> ORGANISM: Artificial Sequence
<220> FEATURE:
<223> OTHER INFORMATION: hsa-miR-135a-3p

<400> SEQUENCE: 6
uauagggauu ggagccgugg cg                                              22

<210> SEQ ID NO 7
<211> LENGTH: 23
<212> TYPE: RNA
<213> ORGANISM: Artificial Sequence
<220> FEATURE:
<223> OTHER INFORMATION: hsa-miR-135b-5p

<400> SEQUENCE: 7
uauggcuuuu cauuccuaug uga                                             23

<210> SEQ ID NO 8
<211> LENGTH: 22
<212> TYPE: RNA
<213> ORGANISM: Artificial Sequence
<220> FEATURE:
<223> OTHER INFORMATION: hsa-miR-135b-3p

<400> SEQUENCE: 8
auguagggcu aaaagccaug gg                                              22

<210> SEQ ID NO 9
<211> LENGTH: 22
<212> TYPE: RNA
<213> ORGANISM: Artificial Sequence
<220> FEATURE:
<223> OTHER INFORMATION: hsa-miR-196a-5p

<400> SEQUENCE: 9
uagguaguuu cauguuguug gg                                              22

<210> SEQ ID NO 10
<211> LENGTH: 217
<212> TYPE: DNA
<213> ORGANISM: Artificial Sequence
<220> FEATURE:
<223> OTHER INFORMATION: hsa-miR-135a-1

<400> SEQUENCE: 10
tccacaccct cagggaggag gggagggttg gggtggaaga agtgcctgca agagcagccc     60
caggcctcgc tgttctctat ggcttttat tcctatgtga ttctactgct cactcatata    120
gggattggag ccgtggcgca cggcgggac agccagcgga gggttctgac actgagcaag    180
ggggctcaaa aggaggcagg acagtggcac ctccctc                             217

<210> SEQ ID NO 11
<211> LENGTH: 204
<212> TYPE: DNA
<213> ORGANISM: Artificial Sequence
<220> FEATURE:
<223> OTHER INFORMATION: hsa-miR-135a-2

<400> SEQUENCE: 11
gctttgaaat ggttgtgaag tcatgtgaag aaaataagtt ttgcatccga ccaagataaa     60
ttcactctag tgcttatgg ctttttattc ctatgtgata gtaataaagt ctcatgtagg    120
gatggaagcc atgaaataca ttgtgaaaaa tcatcaacta agaaggggcc atcagtatag    180
agaacgttag cctgtggagc tgtg                                           204
```

```
<210> SEQ ID NO 12
<211> LENGTH: 209
<212> TYPE: DNA
<213> ORGANISM: Artificial Sequence
<220> FEATURE:
<223> OTHER INFORMATION: hsa-miR-135b

<400> SEQUENCE: 12
ctcgcttccc tatgagattc ctgccgctgg acccctccac tctgctgtgg cctatggctt      60
ttcattccta tgtgattgct gtcccaaact catgtagggc taaaagccat gggctacagt     120
gaggggcgag ctccttctcc tgcgcagctg cacctcccat gggaccaggt tcggagccag     180
ccaccaaggg gcaccagaag gaggctttg                                       209

<210> SEQ ID NO 13
<211> LENGTH: 152
<212> TYPE: DNA
<213> ORGANISM: Artificial Sequence
<220> FEATURE:
<223> OTHER INFORMATION: hsa-miR-196a-1

<400> SEQUENCE: 13
cccccagtga gctcttgacc tagagcttga attggaactg ctgagtgaat taggtagttt      60
catgttgttg ggcctgggtt tctgaacaca acaacattaa accaccgat  tcacggcagt     120 tactgctcct cgcttagctg gaggagttgg gg                                   152

<210> SEQ ID NO 14
<211> LENGTH: 7
<212> TYPE: RNA
<213> ORGANISM: Artificial Sequence
<220> FEATURE:
<223> OTHER INFORMATION: hsa-miR-135a-5p

<400> SEQUENCE: 14 auggcuu                                                                 7

<210> SEQ ID NO 15
<211> LENGTH: 7
<212> TYPE: RNA
<213> ORGANISM: Artificial Sequence
<220> FEATURE:
<223> OTHER INFORMATION: hsa-miR-135a-3p

<400> SEQUENCE: 15 auaggga                                                                 7

<210> SEQ ID NO 16
<211> LENGTH: 7
<212> TYPE: RNA
<213> ORGANISM: Artificial Sequence
<220> FEATURE:
<223> OTHER INFORMATION: hsa-miR-135b-5p

<400> SEQUENCE: 16 auggcuu                                                                 7

<210> SEQ ID NO 17
<211> LENGTH: 7
<212> TYPE: RNA
<213> ORGANISM: Artificial Sequence
<220> FEATURE:
<223> OTHER INFORMATION: hsa-miR-135b-3p
```

```
<400> SEQUENCE: 17 uguaggg                                                              7

<210> SEQ ID NO 18
<211> LENGTH: 7
<212> TYPE: RNA
<213> ORGANISM: Artificial Sequence
<220> FEATURE:
<223> OTHER INFORMATION: hsa-miR-196a-5p

<400> SEQUENCE: 18 agguagu                                                              7

<210> SEQ ID NO 19
<211> LENGTH: 7
<212> TYPE: RNA
<213> ORGANISM: Artificial Sequence
<220> FEATURE:
<223> OTHER INFORMATION: hsa-miR-135a-5p seed

<400> SEQUENCE: 19 auggcuu                                                              7

<210> SEQ ID NO 20
<211> LENGTH: 7
<212> TYPE: RNA
<213> ORGANISM: Artificial Sequence
<220> FEATURE:
<223> OTHER INFORMATION: hsa-miR-135a-5p seed

<400> SEQUENCE: 20 uggcuuu                                                              7

<210> SEQ ID NO 21
<211> LENGTH: 7
<212> TYPE: RNA
<213> ORGANISM: Artificial Sequence
<220> FEATURE:
<223> OTHER INFORMATION: hsa-miR-135a-5p seed

<400> SEQUENCE: 21 ggcuuuu                                                              7

<210> SEQ ID NO 22
<211> LENGTH: 7
<212> TYPE: RNA
<213> ORGANISM: Artificial Sequence
<220> FEATURE:
<223> OTHER INFORMATION: hsa-miR-135a-5p seed

<400> SEQUENCE: 22 gcuuuuu                                                              7

<210> SEQ ID NO 23
<211> LENGTH: 7
<212> TYPE: RNA
<213> ORGANISM: Artificial Sequence
<220> FEATURE:
<223> OTHER INFORMATION: hsa-miR-135a-5p seed

<400> SEQUENCE: 23 cuuuuua                                                              7

<210> SEQ ID NO 24
<211> LENGTH: 7
```

```
<212> TYPE: RNA
<213> ORGANISM: Artificial Sequence
<220> FEATURE:
<223> OTHER INFORMATION: hsa-miR-135a-5p seed

<400> SEQUENCE: 24 uuuuuau                                                                    7

<210> SEQ ID NO 25
<211> LENGTH: 7
<212> TYPE: RNA
<213> ORGANISM: Artificial Sequence
<220> FEATURE:
<223> OTHER INFORMATION: hsa-miR-135a-5p seed

<400> SEQUENCE: 25 uuuuauu                                                                    7

<210> SEQ ID NO 26
<211> LENGTH: 7
<212> TYPE: RNA
<213> ORGANISM: Artificial Sequence
<220> FEATURE:
<223> OTHER INFORMATION: hsa-miR-135a-5p seed

<400> SEQUENCE: 26 uuuauuc                                                                    7

<210> SEQ ID NO 27
<211> LENGTH: 7
<212> TYPE: RNA
<213> ORGANISM: Artificial Sequence
<220> FEATURE:
<223> OTHER INFORMATION: hsa-miR-135a-5p seed

<400> SEQUENCE: 27 uuauucc                                                                    7

<210> SEQ ID NO 28
<211> LENGTH: 7
<212> TYPE: RNA
<213> ORGANISM: Artificial Sequence
<220> FEATURE:
<223> OTHER INFORMATION: hsa-miR-135a-3p seed

<400> SEQUENCE: 28 auaggga                                                                    7

<210> SEQ ID NO 29
<211> LENGTH: 7
<212> TYPE: RNA
<213> ORGANISM: Artificial Sequence
<220> FEATURE:
<223> OTHER INFORMATION: hsa-miR-135a-3p seed

<400> SEQUENCE: 29 uauaggg                                                                    7

<210> SEQ ID NO 30
<211> LENGTH: 7
<212> TYPE: RNA
<213> ORGANISM: Artificial Sequence
<220> FEATURE:
<223> OTHER INFORMATION: hsa-miR-135a-3p seed

<400> SEQUENCE: 30
``` auauagg                                                                  7

<210> SEQ ID NO 31
<211> LENGTH: 7
<212> TYPE: RNA
<213> ORGANISM: Artificial Sequence
<220> FEATURE:
<223> OTHER INFORMATION: hsa-miR-135a-3p seed

<400> SEQUENCE: 31 uagggau                                                                  7

<210> SEQ ID NO 32
<211> LENGTH: 7
<212> TYPE: RNA
<213> ORGANISM: Artificial Sequence
<220> FEATURE:
<223> OTHER INFORMATION: hsa-miR-135b-5p seed

<400> SEQUENCE: 32 auggcuu                                                                  7

<210> SEQ ID NO 33
<211> LENGTH: 7
<212> TYPE: RNA
<213> ORGANISM: Artificial Sequence
<220> FEATURE:
<223> OTHER INFORMATION: hsa-miR-135b-5p seed

<400> SEQUENCE: 33 uggcuuu                                                                  7

<210> SEQ ID NO 34
<211> LENGTH: 7
<212> TYPE: RNA
<213> ORGANISM: Artificial Sequence
<220> FEATURE:
<223> OTHER INFORMATION: hsa-miR-135b-5p seed

<400> SEQUENCE: 34 ggcuuuu                                                                  7

<210> SEQ ID NO 35
<211> LENGTH: 7
<212> TYPE: RNA
<213> ORGANISM: Artificial Sequence
<220> FEATURE:
<223> OTHER INFORMATION: hsa-miR-135b-5p seed

<400> SEQUENCE: 35 cuuuuca                                                                  7

<210> SEQ ID NO 36
<211> LENGTH: 7
<212> TYPE: RNA
<213> ORGANISM: Artificial Sequence
<220> FEATURE:
<223> OTHER INFORMATION: hsa-miR-135b-5p seed

<400> SEQUENCE: 36 uuuucau                                                                  7

<210> SEQ ID NO 37
<211> LENGTH: 7
<212> TYPE: RNA
<213> ORGANISM: Artificial Sequence

```
<220> FEATURE:
<223> OTHER INFORMATION: hsa-miR-135b-5p seed

<400> SEQUENCE: 37 uuucauu                                                                  7

<210> SEQ ID NO 38
<211> LENGTH: 7
<212> TYPE: RNA
<213> ORGANISM: Artificial Sequence
<220> FEATURE:
<223> OTHER INFORMATION: hsa-miR-135b-5p seed

<400> SEQUENCE: 38 uucauuc                                                                  7

<210> SEQ ID NO 39
<211> LENGTH: 7
<212> TYPE: RNA
<213> ORGANISM: Artificial Sequence
<220> FEATURE:
<223> OTHER INFORMATION: hsa-miR-135b-5p seed

<400> SEQUENCE: 39 uauggcu                                                                  7

<210> SEQ ID NO 40
<211> LENGTH: 7
<212> TYPE: RNA
<213> ORGANISM: Artificial Sequence
<220> FEATURE:
<223> OTHER INFORMATION: hsa-miR-135b-3p seed

<400> SEQUENCE: 40 uguaggg                                                                  7

<210> SEQ ID NO 41
<211> LENGTH: 7
<212> TYPE: RNA
<213> ORGANISM: Artificial Sequence
<220> FEATURE:
<223> OTHER INFORMATION: hsa-miR-135b-3p seed

<400> SEQUENCE: 41 guagggc                                                                  7

<210> SEQ ID NO 42
<211> LENGTH: 7
<212> TYPE: RNA
<213> ORGANISM: Artificial Sequence
<220> FEATURE:
<223> OTHER INFORMATION: hsa-miR-135b-3p seed

<400> SEQUENCE: 42 ggcuaaa                                                                  7

<210> SEQ ID NO 43
<211> LENGTH: 7
<212> TYPE: RNA
<213> ORGANISM: Artificial Sequence
<220> FEATURE:
<223> OTHER INFORMATION: hsa-miR-196a-5p seed

<400> SEQUENCE: 43 agguagu                                                                  7
```

```
<210> SEQ ID NO 44
<211> LENGTH: 7
<212> TYPE: RNA
<213> ORGANISM: Artificial Sequence
<220> FEATURE:
<223> OTHER INFORMATION: hsa-miR-196a-5p seed

<400> SEQUENCE: 44 gguaguu                                                                    7

<210> SEQ ID NO 45
<211> LENGTH: 7
<212> TYPE: RNA
<213> ORGANISM: Artificial Sequence
<220> FEATURE:
<223> OTHER INFORMATION: hsa-miR-196a-5p seed

<400> SEQUENCE: 45 guaguuu                                                                    7

<210> SEQ ID NO 46
<211> LENGTH: 7
<212> TYPE: RNA
<213> ORGANISM: Artificial Sequence
<220> FEATURE:
<223> OTHER INFORMATION: hsa-miR-196a-5p seed

<400> SEQUENCE: 46 uaguuuc                                                                    7

<210> SEQ ID NO 47
<211> LENGTH: 7
<212> TYPE: RNA
<213> ORGANISM: Artificial Sequence
<220> FEATURE:
<223> OTHER INFORMATION: hsa-miR-196a-5p seed

<400> SEQUENCE: 47 aguuuca                                                                    7

<210> SEQ ID NO 48
<211> LENGTH: 7
<212> TYPE: RNA
<213> ORGANISM: Artificial Sequence
<220> FEATURE:
<223> OTHER INFORMATION: hsa-miR-196a-5p seed

<400> SEQUENCE: 48 guuucau                                                                    7

<210> SEQ ID NO 49
<211> LENGTH: 7
<212> TYPE: RNA
<213> ORGANISM: Artificial Sequence
<220> FEATURE:
<223> OTHER INFORMATION: hsa-miR-196a-5p seed

<400> SEQUENCE: 49 uucaugu                                                                    7

<210> SEQ ID NO 50
<211> LENGTH: 7
<212> TYPE: RNA
<213> ORGANISM: Artificial Sequence
<220> FEATURE:
<223> OTHER INFORMATION: hsa-miR-196a-5p seed
```

```
<400> SEQUENCE: 50 uuaggua                                                              7

<210> SEQ ID NO 51
<211> LENGTH: 7
<212> TYPE: RNA
<213> ORGANISM: Artificial Sequence
<220> FEATURE:
<223> OTHER INFORMATION: hsa-miR-196a-5p seed

<400> SEQUENCE: 51 uagguag                                                              7

<210> SEQ ID NO 52
<211> LENGTH: 7
<212> TYPE: RNA
<213> ORGANISM: Artificial Sequence
<220> FEATURE:
<223> OTHER INFORMATION: hsa-miR-135a-5p

<400> SEQUENCE: 52 auggcuu                                                              7

<210> SEQ ID NO 53
<211> LENGTH: 7
<212> TYPE: RNA
<213> ORGANISM: Artificial Sequence
<220> FEATURE:
<223> OTHER INFORMATION: hsa-miR-135a-3p

<400> SEQUENCE: 53 auaggga                                                              7

<210> SEQ ID NO 54
<211> LENGTH: 7
<212> TYPE: RNA
<213> ORGANISM: Artificial Sequence
<220> FEATURE:
<223> OTHER INFORMATION: hsa-miR-135b-5p

<400> SEQUENCE: 54 auggcuu                                                              7

<210> SEQ ID NO 55
<211> LENGTH: 7
<212> TYPE: RNA
<213> ORGANISM: Artificial Sequence
<220> FEATURE:
<223> OTHER INFORMATION: hsa-miR-135b-3p

<400> SEQUENCE: 55 uguaggg                                                              7

<210> SEQ ID NO 56
<211> LENGTH: 7
<212> TYPE: RNA
<213> ORGANISM: Artificial Sequence
<220> FEATURE:
<223> OTHER INFORMATION: hsa-miR-196a-5p

<400> SEQUENCE: 56 agguagu                                                              7

<210> SEQ ID NO 57
```

```
<211> LENGTH: 26
<212> TYPE: RNA
<213> ORGANISM: Artificial Sequence
<220> FEATURE:
<223> OTHER INFORMATION: hsa-miR-135a-5p isomiR

<400> SEQUENCE: 57
uauggcuuuu uauuccuaug ugauag                                              26

<210> SEQ ID NO 58
<211> LENGTH: 26
<212> TYPE: RNA
<213> ORGANISM: Artificial Sequence
<220> FEATURE:
<223> OTHER INFORMATION: hsa-miR-135a-5p isomiR

<400> SEQUENCE: 58
uauggcuuuu uauuccuaug ugauuc                                              26

<210> SEQ ID NO 59
<211> LENGTH: 25
<212> TYPE: RNA
<213> ORGANISM: Artificial Sequence
<220> FEATURE:
<223> OTHER INFORMATION: hsa-miR-135a-5p isomiR

<400> SEQUENCE: 59
uauggcuuuu uauuccuaug ugaua                                               25

<210> SEQ ID NO 60
<211> LENGTH: 24
<212> TYPE: RNA
<213> ORGANISM: Artificial Sequence
<220> FEATURE:
<223> OTHER INFORMATION: hsa-miR-135a-5p isomiR

<400> SEQUENCE: 60
uauggcuuuu uauuccuaug ugau                                                24

<210> SEQ ID NO 61
<211> LENGTH: 22
<212> TYPE: RNA
<213> ORGANISM: Artificial Sequence
<220> FEATURE:
<223> OTHER INFORMATION: hsa-miR-135a-5p isomiR

<400> SEQUENCE: 61
uauggcuuuu uauuccuaug ug                                                  22

<210> SEQ ID NO 62
<211> LENGTH: 21
<212> TYPE: RNA
<213> ORGANISM: Artificial Sequence
<220> FEATURE:
<223> OTHER INFORMATION: hsa-miR-135a-5p isomiR

<400> SEQUENCE: 62
uauggcuuuu uauuccuaug u                                                   21

<210> SEQ ID NO 63
<211> LENGTH: 20
<212> TYPE: RNA
<213> ORGANISM: Artificial Sequence
<220> FEATURE:
<223> OTHER INFORMATION: hsa-miR-135a-5p isomiR

<400> SEQUENCE: 63
```
uauggcuuuu uauuccuaug                                              20

<210> SEQ ID NO 64
<211> LENGTH: 19
<212> TYPE: RNA
<213> ORGANISM: Artificial Sequence
<220> FEATURE:
<223> OTHER INFORMATION: hsa-miR-135a-5p isomiR

<400> SEQUENCE: 64
uauggcuuuu uauuccuau                                               19

<210> SEQ ID NO 65
<211> LENGTH: 18
<212> TYPE: RNA
<213> ORGANISM: Artificial Sequence
<220> FEATURE:
<223> OTHER INFORMATION: hsa-miR-135a-5p isomiR

<400> SEQUENCE: 65
uauggcuuuu uauuccua                                                18

<210> SEQ ID NO 66
<211> LENGTH: 15
<212> TYPE: RNA
<213> ORGANISM: Artificial Sequence
<220> FEATURE:
<223> OTHER INFORMATION: hsa-miR-135a-5p isomiR

<400> SEQUENCE: 66
uauggcuuuu uauuc                                                   15

<210> SEQ ID NO 67
<211> LENGTH: 17
<212> TYPE: RNA
<213> ORGANISM: Artificial Sequence
<220> FEATURE:
<223> OTHER INFORMATION: hsa-miR-135a-5p isomiR

<400> SEQUENCE: 67
uauggcuuuu uauuccu                                                 17

<210> SEQ ID NO 68
<211> LENGTH: 23
<212> TYPE: RNA
<213> ORGANISM: Artificial Sequence
<220> FEATURE:
<223> OTHER INFORMATION: hsa-miR-135a-5p isomiR

<400> SEQUENCE: 68
auggcuuuuu auuccuaugu gau                                          23

<210> SEQ ID NO 69
<211> LENGTH: 22
<212> TYPE: RNA
<213> ORGANISM: Artificial Sequence
<220> FEATURE:
<223> OTHER INFORMATION: hsa-miR-135a-5p isomiR

<400> SEQUENCE: 69
auggcuuuuu auuccuaugu ga                                           22

<210> SEQ ID NO 70
<211> LENGTH: 21
<212> TYPE: RNA

```
<213> ORGANISM: Artificial Sequence
<220> FEATURE:
<223> OTHER INFORMATION: hsa-miR-135a-5p isomiR

<400> SEQUENCE: 70
auggcuuuuu auuccuaugu g                                               21

<210> SEQ ID NO 71
<211> LENGTH: 20
<212> TYPE: RNA
<213> ORGANISM: Artificial Sequence
<220> FEATURE:
<223> OTHER INFORMATION: hsa-miR-135a-5p isomiR

<400> SEQUENCE: 71
auggcuuuuu auuccuaugu                                                 20

<210> SEQ ID NO 72
<211> LENGTH: 22
<212> TYPE: RNA
<213> ORGANISM: Artificial Sequence
<220> FEATURE:
<223> OTHER INFORMATION: hsa-miR-135a-5p isomiR

<400> SEQUENCE: 72
uggcuuuuua uuccaugug au                                               22

<210> SEQ ID NO 73
<211> LENGTH: 21
<212> TYPE: RNA
<213> ORGANISM: Artificial Sequence
<220> FEATURE:
<223> OTHER INFORMATION: hsa-miR-135a-5p isomiR

<400> SEQUENCE: 73
uggcuuuuua uuccuaugug a                                               21

<210> SEQ ID NO 74
<211> LENGTH: 20
<212> TYPE: RNA
<213> ORGANISM: Artificial Sequence
<220> FEATURE:
<223> OTHER INFORMATION: hsa-miR-135a-5p isomiR

<400> SEQUENCE: 74
uggcuuuuua uuccuaugug                                                 20

<210> SEQ ID NO 75
<211> LENGTH: 20
<212> TYPE: RNA
<213> ORGANISM: Artificial Sequence
<220> FEATURE:
<223> OTHER INFORMATION: hsa-miR-135a-5p isomiR

<400> SEQUENCE: 75
ggcuuuuuau uccuauguga                                                 20

<210> SEQ ID NO 76
<211> LENGTH: 19
<212> TYPE: RNA
<213> ORGANISM: Artificial Sequence
<220> FEATURE:
<223> OTHER INFORMATION: hsa-miR-135a-5p isomiR

<400> SEQUENCE: 76
gcuuuuuauu ccuauguga                                                  19
```

<210> SEQ ID NO 77
<211> LENGTH: 18
<212> TYPE: RNA
<213> ORGANISM: Artificial Sequence
<220> FEATURE:
<223> OTHER INFORMATION: hsa-miR-135a-5p isomiR

<400> SEQUENCE: 77 gcuuuuauu ccaugug                                                        18

<210> SEQ ID NO 78
<211> LENGTH: 17
<212> TYPE: RNA
<213> ORGANISM: Artificial Sequence
<220> FEATURE:
<223> OTHER INFORMATION: hsa-miR-135a-5p isomiR

<400> SEQUENCE: 78 gcuuuuauu ccaugu                                                         17

<210> SEQ ID NO 79
<211> LENGTH: 18
<212> TYPE: RNA
<213> ORGANISM: Artificial Sequence
<220> FEATURE:
<223> OTHER INFORMATION: hsa-miR-135a-5p isomiR

<400> SEQUENCE: 79 cuuuuauuc cuauguga                                                       18

<210> SEQ ID NO 80
<211> LENGTH: 17
<212> TYPE: RNA
<213> ORGANISM: Artificial Sequence
<220> FEATURE:
<223> OTHER INFORMATION: hsa-miR-135a-5p isomiR

<400> SEQUENCE: 80 cuuuuauuc cuaugug                                                        17

<210> SEQ ID NO 81
<211> LENGTH: 15
<212> TYPE: RNA
<213> ORGANISM: Artificial Sequence
<220> FEATURE:
<223> OTHER INFORMATION: hsa-miR-135a-5p isomiR

<400> SEQUENCE: 81 cuuuuauuc cuaug                                                          15

<210> SEQ ID NO 82
<211> LENGTH: 16
<212> TYPE: RNA
<213> ORGANISM: Artificial Sequence
<220> FEATURE:
<223> OTHER INFORMATION: hsa-miR-135a-5p isomiR

<400> SEQUENCE: 82 cuuuuauuc cuaugu                                                         16

<210> SEQ ID NO 83
<211> LENGTH: 17
<212> TYPE: RNA
<213> ORGANISM: Artificial Sequence
<220> FEATURE:

<223> OTHER INFORMATION: hsa-miR-135a-5p isomiR

<400> SEQUENCE: 83
uuuuuauucc uauguga                                                     17

<210> SEQ ID NO 84
<211> LENGTH: 15
<212> TYPE: RNA
<213> ORGANISM: Artificial Sequence
<220> FEATURE:
<223> OTHER INFORMATION: hsa-miR-135a-5p isomiR

<400> SEQUENCE: 84
uuuuuauucc uaugu                                                       15

<210> SEQ ID NO 85
<211> LENGTH: 16
<212> TYPE: RNA
<213> ORGANISM: Artificial Sequence
<220> FEATURE:
<223> OTHER INFORMATION: hsa-miR-135a-5p isomiR

<400> SEQUENCE: 85
uuuuuauucc uaugug                                                      16

<210> SEQ ID NO 86
<211> LENGTH: 16
<212> TYPE: RNA
<213> ORGANISM: Artificial Sequence
<220> FEATURE:
<223> OTHER INFORMATION: hsa-miR-135a-5p isomiR

<400> SEQUENCE: 86
uuuuauuccu auguga                                                      16

<210> SEQ ID NO 87
<211> LENGTH: 15
<212> TYPE: RNA
<213> ORGANISM: Artificial Sequence
<220> FEATURE:
<223> OTHER INFORMATION: hsa-miR-135a-5p isomiR

<400> SEQUENCE: 87
uuuuauuccu augug                                                       15

<210> SEQ ID NO 88
<211> LENGTH: 15
<212> TYPE: RNA
<213> ORGANISM: Artificial Sequence
<220> FEATURE:
<223> OTHER INFORMATION: hsa-miR-135a-5p isomiR

<400> SEQUENCE: 88
uuuauuccua uguga                                                       15

<210> SEQ ID NO 89
<211> LENGTH: 21
<212> TYPE: RNA
<213> ORGANISM: Artificial Sequence
<220> FEATURE:
<223> OTHER INFORMATION: hsa-miR-135a-3p isomiR

<400> SEQUENCE: 89
uauagggauu ggagccgugg c                                                21

<210> SEQ ID NO 90
<211> LENGTH: 20
<212> TYPE: RNA
<213> ORGANISM: Artificial Sequence
<220> FEATURE:
<223> OTHER INFORMATION: hsa-miR-135a-3p isomiR

<400> SEQUENCE: 90
uauagggauu ggagccgugg                                               20

<210> SEQ ID NO 91
<211> LENGTH: 22
<212> TYPE: RNA
<213> ORGANISM: Artificial Sequence
<220> FEATURE:
<223> OTHER INFORMATION: hsa-miR-135a-3p isomiR

<400> SEQUENCE: 91
auauagggau uggagccgug gc                                            22

<210> SEQ ID NO 92
<211> LENGTH: 21
<212> TYPE: RNA
<213> ORGANISM: Artificial Sequence
<220> FEATURE:
<223> OTHER INFORMATION: hsa-miR-135a-3p isomiR

<400> SEQUENCE: 92
auauagggau uggagccgug g                                             21

<210> SEQ ID NO 93
<211> LENGTH: 20
<212> TYPE: RNA
<213> ORGANISM: Artificial Sequence
<220> FEATURE:
<223> OTHER INFORMATION: hsa-miR-135a-3p isomiR

<400> SEQUENCE: 93
auauagggau uggagccgug                                               20

<210> SEQ ID NO 94
<211> LENGTH: 24
<212> TYPE: RNA
<213> ORGANISM: Artificial Sequence
<220> FEATURE:
<223> OTHER INFORMATION: hsa-miR-135a-3p isomiR

<400> SEQUENCE: 94
cauauaggga uuggagccgu ggcg                                          24

<210> SEQ ID NO 95
<211> LENGTH: 20
<212> TYPE: RNA
<213> ORGANISM: Artificial Sequence
<220> FEATURE:
<223> OTHER INFORMATION: hsa-miR-135a-3p isomiR

<400> SEQUENCE: 95
auagggauug gagccguggc                                               20

<210> SEQ ID NO 96
<211> LENGTH: 20
<212> TYPE: RNA
<213> ORGANISM: Artificial Sequence
<220> FEATURE:
<223> OTHER INFORMATION: hsa-miR-135b-5p isomiR

```
<400> SEQUENCE: 96
uauggcuuuu cauuccuaug                                               20

<210> SEQ ID NO 97
<211> LENGTH: 19
<212> TYPE: RNA
<213> ORGANISM: Artificial Sequence
<220> FEATURE:
<223> OTHER INFORMATION: hsa-miR-135b-5p isomiR

<400> SEQUENCE: 97
uauggcuuuu cauuccuau                                                19

<210> SEQ ID NO 98
<211> LENGTH: 18
<212> TYPE: RNA
<213> ORGANISM: Artificial Sequence
<220> FEATURE:
<223> OTHER INFORMATION: hsa-miR-135b-5p isomiR

<400> SEQUENCE: 98
uauggcuuuu cauucca                                                  18

<210> SEQ ID NO 99
<211> LENGTH: 23
<212> TYPE: RNA
<213> ORGANISM: Artificial Sequence
<220> FEATURE:
<223> OTHER INFORMATION: hsa-miR-135b-5p isomiR

<400> SEQUENCE: 99
auggcuuuuc auuccuaugu gau                                           23

<210> SEQ ID NO 100
<211> LENGTH: 22
<212> TYPE: RNA
<213> ORGANISM: Artificial Sequence
<220> FEATURE:
<223> OTHER INFORMATION: hsa-miR-135b-5p isomiR

<400> SEQUENCE: 100
auggcuuuuc auuccuaugu ga                                            22

<210> SEQ ID NO 101
<211> LENGTH: 21
<212> TYPE: RNA
<213> ORGANISM: Artificial Sequence
<220> FEATURE:
<223> OTHER INFORMATION: hsa-miR-135b-5p isomiR

<400> SEQUENCE: 101
auggcuuuuc auuccuaugu g                                             21

<210> SEQ ID NO 102
<211> LENGTH: 20
<212> TYPE: RNA
<213> ORGANISM: Artificial Sequence
<220> FEATURE:
<223> OTHER INFORMATION: hsa-miR-135b-5p isomiR

<400> SEQUENCE: 102
auggcuuuuc auuccuaugu                                               20

<210> SEQ ID NO 103
<211> LENGTH: 21
```

```
<212> TYPE: RNA
<213> ORGANISM: Artificial Sequence
<220> FEATURE:
<223> OTHER INFORMATION: hsa-miR-135b-5p isomiR

<400> SEQUENCE: 103
uggcuuuuca uuccuaugug a                                        21

<210> SEQ ID NO 104
<211> LENGTH: 19
<212> TYPE: RNA
<213> ORGANISM: Artificial Sequence
<220> FEATURE:
<223> OTHER INFORMATION: hsa-miR-135b-5p isomiR

<400> SEQUENCE: 104
gcuuuucauu ccauguga                                            19

<210> SEQ ID NO 105
<211> LENGTH: 18
<212> TYPE: RNA
<213> ORGANISM: Artificial Sequence
<220> FEATURE:
<223> OTHER INFORMATION: hsa-miR-135b-5p isomiR

<400> SEQUENCE: 105
cuuuucauuc cuauguga                                            18

<210> SEQ ID NO 106
<211> LENGTH: 16
<212> TYPE: RNA
<213> ORGANISM: Artificial Sequence
<220> FEATURE:
<223> OTHER INFORMATION: hsa-miR-135b-5p isomiR

<400> SEQUENCE: 106
cuuuucauuc cuaugu                                              16

<210> SEQ ID NO 107
<211> LENGTH: 17
<212> TYPE: RNA
<213> ORGANISM: Artificial Sequence
<220> FEATURE:
<223> OTHER INFORMATION: hsa-miR-135b-5p isomiR

<400> SEQUENCE: 107
cuuuucauuc cuaugug                                             17

<210> SEQ ID NO 108
<211> LENGTH: 15
<212> TYPE: RNA
<213> ORGANISM: Artificial Sequence
<220> FEATURE:
<223> OTHER INFORMATION: hsa-miR-135b-5p isomiR

<400> SEQUENCE: 108
cuuuucauuc cuaug                                               15

<210> SEQ ID NO 109
<211> LENGTH: 17
<212> TYPE: RNA
<213> ORGANISM: Artificial Sequence
<220> FEATURE:
<223> OTHER INFORMATION: hsa-miR-135b-5p isomiR

<400> SEQUENCE: 109
```

| | |
|---|---|
| uuuucauucc uauguga | 17 |

<210> SEQ ID NO 110
<211> LENGTH: 15
<212> TYPE: RNA
<213> ORGANISM: Artificial Sequence
<220> FEATURE:
<223> OTHER INFORMATION: hsa-miR-135b-5p isomiR

<400> SEQUENCE: 110

| | |
|---|---|
| uuuucauucc uaugu | 15 |

<210> SEQ ID NO 111
<211> LENGTH: 16
<212> TYPE: RNA
<213> ORGANISM: Artificial Sequence
<220> FEATURE:
<223> OTHER INFORMATION: hsa-miR-135b-5p isomiR

<400> SEQUENCE: 111

| | |
|---|---|
| uuuucauucc uaugug | 16 |

<210> SEQ ID NO 112
<211> LENGTH: 16
<212> TYPE: RNA
<213> ORGANISM: Artificial Sequence
<220> FEATURE:
<223> OTHER INFORMATION: hsa-miR-135b-5p isomiR

<400> SEQUENCE: 112

| | |
|---|---|
| uuucauuccu auguga | 16 |

<210> SEQ ID NO 113
<211> LENGTH: 15
<212> TYPE: RNA
<213> ORGANISM: Artificial Sequence
<220> FEATURE:
<223> OTHER INFORMATION: hsa-miR-135b-5p isomiR

<400> SEQUENCE: 113

| | |
|---|---|
| uuucauuccu augug | 15 |

<210> SEQ ID NO 114
<211> LENGTH: 22
<212> TYPE: RNA
<213> ORGANISM: Artificial Sequence
<220> FEATURE:
<223> OTHER INFORMATION: hsa-miR-135b-5p isomiR

<400> SEQUENCE: 114

| | |
|---|---|
| cuauggcuuu ucauuccuau gu | 22 |

<210> SEQ ID NO 115
<211> LENGTH: 23
<212> TYPE: RNA
<213> ORGANISM: Artificial Sequence
<220> FEATURE:
<223> OTHER INFORMATION: hsa-miR-135b-3p isomiR

<400> SEQUENCE: 115

| | |
|---|---|
| auguagggcu aaaagccaug ggc | 23 |

<210> SEQ ID NO 116
<211> LENGTH: 21
<212> TYPE: RNA
<213> ORGANISM: Artificial Sequence

```
<220> FEATURE:
<223> OTHER INFORMATION: hsa-miR-135b-3p isomiR

<400> SEQUENCE: 116
auguagggcu aaaagccaug g                                          21

<210> SEQ ID NO 117
<211> LENGTH: 15
<212> TYPE: RNA
<213> ORGANISM: Artificial Sequence
<220> FEATURE:
<223> OTHER INFORMATION: hsa-miR-135b-3p isomiR

<400> SEQUENCE: 117
auguagggcu aaaag                                                 15

<210> SEQ ID NO 118
<211> LENGTH: 23
<212> TYPE: RNA
<213> ORGANISM: Artificial Sequence
<220> FEATURE:
<223> OTHER INFORMATION: hsa-miR-135b-3p isomiR

<400> SEQUENCE: 118
uguagggcua aaagccaugg gcu                                        23

<210> SEQ ID NO 119
<211> LENGTH: 22
<212> TYPE: RNA
<213> ORGANISM: Artificial Sequence
<220> FEATURE:
<223> OTHER INFORMATION: hsa-miR-135b-3p isomiR

<400> SEQUENCE: 119
uguagggcua aaagccaugg gc                                         22

<210> SEQ ID NO 120
<211> LENGTH: 17
<212> TYPE: RNA
<213> ORGANISM: Artificial Sequence
<220> FEATURE:
<223> OTHER INFORMATION: hsa-miR-135b-3p isomiR

<400> SEQUENCE: 120
gggcuaaaag ccauggg                                               17

<210> SEQ ID NO 121
<211> LENGTH: 24
<212> TYPE: RNA
<213> ORGANISM: Artificial Sequence
<220> FEATURE:
<223> OTHER INFORMATION: hsa-miR-196a-5p isomiR

<400> SEQUENCE: 121
uagguaguuu cauguuguug ggcc                                       24

<210> SEQ ID NO 122
<211> LENGTH: 23
<212> TYPE: RNA
<213> ORGANISM: Artificial Sequence
<220> FEATURE:
<223> OTHER INFORMATION: hsa-miR-196a-5p isomiR

<400> SEQUENCE: 122
uagguaguuu cauguuguug ggc                                        23
```

<210> SEQ ID NO 123
<211> LENGTH: 21
<212> TYPE: RNA
<213> ORGANISM: Artificial Sequence
<220> FEATURE:
<223> OTHER INFORMATION: hsa-miR-196a-5p isomiR

<400> SEQUENCE: 123
uagguaguuu cauguuguug g                                              21

<210> SEQ ID NO 124
<211> LENGTH: 20
<212> TYPE: RNA
<213> ORGANISM: Artificial Sequence
<220> FEATURE:
<223> OTHER INFORMATION: hsa-miR-196a-5p isomiR

<400> SEQUENCE: 124
uagguaguuu cauguuguug                                                20

<210> SEQ ID NO 125
<211> LENGTH: 19
<212> TYPE: RNA
<213> ORGANISM: Artificial Sequence
<220> FEATURE:
<223> OTHER INFORMATION: hsa-miR-196a-5p isomiR

<400> SEQUENCE: 125
uagguaguuu cauguuguu                                                 19

<210> SEQ ID NO 126
<211> LENGTH: 18
<212> TYPE: RNA
<213> ORGANISM: Artificial Sequence
<220> FEATURE:
<223> OTHER INFORMATION: hsa-miR-196a-5p isomiR

<400> SEQUENCE: 126
uagguaguuu cauguugu                                                  18

<210> SEQ ID NO 127
<211> LENGTH: 17
<212> TYPE: RNA
<213> ORGANISM: Artificial Sequence
<220> FEATURE:
<223> OTHER INFORMATION: hsa-miR-196a-5p isomiR

<400> SEQUENCE: 127
uagguaguuu cauguug                                                   17

<210> SEQ ID NO 128
<211> LENGTH: 16
<212> TYPE: RNA
<213> ORGANISM: Artificial Sequence
<220> FEATURE:
<223> OTHER INFORMATION: hsa-miR-196a-5p isomiR

<400> SEQUENCE: 128
uagguaguuu cauguu                                                    16

<210> SEQ ID NO 129
<211> LENGTH: 15
<212> TYPE: RNA
<213> ORGANISM: Artificial Sequence
<220> FEATURE:
<223> OTHER INFORMATION: hsa-miR-196a-5p isomiR

```
<400> SEQUENCE: 129
uagguaguuu caugu                                                15

<210> SEQ ID NO 130
<211> LENGTH: 23
<212> TYPE: RNA
<213> ORGANISM: Artificial Sequence
<220> FEATURE:
<223> OTHER INFORMATION: hsa-miR-196a-5p isomiR

<400> SEQUENCE: 130
agguaguuuc auguuguugg gcc                                       23

<210> SEQ ID NO 131
<211> LENGTH: 22
<212> TYPE: RNA
<213> ORGANISM: Artificial Sequence
<220> FEATURE:
<223> OTHER INFORMATION: hsa-miR-196a-5p isomiR

<400> SEQUENCE: 131
agguaguuuc auguuguugg gc                                        22

<210> SEQ ID NO 132
<211> LENGTH: 21
<212> TYPE: RNA
<213> ORGANISM: Artificial Sequence
<220> FEATURE:
<223> OTHER INFORMATION: hsa-miR-196a-5p isomiR

<400> SEQUENCE: 132
agguaguuuc auguuguugg g                                         21

<210> SEQ ID NO 133
<211> LENGTH: 20
<212> TYPE: RNA
<213> ORGANISM: Artificial Sequence
<220> FEATURE:
<223> OTHER INFORMATION: hsa-miR-196a-5p isomiR

<400> SEQUENCE: 133
agguaguuuc auguuguugg                                           20

<210> SEQ ID NO 134
<211> LENGTH: 20
<212> TYPE: RNA
<213> ORGANISM: Artificial Sequence
<220> FEATURE:
<223> OTHER INFORMATION: hsa-miR-196a-5p isomiR

<400> SEQUENCE: 134
gguaguuuca uguuguuggg                                           20

<210> SEQ ID NO 135
<211> LENGTH: 19
<212> TYPE: RNA
<213> ORGANISM: Artificial Sequence
<220> FEATURE:
<223> OTHER INFORMATION: hsa-miR-196a-5p isomiR

<400> SEQUENCE: 135
gguaguuuca uguuguugg                                            19

<210> SEQ ID NO 136
```

```
<211> LENGTH: 19
<212> TYPE: RNA
<213> ORGANISM: Artificial Sequence
<220> FEATURE:
<223> OTHER INFORMATION: hsa-miR-196a-5p isomiR

<400> SEQUENCE: 136
guaguuucau guuguuggg                                             19

<210> SEQ ID NO 137
<211> LENGTH: 18
<212> TYPE: RNA
<213> ORGANISM: Artificial Sequence
<220> FEATURE:
<223> OTHER INFORMATION: hsa-miR-196a-5p isomiR

<400> SEQUENCE: 137
guaguuucau guuguugg                                              18

<210> SEQ ID NO 138
<211> LENGTH: 18
<212> TYPE: RNA
<213> ORGANISM: Artificial Sequence
<220> FEATURE:
<223> OTHER INFORMATION: hsa-miR-196a-5p isomiR

<400> SEQUENCE: 138
uaguuucaug uuguuggg                                              18

<210> SEQ ID NO 139
<211> LENGTH: 17
<212> TYPE: RNA
<213> ORGANISM: Artificial Sequence
<220> FEATURE:
<223> OTHER INFORMATION: hsa-miR-196a-5p isomiR

<400> SEQUENCE: 139
uaguuucaug uuguugg                                               17

<210> SEQ ID NO 140
<211> LENGTH: 17
<212> TYPE: RNA
<213> ORGANISM: Artificial Sequence
<220> FEATURE:
<223> OTHER INFORMATION: hsa-miR-196a-5p isomiR

<400> SEQUENCE: 140
aguuucaugu uguuggg                                               17

<210> SEQ ID NO 141
<211> LENGTH: 16
<212> TYPE: RNA
<213> ORGANISM: Artificial Sequence
<220> FEATURE:
<223> OTHER INFORMATION: hsa-miR-196a-5p isomiR

<400> SEQUENCE: 141
aguuucaugu uguugg                                                16

<210> SEQ ID NO 142
<211> LENGTH: 16
<212> TYPE: RNA
<213> ORGANISM: Artificial Sequence
<220> FEATURE:
<223> OTHER INFORMATION: hsa-miR-196a-5p isomiR

<400> SEQUENCE: 142
```
uuucauguug uugggc         16

<210> SEQ ID NO 143
<211> LENGTH: 15
<212> TYPE: RNA
<213> ORGANISM: Artificial Sequence
<220> FEATURE:
<223> OTHER INFORMATION: hsa-miR-196a-5p isomiR

<400> SEQUENCE: 143
uuucauguug uuggg         15

<210> SEQ ID NO 144
<211> LENGTH: 22
<212> TYPE: RNA
<213> ORGANISM: Artificial Sequence
<220> FEATURE:
<223> OTHER INFORMATION: hsa-miR-196a-5p isomiR

<400> SEQUENCE: 144
auuagguagu uucauguugu ug         22

<210> SEQ ID NO 145
<211> LENGTH: 23
<212> TYPE: RNA
<213> ORGANISM: Artificial Sequence
<220> FEATURE:
<223> OTHER INFORMATION: hsa-miR-196a-5p isomiR

<400> SEQUENCE: 145
uuagguaguu ucauguuguu ggg         23

<210> SEQ ID NO 146
<211> LENGTH: 22
<212> TYPE: RNA
<213> ORGANISM: Artificial Sequence
<220> FEATURE:
<223> OTHER INFORMATION: hsa-miR-196a-5p isomiR

<400> SEQUENCE: 146
uuagguaguu ucauguuguu gg         22

<210> SEQ ID NO 147
<211> LENGTH: 23
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 147
uauggcuuuu uauuccuaug uga         23

<210> SEQ ID NO 148
<211> LENGTH: 26
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 148
uauggcuuuu uauuccuaug ugauag         26

<210> SEQ ID NO 149
<211> LENGTH: 26
<212> TYPE: RNA

<213> ORGANISM: Artificial Sequence
<220> FEATURE:
<223> OTHER INFORMATION: hsa-miR-135a-5p miRNA or isomiR

<400> SEQUENCE: 149
uauggcuuuu uauuccuaug ugauuc                                          26

<210> SEQ ID NO 150
<211> LENGTH: 25
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 150
uauggcuuuu uauuccuaug ugaua                                           25

<210> SEQ ID NO 151
<211> LENGTH: 24
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 151
uauggcuuuu uauuccuaug ugau                                            24

<210> SEQ ID NO 152
<211> LENGTH: 22
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 152
uauggcuuuu uauuccuaug ug                                              22

<210> SEQ ID NO 153
<211> LENGTH: 21
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 153
uauggcuuuu uauuccuaug u                                               21

<210> SEQ ID NO 154
<211> LENGTH: 20
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 154
uauggcuuuu uauuccuaug                                                 20

<210> SEQ ID NO 155
<211> LENGTH: 19
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 155
uauggcuuuu uauuccuau                                                  19

-continued

<210> SEQ ID NO 156
<211> LENGTH: 18
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 156
uauggcuuuu uauuccua                                                   18

<210> SEQ ID NO 157
<211> LENGTH: 17
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 157
uauggcuuuu uauuccu                                                    17

<210> SEQ ID NO 158
<211> LENGTH: 15
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 158
uauggcuuuu uauuc                                                      15

<210> SEQ ID NO 159
<211> LENGTH: 23
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 159
auggcuuuuu auuccuaugu gau                                             23

<210> SEQ ID NO 160
<211> LENGTH: 22
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 160
auggcuuuuu auuccuaugu ga                                              22

<210> SEQ ID NO 161
<211> LENGTH: 21
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 161
auggcuuuuu auuccuaugu g                                               21

<210> SEQ ID NO 162
<211> LENGTH: 20
<212> TYPE: RNA
<213> ORGANISM: Artificial Sequence
<220> FEATURE:

-continued

<223> OTHER INFORMATION: hsa-miR-135a-5p miRNA or isomiR

<400> SEQUENCE: 162
auggcuuuuu auuccuaugu                                            20

<210> SEQ ID NO 163
<211> LENGTH: 22
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 163
uggcuuuuua uuccuaugug au                                         22

<210> SEQ ID NO 164
<211> LENGTH: 21
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 164
uggcuuuuua uuccuaugug a                                          21

<210> SEQ ID NO 165
<211> LENGTH: 20
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 165
uggcuuuuua uuccuaugug                                            20

<210> SEQ ID NO 166
<211> LENGTH: 20
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 166
ggcuuuuuau uccuauguga                                            20

<210> SEQ ID NO 167
<211> LENGTH: 19
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 167
gcuuuuuauu ccuauguga                                             19

<210> SEQ ID NO 168
<211> LENGTH: 18
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 168
gcuuuuuauu ccuaugug                                              18

-continued

```
<210> SEQ ID NO 169
<211> LENGTH: 17
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 169
gcuuuuuauu ccuaugu                                                    17

<210> SEQ ID NO 170
<211> LENGTH: 18
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 170
cuuuuuauuc cuauguga                                                   18

<210> SEQ ID NO 171
<211> LENGTH: 17
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 171
cuuuuuauuc cuaugug                                                    17

<210> SEQ ID NO 172
<211> LENGTH: 15
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 172
cuuuuuauuc cuaug                                                      15

<210> SEQ ID NO 173
<211> LENGTH: 16
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 173
cuuuuuauuc cuaugu                                                     16

<210> SEQ ID NO 174
<211> LENGTH: 17
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 174
uuuuuauucc uauguga                                                    17

<210> SEQ ID NO 175
<211> LENGTH: 15
<212> TYPE: RNA
<213> ORGANISM: Artificial Sequence
<220> FEATURE:
<223> OTHER INFORMATION: hsa-miR-135a-5p miRNA or isomiR
```

```
<400> SEQUENCE: 175
uuuuuauucc uaugu                                              15

<210> SEQ ID NO 176
<211> LENGTH: 16
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 176
uuuuuauucc uaugug                                             16

<210> SEQ ID NO 177
<211> LENGTH: 16
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 177
uuuuauuccu auguga                                             16

<210> SEQ ID NO 178
<211> LENGTH: 15
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 178
uuuuauuccu augug                                              15

<210> SEQ ID NO 179
<211> LENGTH: 15
<212> TYPE: RNA
<213> ORGANISM: Artificial Sequence
<220> FEATURE:
<223> OTHER INFORMATION: hsa-miR-135a-5p miRNA or isomiR

<400> SEQUENCE: 179
uuuauuccua uguga                                              15

<210> SEQ ID NO 180
<211> LENGTH: 22
<212> TYPE: RNA
<213> ORGANISM: Artificial Sequence
<220> FEATURE:
<223> OTHER INFORMATION: hsa-miR-135a-3p isomiR or miRNA

<400> SEQUENCE: 180
uauagggauu ggagccgugg cg                                      22

<210> SEQ ID NO 181
<211> LENGTH: 21
<212> TYPE: RNA
<213> ORGANISM: Artificial Sequence
<220> FEATURE:
<223> OTHER INFORMATION: hsa-miR-135a-3p isomiR or miRNA

<400> SEQUENCE: 181
uauagggauu ggagccgugg c                                       21

<210> SEQ ID NO 182
<211> LENGTH: 20
```

```
<212> TYPE: RNA
<213> ORGANISM: Artificial Sequence
<220> FEATURE:
<223> OTHER INFORMATION: hsa-miR-135a-3p isomiR or miRNA

<400> SEQUENCE: 182
uauagggauu ggagccgugg                                                       20

<210> SEQ ID NO 183
<211> LENGTH: 22
<212> TYPE: RNA
<213> ORGANISM: Artificial Sequence
<220> FEATURE:
<223> OTHER INFORMATION: hsa-miR-135a-3p isomiR or miRNA

<400> SEQUENCE: 183
auauagggau uggagccgug gc                                                    22

<210> SEQ ID NO 184
<211> LENGTH: 21
<212> TYPE: RNA
<213> ORGANISM: Artificial Sequence
<220> FEATURE:
<223> OTHER INFORMATION: hsa-miR-135a-3p isomiR or miRNA

<400> SEQUENCE: 184
auauagggau uggagccgug g                                                     21

<210> SEQ ID NO 185
<211> LENGTH: 20
<212> TYPE: RNA
<213> ORGANISM: Artificial Sequence
<220> FEATURE:
<223> OTHER INFORMATION: hsa-miR-135a-3p isomiR or miRNA

<400> SEQUENCE: 185
auauagggau uggagccgug                                                       20

<210> SEQ ID NO 186
<211> LENGTH: 24
<212> TYPE: RNA
<213> ORGANISM: Artificial Sequence
<220> FEATURE:
<223> OTHER INFORMATION: hsa-miR-135a-3p isomiR or miRNA

<400> SEQUENCE: 186
cauauaggga uuggagccgu ggcg                                                  24

<210> SEQ ID NO 187
<211> LENGTH: 20
<212> TYPE: RNA
<213> ORGANISM: Artificial Sequence
<220> FEATURE:
<223> OTHER INFORMATION: hsa-miR-135a-3p isomiR or miRNA

<400> SEQUENCE: 187
auagggauug gagccguggc                                                       20

<210> SEQ ID NO 188
<211> LENGTH: 23
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 188
```
uauggcuuuu cauuccuaug uga                                    23

<210> SEQ ID NO 189
<211> LENGTH: 20
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 189
uauggcuuuu cauuccuaug                                        20

<210> SEQ ID NO 190
<211> LENGTH: 19
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 190
uauggcuuuu cauuccuau                                         19

<210> SEQ ID NO 191
<211> LENGTH: 18
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 191
uauggcuuuu cauuccua                                          18

<210> SEQ ID NO 192
<211> LENGTH: 23
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 192
auggcuuuuc auuccuaugu gau                                    23

<210> SEQ ID NO 193
<211> LENGTH: 22
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 193
auggcuuuuc auuccuaugu ga                                     22

<210> SEQ ID NO 194
<211> LENGTH: 21
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 194
auggcuuuuc auuccuaugu g                                      21

<210> SEQ ID NO 195
<211> LENGTH: 20
<212> TYPE: RNA
<213> ORGANISM: Artificial Sequence

```
<220> FEATURE:
<223> OTHER INFORMATION: hsa-miR-135b-5p miRNA or isomiR

<400> SEQUENCE: 195
auggcuuuuc auuccuaugu                                                   20

<210> SEQ ID NO 196
<211> LENGTH: 21
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 196
uggcuuuuca uuccuaugug a                                                 21

<210> SEQ ID NO 197
<211> LENGTH: 19
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 197
gcuuuucauu ccauguga                                                     19

<210> SEQ ID NO 198
<211> LENGTH: 18
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 198
cuuuucauuc cuauguga                                                     18

<210> SEQ ID NO 199
<211> LENGTH: 16
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 199
cuuuucauuc cuaugu                                                       16

<210> SEQ ID NO 200
<211> LENGTH: 17
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 200
cuuuucauuc cuaugug                                                      17

<210> SEQ ID NO 201
<211> LENGTH: 15
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 201
cuuuucauuc cuaug                                                        15
```

<210> SEQ ID NO 202
<211> LENGTH: 17
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 202
uuuucauucc uauguga                                                  17

<210> SEQ ID NO 203
<211> LENGTH: 15
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 203
uuuucauucc uaugu                                                    15

<210> SEQ ID NO 204
<211> LENGTH: 16
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 204
uuuucauucc uaugug                                                   16

<210> SEQ ID NO 205
<211> LENGTH: 16
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 205
uuucauuccu auguga                                                   16

<210> SEQ ID NO 206
<211> LENGTH: 15
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 206
uuucauuccu augug                                                    15

<210> SEQ ID NO 207
<211> LENGTH: 22
<212> TYPE: RNA
<213> ORGANISM: Artificial Sequence
<220> FEATURE:
<223> OTHER INFORMATION: hsa-miR-135b-5p miRNA or isomiR

<400> SEQUENCE: 207
cuauggcuuu ucauuccuau gu                                            22

<210> SEQ ID NO 208
<211> LENGTH: 22
<212> TYPE: RNA
<213> ORGANISM: Artificial Sequence
<220> FEATURE:
<223> OTHER INFORMATION: hsa-miR-135b-3p miRNA or isomiR

<400> SEQUENCE: 208
auguagggcu aaaagccaug gg    22

<210> SEQ ID NO 209
<211> LENGTH: 23
<212> TYPE: RNA
<213> ORGANISM: Artificial Sequence
<220> FEATURE:
<223> OTHER INFORMATION: hsa-miR-135b-3p miRNA or isomiR

<400> SEQUENCE: 209
auguagggcu aaaagccaug ggc    23

<210> SEQ ID NO 210
<211> LENGTH: 21
<212> TYPE: RNA
<213> ORGANISM: Artificial Sequence
<220> FEATURE:
<223> OTHER INFORMATION: hsa-miR-135b-3p miRNA or isomiR

<400> SEQUENCE: 210
auguagggcu aaaagccaug g    21

<210> SEQ ID NO 211
<211> LENGTH: 15
<212> TYPE: RNA
<213> ORGANISM: Artificial Sequence
<220> FEATURE:
<223> OTHER INFORMATION: hsa-miR-135b-3p miRNA or isomiR

<400> SEQUENCE: 211
auguagggcu aaaag    15

<210> SEQ ID NO 212
<211> LENGTH: 23
<212> TYPE: RNA
<213> ORGANISM: Artificial Sequence
<220> FEATURE:
<223> OTHER INFORMATION: hsa-miR-135b-3p miRNA or isomiR

<400> SEQUENCE: 212
uguagggcua aaagccaugg gcu    23

<210> SEQ ID NO 213
<211> LENGTH: 22
<212> TYPE: RNA
<213> ORGANISM: Artificial Sequence
<220> FEATURE:
<223> OTHER INFORMATION: hsa-miR-135b-3p miRNA or isomiR

<400> SEQUENCE: 213
uguagggcua aaagccaugg gc    22

<210> SEQ ID NO 214
<211> LENGTH: 17
<212> TYPE: RNA
<213> ORGANISM: Artificial Sequence
<220> FEATURE:
<223> OTHER INFORMATION: hsa-miR-135b-3p miRNA or isomiR

<400> SEQUENCE: 214
gggcuaaaag ccauggg    17

<210> SEQ ID NO 215

-continued

```
<211> LENGTH: 22
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 215
uagguaguuu cauguuguug gg                                               22

<210> SEQ ID NO 216
<211> LENGTH: 22
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 216
gguaguuuca uguuguuggg cc                                               22

<210> SEQ ID NO 217
<211> LENGTH: 23
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 217
uagguaguuu cauguuguug ggc                                              23

<210> SEQ ID NO 218
<211> LENGTH: 21
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 218
uagguaguuu cauguuguug g                                                21

<210> SEQ ID NO 219
<211> LENGTH: 20
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 219
uagguaguuu cauguuguug                                                  20

<210> SEQ ID NO 220
<211> LENGTH: 19
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 220
uagguaguuu cauguuguu                                                   19

<210> SEQ ID NO 221
<211> LENGTH: 18
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 221
```
uagguaguuu cauguugu                                                18

<210> SEQ ID NO 222
<211> LENGTH: 17
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 222
uagguaguuu cauguug                                                 17

<210> SEQ ID NO 223
<211> LENGTH: 16
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 223
uagguaguuu cauguu                                                  16

<210> SEQ ID NO 224
<211> LENGTH: 15
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 224
uagguaguuu caugu                                                   15

<210> SEQ ID NO 225
<211> LENGTH: 23
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 225
agguaguuuc auuguuugg gcc                                           23

<210> SEQ ID NO 226
<211> LENGTH: 22
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 226
agguaguuuc auguuguugg gc                                           22

<210> SEQ ID NO 227
<211> LENGTH: 21
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 227
agguaguuuc auguuguugg g                                            21

<210> SEQ ID NO 228
<211> LENGTH: 20
<212> TYPE: RNA

<213> ORGANISM: Artificial Sequence
<220> FEATURE:
<223> OTHER INFORMATION: hsa-miR-196a-5p miRNA or isomiR

<400> SEQUENCE: 228
agguaguuuc auguuguugg                                               20

<210> SEQ ID NO 229
<211> LENGTH: 20
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 229
gguaguuuca uguuguuggg                                               20

<210> SEQ ID NO 230
<211> LENGTH: 19
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 230
gguaguuuca uguuguugg                                                19

<210> SEQ ID NO 231
<211> LENGTH: 19
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 231
guaguuucau guuguuggg                                                19

<210> SEQ ID NO 232
<211> LENGTH: 18
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 232
guaguuucau guuguugg                                                 18

<210> SEQ ID NO 233
<211> LENGTH: 18
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 233
uaguuucaug uuguuggg                                                 18

<210> SEQ ID NO 234
<211> LENGTH: 17
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 234
uaguuucaug uuguugg                                                  17

-continued

```
<210> SEQ ID NO 235
<211> LENGTH: 17
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 235
aguuucaugu uguuggg                                                   17

<210> SEQ ID NO 236
<211> LENGTH: 16
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 236
aguuucaugu uguugg                                                    16

<210> SEQ ID NO 237
<211> LENGTH: 16
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 237
uuucauguug uugggc                                                    16

<210> SEQ ID NO 238
<211> LENGTH: 15
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 238
uuucauguug uuggg                                                     15

<210> SEQ ID NO 239
<211> LENGTH: 22
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 239
auuagguagu uucauguugu ug                                             22

<210> SEQ ID NO 240
<211> LENGTH: 23
<212> TYPE: RNA
<213> ORGANISM: Artificial Sequence
<220> FEATURE:
<223> OTHER INFORMATION: hsa-miR-196a-5p miRNA or isomiR

<400> SEQUENCE: 240
uuagguaguu ucauguuguu ggg                                            23

<210> SEQ ID NO 241
<211> LENGTH: 22
<212> TYPE: RNA
<213> ORGANISM: Artificial Sequence
<220> FEATURE:
```

<223> OTHER INFORMATION: hsa-miR-196a-5p miRNA or isomiR

<400> SEQUENCE: 241
uuagguaguu ucauguuguu gg                                                22

<210> SEQ ID NO 242
<211> LENGTH: 23
<212> TYPE: DNA
<213> ORGANISM: Artificial Sequence
<220> FEATURE:
<223> OTHER INFORMATION: hsa-miR-135a-5p antagomir

<400> SEQUENCE: 242
tcacatagga ataaaaagcc ata                                               23

<210> SEQ ID NO 243
<211> LENGTH: 22
<212> TYPE: DNA
<213> ORGANISM: Artificial Sequence
<220> FEATURE:
<223> OTHER INFORMATION: hsa-miR-135a-3p antagomir

<400> SEQUENCE: 243
cgccacggct ccaatcccta ta                                                22

<210> SEQ ID NO 244
<211> LENGTH: 23
<212> TYPE: DNA
<213> ORGANISM: Artificial Sequence
<220> FEATURE:
<223> OTHER INFORMATION: hsa-miR-135b-5p antagomir

<400> SEQUENCE: 244
tcacatagga atgaaaagcc ata                                               23

<210> SEQ ID NO 245
<211> LENGTH: 22
<212> TYPE: DNA
<213> ORGANISM: Artificial Sequence
<220> FEATURE:
<223> OTHER INFORMATION: hsa-miR-135b-3p antagomir

<400> SEQUENCE: 245
cccatggctt ttagccctac at                                                22

<210> SEQ ID NO 246
<211> LENGTH: 22
<212> TYPE: DNA
<213> ORGANISM: Artificial Sequence
<220> FEATURE:
<223> OTHER INFORMATION: hsa-miR-196a-5p antagomir

<400> SEQUENCE: 246
cccaacaaca tgaaactacc ta                                                22

<210> SEQ ID NO 247
<211> LENGTH: 23
<212> TYPE: DNA
<213> ORGANISM: Artificial Sequence
<220> FEATURE:
<223> OTHER INFORMATION: hsa-miR-135a-5p antagomir

<400> SEQUENCE: 247
tcacatagga ataaaaagcc ata                                               23

```
<210> SEQ ID NO 248
<211> LENGTH: 26
<212> TYPE: DNA
<213> ORGANISM: Artificial Sequence
<220> FEATURE:
<223> OTHER INFORMATION: hsa-miR-135a-5p antagomir

<400> SEQUENCE: 248
ctatcacata ggaataaaaa gccata                                        26

<210> SEQ ID NO 249
<211> LENGTH: 26
<212> TYPE: DNA
<213> ORGANISM: Artificial Sequence
<220> FEATURE:
<223> OTHER INFORMATION: hsa-miR-135a-5p antagomir

<400> SEQUENCE: 249
gaatcacata ggaataaaaa gccata                                        26

<210> SEQ ID NO 250
<211> LENGTH: 25
<212> TYPE: DNA
<213> ORGANISM: Artificial Sequence
<220> FEATURE:
<223> OTHER INFORMATION: hsa-miR-135a-5p antagomir

<400> SEQUENCE: 250
tatcacatag gaataaaaag ccata                                         25

<210> SEQ ID NO 251
<211> LENGTH: 24
<212> TYPE: DNA
<213> ORGANISM: Artificial Sequence
<220> FEATURE:
<223> OTHER INFORMATION: hsa-miR-135a-5p antagomir

<400> SEQUENCE: 251
atcacatagg aataaaaagc cata                                          24

<210> SEQ ID NO 252
<211> LENGTH: 22
<212> TYPE: DNA
<213> ORGANISM: Artificial Sequence
<220> FEATURE:
<223> OTHER INFORMATION: hsa-miR-135a-5p antagomir

<400> SEQUENCE: 252
cacataggaa taaaaagcca ta                                            22

<210> SEQ ID NO 253
<211> LENGTH: 21
<212> TYPE: DNA
<213> ORGANISM: Artificial Sequence
<220> FEATURE:
<223> OTHER INFORMATION: hsa-miR-135a-5p antagomir

<400> SEQUENCE: 253
acataggaat aaaaagccat a                                             21

<210> SEQ ID NO 254
<211> LENGTH: 20
<212> TYPE: DNA
<213> ORGANISM: Artificial Sequence
<220> FEATURE:
<223> OTHER INFORMATION: hsa-miR-135a-5p antagomir
```

```
<400> SEQUENCE: 254
cataggaata aaaagccata                                              20

<210> SEQ ID NO 255
<211> LENGTH: 19
<212> TYPE: DNA
<213> ORGANISM: Artificial Sequence
<220> FEATURE:
<223> OTHER INFORMATION: hsa-miR-135a-5p antagomir

<400> SEQUENCE: 255
ataggaataa aaagccata                                               19

<210> SEQ ID NO 256
<211> LENGTH: 18
<212> TYPE: DNA
<213> ORGANISM: Artificial Sequence
<220> FEATURE:
<223> OTHER INFORMATION: hsa-miR-135a-5p antagomir

<400> SEQUENCE: 256
taggaataaa aagccata                                                18

<210> SEQ ID NO 257
<211> LENGTH: 17
<212> TYPE: DNA
<213> ORGANISM: Artificial Sequence
<220> FEATURE:
<223> OTHER INFORMATION: hsa-miR-135a-5p antagomir

<400> SEQUENCE: 257
aggaataaaa agccata                                                 17

<210> SEQ ID NO 258
<211> LENGTH: 15
<212> TYPE: DNA
<213> ORGANISM: Artificial Sequence
<220> FEATURE:
<223> OTHER INFORMATION: hsa-miR-135a-5p antagomir

<400> SEQUENCE: 258
gaataaaaag ccata                                                   15

<210> SEQ ID NO 259
<211> LENGTH: 23
<212> TYPE: DNA
<213> ORGANISM: Artificial Sequence
<220> FEATURE:
<223> OTHER INFORMATION: hsa-miR-135a-5p antagomir

<400> SEQUENCE: 259
atcacatagg aataaaaagc cat                                          23

<210> SEQ ID NO 260
<211> LENGTH: 22
<212> TYPE: DNA
<213> ORGANISM: Artificial Sequence
<220> FEATURE:
<223> OTHER INFORMATION: hsa-miR-135a-5p antagomir

<400> SEQUENCE: 260
tcacatagga ataaaaagcc at                                           22

<210> SEQ ID NO 261
<211> LENGTH: 21
```

```
<212> TYPE: DNA
<213> ORGANISM: Artificial Sequence
<220> FEATURE:
<223> OTHER INFORMATION: hsa-miR-135a-5p antagomir

<400> SEQUENCE: 261
cacataggaa taaaaagcca t                                          21

<210> SEQ ID NO 262
<211> LENGTH: 20
<212> TYPE: DNA
<213> ORGANISM: Artificial Sequence
<220> FEATURE:
<223> OTHER INFORMATION: hsa-miR-135a-5p antagomir

<400> SEQUENCE: 262
acataggaat aaaaagccat                                            20

<210> SEQ ID NO 263
<211> LENGTH: 22
<212> TYPE: DNA
<213> ORGANISM: Artificial Sequence
<220> FEATURE:
<223> OTHER INFORMATION: hsa-miR-135a-5p antagomir

<400> SEQUENCE: 263
atcacatagg aataaaaagc ca                                         22

<210> SEQ ID NO 264
<211> LENGTH: 21
<212> TYPE: DNA
<213> ORGANISM: Artificial Sequence
<220> FEATURE:
<223> OTHER INFORMATION: hsa-miR-135a-5p antagomir

<400> SEQUENCE: 264
tcacatagga ataaaaagcc a                                          21

<210> SEQ ID NO 265
<211> LENGTH: 20
<212> TYPE: DNA
<213> ORGANISM: Artificial Sequence
<220> FEATURE:
<223> OTHER INFORMATION: hsa-miR-135a-5p antagomir

<400> SEQUENCE: 265
cacataggaa taaaaagcca                                            20

<210> SEQ ID NO 266
<211> LENGTH: 20
<212> TYPE: DNA
<213> ORGANISM: Artificial Sequence
<220> FEATURE:
<223> OTHER INFORMATION: hsa-miR-135a-5p antagomir

<400> SEQUENCE: 266
tcacatagga ataaaaagcc                                            20

<210> SEQ ID NO 267
<211> LENGTH: 19
<212> TYPE: DNA
<213> ORGANISM: Artificial Sequence
<220> FEATURE:
<223> OTHER INFORMATION: hsa-miR-135a-5p antagomir

<400> SEQUENCE: 267
```
tcacatagga ataaaaagc                                              19

<210> SEQ ID NO 268
<211> LENGTH: 18
<212> TYPE: DNA
<213> ORGANISM: Artificial Sequence
<220> FEATURE:
<223> OTHER INFORMATION: hsa-miR-135a-5p antagomir

<400> SEQUENCE: 268
cacataggaa taaaaagc                                               18

<210> SEQ ID NO 269
<211> LENGTH: 17
<212> TYPE: DNA
<213> ORGANISM: Artificial Sequence
<220> FEATURE:
<223> OTHER INFORMATION: hsa-miR-135a-5p antagomir

<400> SEQUENCE: 269
acataggaat aaaagc                                                 17

<210> SEQ ID NO 270
<211> LENGTH: 18
<212> TYPE: DNA
<213> ORGANISM: Artificial Sequence
<220> FEATURE:
<223> OTHER INFORMATION: hsa-miR-135a-5p antagomir

<400> SEQUENCE: 270
tcacatagga ataaaaag                                               18

<210> SEQ ID NO 271
<211> LENGTH: 17
<212> TYPE: DNA
<213> ORGANISM: Artificial Sequence
<220> FEATURE:
<223> OTHER INFORMATION: hsa-miR-135a-5p antagomir

<400> SEQUENCE: 271
cacataggaa taaaaag                                                17

<210> SEQ ID NO 272
<211> LENGTH: 15
<212> TYPE: DNA
<213> ORGANISM: Artificial Sequence
<220> FEATURE:
<223> OTHER INFORMATION: hsa-miR-135a-5p antagomir

<400> SEQUENCE: 272
cataggaata aaaag                                                  15

<210> SEQ ID NO 273
<211> LENGTH: 16
<212> TYPE: DNA
<213> ORGANISM: Artificial Sequence
<220> FEATURE:
<223> OTHER INFORMATION: hsa-miR-135a-5p antagomir

<400> SEQUENCE: 273
acataggaat aaaaag                                                 16

<210> SEQ ID NO 274
<211> LENGTH: 17
<212> TYPE: DNA
<213> ORGANISM: Artificial Sequence

```
<220> FEATURE:
<223> OTHER INFORMATION: hsa-miR-135a-5p antagomir

<400> SEQUENCE: 274
tcacatagga ataaaaa                                                  17

<210> SEQ ID NO 275
<211> LENGTH: 15
<212> TYPE: DNA
<213> ORGANISM: Artificial Sequence
<220> FEATURE:
<223> OTHER INFORMATION: hsa-miR-135a-5p antagomir

<400> SEQUENCE: 275
acataggaat aaaaa                                                    15

<210> SEQ ID NO 276
<211> LENGTH: 16
<212> TYPE: DNA
<213> ORGANISM: Artificial Sequence
<220> FEATURE:
<223> OTHER INFORMATION: hsa-miR-135a-5p antagomir

<400> SEQUENCE: 276
cacataggaa taaaaa                                                   16

<210> SEQ ID NO 277
<211> LENGTH: 16
<212> TYPE: DNA
<213> ORGANISM: Artificial Sequence
<220> FEATURE:
<223> OTHER INFORMATION: hsa-miR-135a-5p antagomir

<400> SEQUENCE: 277
tcacatagga ataaaa                                                   16

<210> SEQ ID NO 278
<211> LENGTH: 15
<212> TYPE: DNA
<213> ORGANISM: Artificial Sequence
<220> FEATURE:
<223> OTHER INFORMATION: hsa-miR-135a-5p antagomir

<400> SEQUENCE: 278
cacataggaa taaaa                                                    15

<210> SEQ ID NO 279
<211> LENGTH: 15
<212> TYPE: DNA
<213> ORGANISM: Artificial Sequence
<220> FEATURE:
<223> OTHER INFORMATION: hsa-miR-135a-5p antagomir

<400> SEQUENCE: 279
tcacatagga ataaa                                                    15

<210> SEQ ID NO 280
<211> LENGTH: 22
<212> TYPE: DNA
<213> ORGANISM: Artificial Sequence
<220> FEATURE:
<223> OTHER INFORMATION: hsa-miR-135a-3p antagomir

<400> SEQUENCE: 280
cgccacggct ccaatcccta ta                                            22
```

```
<210> SEQ ID NO 281
<211> LENGTH: 21
<212> TYPE: DNA
<213> ORGANISM: Artificial Sequence
<220> FEATURE:
<223> OTHER INFORMATION: hsa-miR-135a-3p antagomir

<400> SEQUENCE: 281
gccacggctc caatccctat a                                              21

<210> SEQ ID NO 282
<211> LENGTH: 20
<212> TYPE: DNA
<213> ORGANISM: Artificial Sequence
<220> FEATURE:
<223> OTHER INFORMATION: hsa-miR-135a-3p antagomir

<400> SEQUENCE: 282
ccacggctcc aatccctata                                                20

<210> SEQ ID NO 283
<211> LENGTH: 22
<212> TYPE: DNA
<213> ORGANISM: Artificial Sequence
<220> FEATURE:
<223> OTHER INFORMATION: hsa-miR-135a-3p antagomir

<400> SEQUENCE: 283
gccacggctc caatccctat at                                             22

<210> SEQ ID NO 284
<211> LENGTH: 21
<212> TYPE: DNA
<213> ORGANISM: Artificial Sequence
<220> FEATURE:
<223> OTHER INFORMATION: hsa-miR-135a-3p antagomir

<400> SEQUENCE: 284
ccacggctcc aatccctata t                                              21

<210> SEQ ID NO 285
<211> LENGTH: 20
<212> TYPE: DNA
<213> ORGANISM: Artificial Sequence
<220> FEATURE:
<223> OTHER INFORMATION: hsa-miR-135a-3p antagomir

<400> SEQUENCE: 285
cacggctcca atccctatat                                                20

<210> SEQ ID NO 286
<211> LENGTH: 24
<212> TYPE: DNA
<213> ORGANISM: Artificial Sequence
<220> FEATURE:
<223> OTHER INFORMATION: hsa-miR-135a-3p antagomir

<400> SEQUENCE: 286
cgccacggct ccaatcccta tatg                                           24

<210> SEQ ID NO 287
<211> LENGTH: 20
<212> TYPE: DNA
<213> ORGANISM: Artificial Sequence
<220> FEATURE:
<223> OTHER INFORMATION: hsa-miR-135a-3p antagomir
```

<400> SEQUENCE: 287
gccacggctc caatccctat                                          20

<210> SEQ ID NO 288
<211> LENGTH: 23
<212> TYPE: DNA
<213> ORGANISM: Artificial Sequence
<220> FEATURE:
<223> OTHER INFORMATION: hsa-miR-135b-5p antagomir

<400> SEQUENCE: 288
tcacatagga atgaaaagcc ata                                      23

<210> SEQ ID NO 289
<211> LENGTH: 20
<212> TYPE: DNA
<213> ORGANISM: Artificial Sequence
<220> FEATURE:
<223> OTHER INFORMATION: hsa-miR-135b-5p antagomir

<400> SEQUENCE: 289
cataggaatg aaaagccata                                          20

<210> SEQ ID NO 290
<211> LENGTH: 19
<212> TYPE: DNA
<213> ORGANISM: Artificial Sequence
<220> FEATURE:
<223> OTHER INFORMATION: hsa-miR-135b-5p antagomir

<400> SEQUENCE: 290
ataggaatga aaagccata                                           19

<210> SEQ ID NO 291
<211> LENGTH: 18
<212> TYPE: DNA
<213> ORGANISM: Artificial Sequence
<220> FEATURE:
<223> OTHER INFORMATION: hsa-miR-135b-5p antagomir

<400> SEQUENCE: 291
taggaatgaa aagccata                                            18

<210> SEQ ID NO 292
<211> LENGTH: 23
<212> TYPE: DNA
<213> ORGANISM: Artificial Sequence
<220> FEATURE:
<223> OTHER INFORMATION: hsa-miR-135b-5p antagomir

<400> SEQUENCE: 292
atcacatagg aatgaaaagc cat                                      23

<210> SEQ ID NO 293
<211> LENGTH: 22
<212> TYPE: DNA
<213> ORGANISM: Artificial Sequence
<220> FEATURE:
<223> OTHER INFORMATION: hsa-miR-135b-5p antagomir

<400> SEQUENCE: 293
tcacatagga atgaaaagcc at                                       22

<210> SEQ ID NO 294

```
<211> LENGTH: 21
<212> TYPE: DNA
<213> ORGANISM: Artificial Sequence
<220> FEATURE:
<223> OTHER INFORMATION: hsa-miR-135b-5p antagomir

<400> SEQUENCE: 294
cacataggaa tgaaaagcca t                                              21

<210> SEQ ID NO 295
<211> LENGTH: 20
<212> TYPE: DNA
<213> ORGANISM: Artificial Sequence
<220> FEATURE:
<223> OTHER INFORMATION: hsa-miR-135b-5p antagomir

<400> SEQUENCE: 295
acataggaat gaaaagccat                                                20

<210> SEQ ID NO 296
<211> LENGTH: 21
<212> TYPE: DNA
<213> ORGANISM: Artificial Sequence
<220> FEATURE:
<223> OTHER INFORMATION: hsa-miR-135b-5p antagomir

<400> SEQUENCE: 296
tcacatagga atgaaaagcc a                                              21

<210> SEQ ID NO 297
<211> LENGTH: 19
<212> TYPE: DNA
<213> ORGANISM: Artificial Sequence
<220> FEATURE:
<223> OTHER INFORMATION: hsa-miR-135b-5p antagomir

<400> SEQUENCE: 297
tcacatagga atgaaaagc                                                 19

<210> SEQ ID NO 298
<211> LENGTH: 18
<212> TYPE: DNA
<213> ORGANISM: Artificial Sequence
<220> FEATURE:
<223> OTHER INFORMATION: hsa-miR-135b-5p antagomir

<400> SEQUENCE: 298
tcacatagga atgaaaag                                                  18

<210> SEQ ID NO 299
<211> LENGTH: 16
<212> TYPE: DNA
<213> ORGANISM: Artificial Sequence
<220> FEATURE:
<223> OTHER INFORMATION: hsa-miR-135b-5p antagomir

<400> SEQUENCE: 299
acataggaat gaaaag                                                    16

<210> SEQ ID NO 300
<211> LENGTH: 17
<212> TYPE: DNA
<213> ORGANISM: Artificial Sequence
<220> FEATURE:
<223> OTHER INFORMATION: hsa-miR-135b-5p antagomir

<400> SEQUENCE: 300
```

-continued

```
<210> SEQ ID NO 301
<211> LENGTH: 15
<212> TYPE: DNA
<213> ORGANISM: Artificial Sequence
<220> FEATURE:
<223> OTHER INFORMATION: hsa-miR-135b-5p antagomir

<400> SEQUENCE: 301
cataggaatg aaaag                                                      15

<210> SEQ ID NO 302
<211> LENGTH: 17
<212> TYPE: DNA
<213> ORGANISM: Artificial Sequence
<220> FEATURE:
<223> OTHER INFORMATION: hsa-miR-135b-5p antagomir

<400> SEQUENCE: 302
tcacatagga atgaaaa                                                    17

<210> SEQ ID NO 303
<211> LENGTH: 15
<212> TYPE: DNA
<213> ORGANISM: Artificial Sequence
<220> FEATURE:
<223> OTHER INFORMATION: hsa-miR-135b-5p antagomir

<400> SEQUENCE: 303
acataggaat gaaaa                                                      15

<210> SEQ ID NO 304
<211> LENGTH: 16
<212> TYPE: DNA
<213> ORGANISM: Artificial Sequence
<220> FEATURE:
<223> OTHER INFORMATION: hsa-miR-135b-5p antagomir

<400> SEQUENCE: 304
cacataggaa tgaaaa                                                     16

<210> SEQ ID NO 305
<211> LENGTH: 16
<212> TYPE: DNA
<213> ORGANISM: Artificial Sequence
<220> FEATURE:
<223> OTHER INFORMATION: hsa-miR-135b-5p antagomir

<400> SEQUENCE: 305
tcacatagga atgaaa                                                     16

<210> SEQ ID NO 306
<211> LENGTH: 15
<212> TYPE: DNA
<213> ORGANISM: Artificial Sequence
<220> FEATURE:
<223> OTHER INFORMATION: hsa-miR-135b-5p antagomir

<400> SEQUENCE: 306
cacataggaa tgaaa                                                      15

<210> SEQ ID NO 307
<211> LENGTH: 22
<212> TYPE: DNA
```

(preceding entry on page: `cacataggaa tgaaaag` 17)

```
<213> ORGANISM: Artificial Sequence
<220> FEATURE:
<223> OTHER INFORMATION: hsa-miR-135b-5p antagomir

<400> SEQUENCE: 307
acataggaat gaaaagccat ag                                          22

<210> SEQ ID NO 308
<211> LENGTH: 22
<212> TYPE: DNA
<213> ORGANISM: Artificial Sequence
<220> FEATURE:
<223> OTHER INFORMATION: hsa-miR-135b-3p antagomir

<400> SEQUENCE: 308
cccatggctt ttagccctac at                                          22

<210> SEQ ID NO 309
<211> LENGTH: 23
<212> TYPE: DNA
<213> ORGANISM: Artificial Sequence
<220> FEATURE:
<223> OTHER INFORMATION: hsa-miR-135b-3p antagomir

<400> SEQUENCE: 309
gcccatggct tttagcccta cat                                         23

<210> SEQ ID NO 310
<211> LENGTH: 21
<212> TYPE: DNA
<213> ORGANISM: Artificial Sequence
<220> FEATURE:
<223> OTHER INFORMATION: hsa-miR-135b-3p antagomir

<400> SEQUENCE: 310
ccatggcttt tagccctaca t                                           21

<210> SEQ ID NO 311
<211> LENGTH: 15
<212> TYPE: DNA
<213> ORGANISM: Artificial Sequence
<220> FEATURE:
<223> OTHER INFORMATION: hsa-miR-135b-3p antagomir

<400> SEQUENCE: 311
cttttagccc tacat                                                  15

<210> SEQ ID NO 312
<211> LENGTH: 23
<212> TYPE: DNA
<213> ORGANISM: Artificial Sequence
<220> FEATURE:
<223> OTHER INFORMATION: hsa-miR-135b-3p antagomir

<400> SEQUENCE: 312
agcccatggc ttttagccct aca                                         23

<210> SEQ ID NO 313
<211> LENGTH: 22
<212> TYPE: DNA
<213> ORGANISM: Artificial Sequence
<220> FEATURE:
<223> OTHER INFORMATION: hsa-miR-135b-3p antagomir

<400> SEQUENCE: 313
gcccatggct tttagcccta ca                                          22
```

<210> SEQ ID NO 314
<211> LENGTH: 17
<212> TYPE: DNA
<213> ORGANISM: Artificial Sequence
<220> FEATURE:
<223> OTHER INFORMATION: hsa-miR-135b-3p antagomir

<400> SEQUENCE: 314
cccatggctt ttagccc                                                17

<210> SEQ ID NO 315
<211> LENGTH: 22
<212> TYPE: DNA
<213> ORGANISM: Artificial Sequence
<220> FEATURE:
<223> OTHER INFORMATION: hsa-miR-196a-5p antagomir

<400> SEQUENCE: 315
cccaacaaca tgaaactacc ta                                          22

<210> SEQ ID NO 316
<211> LENGTH: 22
<212> TYPE: DNA
<213> ORGANISM: Artificial Sequence
<220> FEATURE:
<223> OTHER INFORMATION: hsa-miR-196a-5p antagomir

<400> SEQUENCE: 316
ggcccaacaa catgaaacta cc                                          22

<210> SEQ ID NO 317
<211> LENGTH: 23
<212> TYPE: DNA
<213> ORGANISM: Artificial Sequence
<220> FEATURE:
<223> OTHER INFORMATION: hsa-miR-196a-5p antagomir

<400> SEQUENCE: 317
gcccaacaac atgaaactac cta                                         23

<210> SEQ ID NO 318
<211> LENGTH: 21
<212> TYPE: DNA
<213> ORGANISM: Artificial Sequence
<220> FEATURE:
<223> OTHER INFORMATION: hsa-miR-196a-5p antagomir

<400> SEQUENCE: 318
ccaacaacat gaaactacct a                                           21

<210> SEQ ID NO 319
<211> LENGTH: 20
<212> TYPE: DNA
<213> ORGANISM: Artificial Sequence
<220> FEATURE:
<223> OTHER INFORMATION: hsa-miR-196a-5p antagomir

<400> SEQUENCE: 319
caacaacatg aaactaccta                                             20

<210> SEQ ID NO 320
<211> LENGTH: 19
<212> TYPE: DNA
<213> ORGANISM: Artificial Sequence
<220> FEATURE:

<223> OTHER INFORMATION: hsa-miR-196a-5p antagomir

<400> SEQUENCE: 320
aacaacatga aactaccta                             19

<210> SEQ ID NO 321
<211> LENGTH: 18
<212> TYPE: DNA
<213> ORGANISM: Artificial Sequence
<220> FEATURE:
<223> OTHER INFORMATION: hsa-miR-196a-5p antagomir

<400> SEQUENCE: 321
acaacatgaa actaccta                              18

<210> SEQ ID NO 322
<211> LENGTH: 17
<212> TYPE: DNA
<213> ORGANISM: Artificial Sequence
<220> FEATURE:
<223> OTHER INFORMATION: hsa-miR-196a-5p antagomir

<400> SEQUENCE: 322
caacatgaaa ctaccta                               17

<210> SEQ ID NO 323
<211> LENGTH: 16
<212> TYPE: DNA
<213> ORGANISM: Artificial Sequence
<220> FEATURE:
<223> OTHER INFORMATION: hsa-miR-196a-5p antagomir

<400> SEQUENCE: 323
aacatgaaac taccta                                16

<210> SEQ ID NO 324
<211> LENGTH: 15
<212> TYPE: DNA
<213> ORGANISM: Artificial Sequence
<220> FEATURE:
<223> OTHER INFORMATION: hsa-miR-196a-5p antagomir

<400> SEQUENCE: 324
acatgaaact accta                                 15

<210> SEQ ID NO 325
<211> LENGTH: 23
<212> TYPE: DNA
<213> ORGANISM: Artificial Sequence
<220> FEATURE:
<223> OTHER INFORMATION: hsa-miR-196a-5p antagomir

<400> SEQUENCE: 325
ggcccaacaa catgaaacta cct                        23

<210> SEQ ID NO 326
<211> LENGTH: 22
<212> TYPE: DNA
<213> ORGANISM: Artificial Sequence
<220> FEATURE:
<223> OTHER INFORMATION: hsa-miR-196a-5p antagomir

<400> SEQUENCE: 326
gcccaacaac atgaaactac ct                         22

```
<210> SEQ ID NO 327
<211> LENGTH: 21
<212> TYPE: DNA
<213> ORGANISM: Artificial Sequence
<220> FEATURE:
<223> OTHER INFORMATION: hsa-miR-196a-5p antagomir

<400> SEQUENCE: 327
cccaacaaca tgaaactacc t                                          21

<210> SEQ ID NO 328
<211> LENGTH: 20
<212> TYPE: DNA
<213> ORGANISM: Artificial Sequence
<220> FEATURE:
<223> OTHER INFORMATION: hsa-miR-196a-5p antagomir

<400> SEQUENCE: 328
ccaacaacat gaaactacct                                            20

<210> SEQ ID NO 329
<211> LENGTH: 20
<212> TYPE: DNA
<213> ORGANISM: Artificial Sequence
<220> FEATURE:
<223> OTHER INFORMATION: hsa-miR-196a-5p antagomir

<400> SEQUENCE: 329
cccaacaaca tgaaactacc                                            20

<210> SEQ ID NO 330
<211> LENGTH: 19
<212> TYPE: DNA
<213> ORGANISM: Artificial Sequence
<220> FEATURE:
<223> OTHER INFORMATION: hsa-miR-196a-5p antagomir

<400> SEQUENCE: 330
ccaacaacat gaaactacc                                             19

<210> SEQ ID NO 331
<211> LENGTH: 19
<212> TYPE: DNA
<213> ORGANISM: Artificial Sequence
<220> FEATURE:
<223> OTHER INFORMATION: hsa-miR-196a-5p antagomir

<400> SEQUENCE: 331
cccaacaaca tgaaactac                                             19

<210> SEQ ID NO 332
<211> LENGTH: 18
<212> TYPE: DNA
<213> ORGANISM: Artificial Sequence
<220> FEATURE:
<223> OTHER INFORMATION: hsa-miR-196a-5p antagomir

<400> SEQUENCE: 332
ccaacaacat gaaactac                                              18

<210> SEQ ID NO 333
<211> LENGTH: 18
<212> TYPE: DNA
<213> ORGANISM: Artificial Sequence
<220> FEATURE:
<223> OTHER INFORMATION: hsa-miR-196a-5p antagomir
```

```
<400> SEQUENCE: 333
cccaacaaca tgaaacta                                               18

<210> SEQ ID NO 334
<211> LENGTH: 17
<212> TYPE: DNA
<213> ORGANISM: Artificial Sequence
<220> FEATURE:
<223> OTHER INFORMATION: hsa-miR-196a-5p antagomir

<400> SEQUENCE: 334
ccaacaacat gaaacta                                                17

<210> SEQ ID NO 335
<211> LENGTH: 17
<212> TYPE: DNA
<213> ORGANISM: Artificial Sequence
<220> FEATURE:
<223> OTHER INFORMATION: hsa-miR-196a-5p antagomir

<400> SEQUENCE: 335
cccaacaaca tgaaact                                                17

<210> SEQ ID NO 336
<211> LENGTH: 16
<212> TYPE: DNA
<213> ORGANISM: Artificial Sequence
<220> FEATURE:
<223> OTHER INFORMATION: hsa-miR-196a-5p antagomir

<400> SEQUENCE: 336
ccaacaacat gaaact                                                 16

<210> SEQ ID NO 337
<211> LENGTH: 16
<212> TYPE: DNA
<213> ORGANISM: Artificial Sequence
<220> FEATURE:
<223> OTHER INFORMATION: hsa-miR-196a-5p antagomir

<400> SEQUENCE: 337
gcccaacaac atgaaa                                                 16

<210> SEQ ID NO 338
<211> LENGTH: 15
<212> TYPE: DNA
<213> ORGANISM: Artificial Sequence
<220> FEATURE:
<223> OTHER INFORMATION: hsa-miR-196a-5p antagomir

<400> SEQUENCE: 338
cccaacaaca tgaaa                                                  15

<210> SEQ ID NO 339
<211> LENGTH: 22
<212> TYPE: DNA
<213> ORGANISM: Artificial Sequence
<220> FEATURE:
<223> OTHER INFORMATION: hsa-miR-196a-5p antagomir

<400> SEQUENCE: 339
caacaacatg aaactaccta at                                          22

<210> SEQ ID NO 340
<211> LENGTH: 23
```

```
<212> TYPE: DNA
<213> ORGANISM: Artificial Sequence
<220> FEATURE:
<223> OTHER INFORMATION: hsa-miR-196a-5p antagomir

<400> SEQUENCE: 340
cccaacaaca tgaaactacc taa                                            23

<210> SEQ ID NO 341
<211> LENGTH: 22
<212> TYPE: DNA
<213> ORGANISM: Artificial Sequence
<220> FEATURE:
<223> OTHER INFORMATION: hsa-miR-196a-5p antagomir

<400> SEQUENCE: 341
ccaacaacat gaaactacct aa                                             22

<210> SEQ ID NO 342
<211> LENGTH: 23
<212> TYPE: RNA
<213> ORGANISM: Artificial Sequence
<220> FEATURE:
<223> OTHER INFORMATION: miRNA-135b

<400> SEQUENCE: 342
uauggcuuuu cauuccuaug uga                                            23

<210> SEQ ID NO 343
<211> LENGTH: 23
<212> TYPE: RNA
<213> ORGANISM: Artificial Sequence
<220> FEATURE:
<223> OTHER INFORMATION: miRNA-135a

<400> SEQUENCE: 343
uauggcuuuu uauuccuaug uga                                            23

<210> SEQ ID NO 344
<211> LENGTH: 23
<212> TYPE: DNA
<213> ORGANISM: Artificial Sequence
<220> FEATURE:
<223> OTHER INFORMATION: pCDH-fwd primer

<400> SEQUENCE: 344
cacgctgttt tgacctccat aga                                            23

<210> SEQ ID NO 345
<211> LENGTH: 18
<212> TYPE: DNA
<213> ORGANISM: Artificial Sequence
<220> FEATURE:
<223> OTHER INFORMATION: pCDH-rev primer

<400> SEQUENCE: 345
cactgacggg caccggag                                                  18

<210> SEQ ID NO 346
<211> LENGTH: 28
<212> TYPE: DNA
<213> ORGANISM: Artificial Sequence
<220> FEATURE:
<223> OTHER INFORMATION: pCDH-seq

<400> SEQUENCE: 346
```
gacctccata gaagattcta gagctagc                                              28

<210> SEQ ID NO 347
<211> LENGTH: 20
<212> TYPE: RNA
<213> ORGANISM: Homo sapiens

<400> SEQUENCE: 347
uaaggcacgc ggugaaugcc                                                       20

<210> SEQ ID NO 348
<211> LENGTH: 22
<212> TYPE: RNA
<213> ORGANISM: Homo sapiens

<400> SEQUENCE: 348
cguguucaca gcggaccuug au                                                    22

<210> SEQ ID NO 349
<211> LENGTH: 7
<212> TYPE: RNA
<213> ORGANISM: Artificial sequence
<220> FEATURE:
<223> OTHER INFORMATION: miRNA-124-3p seed

<400> SEQUENCE: 349 aaggcac                                                                      7

<210> SEQ ID NO 350
<211> LENGTH: 7
<212> TYPE: RNA
<213> ORGANISM: Artificial sequence
<220> FEATURE:
<223> OTHER INFORMATION: miRNA-124-5p seed

<400> SEQUENCE: 350 guguuca                                                                      7

<210> SEQ ID NO 351
<211> LENGTH: 35
<212> TYPE: DNA
<213> ORGANISM: Artificial Sequence
<220> FEATURE:
<223> OTHER INFORMATION: MEF2A-135a-fw primer

<400> SEQUENCE: 351
tcgagagcag aaccttggaa aaaaaaagcc atggc                                      35

<210> SEQ ID NO 352
<211> LENGTH: 35
<212> TYPE: DNA
<213> ORGANISM: Artificial Sequence
<220> FEATURE:
<223> OTHER INFORMATION: MEF2A-135a-reverse primer

<400> SEQUENCE: 352
ggccgccatg gcttttttttt tccaaggttc tgctc                                     35

<210> SEQ ID NO 353
<211> LENGTH: 35
<212> TYPE: DNA
<213> ORGANISM: Artificial Sequence
<220> FEATURE:
<223> OTHER INFORMATION: MEF2A-135aMut-fw

<400> SEQUENCE: 353

```
tcgagagcag aaccttggaa aaaaaaaggc ttggc                              35
```

<210> SEQ ID NO 354
<211> LENGTH: 35
<212> TYPE: DNA
<213> ORGANISM: Artificial Sequence
<220> FEATURE:
<223> OTHER INFORMATION: MEF2A-135aMut-reverse primer

<400> SEQUENCE: 354

```
ggccgccaag ccttttttt tccaaggttc tgctc                               35
```

<210> SEQ ID NO 355
<211> LENGTH: 21
<212> TYPE: DNA
<213> ORGANISM: Artificial Sequence
<220> FEATURE:
<223> OTHER INFORMATION: Pre-miR-135a1 human primer forward

<400> SEQUENCE: 355

```
tcgctgttct ctatggcttt t                                             21
```

<210> SEQ ID NO 356
<211> LENGTH: 20
<212> TYPE: DNA
<213> ORGANISM: Artificial Sequence
<220> FEATURE:
<223> OTHER INFORMATION: Pre-miR-135a1 human primer reverse

<400> SEQUENCE: 356

```
cggctccaat ccctatatga                                               20
```

<210> SEQ ID NO 357
<211> LENGTH: 22
<212> TYPE: DNA
<213> ORGANISM: Artificial Sequence
<220> FEATURE:
<223> OTHER INFORMATION: Pre-miR-135a2 human primer forward

<400> SEQUENCE: 357

```
tgctttatgg cttttattc ct                                             22
```

<210> SEQ ID NO 358
<211> LENGTH: 20
<212> TYPE: DNA
<213> ORGANISM: Artificial Sequence
<220> FEATURE:
<223> OTHER INFORMATION: Pre-miR-135a2 human primer reverse

<400> SEQUENCE: 358

```
tggcttccat ccctacatga                                               20
```

<210> SEQ ID NO 359
<211> LENGTH: 23
<212> TYPE: DNA
<213> ORGANISM: Artificial Sequence
<220> FEATURE:
<223> OTHER INFORMATION: Pre-miR-135a1 mouse primer forward

<400> SEQUENCE: 359

```
gcctcactgt tctctatggc ttt                                           23
```

<210> SEQ ID NO 360
<211> LENGTH: 23
<212> TYPE: DNA

```
<213> ORGANISM: Artificial Sequence
<220> FEATURE:
<223> OTHER INFORMATION: Pre-miR-135a1 mouse primer reverse

<400> SEQUENCE: 360
ccacggctcc aatccctata tga                                              23

<210> SEQ ID NO 361
<211> LENGTH: 20
<212> TYPE: DNA
<213> ORGANISM: Artificial Sequence
<220> FEATURE:
<223> OTHER INFORMATION: Pre-miR-135a2 mouse primer forward

<400> SEQUENCE: 361
tgctttatgg ctttttattc                                                  20

<210> SEQ ID NO 362
<211> LENGTH: 22
<212> TYPE: DNA
<213> ORGANISM: Artificial Sequence
<220> FEATURE:
<223> OTHER INFORMATION: Pre-miR-135a2 mouse primer reverse

<400> SEQUENCE: 362
catccctaca tgagacttta tt                                               22

<210> SEQ ID NO 363
<211> LENGTH: 20
<212> TYPE: DNA
<213> ORGANISM: Artificial Sequence
<220> FEATURE:
<223> OTHER INFORMATION: GAPDH Human primer Fw

<400> SEQUENCE: 363
tggaaggact catgaccaca                                                  20

<210> SEQ ID NO 364
<211> LENGTH: 20
<212> TYPE: DNA
<213> ORGANISM: Artificial Sequence
<220> FEATURE:
<223> OTHER INFORMATION: GAPDH Human primer Rv

<400> SEQUENCE: 364
gggatgatgt tctggagagc                                                  20

<210> SEQ ID NO 365
<211> LENGTH: 20
<212> TYPE: DNA
<213> ORGANISM: Artificial Sequence
<220> FEATURE:
<223> OTHER INFORMATION: Beta-actin Mouse primer Fw

<400> SEQUENCE: 365
agccatgtac gtagccatcc                                                  20

<210> SEQ ID NO 366
<211> LENGTH: 20
<212> TYPE: DNA
<213> ORGANISM: Artificial Sequence
<220> FEATURE:
<223> OTHER INFORMATION: Beta-actin Mouse primer Rv

<400> SEQUENCE: 366
ctctcagctg tggtggtgaa                                                  20
```

<210> SEQ ID NO 367
<211> LENGTH: 20
<212> TYPE: DNA
<213> ORGANISM: Artificial Sequence
<220> FEATURE:
<223> OTHER INFORMATION: GR primer Fw

<400> SEQUENCE: 367
ggggaagcgt gatggacttg                                                    20

<210> SEQ ID NO 368
<211> LENGTH: 20
<212> TYPE: DNA
<213> ORGANISM: Artificial Sequence
<220> FEATURE:
<223> OTHER INFORMATION: GR primer Rv

<400> SEQUENCE: 368
cagcagccac tgagggtgaa                                                    20

<210> SEQ ID NO 369
<211> LENGTH: 20
<212> TYPE: DNA
<213> ORGANISM: Artificial Sequence
<220> FEATURE:
<223> OTHER INFORMATION: KLF5 primer Fw

<400> SEQUENCE: 369
gagttcctcc gtcatttcca                                                    20

<210> SEQ ID NO 370
<211> LENGTH: 20
<212> TYPE: DNA
<213> ORGANISM: Artificial Sequence
<220> FEATURE:
<223> OTHER INFORMATION: KLF5 primer Rv

<400> SEQUENCE: 370
gtcgccatta cccttgtcac                                                    20

<210> SEQ ID NO 371
<211> LENGTH: 20
<212> TYPE: DNA
<213> ORGANISM: Artificial Sequence
<220> FEATURE:
<223> OTHER INFORMATION: Mef2a primer Fw

<400> SEQUENCE: 371
agcagcacca tctaggacaa                                                    20

<210> SEQ ID NO 372
<211> LENGTH: 20
<212> TYPE: DNA
<213> ORGANISM: Artificial Sequence
<220> FEATURE:
<223> OTHER INFORMATION: Mef2a primer Rv

<400> SEQUENCE: 372
ctgctgttgg aagcctgatg                                                    20

<210> SEQ ID NO 373
<211> LENGTH: 20
<212> TYPE: DNA
<213> ORGANISM: Artificial Sequence
<220> FEATURE:

<223> OTHER INFORMATION: Mtss1 primer Fw

<400> SEQUENCE: 373
acagcaccca gaccaccacc                                                    20

<210> SEQ ID NO 374
<211> LENGTH: 20
<212> TYPE: DNA
<213> ORGANISM: Artificial Sequence
<220> FEATURE:
<223> OTHER INFORMATION: Mtss1 primer Rv

<400> SEQUENCE: 374
tgcctcctgg tcgccactta                                                    20

<210> SEQ ID NO 375
<211> LENGTH: 18
<212> TYPE: DNA
<213> ORGANISM: Artificial Sequence
<220> FEATURE:
<223> OTHER INFORMATION: PlxnA4 primer Fw

<400> SEQUENCE: 375
tctcagtaca acgtgctg                                                      18

<210> SEQ ID NO 376
<211> LENGTH: 19
<212> TYPE: DNA
<213> ORGANISM: Artificial Sequence
<220> FEATURE:
<223> OTHER INFORMATION: PlxnA4 primer Rv

<400> SEQUENCE: 376
tagcactgga tctgattgc                                                     19

<210> SEQ ID NO 377
<211> LENGTH: 20
<212> TYPE: DNA
<213> ORGANISM: Artificial Sequence
<220> FEATURE:
<223> OTHER INFORMATION: Slit2 primer fw

<400> SEQUENCE: 377
cagtcattca tggctccctc                                                    20

<210> SEQ ID NO 378
<211> LENGTH: 20
<212> TYPE: DNA
<213> ORGANISM: Artificial Sequence
<220> FEATURE:
<223> OTHER INFORMATION: Slit2 primer Rv

<400> SEQUENCE: 378
ttccctcggc agtctacaat                                                    20

<210> SEQ ID NO 379
<211> LENGTH: 22
<212> TYPE: DNA
<213> ORGANISM: Artificial Sequence
<220> FEATURE:
<223> OTHER INFORMATION: Tsc1 primer Fw

<400> SEQUENCE: 379
caggagttac agacaaagct gg                                                 22

```
<210> SEQ ID NO 380
<211> LENGTH: 20
<212> TYPE: DNA
<213> ORGANISM: Artificial Sequence
<220> FEATURE:
<223> OTHER INFORMATION: Tsc1 primer Rv

<400> SEQUENCE: 380
agcttctgag agacctggct                                                 20
```